(12) United States Patent
Mills et al.

(10) Patent No.: US 12,280,027 B2
(45) Date of Patent: Apr. 22, 2025

(54) TRANSDERMAL ANALGESIC FORMULATION

(71) Applicant: MEAT & LIVESTOCK AUSTRALIA LTD, North Sydney (AU)

(72) Inventors: Paul Mills, North Sydney (AU); Nana Satake, North Sydney (AU)

(73) Assignee: MEAT & LIVESTOCK AUSTRALIA LTD, North Sydney (AU)

( * ) Notice: Subject to any disclaimer, the term of this patent is extended or adjusted under 35 U.S.C. 154(b) by 161 days.

(21) Appl. No.: 16/772,027

(22) PCT Filed: Dec. 11, 2018

(86) PCT No.: PCT/AU2018/000255
§ 371 (c)(1),
(2) Date: Jun. 11, 2020

(87) PCT Pub. No.: WO2019/113625
PCT Pub. Date: Jun. 20, 2019

(65) Prior Publication Data
US 2021/0069137 A1    Mar. 11, 2021

(30) Foreign Application Priority Data
Dec. 11, 2017 (AU) .............................. 2017904975

(51) Int. Cl.
| | | |
|---|---|---|
| *A61K 31/192* | (2006.01) | |
| *A61K 9/00* | (2006.01) | |
| *A61K 31/196* | (2006.01) | |
| *A61K 31/44* | (2006.01) | |
| *A61K 47/10* | (2017.01) | |
| *A61K 47/14* | (2017.01) | |
| *A61K 47/44* | (2017.01) | |
| *A61P 29/00* | (2006.01) | |

(52) U.S. Cl.
CPC .......... *A61K 31/192* (2013.01); *A61K 9/0017* (2013.01); *A61K 31/196* (2013.01); *A61K 31/44* (2013.01); *A61K 47/10* (2013.01); *A61K 47/14* (2013.01); *A61K 47/44* (2013.01); *A61P 29/00* (2018.01)

(58) Field of Classification Search
CPC .... A61K 31/192; A61K 31/196; A61K 31/44; A61K 47/10; A61K 47/14; A61K 47/44; A61K 9/0017; A61P 29/00
See application file for complete search history.

(56) References Cited

U.S. PATENT DOCUMENTS

2016/0303065 A1    10/2016    Ewin et al.

FOREIGN PATENT DOCUMENTS

| | | | |
|---|---|---|---|
| CA | 2728727 | C | 12/2009 |
| EP | 1201230 | A2 | 5/2002 |
| WO | WO9523596 | * | 9/1995 |
| WO | WO 2000/053228 | A2 | 9/2000 |
| WO | WO 01/02015 | A1 | 1/2001 |
| WO | WO 2009/063378 | A2 | 5/2009 |
| WO | WO 2010/087947 | A2 | 8/2010 |
| WO | WO 2012/022837 | A1 | 2/2012 |

OTHER PUBLICATIONS

Balarezo et al., Essential topic oils on the prevention and treatment of mastitis. Engormix, published online Jun. 5, 2014.*
Sebei et al., Chemical composition and antibacterial activities of seven *Eucalyptus* species essential oils leaves. Biological Research, 48(7) (Year: 2015).*
Shpigel et al., Anti-inflammatory ketoprofen in the treatment of field cases of bovine mastitis. Research in Veterinary Science, vol. 56, pp. 62-68 (Year: 1994).*
Ting et al., Effect of ketoprofen, lidocaine local anesthesia, and combined xylazine and lidocaine caudal epidural anesthesia during castration of beef cattle on stress responses, immunity, growth, and behavior. Journal of Animal Science, vol. 81(5), pp. 1281-1293 (Year: 2003).*
European Patent Office, Extended European Search Report in European Patent Application No. 18887975.3, mailed on Sep. 29, 2021.
International Bureau, International Search Report and Written Opinion in International Application No. PCT/AU2018/000255, mailed Feb. 19, 2019.
Ma et al., "Effect of Counter-Ions and Penetration Enhancers on the Skin Permeation of Flurbiprofen," J. Pharm. Sci., 99(4): 1826-1837 (2010).
Dhawan et al., "Enhanced transdermal permeability of piroxicam through novel nanoemulgel formulation", *International Journal of Pharmaceutical Investigation*, 4(2): 65-76 (2014).
Mills et al., "Transdermal drug delivery: Basic principles for the veterinarian", *The Veterinary Journal*, 172: 218-233 (2006).
Monteiro-Riviere et al., "Interspecies and Interregional Analysis of the Comparative Histologic Thickness and Laser Doppler Blood Flow Measurements at Five Cutaneous Sites in Nine Species", *The Journal of Investigative Dermatology*, 95(5): 582-586 (1990).

* cited by examiner

*Primary Examiner* — Barbara P Badio
(74) *Attorney, Agent, or Firm* — Leydig, Voit & Mayer, Ltd.

(57) ABSTRACT

Provided herein is a transdermal liquid formulation that includes a propionic acid-based non-steroidal anti-inflammatory agent, such as ketoprofen, and a dermal penetration enhancer containing an alcohol, an emollient and an essential oil. Methods of using and making the aforementioned transdermal liquid formulation are also provided herein.

6 Claims, 21 Drawing Sheets

TRANSDERMAL ANALGESIC FORMULATION

CROSS-REFERENCE TO RELATED APPLICATIONS

This patent application is the U.S. national stage of PCT/AU2018/000255, filed Dec. 11, 2018, which claims the benefit of Australian Patent Application No. 2017904975, filed Dec. 11, 2017, each of which is incorporated by reference in its entirety herein.

TECHNICAL FIELD

THIS INVENTION relates to a transdermal analgesic formulation for application to the skin of animals, and more particularly cattle.

BACKGROUND

Cattle typically undergo a range of necessary surgical husbandry procedures, including dehorning, castration and ovariectomy. Analgesia may be insufficient during these procedures, especially in extensive properties where access to veterinary assistance is limited. However, public interest groups and welfare advocates are increasingly concerned about the welfare of animals undergoing potentially painful procedures, while production will also suffer if insufficient analgesia is available. It would therefore be highly advantageous if analgesics were available and able to be administered without veterinary assistance.

The transdermal route of drug administration offers many advantages, including avoiding first pass effects and the high costs of producing parenteral formulations (particularly sterility), plus can be easily administered by lay personnel. The problem arises that such formulations cannot be extrapolated between species and movement through skin is strongly dependent on the specific active drug and the vehicle the drug is dissolved in. Accordingly, there remains a need for improved transdermal analgesic formulations for administration to the skin of animals, such as cattle.

SUMMARY

The present invention is broadly directed to a transdermal liquid formulation that includes a propionic acid-based non-steroidal anti-inflammatory agent, and more particularly ketoprofen, an alcohol, an emollient and an essential oil, as well as methods of use thereof. The transdermal absorption of the propionic acid-based non-steroidal anti-inflammatory agent can be advantageously enhanced by the inclusion of such a combination of penetration enhancers, such that therapeutically relevant concentrations of the anti-inflammatory agent can be rapidly achieved in treated animals.

In a first aspect, the invention provides a transdermal liquid formulation comprising:
(a) a therapeutically effective amount of a propionic acid-based non-steroidal anti-inflammatory agent; and
(b) a dermal penetration enhancer comprising an alcohol, an emollient and an essential oil.

Suitably, the propionic acid-based anti-inflammatory agent is selected from the group consisting of ketoprofen, alminoprofen, ibuprofen, oxaprozin, zaltoprofen, tiaprofenic acid, naproxen, fenoprofen, flurbiprofen, pranoprofen, dexibuprofen, dexketoprofen, loxoprofen and any combination thereof. Preferably, the propionic acid-based non-steroidal anti-inflammatory agent is or comprises ketoprofen or a pharmaceutically acceptable salt thereof.

In certain embodiments, the propionic acid-based non-steroidal anti-inflammatory agent is present in an amount from about 100 mg/mL to about 300 mg/mL.

The alcohol is suitably selected from the group consisting of a primary alcohol, a secondary alcohol and any combination thereof. Preferably, the alcohol is selected from the group consisting of ethanol, isopropanol and any combination thereof. More preferably, the alcohol is or comprises ethanol.

In one embodiment, the alcohol is present in an amount from about 100 mL/L to about 700 mL/L.

Suitably, the emollient is selected from the group consisting of a glycol, an unsaturated fatty alcohol, a sorbitol derivative, a myristate, an alkoxylated di-ester of myristyl alcohol and adipic acid, a pyrrolidone, and any combination thereof. In particular preferred embodiments, the emollient is selected from the group consisting of propylene glycol, oleyl alcohol, dimethyl isosorbide, PPG-3 benzyl ether myristate, di-PPG2-myreth-10-adipate, 1-ethyl-2-pryrrolidone, isomyristate, isopropyl myristate and any combination thereof. Even more preferably, the emollient is or comprises isopropyl myristate.

In one embodiment, the emollient is present in an amount from about 100 mL/L to about 700 mL/L.

Suitably, the essential oil is or comprises menthol, a cineole-based oil or any combination thereof. Preferably, the cineole-based oil is or comprises *eucalyptus* oil, eucalyptol or any combination thereof.

In one embodiment, the essential oil is present in an amount from about 25 mL/L to about 150 mL/L.

In particular embodiments, the transdermal liquid formulation is for use in cattle.

In one embodiment, the transdermal liquid formulation is for use as a pour-on preparation.

In one preferred embodiment, the transdermal liquid formulation comprises:
(a) ketoprofen at a concentration of about 100 mg/mL to about 300 mg/mL;
(b) ethanol at a concentration of about 300 mL/L to about 600 mL/L;
(c) isopropyl myristate at a concentration of about 300 mL/L to about 600 mL/L; and
(d) *eucalyptus* oil at a concentration of about 50 mL/L to about 150 mL/L.

In a second aspect, the invention provides a method of preventing and/or treating inflammation in a subject, the method including the step of administering to the subject a therapeutically effective amount of the transdermal liquid formulation of the first aspect to thereby prevent and/or treat inflammation in the subject.

In a third aspect, the invention provides a method of preventing and/or treating pain in a subject, the method including the step of administering to the subject a therapeutically effective amount of the transdermal liquid formulation of the first aspect to thereby prevent and/or treat pain in the subject.

In a fourth aspect, the invention provides a method of preventing and/or treating a lameness and/or a loss of mobility in a subject, the method including the step of administering to the subject a therapeutically effective amount of the transdermal liquid formulation of the first aspect to thereby prevent and/or treat the lameness and/or the loss of mobility in the subject.

With respect to the three aforementioned aspects, the transdermal liquid formulation is suitably administered by a spray device, a pour-on device, a spot-on device and/or a transdermal patch.

In a fifth aspect, the invention provides a method of administering a transdermal liquid preparation to a subject in need thereof, including the step of administering a therapeutically effective amount of the transdermal liquid preparation of the first aspect to the subject by an application device.

Suitably, the application device is selected from the group consisting of a spray device, a pour-on device, a spot-on device and a transdermal patch.

In one embodiment, the present method includes the further step of adding the transdermal liquid preparation to the application device.

With respect to the second, third, fourth and fifth aspects, the subject is preferably a mammal. More preferably, the subject is bovine.

In a sixth aspect, the invention provides a method of preparing a transdermal liquid formulation, including the steps of:
(a) combining a therapeutically effective amount of a propionic acid-based non-steroidal anti-inflammatory agent and a dermal penetration enhancer comprising an alcohol, an emollient and an essential oil; and
(b) mixing the mixture of step (a) to thereby prepare the transdermal liquid formulation.

Suitably, the transdermal liquid formulation is that of the first aspect.

In a seventh aspect, the invention provides, a transdermal liquid formulation prepared by the method of the sixth aspect.

As used herein, except where the context requires otherwise, the term "comprise" and variations of the term, such as "comprising", "comprises" and "comprised", are not intended to exclude further elements, components, integers or steps but may include one or more unstated further elements, components, integers or steps.

It will be appreciated that the indefinite articles "a" and "an" are not to be read as singular indefinite articles or as otherwise excluding more than one or more than a single subject to which the indefinite article refers. For example, "a" cell includes one cell, one or more cells and a plurality of cells.

BRIEF DESCRIPTION OF THE DRAWINGS

By way of example only, embodiments of the invention are described more fully hereinafter with reference to the accompanying drawing, in which:—

DETAILED DESCRIPTION

Figure 1:
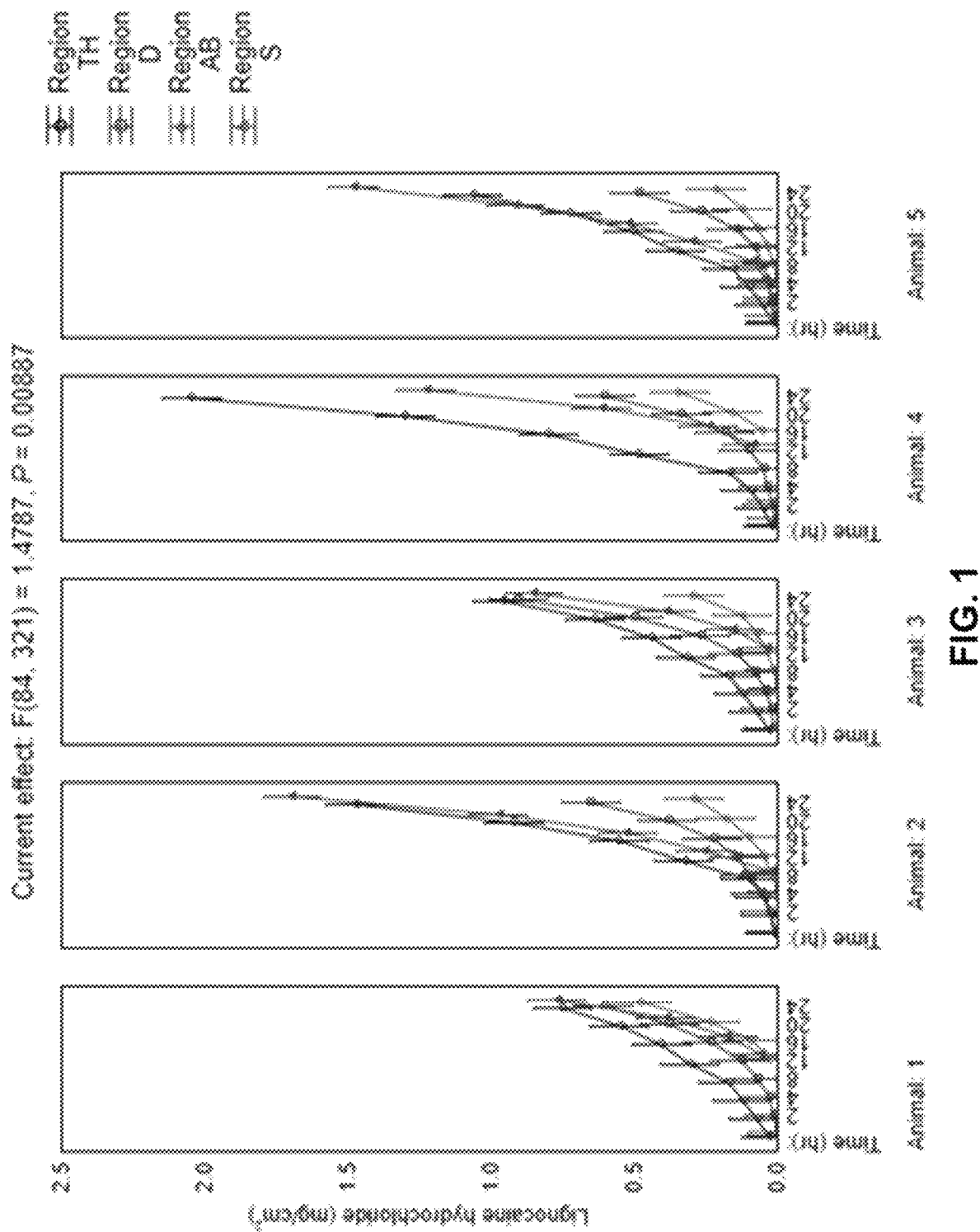
FIG. 1: Permeation profiles of lignocaine hydrochloride through skin obtained from the thorax (TH), dorsal midline (D), ventral abdomen (AB) and scrotum (S). The cumulative amount is marked on the y-axis. Each data point represents a mean value and standard error of mean from a number of replicates (n=3).

The present invention is predicated, at least in part, on the surprising discovery that the transdermal application of ketoprofen together with specific penetration enhancing agents (i.e., an alcohol, an emollient and an essential oil) to cattle rapidly resulted in therapeutically relevant systemic concentrations of the anti-inflammatory agent and provided analgesia that seemed equivalent or even superior to intramuscular injections of ketoprofen. Therefore, the formulations of the present invention can be used to prevent or reduce pain or inflammation associated with an infectious disease, surgery, injury, or another cause.

Accordingly, in one aspect, the invention provides a transdermal liquid formulation comprising:
(a) a therapeutically effective amount of a propionic acid-based non-steroidal anti-inflammatory agent; and
(b) a dermal penetration enhancer comprising an alcohol, an emollient and an essential oil.

As generally used herein, the terms "transdermal", "transdermally" or similar refer to the passage or migration into and/or through the various layers of skin (e.g. stratum corneum, dermis, cutis and subcutis) and/or mucosa for localized or systemic delivery of an active agent to a subject.

Transdermal application of the formulation of the present aspect is intended to encompass all such methods known for allowing a pharmaceutically active ingredient to be delivered at least partially through the skin or mucosa. It would be appreciated that this is typically achieved by applying the composition containing the active ingredient and formulation excipients externally to the surface, i.e. skin, fur, etc. of a subject and allowing sufficient time for absorption through the dermal layers of the subject being treated. Exemplary methods of administration include pour-on, spot-on, spray, dip, wipe, or other methods apparent to those skilled in the art. In addition to this, it is contemplated that the transdermal liquid formulation may be incorporated into a transdermal therapeutic system (TTS), such as a patch, as are known in the art.

In one preferred embodiment, the transdermal liquid formulation is suitable or formulated for use as a pour-on preparation. Typically, "pour-on" formulations are referred to as such because they are poured-on the animal's back, usually from the withers to the tail of an animal, such as cattle, sheep or horses.

The term "therapeutically effective amount" describes a quantity of a specified agent sufficient to achieve a desired effect in a subject being treated with that agent. For example, this can be the amount of the propionic acid-based non-steroidal anti-inflammatory agent necessary to reduce, alleviate and/or prevent inflammation and/or pain. In some embodiments, a "therapeutically effective amount" is sufficient to reduce or eliminate a symptom of inflammation and/or pain. In other embodiments, a "therapeutically effective amount" is an amount sufficient to achieve a desired biological effect, such as an amount that is effective to prevent or decrease redness, heat, swelling, and/or pain associated with inflammation or an inflammatory disease, disorder or condition.

Ideally, a therapeutically effective amount of an agent is an amount sufficient to induce the desired result without causing a substantial cytotoxic effect in the subject. The effective amount of an agent, such as the propionic acid-based non-steroidal anti-inflammatory agent, useful for reducing, alleviating and/or preventing inflammation and/or pain will be dependent on the subject being treated, the type and severity of any associated disease, disorder and/or condition, and the manner of administration of the therapeutic composition.

A therapeutically effective amount of a transdermal liquid formulation comprising the propionic acid-based non-steroidal anti-inflammatory agent may be administered in a single dose, or in several doses, for example daily or every other day, during a course of treatment. However, the frequency of administration is dependent on the preparation applied, the subject being treated, the severity of inflammation, and the manner of administration of the therapy or composition.

In particular embodiments, the amount of the transdermal liquid formulation to be administered to a subject, including cattle, is from about 0.5 to about 20 mg (e.g., about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0 mg/kg or any range therein) of the propionic acid-based non-steroidal anti-inflammatory agent (e.g., ketoprofen) per kilogram of body weight of the subject per day or dose. With respect to cattle, the transdermal liquid formulation is preferably administered to cattle at from about 1 mg to about 5 mg and more preferably about 1.5 mg to about 3.5 mg of the propionic acid-based non-steroidal anti-inflammatory agent (e.g., ketoprofen) per kilogram of body weight.

It will be appreciated that propionic acid-based non-steroidal anti-inflammatory agents represent an effective class of non-steroidal anti-inflammatory drugs (NSAIDs) that are structurally derived from propionic acids. Exemplary propionic acid-based anti-inflammatory agents include ketoprofen, alminoprofen, ibuprofen, oxaprozin, zaltoprofen, tiaprofenic acid, naproxen, fenoprofen, flurbiprofen, pranoprofen, dexibuprofen, dexketoprofen and loxoprofen, inclusive of pharmaceutically acceptable salts thereof. In one particularly preferred embodiment, the propionic acid-based non-steroidal anti-inflammatory agent is or comprises ketoprofen or a pharmaceutically acceptable salt thereof.

The propionic acid-based non-steroidal anti-inflammatory agent of the transdermal liquid formulation of the invention is suitably to be present in an amount from about 10 mg/mL (i.e., about 1% w/v) to about 500 mg/mL (i.e., about 50% w/v) or any range therein such as, but not limited to, about 50 mg/mL to about 300 mg/mL, or about 100 mg/mL to about 250 mg/mL. In particular embodiments of the present invention, the propionic acid-based non-steroidal anti-inflammatory agent is present in an amount of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 mg/mL or any range therein, of the transdermal liquid formulation. In certain embodiments of the present invention, the propionic acid-based non-steroidal anti-inflammatory agent is present in an amount from about 100 mg/mL to about 300 mg/mL.

The term "dermal penetration enhancer" is used herein in its broadest sense to refer to an agent or compound which promotes or improves the rate of percutaneous transport of an active agent, such as the propionic acid-based non-steroidal anti-inflammatory agent, across the skin of a subject for systemic or local delivery thereto.

With respect to the dermal penetration enhancer, the alcohol may be any one or more alcohols as are known in the art and may include one or more primary, secondary and/or tertiary alcohols. More particularly, the alcohol is suitably a primary alcohol, such as methanol, ethanol, propanol, butanol and the like, or a secondary alcohol, such as isopropanol, butan-2-ol and the like. In one particular embodiment, the alcohol is or comprises ethanol, isopropanol or any combination thereof.

The alcohol of the dermal penetration enhancer is suitably present in an amount from about 10 mL/L (i.e., about 1% v/v) to about 950 mL/L (i.e., about 95% v/v) or any range therein such as, but not limited to, about 50 to about 700 mL/L, or about 200 to about 500 mL/L. In particular embodiments of the present invention, the alcohol is present in an amount of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950 mL/L or any range therein, of the transdermal liquid formulation. In certain embodiments of the present invention, the alcohol is present in an amount from about 100 mL/L to about 600 mL/L.

It will be appreciated that the term "emollient" refers to a chemical agent (or a mixture of compounds) which increase skin hydration, thereby softening the external layers of the skin. Emollients may be active (i.e., by delivering water molecules into the skin) or passive (i.e., by reducing and/or preventing water evaporation from the skin). Additionally, emollients can provide a softening or soothing effect to the skin surface. Emollients can be either solid or liquid at 25° C. and may be used individually or as a blend of emollients with melting points above and below 25° C.

The emollient may be any one or more emollients as are known in the art. Exemplary emollients include fatty acid triglycerides, such as mixtures of caprylic and capric triglycerides (e.g., CRODAMOL™ GTCC-LQ, MIGLYOL®, CAPTEX®, LABRAFAC™ Lipophile WL), palmitic triglyceride, oleic triglyceride, caprylic triglyceride, capric triglyceride, and linoleic triglyceride; fatty acid esters, such as isopropyl myristate, isopropyl palmitate, dibutyl adipate, and dibutyl phthalate; polyhydric alcohols such as propylene glycol, butylene glycol, polyethylene glycol, glycerol, and sorbitol; fatty acids such as lauric, myristic, palmitic, stearic, behenic, oleic, linoleic, linolenic, lanolic, isostearic, arachidonic and poly unsaturated fatty acids (PUFA); oils such as mineral oil, lanolin oil, coconut oil, cocoa butter, olive oil, jojoba oil, castor oil, silicone oil (such as linear and cyclic polydimethylsiloxanes); higher alcohols, such as lauryl, cetyl, stearyl, oleyl, behenyl, cholesterol and 2-hexydecanol alcohol; esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; cyclomethicone; hydrogenated lanolin; waxes; lecithin, or mixtures thereof.

Suitably, the emollient is selected from the group consisting of a glycol, an unsaturated fatty alcohol, a sorbitol derivative, a myristate, an alkoxylated di-ester of myristyl alcohol and adipic acid, a pyrrolidone, and any combination thereof. In particular preferred embodiments, the emollient is selected from the group consisting of propylene glycol, oleyl alcohol, dimethyl isosorbide, PPG-3 benzyl ether myristate, di-PPG2-myreth-10-adipate, 1-ethyl-2-pryrrolidone, isomyristate, isopropyl myristate and any combination thereof. In alternative embodiments, the emollient (and the alcohol) is not oleyl alcohol.

The emollient of the transdermal liquid formulation is suitably present in an amount from about 10 mL/L (i.e., about 1% v/v) to about 950 mL/L (i.e., about 95% v/v) or any range therein such as, but not limited to, about 50 mL/L to about 700 mL/L, or about 200 mL/L to about 500 mL/L. In particular embodiments of the present invention, the emollient is present in an amount of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950 mL/L or any range therein, of the transdermal liquid formulation. In certain embodiments of the present invention, the emollient is present in an amount from about 100 mL/L to about 600 mL/L.

As used herein, the term "essential oil" means a volatile oil derived from the leaves, stem, flower or twigs of plants or synthetically-made compounds that have the same chemical attributes. The essential oil usually carries the odour or flavour of the plant. Chemically, each plant essential oil or derivative thereof, which may be extracted from natural sources or synthetically made, generally contains, as a major constituent, an acyclic monoterpene alcohol or aldehyde, a benzenoid aromatic compound containing at least one oxygenated substituent or side chain, or a monocarbocyclic terpene generally having a six-membered ring bearing one or more oxygenated substituents. An essential oil also includes within its scope derivatives thereof, including racemic mixtures, enantiomers, diastereomers, hydrates, salts, solvates, metabolites, analogs, synthetic derivatives and homologs.

Non-limiting examples of essential oils include mentha, jasmine, camphor, white cedar, bitter orange peel, ryu, turpentine, cinnamon, bergamot, citrus unshiu, calamus, pine, lavender, bay, clove, hiba, *eucalyptus*, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, *ginseng*, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils. In particular embodiments, the essential oil is or comprises menthol, a cineole-based oil, such as *eucalyptus* oil and/or eucalyptol, or any combination thereof. In alternative embodiments, the essential oil is not menthol.

The essential oil of the dermal penetration enhancer is suitably present in an amount from about 10 mL/L (i.e., about 1% v/v) to about 300 mL/L (i.e., about 30% v/v) or any range therein such as, but not limited to, about 20 mL/L to about 250 mL/L, or about 50 mL/L to about 150 mL/L. In particular embodiments of the present invention, the essential oil is present in an amount of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 mL/L or any range therein, of the transdermal liquid formulation. In certain embodiments of the present invention, the essential oil is present in an amount from about 25 mL/L to about 150 mL/L.

The present composition can also optionally include a further pharmaceutically active agent. It will be appreciated that a wide variety of pharmaceutically active agents can be included with the transdermal liquid formulation described herein, such as a further anti-inflammatory agent (e.g., a further NSAID besides the propionic acid-based non-steroidal anti-inflammatory agent or a corticosteroid), an antimicrobial, an anthelmintic, a hormone (e.g., synthetic and/or purified), a growth enhancer, an anxiolytic, an antihistamine, an immune stimulant, a vaccine, oxytocin and the like as are known in the art. Preferably, the further pharmaceutically active agent does not significantly interact with or significantly diminish the activity and/or transdermal absorption of the propionic acid-based non-steroidal anti-inflammatory agent. In particular embodiments, the transdermal liquid formulation does not further include flunixin or a pharmaceutically acceptable salt thereof.

Other additives or agents can also be added to the present transdermal liquid formulation, as required. Such agents can include preservatives, chelating agents, antioxidants, buffering agents and viscosity modifying agents. Exemplary preservatives include without limitation methyl p-hydroxybenzoate (methylparaben) and propyl p-hydroxybenzoate (propylparaben), added in an appropriate quantity known to one skilled in the art. Exemplary chelating agents include without limitation edetate disodium and EDTA. Exemplary antioxidants include without limitation butylated hydroxyanisole, ascorbic acid, and sodium monothioglycerol, added in an appropriate quantity known to one skilled in the art. Suitable viscosity modifying agents include, without limitation, water, ethanol, isopropanol, propylene glycol, dimethylisosorbide, triacetin, or glycerol, added in an appropriate quantity known to one skilled in the art. Non-limiting examples of buffering agents include citric acid and maleic acid.

In particular embodiments, the composition further comprises one or more carriers, diluents or excipients. A useful reference describing pharmaceutically acceptable carriers, diluents and excipients is Remington's Pharmaceutical Sciences (Mack Publishing Co. N.J. USA, 1991), which is incorporated herein by reference.

In one embodiment, the transdermal liquid formulation of the present aspect demonstrates a plasma profile following administration to a subject substantially similar to that observed with an injectable formulation of the propionic acid-based anti-inflammatory agent. To this end, the transdermal liquid formulation of the present aspect preferably demonstrates a short onset of activity (e.g., less than 10, 15, 20, 25, 30, 35, 40, 45, 50, 55 or 60 minutes following administration) so as to facilitate a rapid reduction in pain, inflammation and/or one or more clinical signs associated therewith. Additionally, the transdermal liquid formulation of the present aspect preferably demonstrates substantially complete clearance from plasma within, for example, 6, 7, 8, 9, 10, 11, 12, 13, 14, 15, 16, 17, 18, 19, 20, 21, 22, 23 or 24 hours following administration to a subject, and in particular cattle, so as to provide minimal withholding periods with respect to milk and/or meat derived from treated animals.

The formulation described herein may be suitable for administration to any animal, including humans and non-human animals, such as avians inclusive of poultry (e.g., chickens, ducks, geese, pigeons, quails and turkeys), ruminants (e.g., cattle, sheep, goats etc), pigs, horses, donkeys, dogs and cats. In particular embodiments, the transdermal liquid formulation of the present aspect is for use in cattle.

Accordingly, the transdermal liquid formulation according to the present invention is preferably suitable for the treatment of pain and/or an inflammatory disease, disorder or condition in cattle, such as footrot, respiratory disease, acute mastitis, pinkeye (i.e., infectious keratoconjunctivitis), acute pneumonia, metritis and enteritis. It will be understood that the dosage regimen for treatment of such diseases should be appropriate for the particular inflammatory disease, disorder or condition and the age, weight and sex of the animal to be treated.

In another aspect, the invention provides a method of preventing and/or treating inflammation in a subject, the method including the step of administering to the subject a therapeutically effective amount of the transdermal liquid formulation of the previous aspect to thereby prevent and/or treat the inflammation in the subject.

In a related aspect, the invention provides a method of preventing and/or treating pain in a subject, the method including the step of administering to the subject a therapeutically effective amount of the transdermal liquid formulation hereinbefore described to thereby prevent and/or treat the pain in the subject.

In a further related aspect, the invention provides a method of preventing and/or treating lameness and/or loss of mobility in a subject, the method including the step of administering to the subject a therapeutically effective amount of the transdermal liquid formulation of the first aspect to thereby prevent and/or treat the lameness and/or loss of mobility in the subject.

By "reducing", as in reducing inflammation and/or pain in a subject, is meant a lessening or shortening of a symptom, aspect, or characteristic associated with inflammation (e.g., redness, heat, swelling, and/or pain) and/or pain, or of the length of time a subject experiences a symptom, aspect, or characteristic associated with inflammation and/or pain. Such reducing need not be absolute to be beneficial to the subject. By "alleviating", as in alleviating inflammation and/or pain in a subject, is meant a reduction in the severity or seriousness of a symptom, aspect, or characteristic associated with inflammation (e.g., redness, heat, swelling, and/or pain) and/or pain. Such alleviating need not be absolute to be beneficial to the subject. Reduction and/or alleviation of inflammation and/or pain in a subject can be determined using any methods or standards known to the ordinarily skilled artisan, including both qualitative and quantitative methods and standards, such as those hereinafter described.

It is to be understood that reducing or alleviating inflammation and/or pain in a subject is a method of treating inflammation and/or pain in the subject. As used herein, "treating" (or "treat" or "treatment") refers to a therapeutic intervention that ameliorates a sign or symptom of inflammation and/or pain after it has begun to develop. The term "ameliorating," with reference to inflammation and/or pain, refers to any observable beneficial effect of the treatment. The beneficial effect can be determined using any methods or standards known to the ordinarily skilled artisan.

As used herein, "preventing" (or "prevent" or "prevention") refers to a course of action (such as administering a therapeutically effective amount of the transdermal liquid formulation provided herein) initiated prior to the onset of a symptom, aspect, or characteristic of inflammation and/or pain so as to prevent or reduce the symptom, aspect, or characteristic. It is to be understood that such preventing need not be absolute to be beneficial to a subject. A "prophylactic" treatment is a treatment administered to a subject who does not exhibit signs of inflammation and/or pain or exhibits only early signs for the purpose of decreasing the risk of developing a symptom, aspect, or characteristic of inflammation and/or pain.

As used herein, "inflammation" refers to the well known localised response to various types of injury or infection, which is characterised by redness, heat, swelling, and pain, and often also including dysfunction or reduced mobility. Inflammation represents an early defence mechanism to contain an infection and prevent its spread from the initial focus. Major events in inflammation include dilation of capillaries to increase blood flow, changes in the microvasculature structure, leading to escape of plasma and proteins and leukocytes from the circulation, and leukocyte emigration from the capillaries and accumulation at the site of injury or infection.

As used herein, the term "pain" refers to an unpleasant sensory and emotional experience associated with actual or potential tissue damage caused by or resulting in stimulation of nociceptors in the peripheral nervous system, or by damage to or malfunction of the peripheral or central nervous systems and neural voltage channel transmission. This term is inclusive of acute and chronic pain, including pain caused by trauma, surgery and/or inflammation.

The term "lameness" as used herein is defined as an abnormal or irregular gait or locomotion characterized by limping or not bearing full weight on one or more legs of the subject in question, usually associated with pain in the musculoskeletal system. More specifically, lameness typically results from the presence of painful lesions on one or more associated bony structures, cartilages, ligaments, synovial membranes, joints or the connective tissue or from an anomaly of local vascularization of the affected leg or legs. Lameness can manifest itself clinically in an intermittent or continuous manner for several days, several weeks or several months. Further to this, affected subjects may have reduced activity in standing up and moving including limping, sagging or stiffness and lack of flexion, and adoption of unusual postures.

The term "subject" includes both human and veterinary subjects. For example, administration to a subject can include administration to a human subject or a veterinary subject. Preferably, the subject is cattle. However, therapeutic uses according to the invention may also be applicable to all mammals, such as domestic and companion animals, performance animals such as horses, livestock, and laboratory animals.

By "administer", "administration" and "administering" is intended to describe the introduction or application of the transdermal liquid formulation into or onto a subject by a chosen route. As will be appreciated from the present disclosure, the preferred route of administration is transdermally.

In another aspect, the invention provides a method of administering the transdermal liquid preparation of the first mentioned aspect, including the step of administering a therapeutically effective amount of the transdermal liquid formulation to a subject in need thereof with an application device.

In particular embodiments, the application device is selected from the group consisting of a spray device, a pour-on device, a spot-on device and a transdermal patch.

In one embodiment, the method of the present aspect further includes the initial step of adding the transdermal liquid preparation to the application device.

In another aspect, the invention provides a method of preparing a transdermal liquid formulation, including the steps of.
(a) combining a therapeutically effective amount of a propionic acid-based non-steroidal anti-inflammatory agent and a dermal penetration enhancer comprising an alcohol, an emollient, and an essential oil; and
(b) mixing the mixture of step (a) to thereby prepare the transdermal liquid formulation.

For the present aspect, the transdermal liquid formulation is suitably that of the first mentioned aspect.

In a particular embodiments of the present aspect, one or more of the dermal penetration enhancers or a portion thereof, are added to a suitable vessel or chamber, followed by the propionic acid-based non-steroidal anti-inflammatory agent and/or any remaining excipients or additives. The mixture is then mixed until all solids are dissolved. An additional solvent or surfactant to bring the transdermal liquid formulation to a final volume may be added if needed. Additives, such as those hereinbefore provided, may also be included in the vessel and mixed into the transdermal liquid formulation. It will be appreciated that the order of addition of the above dermal penetration enhancers, the propionic acid-based non-steroidal anti-inflammatory agent, excipients, solvents and additives is not critical.

In a related aspect, the invention provides a transdermal liquid formulation prepared by the method of the second aspect.

The methods described herein may be applicable to any animal, including humans and non-human animals, such as avians inclusive of poultry (e.g., chickens, ducks, geese, pigeons, quails and turkeys), ruminants (e.g., cattle, sheep, goats etc.), pigs, horses, donkeys, dogs and cats. Preferably, the subject is bovine.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

So that the present invention may be more readily understood and put into practical effect, the skilled person is referred to the following non-limiting examples.

EXAMPLE

Materials and Methods

To Confirm Transdermal Penetration of Candidate Formulations Using In Vitro Techniques
Regional Differences in Transdermal Drug Penetration Cattle skin was harvested from Black Angus steers (n=5, age 1.5-2 years, 5/5 body condition score and weighing 508-570 kg). Hair was removed using an electric clipper and the subcutaneous fat and musculature carefully trimmed away before the skin was cut into circular sections (approximately 2 cm diameter) using a metal wad punch, and placed in airtight ziplock bags, stored at −20° C. within 5 hr of slaughter.

The skin samples were defrosted immediately prior to use and mounted on Franz diffusion cells. A donor solution of radiolabeled lignocaine (Lidocaine [carbonyl-14C]HCl in ethanol, 0.1 mCi/mmol; American Radiolabeled Chemicals, St. Louis, MO, USA) solution was added, while the receptor solution was phosphate-buffered saline containing 4% Bovine serum albumin (Mills et al., 2003, 2005). The concentration of lignocaine ($C_v$) was 100 mg/mL, resulting in a dose per area of 88.42 mg/cm². A glass cover slip was applied to each donor chamber to prevent evaporation of the donor solution. Samples (200 μL) were collected at regular intervals from the receptor chambers via the sampling port and immediately replenished with equal volumes of fresh receptor solution. At the completion of each study, the diffusions cells were dismantled and the skin discs were rinsed and stored. Both receptor fluid samples and skin samples were analysed for lignocaine concentration using a TRI-CARB® 3110TR Liquid Scintillation Analyser.

The pseudo-steady state flux ($J_{ss}$ or driving force) of lignocaine was derived from the gradient of the regression line through the data points of the linear part of the cumulative amount of lignocaine penetration per skin area against time profile (permeation profile) (Cross et al., 2003b; Mills et al., 2004a). The time lag or delay before drug first appearing in the receptor fluid ($t_{lag}$, which correlates to the initial onset of drug activity) was designated as the x-intercept of the regression line (Ahlstrom et al., 2009) and the permeability of active drug in the specific vehicle ($k_p$ or permeability coefficient) was calculated using the known values of $J_{ss}$ and the concentration of lignocaine hydrochloride in the vehicle ($C_V$) (Williams, 2003; Ahlstrom et al., 2007) as:

$$k_p = J_{ss}/C_v$$

The amount of lignocaine in the receptor cell was analysed with respect to length of freezing and sampling time, using factorial ANOVA on STATISTIC™ (version 12; StatSoft Inc., Tulsa, OK, USA). With respect to the length of freezing, the derived $k_p$ and $t_{lag}$ were analysed with repeated measures ANOVA. The amount of lignocaine retained within the skin each at the end of each experimental was analysed using Kruskal Wallis ANOVA since it had a non-parametric distribution.

Screening of NSAID and Vehicle Combinations to Maximise Active Drug Penetration Through Cattle Skin Four NSAIDs are currently registered for use in Australia: Flunxin meglumine, Ketoprofen, Meloxicam and Tolfenamic acid. In vitro techniques, as decided in 3.1.1, were used to measure the penetration of each of these four NSAIDs in over 150 vehicle combinations. The full list of these combinations of active drug and vehicles can be found in Table 13.

Optimising the Candidate Formulations

Once the relative permeability of each NSAID was determined, the most suitable drug-vehicle formulation was selected and optimised, in terms of additional excipients and active drug concentration, to enhance transdermal drug penetration. The terpenes were the most effective from the preliminary studies, but further investigation revealed that *eucalyptus* oil, also a terpene (containing 1,8 cineole), was even more effective than the Croda-supplied terpenes. Comparing *Eucalyptus* oil itself to pure eucalyptol, the complete oil was significantly better at the transfer of ketoprofen through the cattle skin than pure eucalyptol at 5% (despite the final concentration of 1,8-cineole therefore being lower, which may reflect an addition penetration enhancing effect of *eucalyptus* oil).

Stability Studies of the Final Formulation

Preliminary stability studies were performed on the optimal analgesic formulation to ensure no obvious or major concerns with storing the final formulation. This involved storing the final formulation in glass and plastic (polypropylene) containers at varying temperatures (0, 20 and 40° C.) for 6 months. The samples were examined for visual appearance, precipitation and active drug concentration at 0 (when first prepared), 2, 4 and 6 months.

Analysis of NSAIDs in Biological Samples

Plasma Protein Precipitation:

Cold Acetonitrile (0.2% formic acid) precipitation was added to samples at 1:1 ratio and vortexed for 30 s. Protein crashing carried out by 2 rounds of centrifugation for 15 min at 20,000 g. Interval between "crashing" was 30 min at 4° C. Supernatant of each sample collected and analysed by LCMS/MS.

Ketoprofen Concentration Determination by LC-MS/MS (16 Mar.-28 May 2016)

Instrument: Shimadzu Nexera uHPLC in tandem with LCMS 8030.

CID gas: Argon

Column: Phenomenex Kinetix C18, 1.7 µm pore size.

Mobile phase A: 0.1% formic acid in water

Mobile phase B: 0.1% formic acid in Acetonitrile

LOD: 0.01; QC samples instrument stability (0.1, 2 and 5 µg/mL); Calibration range 0.019-5 µg/mL (similar range to previous experiments in this lab).

Ketoprofen: Test recoveries, using spiked plasma from protein crashing ranged from 91.2-102.6%.

Detection m/z 255.10>105.20 and confirming ion 255.10>194.25

Samples: must be prepared with less than 90% solvent prior to analysis.

Instrument performance and stability: All samples were analysed on the instrument continuously over 4 days. QCs were analysed every 20 samples. Three sets of calibration curves were assessed.

Instrument stability was reasonable.

| Standard | | CV (%) |
|---|---|---|
| QCH | (5 µg/mL) | 9.287 |
| QCM | (2 µg/mL) | 11.274 |
| QCL | (0.1 µg/mL) | 10.385 |
| CC | 0.0195 µg/mL | 14.681 |
| CC | 0.0781 µg/mL | 10.581 |
| CC | 0.3125 µg/mL | 14.148 |
| CC | 1.25 µg/mL | 12.132 |
| CC | 5 µg/mL | 1.84 |

To Determine the Efficacy of Candidate Transdermal Formulations to Control Pain Associated with Surgical Husbandry Formulations Pilot Study 1

The study design consisted of a pre-treatment blood sample being collected, then the formulation applied (10 or 40 mL) along the backline between the withers and lumbar region of four calves. Further blood samples were then collected at 2, 4, 8, 12 and 24 hr later, then analysed for ketoprofen concentrations using UPLC-MS. The calves were all Droughtmasters (approximately 50% *Bos indicus*, 50% *Bos taurus*), as follows:

TABLE 1

Cattle details for Pilot study 1

| Calf ID (mg/kg) | Gender | Weight (kg) | Dose volume (mL) |
|---|---|---|---|
| 3405 | Male | 241 | 40 |
| 3383 | Female | 191 | 40 |
| 3389 | Male | 248 | 10 |
| 3385 | Female | 216 | 10 |

Pilot Study 2

The study design for the second pilot study was the same as the first pilot study, except that all animals received a dose volume of 10 mL. All calves were estimated to be of similar weight and were from the same cohort of calves as the first experiment. Body weight was estimated as per industry standard. The animals were closely observed for any grooming, particularly during the first 2 hr following application. Blood samples were collected at 0, 1, 2, 3, 4 and 6 hr following application.

TABLE 2

Cattle details for Pilot study 2

| Calf ID | Gender | Weight (kg) | Dose volume (mL) | Dose rate (mg/kg) |
|---|---|---|---|---|
| 3401 | Male | ~220 | 10 | ~8 |
| 3415 | Female | ~200 | 10 | ~10 |
| 3417 | female | ~200 | 10 | ~10 |
| 3421 | Female | ~200 | 10 | ~10 |

Bioavailability Study

This was a randomized, non-blinded, crossover pharmacokinetic study. Cattle (n=14, including two spares) of approximately 250-350 kg body weight were selected from the Yarrandoo herd. The cattle were randomized to three treatment groups (A, B and C), each of four individuals. Each group received each treatment once, as described in Table 1. The treatments were: (1) ketoprofen 3 mg/kg IV (Ilium); (2) ketoprofen 3 mg/kg IM (Ilium); (3) ketoprofen 10 mg/kg topical (transdermal ketoprofen formulation). A minimum one week 'washout' period was allowed between each treatment. Cattle receiving the topical treatment were washed, with warm water and shampoo (Fido's Everyday shampoo), applied with a soft brush, and then thoroughly rinsed, 12 hr after application and after all samples had been collected to remove any residual product. The cattle facilities used for handling of topically-treated animals was appropriately washed after all samples had been collected. Cattle receiving the IM and IV treatments were handled using facilities separate to any cattle treated with the topical treatment on the same day.

Blood samples (9 mL) were collected at regular intervals (Table 2). Blood samples were centrifuged and plasma separated for ketoprofen concentration analysis via UPLC-MS to determine pharmacokinetic parameters. The pharmacokinetic analysis was performed using Phoenix WinNonLin and a non-compartmental model.

TABLE 3

Bioavailability study treatment allocation

| | Day | Ketoprofen 3 mg/kg IV | Ketoprofen 3 mg/kg IM | Ketoprofen 10 mg/kg topical |
|---|---|---|---|---|
| $1^{st}$ treatment | 0 | A1* | B1 | C1, C2 |
| | 1 | A2 | B2 | C3, C4 |
| | 2 | A3, A4 | B3, B4 | — |
| $2^{nd}$ treatment | 7 | C1 | A1 | — |
| | 8 | C2 | A2 | B1, B2 |
| | 9 | C3 | A3 | B3, B4 |
| | 10 | C4 | A4 | — |
| $3^{rd}$ treatment | 15 | B1 | C1 | A1, A2 |
| | 16 | B2 | C2 | A3, A4 |
| | 17 | B3, B4 | C3, C4 | — |

*Indicates treatment group and animal (e.g. A1 is animal 1 in Group A)

TABLE 4

Bioavailability study blood sampling times

| Treatment | Blood sampling times (±1 minute) |
|---|---|
| Ketoprofen 3 mg/kg IV | 0, 2, 5, 10, 15, 25, 40 min and 1, 2, 3, 4, 6 and 8 hr |
| Ketoprofen 3 mg/kg IM | 0, 10, 20, 30 and 45 min, then 1, 2, 4, 6, 8 and 12 hr |
| Ketoprofen 10 mg/kg topical | 0, 10, 20, 30 and 45 min, then 1, 2, 4, 6, 8 and 12 hr |

For application of the transdermal formulation, the test item was administered topically once to each individual as a single dose at the dose rate of 10 mg/kg (0.05 mL/kg). Each dose was individually calculated based on the animal's weight, rounded up to the most accurate graduation on the syringe(s). The test item was equilibrated to ambient temperature prior to administration.

Cattle were dry at the time of treatment and remained dry until the completion of blood collection. The dose was administered as a pour-on, using a suitably-sized syringe, applied as a single band along the spine between the shoulders and approximately halfway along the back. Cattle were restrained within a suitable crush at the time of treatment. Elbow-length gloves, fully enclosed boots and overalls were worn as a minimum during administration.

The animals were observed regularly during the bioavailability study. Following treatment on day 0 and during the remainder of the working day, the animals were examined regularly for adverse reactions at the time of blood collections. For animals receiving the topical formulation, the treatment site was specifically examined at approximately 1, 4 and 8 hours post-treatment to ensure no local reactions were evident. Animals receiving the topical formulation were housed individually until the completion of blood collection on the day of administration and specifically observed for grooming behavior. During the study, the cattle were inspected at least daily for general health and well-being.

To Develop a Formulation Containing an NSAID to Control Pain Associated with Routine Surgical Interventions for Up to 24 hr Clinical Study This study was performed at the Queensland Animal Science Precinct (QASP) at the University of Queensland Gatton Campus.

A total of 36 weaners (male and female ~200 kg, Holstein-Fresian calves) were randomly assigned to one of four groups:

(i) Disbudded and placebo transdermal treatment (n=10).
(ii) Disbudded and ketoprofen transdermal (10 mg/kg; n=10).
(iii) Disbudded and ketoprofen intramuscular (3 mg/kg; n=10).
(iv) Sham (handling only) (n=5).

Each group were placed in the holding yard and the treatment applied. The transdermal ketoprofen or placebo (vehicle only) was applied along the backline, approximately from the shoulder to the mid-point of the backline. The IM treatment was administered 30 min before the procedure whilst the animals were restrained in a crush. Once treatment was completed, the animals were moved into the crush (the order of appearance noted for time since treatment) and a blood sample collected. The husbandry procedure (disbudding) was carried out. Subsequent blood samples were collected at 0, 1, 2, 4, 8, 24, 48 and 96 hr. Blood samples were analysed for cortisol and biomarkers once the study was completed.

Calf behaviour was monitored before and after dehorning in suitable time periods. The day before dehorning, the behaviour of all 36 calves were monitored for two hours to record the baseline variation, which was taken as 0 hour observation. Next day after dehorning, behaviour was recorded at 2-4 hour, 4-8 hour, 8-12 hour, 24 hour and 48 hours. There were 12 behaviour parameters recorded, as follows: Head shaking, Ear flicking, Tail wagging, Head rubbing, lying, ruminating, neck extending, grooming, walking, vocalising, feeding and drinking. Each animal was observed for 3 min at each observation period and the frequency of each behaviour parameter during this period was recorded. This protocol was adapted for Petherick et al (2013), with the subsequent Ethogram used to analyse the behavioural changes during this study.

Conventional Parameters to Assessment Pain and Inflammation

The conventional parameters used to assess pain and inflammation included plasma total cortisol concentration (ELISA using a commercial kit), body weight and the behaviour Ethogram.

Proteomic Assessment of Pain and Inflammation

Proteomics is the branch of science that involves identification, quantification and characterization of all proteins in the living individual. It also plays an indispensable role in assessing the changes in protein expression, occurring in response to various physiological state as well as disease conditions. In last few years, proteomics has been increasingly used in development of novel biomarkers for early diagnosis of diseases and monitoring of treatment strategies of different diseases in human medicine as well as in veterinary medicine Mass Spectrometry (MS)-Based Proteomics Over the last two decades technological advancement in the field of proteomics has created a lot of opportunities in exploring the complex biological system of living organism. Especially, MS-based techniques have emerged as the most powerful tool to interpret available genomic information and to create quantitative protein profile from plasma, tissues or cell lines of various species. These techniques also proved useful for analysis of protein-protein interaction, post-translational modifications and gene annotation (Mann and Aebersold, 2003). Mass spectrometry-based proteomics analysis can be broadly divided into two main domains that include discovery proteomics and targeted proteomics. The former enables the unbiased identification and quantification of hundreds to thousands of proteins from complex mixtures using shotgun proteomics techniques (explained below), however, in somewhat stochastic manner whereas targeted proteomics focuses only on the subset of selected protein targets important for the biological process under study. Quantification may be either relative to control sample or on an absolute scale. Targeted proteomics is more and more commonly employed to validate shotgun proteomics findings and started to replace Western blotting approach.

Shotgun (or Discovery) Proteomics

Traditionally, proteomics and especially proteomics in veterinary field, has been associated with 2D gels-based approaches. 2D gels, however suffer from several issues such as lack of reproducibility, being laborious, underrepresentation of certain classes of proteins and most importantly each protein spot in fact consists of multiple proteins. The idea of shotgun proteomics was introduced in order to avoid having to do 2D gels. Shotgun proteomics is one of the most widely used approaches for identification and/or quantification of maximal number of proteins in a given samples. It has achieved high throughput analysis as compared to other conventional MS-based techniques because of advantages associated with it. First is proteolytic digestion of proteins into short peptides followed by liquid chromatography-tandem mass spectrometry (LC-MS/MS) based sequencing, simplifies the sample handling and increase its efficiency of protein identification (Nesvizhskii and Aebersold, 2005). In shotgun proteomics, proteins are denatured, cysteine residues alkylated and the proteins digested into peptides. Various fractionation strategies can be introduced at the protein or peptide level. These peptides are then desalted and analysed by liquid chromatography tandem mass spectrometry (LC-MS/MS) in data dependent acquisition mode (explained below). The most frequently used instruments for shotgun proteomics include ion-trap, hybrid ion-trap/orbitrap, hybrid quadrupole/orbitrap and hybrid quadrupole/TOF mass spectrometer. However, spectra obtained in all these methods vary with regard to their quality (resolution and mass accuracy). There are several other DDA-based quantitative proteomics strategies (label free and label-based, the most popular being spectral counting, SILAC, TMT tags, iTRAQ tags).

Application in Veterinary Science

Shotgun proteomics techniques support formulation of new hypotheses and are ideally suited for discovery studies due to theirs high sensitivity and ability to screen hundreds to thousands of proteins at once. Its use has been increased in veterinary medicine in the last few years especially in farm animals. Either plasma or other body fluids or tissues have been utilized with a various degree of success. Shotgun analysis has been conducted on plasma samples from dairy cattle suffering with foot rot, to understand plasma protein profile and to discover potential disease-associated proteins. Plasma proteins were separated by SDS-PAGE and finally LC-MS/MS was performed. A total of 648 proteins were identified in healthy plasma samples, of which 234 were non-redundant proteins and 123 were high-confidence proteins; and 712 proteins were identified from infected animal plasma, of which 272 were non-redundant proteins and 138 were high-confidence proteins (Sun et al., 2013). Another study has conducted comparison of the bovine uterine flushing (UF) and plasma proteome using iTRAQ labelling and SCX separation of the iTRAQ labelled peptides and finally LC-MS/MS technique have enabled identification of 53 proteins, out of that 35 proteins were higher in UF compared to plasma (Faulkner et al., 2012). Serum proteome has analysed from normal and FMD virus infected piglets using LC-MS/MS after removing high abundance proteins with depletion kit. In control group, 8 proteins were identified while in virus infected piglets total 9 proteins were identified with good reproducibility and 3 proteins appeared after FMD infection which were absent in healthy (control) animal (Liu et al., 2011). In one study of swine, serum proteomic analysis was done using shotgun (LC-MS/MS) approach after depleting high abundance proteins using SeproTip columns. A total of 1,096 proteins were identified and quantified, of which 182 were identified with multiple unique amino acid sequences and high peptide ID confidence (Bell et al., 2010). Finally, data dependent acquisition is critical for spectral library collection used for deconvolution of SWATH data.

Results

To Confirm Transdermal Penetration of Candidate Formulations Using In Vitro Techniques Regional Differences in Transdermal Drug Penetration In all animals, the cumulative amount of lignocaine hydrochloride penetrating through skin significantly increased over time (P<0.001) (see FIG. 1). There was a significantly higher cumulative amount of lignocaine penetrating through the skin from animals 2 and 4, compared to animals 1 and 3 (P<0.001). From a pair-wise comparison, the amount of lignocaine penetrating through the skin in animal 5 did not significantly differ from other animal (P>0.1), except animal 1 (P<0.05)

Figure 2:
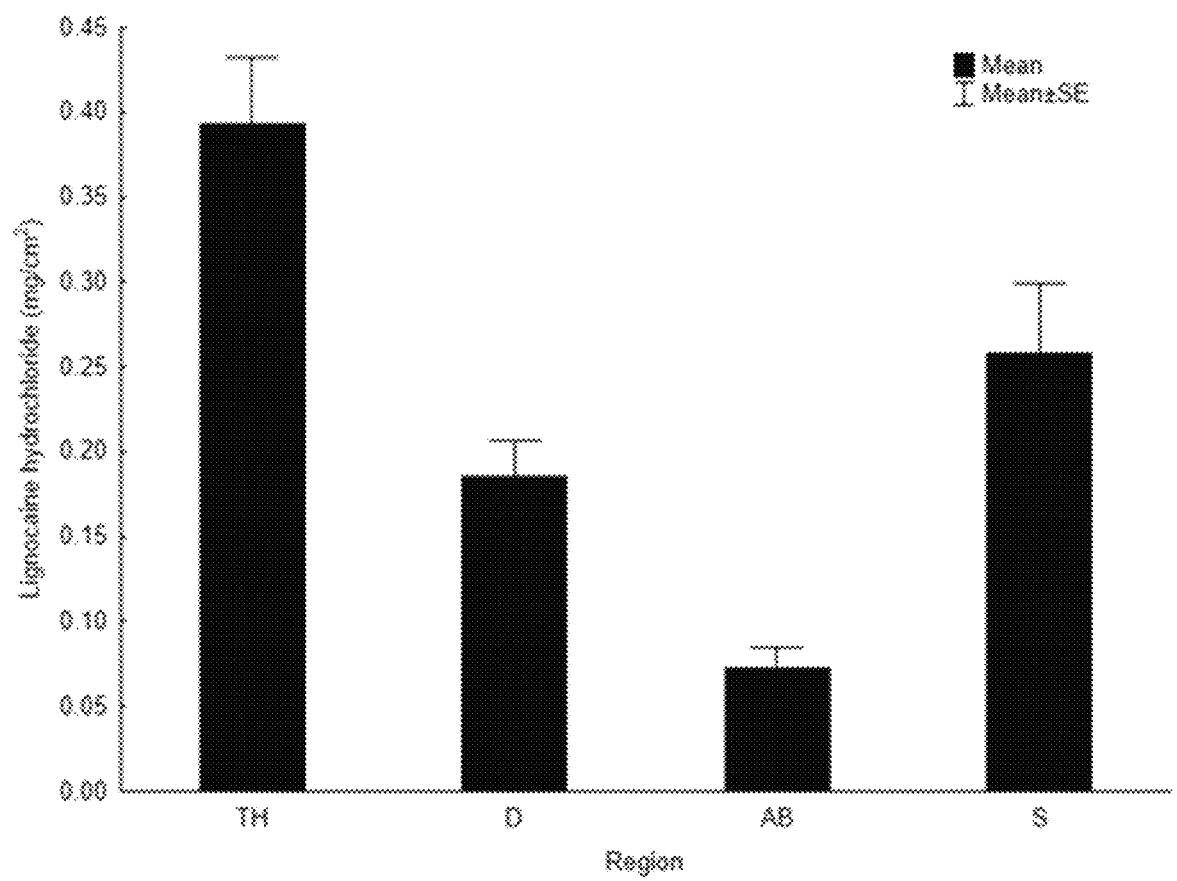
FIG. 2: The mean cumulative of lignocaine hydrochloride in the receptor phase across four regions over 24 hr.
Figure 3:
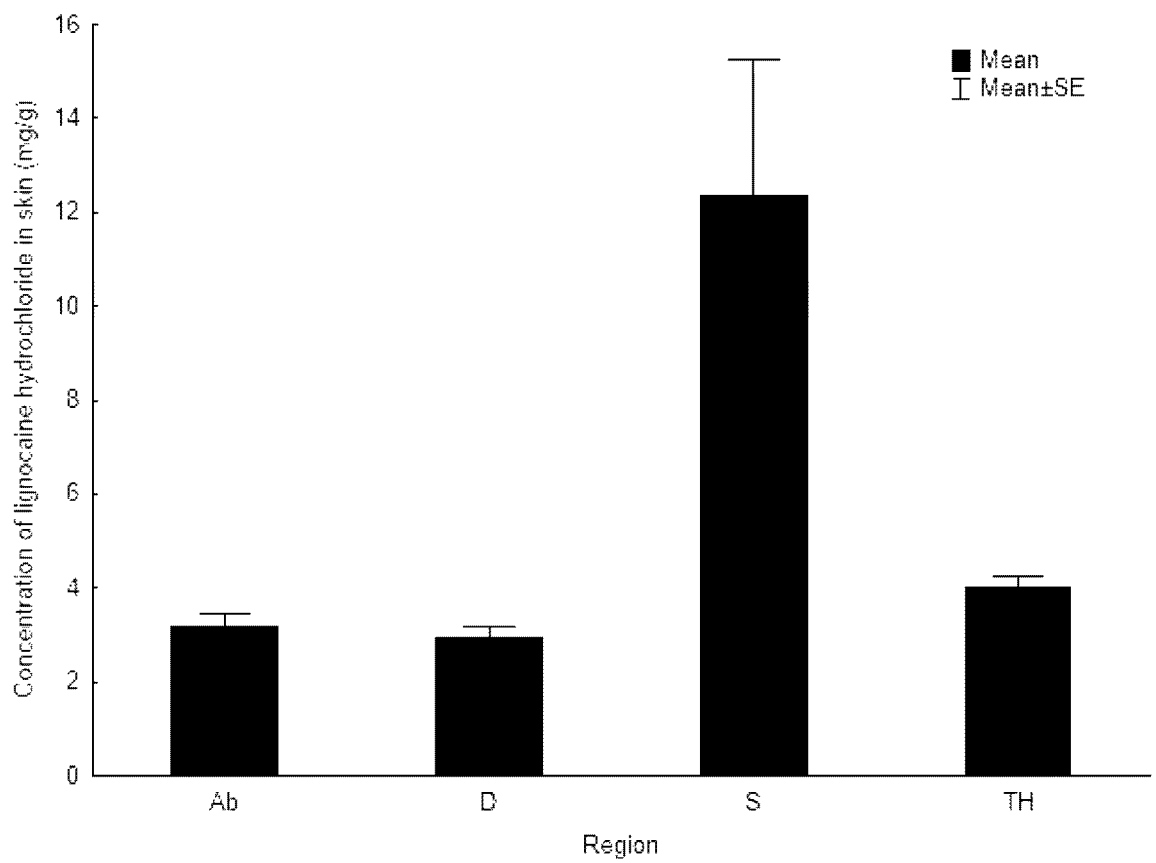
FIG. 3: The mean of the amount of lignocaine hydrochloride retained in the skin at the complete of each experiment.

There were significant differences in the cumulative amount of lignocaine that penetrated through all the skin regions (P<0.001) (See FIG. 2), with the thorax significantly higher than the other three regions (P<0.001). The amount of lignocaine penetrated through the scrotal skin was also significantly higher than the skin from the dorsal midline (P<0.001) and ventral abdomen (P<0.001). After 24 hr exposure, the concentration of lignocaine hydrochloride retained within the scrotal skin was significantly higher than the other regions (P<0.001) (See FIG. 3). The concentrations of lignocaine in the skin from the ventral abdomen, dorsal midline and thorax did not significantly differ (P>0.5).

Figure 4:
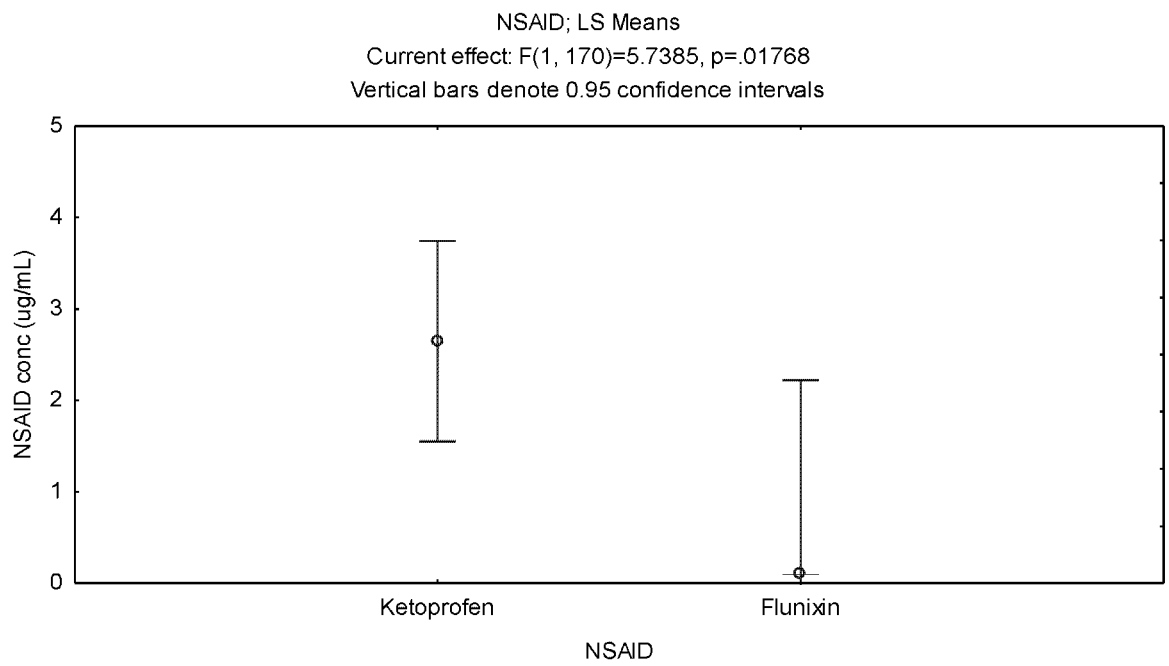
FIG. 4: Movement on NSAIDs through cattle skin in vitro.

Screening of NSAID and Vehicle Combinations to Maximise Active Drug Penetration Through Cattle Skin Over 150 vehicle combinations were screened in this study. Of the four NSAIDS registered for use in cattle in Australia, flunixin appeared to be the most soluble in the majority of vehicles examined. A number of these vehicles were quite effective in moving flunixin through cattle skin in vitro, particularly combinations of ethanol, propylene glycol and *eucalyptus* oil, which were more effective than 100% *eucalyptus* oil. However, there was significantly more ketoprofen penetrating through cattle skin in all of the vehicles used in this study (FIG. 4). Both tolfenamic acid and meloxicam were not particularly soluble in most of the vehicles tested and both drugs also had little to no penetration through cattle skin. A full list of the vehicles and raw data can be found in Table 13.

Optimising the Candidate Formulations

Figure 5:
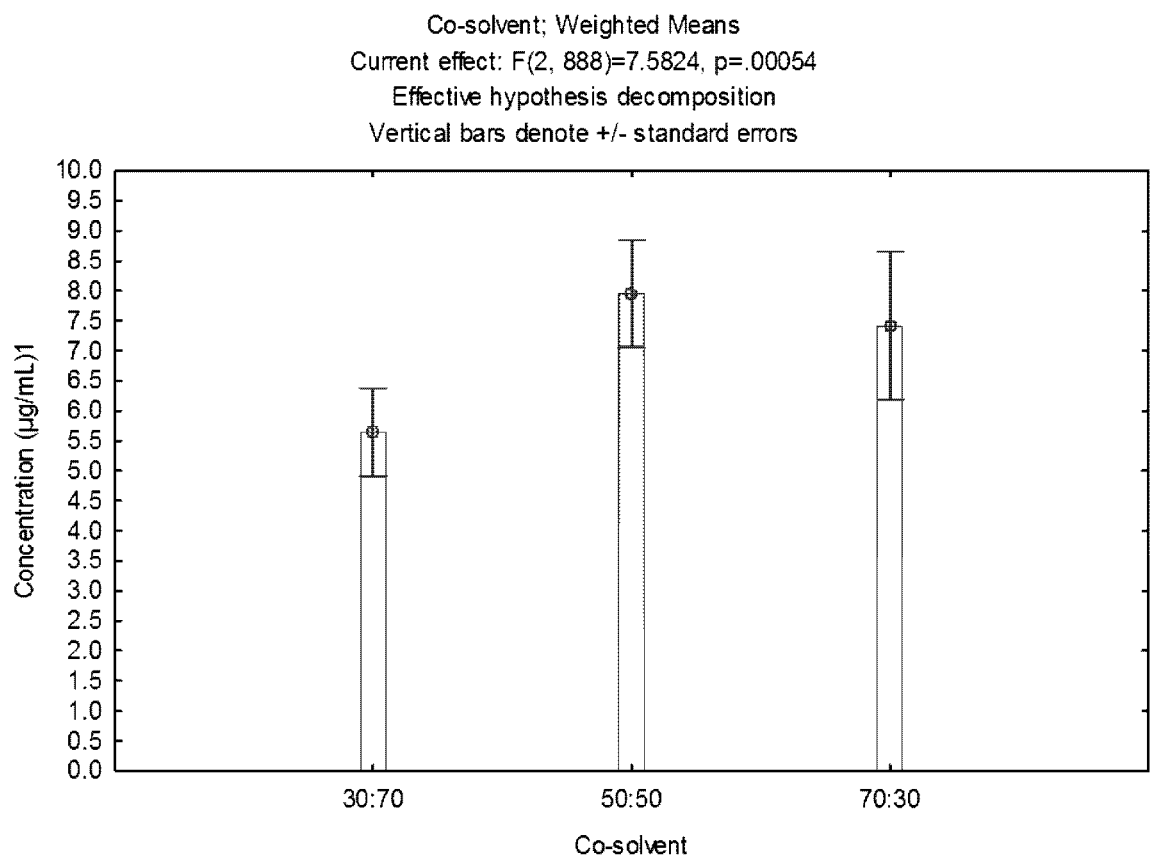
FIG. 5: The effects of various concentrations of ethanol on ketoprofen movement through cattle skin.
Figure 6:
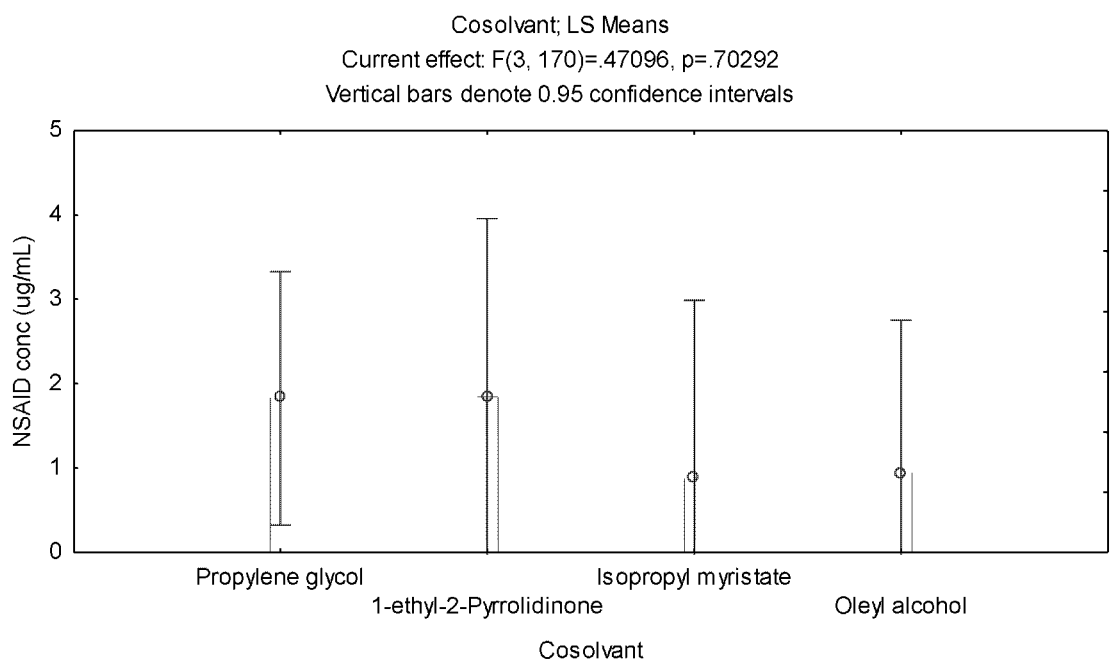
FIG. 6: The effects of various solubilising agents on ketoprofen movement through cattle skin.
Figure 7:
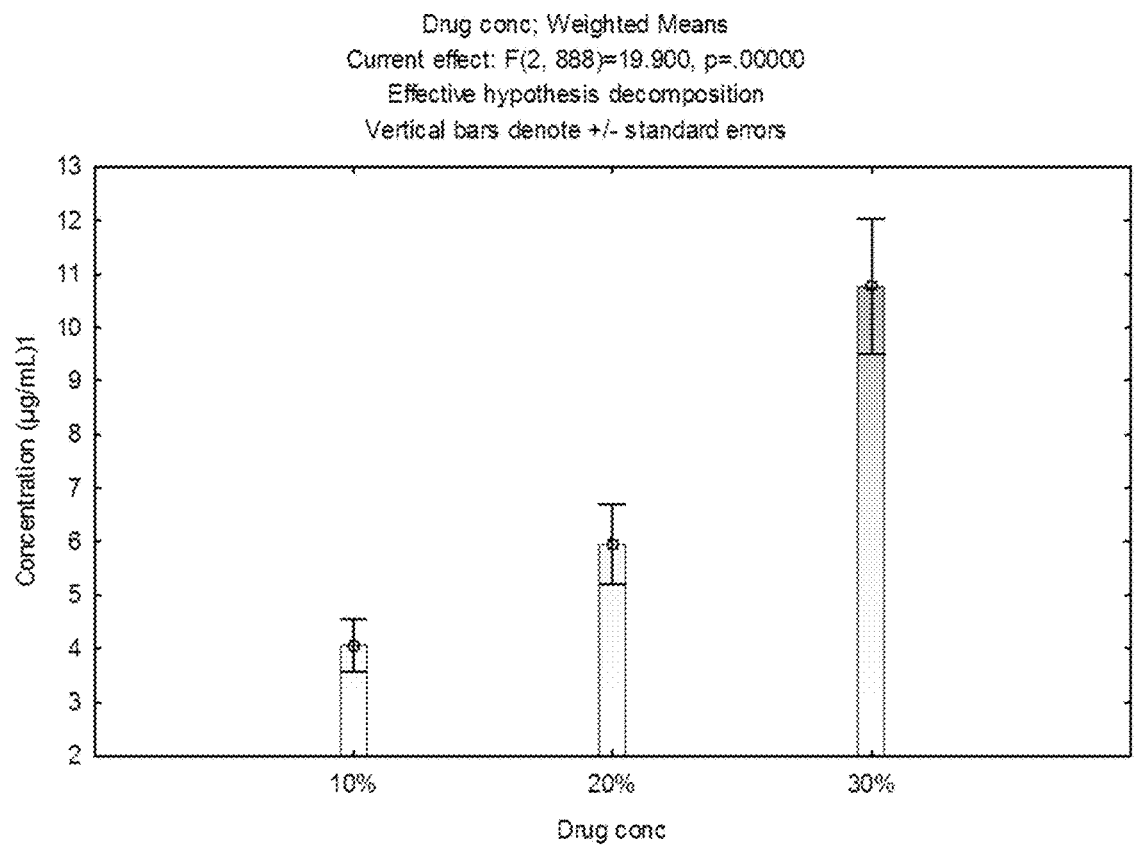
FIG. 7: The effects of increasing concentration of ketoprofen on the amount of drug penetrating through cattle skin.

Once it was decided to move forward with ketoprofen, the vehicles were refined to maximise transdermal drug penetration. A combination of alcohol and *eucalyptus* oil provided the most favourable transdermal drug movement. Ethanol (50-70%) was stable and significantly enhanced penetration compared to other alcohols (FIG. 5). Isopropanol was included in the range of alcohols tested, since it is commonly used in other topical formulations and was considered a safer (less flammable) option. However, isopropanol did not transfer NSAIDs well for any of the actives tested and did not perform as well as ethanol. Several solubilising agents were tested, including propylene glycol (PG), oleyl alcohol and isopropyl myristate (IPM), with IPM proving the more effective (FIG. 6). A final combination of 50:50 ethanol and IPM, mixed with 10% *eucalyptus* oil (~7% 1,8-cineole), meaning that ethanol and IPM are actually at 45% each. A range of active concentrations (10, 20 and 30%) were also considered. Ketoprofen at 30% did result in mild precipitation at room temperature, while 20% seemed quite stable, so was selected as the ideal concentration (FIG. 7).

Stability Studies of the Final Formulation

There was no change in the final formulation at 2 or 4 months storage, in terms of precipitation, crystallisations, colour and evaporation. There was some evidence of evaporation, particularly from the glass vessels, most noticeably in samples containing higher ethanol components (50% and 70%) when stored at 40° C., particularly those with appeared to have evaporated quicker than the others from the glass vessels.

At 6 months, evaporation was evident in all samples stored in glass at 40° C. and some at ambient temperature. A small colour change was observed in samples stored at 40° C.

Figure 8:
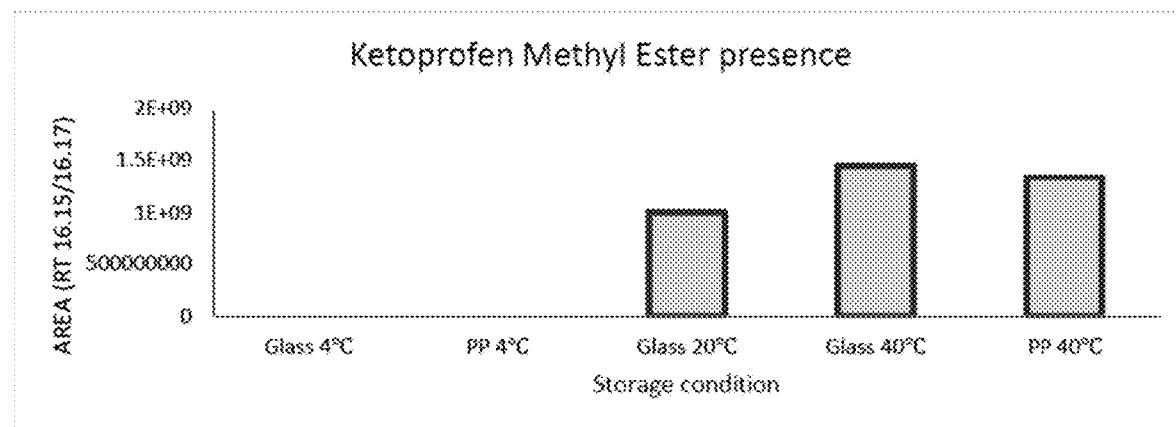
FIG. 8: Appearance of ketoprofen methyl ester in final formulation samples maintained under various conditions.

Concentration of ketoprofen remained stable (20±1%) throughout, although small amounts of ketoprofen methyl ester were detected in some samples stored at 20 and 40° C. (see FIG. 8).

Analysis of Ketoprofen in Biological Samples
Plasma Protein Precipitation:

Cold Acetonitrile (0.2% formic acid) precipitation was added to samples at 1:1 ratio and vortexed for 30 s. Protein crashing carried out by 2 rounds of centrifugation for 15 min at 20,000 g. Interval between "crashing" was 30 min at 4° C. Supernatant of each sample collected and analysed by LCMS/MS.

It is noted that further cleaning and processing of samples will enable better sensitivity to the assessment. For the purpose of continuity method of sample preparation was not changed throughout the project.

Figure 9:
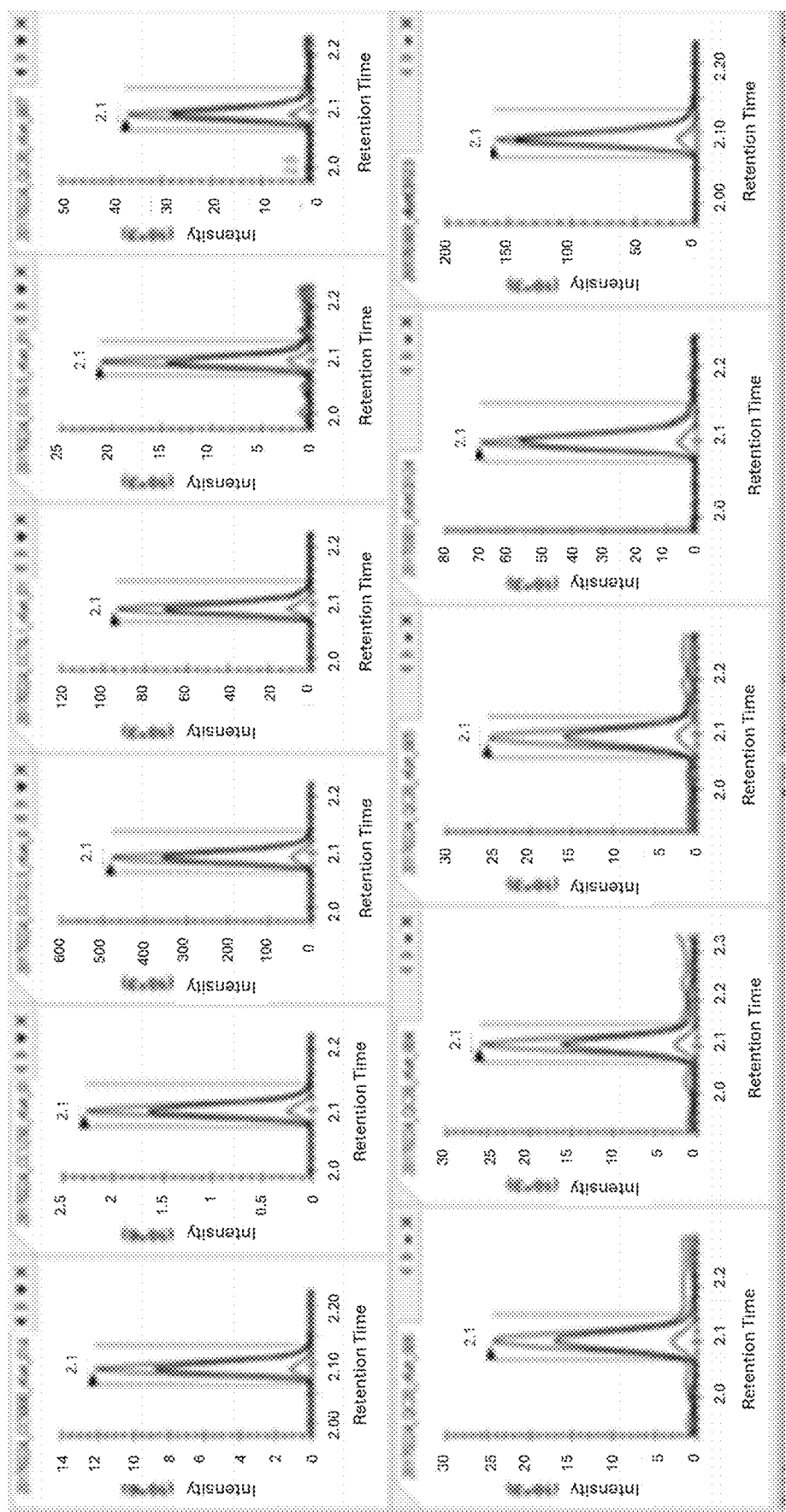
FIG. 9: Co-elution of the ketoprofen transitions and stability of each transition in biological samples.
Figure 9:
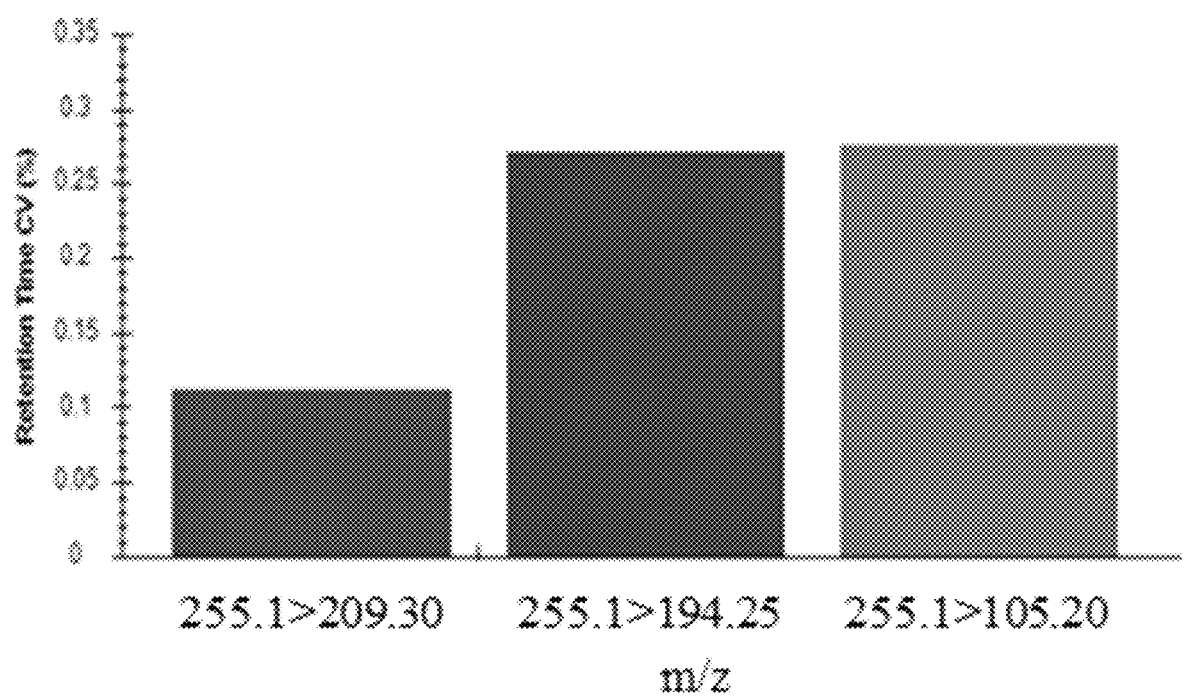
Figure 10:
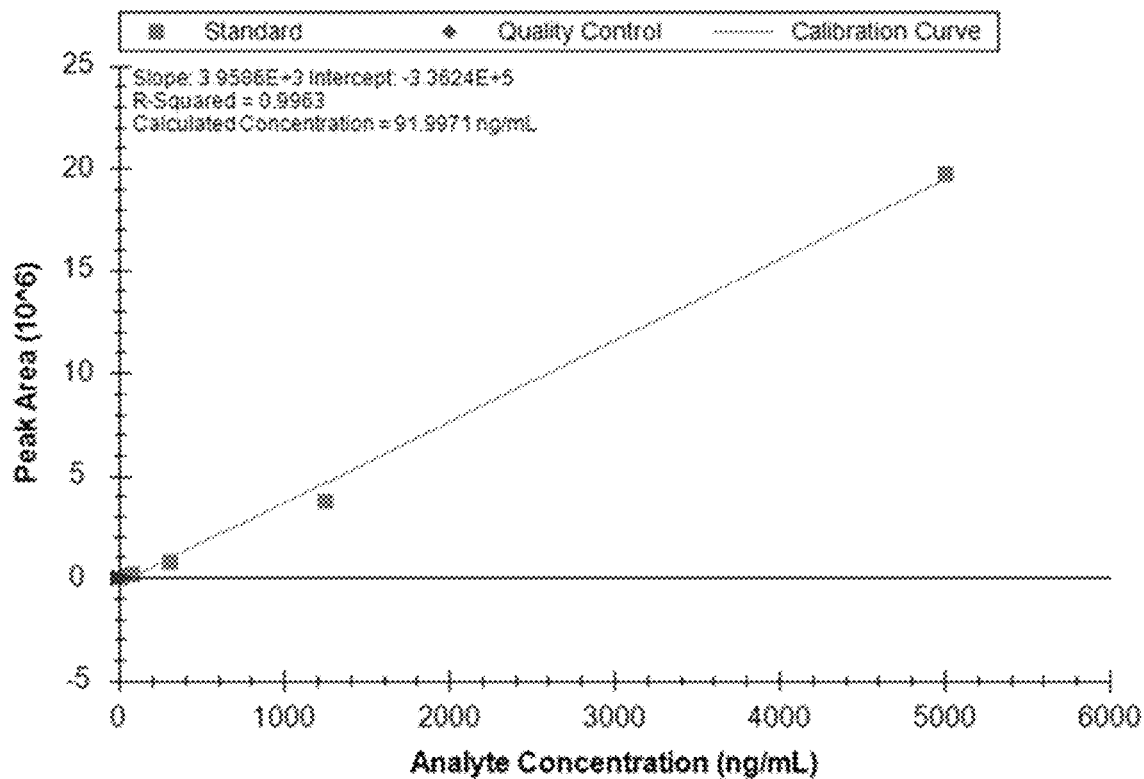
FIG. 10: Calibration curve for analysis of ketoprofen in biological samples.
Figure 11:
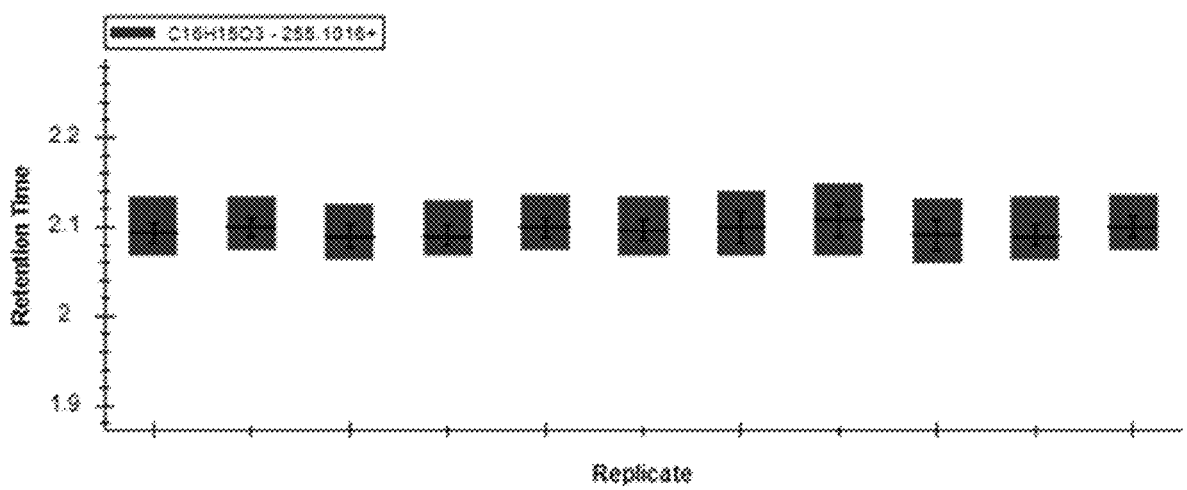
FIG. 11: Retention time stability of ketoprofen analysis in biological samples (n=11 shown).
Figure 12:
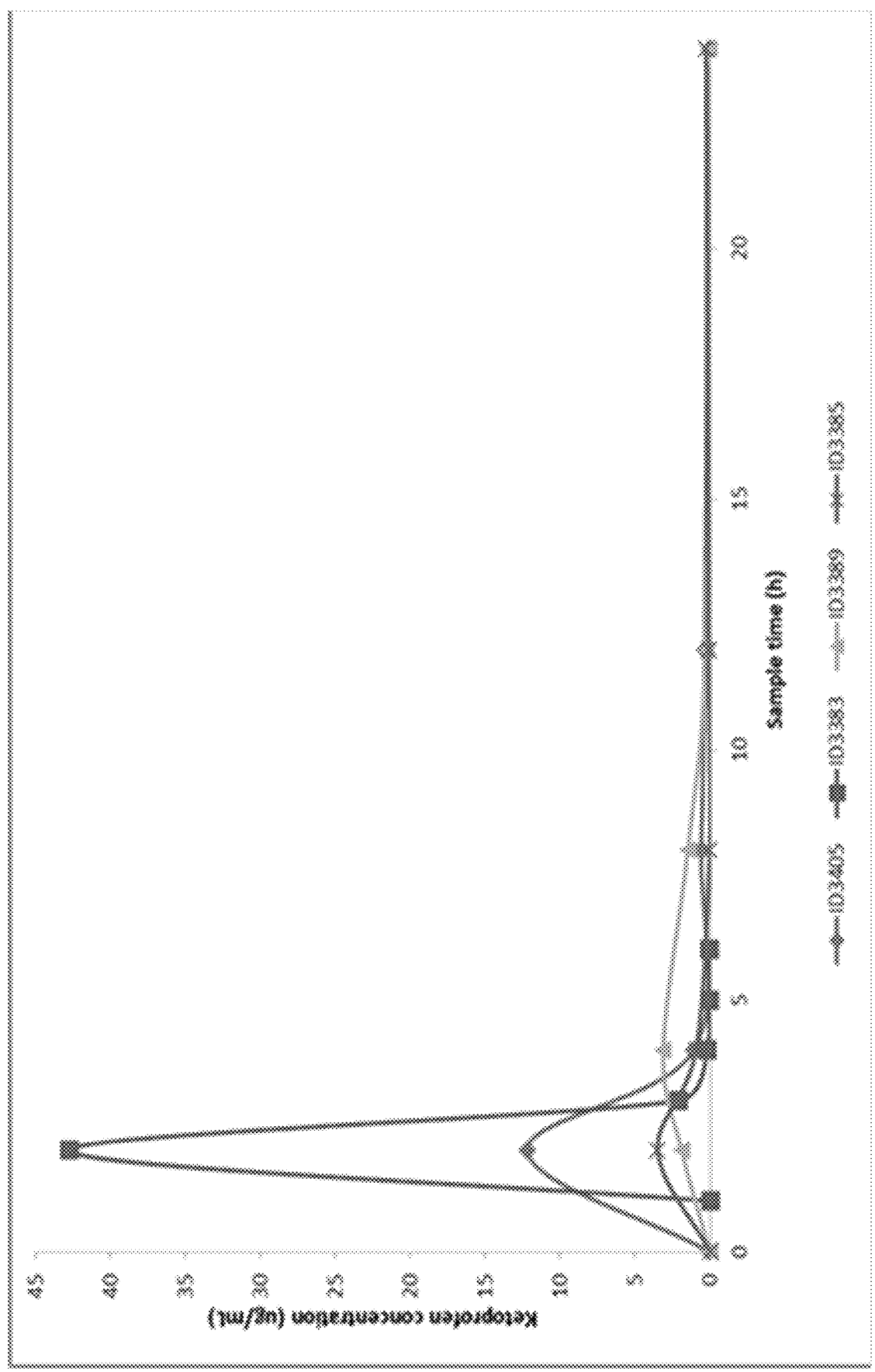
FIG. 12: Ketoprofen concentrations (µg/mL) in plasma after transdermal administration of 10 or 40 mL of formulation to four calves.
Figure 13:
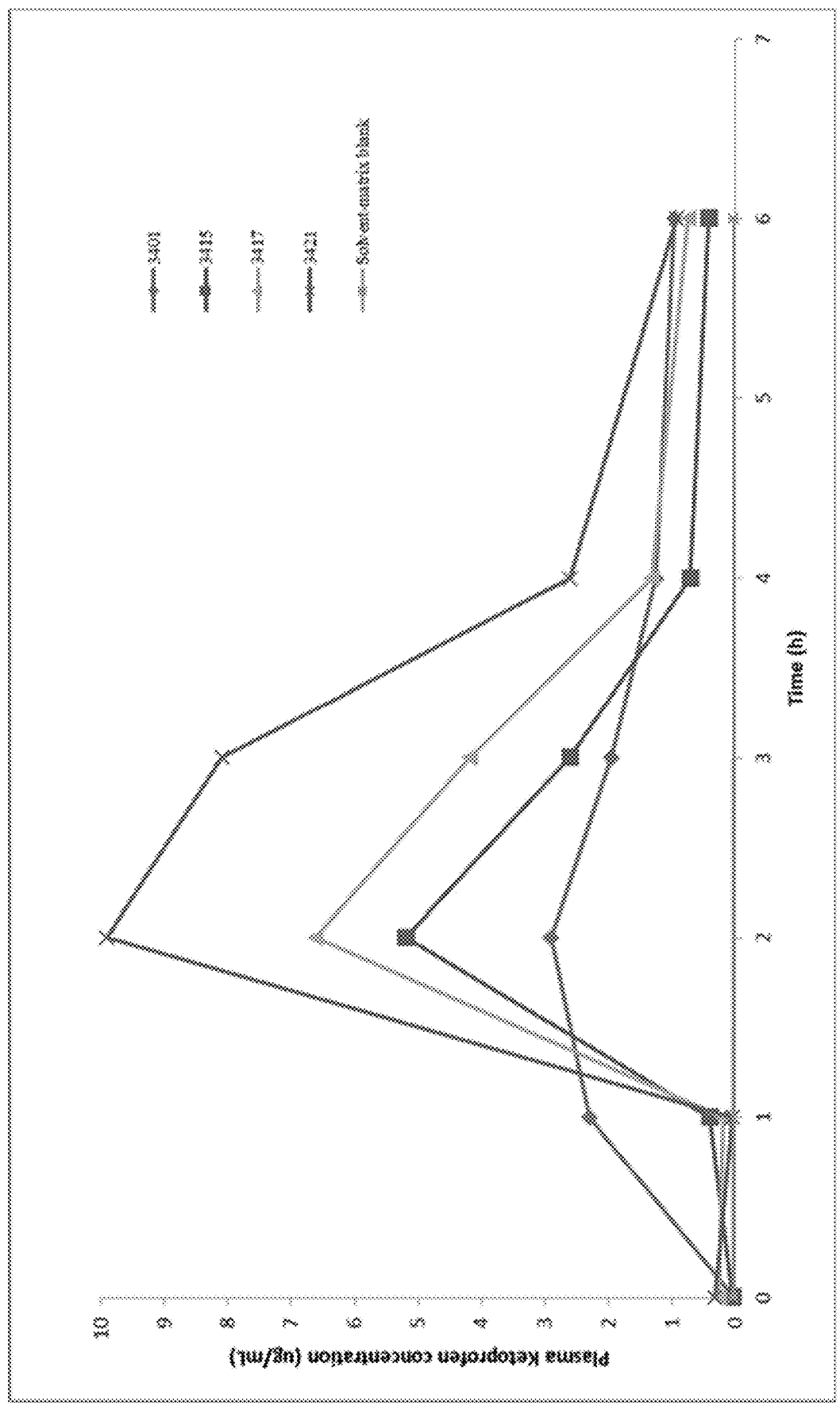
FIG. 13: Ketoprofen concentrations (µg/mL) in plasma after transdermal administration of formulation to four calves.

Ketoprofen Concentration Determination by LC-MS/MS (9-12 Jan. 2017)
    Instrument: Shimadzu Nexera uHPLC in tandem with LCMS 8030.
    CID gas: Argon
    Column: Phenomenex Kinetix Evo C18, 1.7 µm pore size.
    Mobile phase A: 0.1% formic acid in water
    Mobile phase B: 0.1% formic acid in Acetonitrile
    LOD: 2 ppb; QC samples instrument stability at 0.02 µg/mL; Calibration range 0.0049-5 µg/mL.
    Ketoprofen: Detection m/z 255.10>105.20 and confirming ion 255.10>194.25, 255.10>209.30
    Collision energies for each transition was optimised Co-elution of all peaks are checked and verified in all analysis files. The right chart verifies the retention time % CV of each transition across all files.
    ISTD Ibuprofen: Unsuccessful—instrument negative ion mode was out of order and the column length was likely to be too short, and a longer chromatography programme may have been required. Current modifications to be considered is the use of deuterated ketoprofen or another surrogate NSAID to be used as an ISTD.
    Samples: must be prepared with less than 90% solvent prior to analysis.
    Instrument performance and stability: All samples were analysed on the instrument continuously. QC was analysed every 20 samples, CV<5%. Five sets of calibration curves were assessed.
    Calibration curve and retention time of variation: FIG. 9 below illustrates a proportion of the standards FIG. 11 shows QC data alignment of the retention times of Ketoprofen during the analyses.

To Determine the Efficacy of Candidate Transdermal Formulations to Control Pain Associated with Surgical Husbandry Formulations
Pilot Study 1

The plasma ketoprofen concentrations (µg/mL) in each calf were as follows:

| Time (hr) | Calf 3405 | Calf 3383 | Calf 3389 | Calf 3385 |
|---|---|---|---|---|
| 0 | 0.057 | 0.021 | 0.027 | 0.024 |
| 2 | 12.21 | 42.768 | 1.905 | 3.498 |
| 4 | 1.092 | 2.103 | 3.132 | 0.963 |
| 8 | 0.603 | 0.252 | 1.503 | 0.048 |
| 12 | 0.375 | 0.102 | 0.303 | 0.108 |
| 24 | 0.075 | 0.045 | 0.111 | 0.285 |

Plasma ketoprofen concentrations were detectable and approached what may have been expected following IM administration. The lag time (between application and appearance of active in the plasma) was unexpectedly very short (most transdermal formulations exhibit a lag time of several hours). It was uncertain if the peaks for the applications had been missed. It was also unsure if any grooming had contributed to the short lag time but casual observation indicated this was unlikely to have been significant.

Pilot Study 2

The plasma ketoprofen concentrations (µg/mL) were as follows:

| Time (hr) | Calf 3401 | Calf 3415 | Calf 3417 | Calf 3421 |
|---|---|---|---|---|
| 0 | 0.021 | 0.039 | 0.258 | 0.321 |
| 1 | 2.301 | 0.405 | 0.192 | 0.048 |
| 2 | 2.904 | 5.199 | 6.624 | 9.912 |

-continued

| Time (hr) | Calf 3401 | Calf 3415 | Calf 3417 | Calf 3421 |
|---|---|---|---|---|
| 3 | 1.965 | 2.616 | 4.182 | 8.103 |
| 4 | 1.251 | 0.711 | 1.314 | 2.616 |
| 6 | 0.951 | 0.426 | 0.744 | 0.933 |

There was no grooming observed at any stage during the second pilot study. Again, a short lag phase was observed, with peak plasma concentrations ~2 hr following application. Although we did not weigh the calves, there did seem to be a weight-related effect, since the lowest plasma concentrations were in calf 3401 and the highest in calf 3421, which were estimated to be the heaviest and lightest calves, respectively, although calf 3401 was male and there may be some gender differences.

Bioavailability Study

Figure 14:
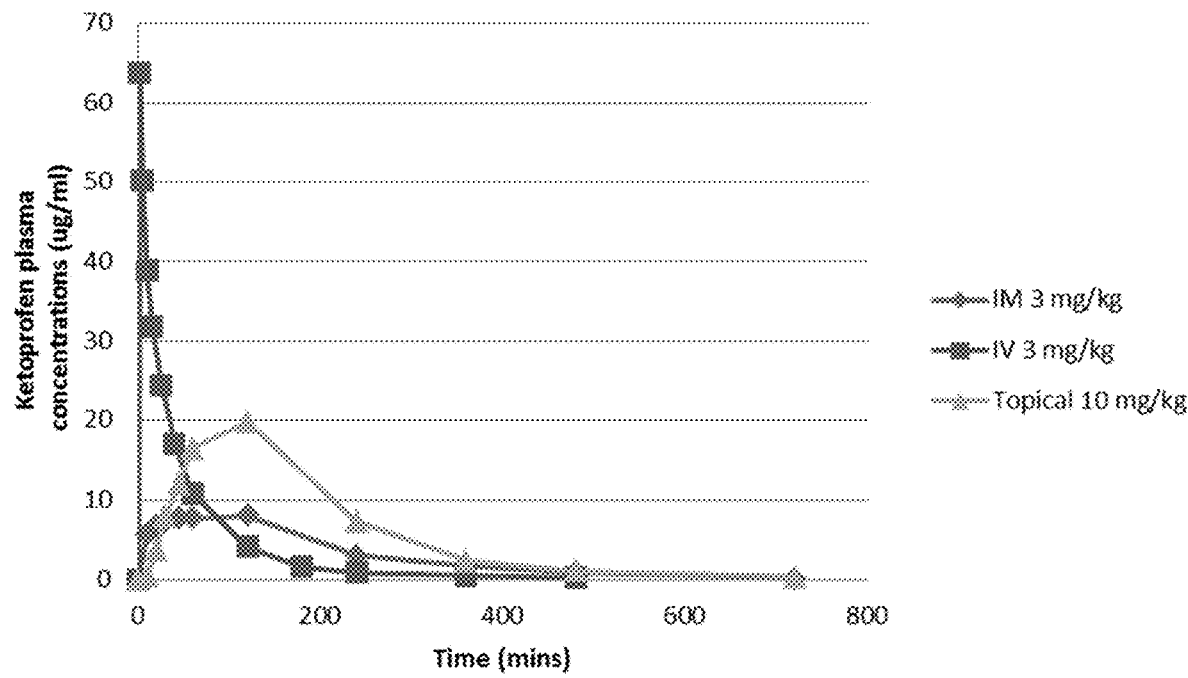
FIG. 14: Plasma concentration vs. time curves for ketoprofen administered to cattle by IV, IM and transdermal routes.
Figure 15:
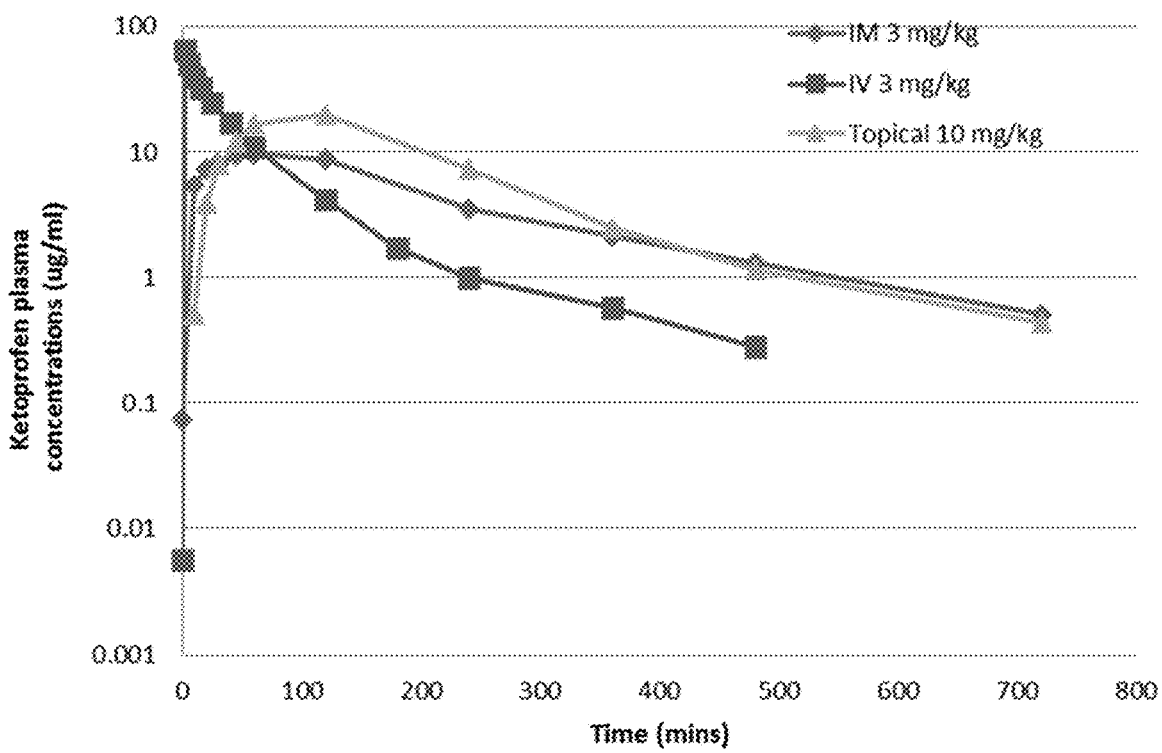
FIG. 15: The semi-log arrhythmic graph of the plasma concentration vs. time curves for ketoprofen administered to cattle by IV, IM and transdermal routes.

The PK results can be seen below in FIGS. 14 and 15, and Table 5. The transdermal formulation had a slower absorption than IM, although the peaks were equivalent at 30 minutes. A peak ($C_{MAX}$) occurred ~2 hr. A bioavailability of 50% and an area under the curve (AUC; 3940 µg·mL/min) exceeding that following IM administration (2376 µg·mL/min) suggested that the transdermal formulation had a greater systemic effect than IM administration.

Figure 16:
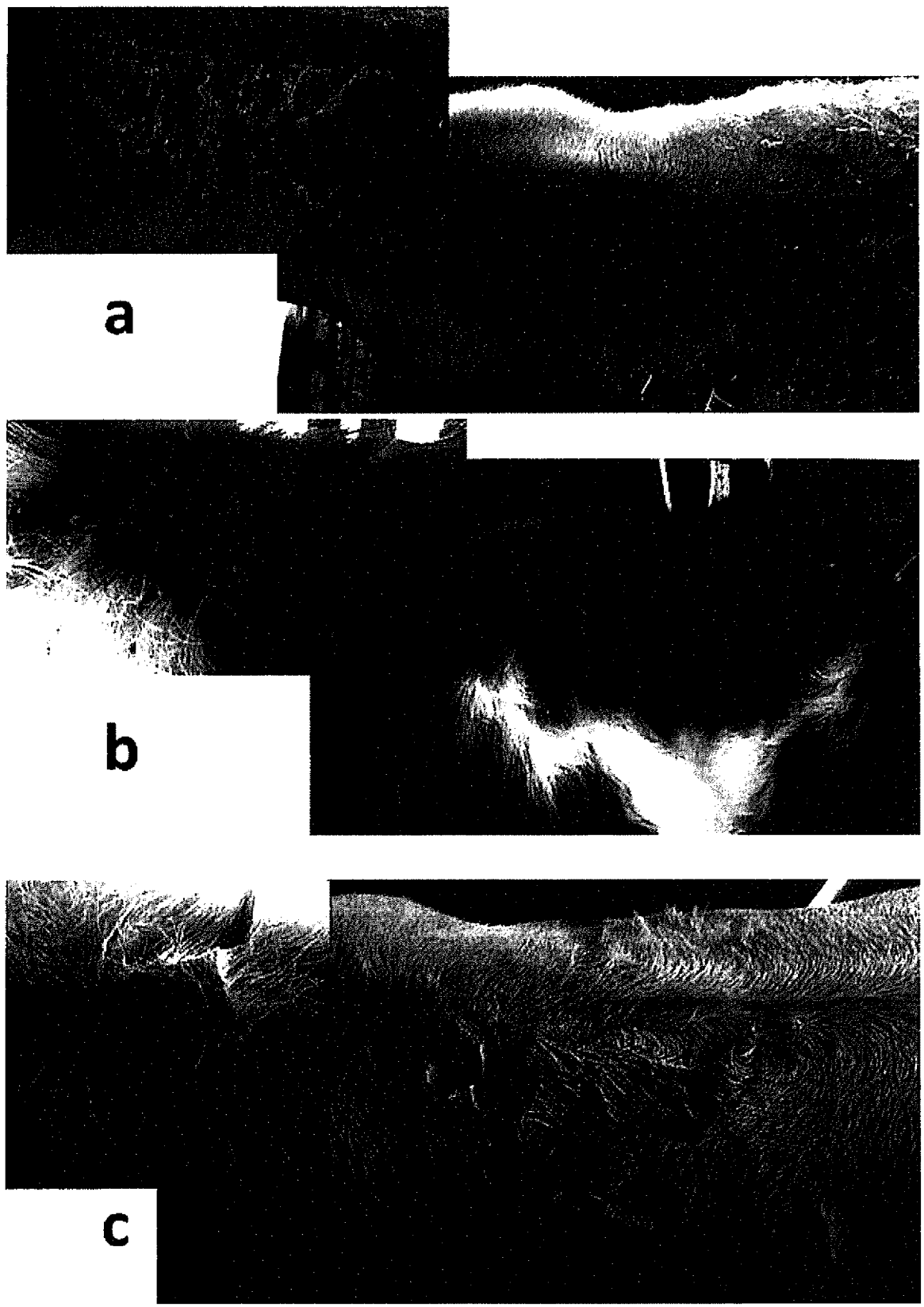
FIG. 16: Skin irritation following administration of transdermal ketoprofen formulation. The figures illustrate the irritation at various time points, with inserts showing a closer view of the actual site of irritation; (a) calf #10, 8 days post application (area shaved for biopsy); (b) calf #169: 14 days post application; (c) calf #181: 27 days post application.

Unfortunately, evidence of skin irritation was observed several days after administration of the transdermal formulation, continuing to marked skin inflammation and excoriation in the 3-4 weeks following application (FIG. 16). It was uncertain if this irritation was due to photosensitisation of the ketoprofen, the fact that the transdermal formulation had been administered three times to each animal or other environmental factors.

TABLE 5

The pharmacokinetic (Pk) parameters for ketoprofen administered to cattle by IV, IM and transdermal routes

| | Dose (mg/kg) | Cmax/ Co | Cmax/ dose | Tmax | AUC Last | 0-AUC Inf/dose | Half-life (mins) | F (%) |
|---|---|---|---|---|---|---|---|---|
| IV | 3 | 77 | 22 | NA | 2363 | 806 | 121 | |
| IM | 3 | 11 | 4 | 74 | 2376 | 856 | 164 | 101 |
| Topical | 10 | 20 | 2 | 115 | 3940 | 404 | 155 | 50 |

To Develop a Formulation Containing an NSAID to Control Pain Associated with Routine Surgical Interventions for Up to 24 hr Clinical Study This study was successfully performed and all 36 animals completed the study. Some calves required attention to continued bleeding from the dehorning site, which was undertaken manually. All animals remained in good health throughout the study.

Conventional Parameters to Assessment Pain and Inflammation

Total Cortisol

The total plasma cortisol concentration (ng/mL) in each animal at each time point can be observed in table 6.

TABLE 6

Total plasma cortisol concentration (ng/mL)

| Group | Animal | 0 | 1 | 2 | 4 | 8 | 24 | 96 |
|---|---|---|---|---|---|---|---|---|
| Placebo | 50 | 3.5 | 18.2 | 8.2 | 27.7 | 4.0 | 5.6 | 16.1 |
| Placebo | 54 | 10.0 | 19.2 | 36.9 | 32.6 | 24.1 | 19.5 | 22.5 |
| Placebo | 60 | 6.4 | 36.6 | 21.4 | 30.0 | 19.8 | 12.9 | 25.7 |
| Placebo | 61 | 2.0 | 17.2 | 21.8 | 24.9 | 21.1 | 24.6 | 7.5 |
| Placebo | 68 | 13.7 | 13.1 | 19.2 | 21.8 | 18.8 | 11.8 | 9.3 |
| Placebo | 76 | 8.4 | 28.4 | 35.7 | 31.8 | 22.9 | 37.8 | 25.6 |
| Placebo | 74 | 16.8 | 29.7 | 24.6 | 34.9 | 37.1 | 30.8 | 19.3 |
| Placebo | 47 | 15.9 | 30.9 | 9.6 | 15.5 | 15.8 | 20.1 | 8.7 |
| Placebo | 44 | 19.0 | 24.2 | 17.6 | 39.9 | 41.9 | 14.6 | 4.8 |
| Placebo | 52 | 6.8 | 8.1 | 46.6 | 8.8 | 5.6 | 7.0 | 6.0 |
| mean | | 10.2 | 22.5 | 24.2 | 26.8 | 21.1 | 18.5 | 14.5 |
| SEM | | 1.8 | 2.8 | 3.9 | 3.0 | 3.7 | 3.3 | 2.6 |
| TransD | 72 | 6.5 | 4.6 | 3.9 | 14.5 | 10.4 | 1.9 | 1.9 |
| TransD | 78 | 4.0 | 6.6 | 1.9 | 4.2 | Missing | 1.9 | 10.9 |
| TransD | 75 | 8.8 | 1.9 | 1.9 | 14.7 | 16.6 | 21.9 | 2.7 |
| TransD | 64 | 1.9 | 28.0 | 2.6 | 6.0 | 19.9 | 2.7 | 19.1 |
| TransD | 48 | 3.2 | 27.5 | 13.4 | 3.1 | 17.0 | 1.9 | 16.7 |
| TransD | 67 | 1.9 | Missing | 4.8 | 22.1 | 14.2 | 16.5 | 9.9 |
| TransD | 39 | 8.0 | 16.5 | 4.8 | 9.0 | 11.4 | 12.7 | 9.9 |
| TransD | 51 | 8.4 | 16.3 | 6.1 | 1.9 | 13.3 | 9.1 | 9.4 |
| TransD | 46 | Missing | 4.0 | 1.9 | 1.9 | 22.8 | 1.9 | 2.3 |
| TransD | 43 | 2.4 | 29.1 | 10.7 | 19.0 | 28.7 | 6.8 | 16.8 |
| mean | | 5.0 | 15.0 | 5.2 | 9.7 | 17.1 | 7.7 | 9.9 |
| SEM | | 1.0 | 3.7 | 1.2 | 2.4 | 2.0 | 2.3 | 2.0 |
| Sham | 69 | 1.9 | 1.9 | 8.5 | 5.4 | 10.1 | 14.0 | 8.2 |
| Sham | 58 | 2.7 | 8.9 | 5.6 | 2.4 | 7.7 | 1.9 | 17.1 |
| Sham | 66 | 1.9 | 2.9 | 1.9 | 7.0 | 12.8 | 4.5 | 6.7 |
| Sham | 49 | 5.1 | 12.1 | 2.4 | 1.9 | 19.5 | 3.8 | 2.6 |
| Sham | 53 | 1.9 | 2.3 | 1.9 | 11.3 | 16.4 | 1.9 | 1.9 |
| Sham | 38 | 1.9 | 1.9 | 2.2 | 1.9 | 1.9 | 1.9 | Missing |
| mean | | 2.6 | 5.0 | 3.7 | 5.0 | 11.4 | 4.7 | 7.3 |
| SEM | | 0.5 | 1.8 | 1.1 | 1.5 | 2.6 | 1.9 | 2.7 |
| IM | 82 | 2.9 | 3.3 | 4.1 | 29.9 | 23.3 | 21.9 | 30.0 |
| IM | 77 | 3.2 | 7.9 | 4.4 | 24.6 | 20.9 | 10.6 | 4.5 |

TABLE 6-continued

Total plasma cortisol concentration (ng/mL)

| Group | Animal | 0 | 1 | 2 | 4 | 8 | 24 | 96 |
|---|---|---|---|---|---|---|---|---|
| IM | 65 | 7.8 | 5.9 | 9.0 | 15.8 | 18.9 | 6.7 | 26.9 |
| IM | 70 | 6.1 | 3.4 | 3.7 | 25.2 | 8.6 | 1.9 | 8.3 |
| IM | 56 | 11.8 | 13.5 | 4.6 | 16.2 | 12.9 | 6.9 | 30.7 |
| IM | 63 | 3.1 | 7.1 | 8.1 | 8.3 | 10.3 | 16.7 | 11.7 |
| IM | 35 | 13.0 | 30.8 | 6.4 | 19.7 | 28.8 | 6.5 | 2.3 |
| IM | 42 | 2.8 | 42.6 | 39.1 | 19.2 | 10.7 | 9.6 | 16.6 |
| IM | 40 | 3.7 | 7.6 | 10.1 | 4.4 | 7.9 | 2.8 | 4.1 |

TABLE 6-continued

Total plasma cortisol concentration (ng/mL)

| Group | Animal | Time | | | | | | |
|---|---|---|---|---|---|---|---|---|
| | | 0 | 1 | 2 | 4 | 8 | 24 | 96 |
| IM | 55 | 4.0 | 6.1 | 15.5 | 6.3 | 18.8 | 22.5 | 16.7 |
| | mean | 5.8 | 12.8 | 10.5 | 17.0 | 16.1 | 10.6 | 15.2 |
| | SEM | 1.2 | 4.2 | 3.4 | 2.7 | 2.2 | 2.3 | 3.4 |

Figure 17:
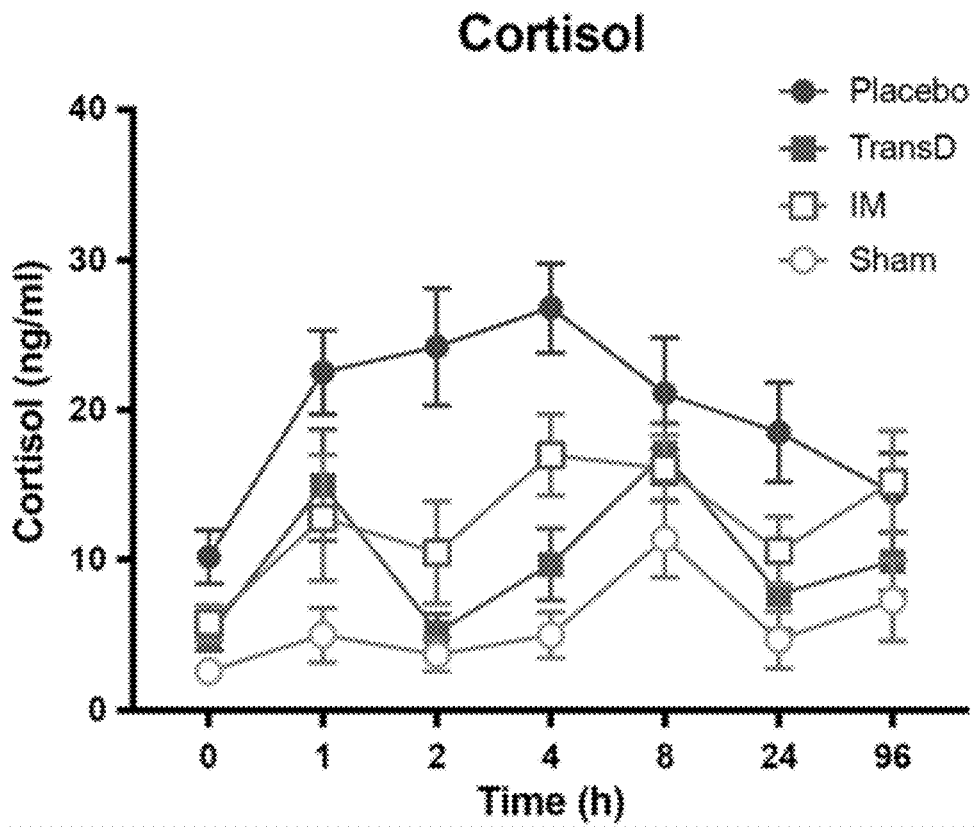
FIG. 17: Total plasma cortisol (ng/mL) over 96 hr.
Figure 18:
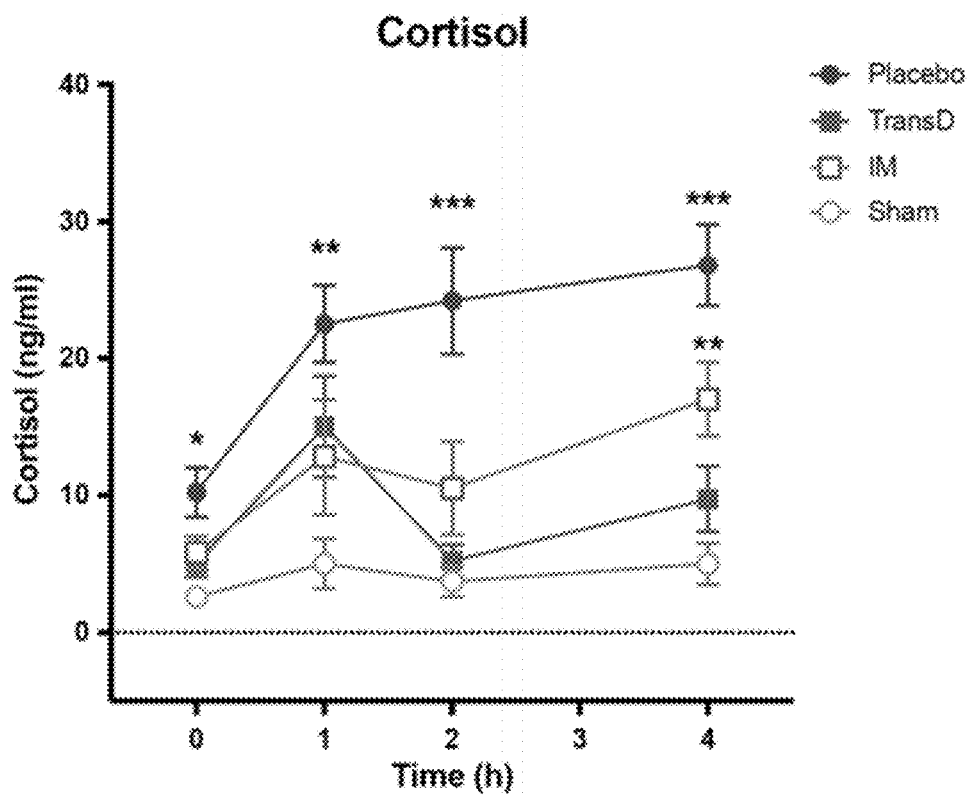
FIG. 18: Total plasma cortisol (ng/mL) during the first 4 hr only.

When looked at graphically, it can be seen that there are differences between the groups when looked at over the entire 96 hr (FIG. 17) and, particularly, during the first 4 hr (FIG. 18).

The most obvious differences are in the first 4 hr. At 8 hr all treatments had an increase and there was no treatment effect post 8 hr. An ANOVA on each time point and the statistical result is shown on the 4 hr (FIG. 18). At the start (time 0) the placebo were slightly higher than others, while placebo increased markedly over time being significant from sham at all time points up to 4 hr.

The IM and Trans D increased from time 0 and were essentially the same (not different from each other at any time point). At 1 hr the Trans D and IM were not different from either sham or placebo (i.e. Intermediate). But at 2 hr both the Trans D and IM were not different from sham, but they were obviously both lower than placebo. At 4 hr the IM increases a bit to become significant from sham, but not Trans D.

These results mean that there was no difference in cortisol concentration between Trans D, sham OR IM at any time point. In Trans D there was a mild NS increase in cortisol at 1 hr compared to sham. There was a significant blunting of the stress response by transD and IM and 1, 2 and 4 hr post dehorning. The increase in cortisol at 8 hr for the sham group may reflect apprehension at repeated sampling.

Body Weight

There were no significant differences between either treatment group and the sham group, while both IM and transdermal groups had significantly (P<0.05) higher body weight gain, compared to the placebo group.

TABLE 7

Body weight changes in dehorned calves compared to sham-treated calves, compared to the effects of ketoprofen, administered IM or transdermally

| Treatment | Animal no. | Animal ID | Body weight | | |
|---|---|---|---|---|---|
| | | | 26 Oct. 2016 | 10 Nov. 2016 | 1 Dec. 2016 |
| Placebo (Y) | 1 | 74 | 89 | 118 | 143 |
| | 2 | 76 | 99 | 125 | 153 |
| | 3 | 68 | 115 | 142 | 160 |
| | 4 | 61 | 135 | 165 | 201 |
| | 5 | 60 | 150 | 169 | 212 |
| | 6 | 54 | 161 | 186 | 190 |
| | 7 | 50 | 177 | 211 | 238 |
| | 8 | 47 | 188 | 205 | 246 |
| | 9 | 44 | 191 | 205 | 249 |
| | 10 | 52 | 212 | 233 | 266 |
| | Mean | | 151.7 | 175.9 | 205.8 |
| | SD | | 41.6 | 38.8 | 43.8 |
| Keto TD (R) | 11 | 72 | 92 | 112 | 132 |
| | 12 | 78 | 98 | 118 | 145 |
| | 13 | 75 | 112 | 139 | 171 |
| | 14 | 64 | 127 | 155 | 184 |
| | 15 | 48 | 150 | 180 | 211 |
| | 16 | 67 | 165 | 195 | 225 |

TABLE 7-continued

Body weight changes in dehorned calves compared to sham-treated calves, compared to the effects of ketoprofen, administered IM or transdermally

| Treatment | Animal no. | Animal ID | Body weight | | |
|---|---|---|---|---|---|
| | | | 26 Oct. 2016 | 10 Nov. 2016 | 1 Dec. 2016 |
| | 17 | 39 | 176 | 213 | 246 |
| | 18 | 51 | 180 | 206 | 241 |
| | 19 | 46 | 205 | 242 | 281 |
| | 20 | 43 | 215 | 252 | 292 |
| | Mean | | 151.9 | 181.2 | 212.8 |
| | SD | | 43.5 | 49.2 | 54.4 |
| Keto IM (B) | 21 | 82 | 93 | 107 | 135 |
| | 22 | 77 | 94 | 120 | 152 |
| | 23 | 65 | 110 | 141 | 164 |
| | 24 | 70 | 116 | 134 | 169 |
| | 25 | 56 | 150 | 179 | 207 |
| | 26 | 63 | 156 | 187 | 224 |
| | 27 | 35 | 191 | 210 | 252 |
| | 28 | 42 | 191 | 216 | 257 |
| | 29 | 40 | 205 | 240 | 278 |
| | 30 | 55 | 212 | 250 | 287 |
| | Mean | | 151.8 | 178.4 | 212.5 |
| | SD | | 46.4 | 50.9 | 55.2 |
| Sham control (G) | 31 | 69 | 104 | 126 | 148 |
| | 32 | 58 | 107 | 126 | 162 |
| | 33 | 66 | 145 | 172 | 208 |
| | 34 | 49 | 149 | 183 | 215 |
| | 35 | 53 | 184 | 216 | 246 |
| | 36 | 38 | 236 | 264 | 311 |
| | Mean | | 154.16 | 181.16 | 215 |
| | SD | | 49.9 | 53.4 | 59.2 |

Behaviour Ethogram and Analysis

The initial challenge was to determine which variables were indicators of pain and these could then be further investigated and compared between groups. The method used to identify those variables was Confirmatory Factor Analysis (CFA) within Structural Equation Modelling Framework (SEM). This method is far more superior to Principal Component Analysis (PCA), Multiple Component Analysis (MCA) or Factorial Analysis (FA) because it permits the use of information from all the variables in the dataset to describe which ones are better predictors of another latent variable, in this case, Pain. SEM is a conceptual map and hypothesis-driven process. Relationships between predictor variables (sems language 'observed variables') have to be plausible for SEM to produce reliable estimates that describe the relationship between the observed variable and the latent variable outcome.

The model output below describe the final, and most stable, models fitted using sems function in STATA 13. Only statistically significant variables remain (P<0.05) in the final model. The conceptual framework of the model is also plotted to make the interpretation of model outcome more accessible to the reader.

In the conceptual model map (FIG. 19), the oval shape is the latent variable (Pain). Square shapes are the observed variables. The circles are the standard error terms of each of our variables. The arrows are pathways between the latent variable and observed variables and between the error terms of the observed variables (i.e. allows for those variables to correlate with each other). The values shown on those arrows are the values estimated from the sem model (variable loading). Those values are standardised across the entire model, and they are used quantify the association between the latent and observed variables. They are interpreted roughly like regression coefficients as a function of standard deviation change in the latent and observed variables.

Seven variables (Ear flick, tail wag, ruminating, head shake, lying, grooming and neck extending) had substantial loading and were statistically significant. The interpretation is as follow: if an animal is One Standard Deviation higher in Pain (or pain score), it will have/score 0.78 Standard Deviation (SD) higher (positive coefficient) Ear flick count, 0.66 SD higher in Tail wag, 0.36 SD lower (negative coefficient) in Rumination and 0.25 SD lower in Grooming. You can also not ignore the negative correlation between tail wagging and laying down, or that between earflick and headrub. This confirms that the model framework is sound and reliable.

These observed variables can then be compared over time and between groups using separate Poisson models. Ideally (i.e. to demonstrate efficacy), there would be lower counts of positively correlated variables with pain and higher counts of those variables negatively correlated with pain.

Fitting Mixed Effect Poisson and Negative Binomial Models

Figure 19:
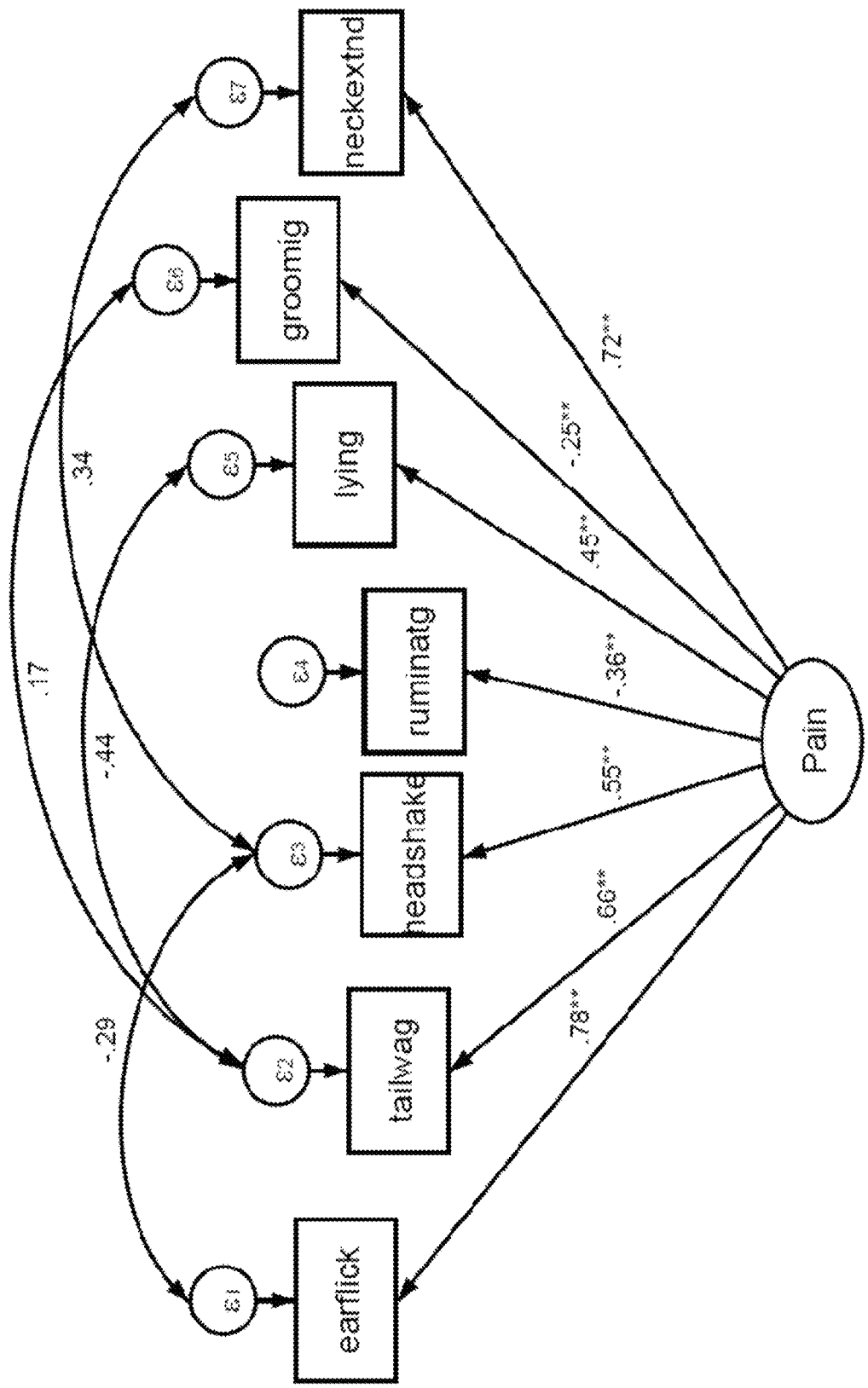
FIG. 19: A conceptual map of the parameters indicating pain.

Separate models were used for each of the observed animal behavioural traits (FIG. 19). A mixed effect Poisson model with an animal fitted as random intercepts and time as random slope, and unstructured error term for the residuals. Behaviours trait at baseline (time 0) was centred and added to the fixed effect part of the model (essentially turning the model into a random slope model too). Overdispersion was assessed and it was ruled out as being problematic (the scale is ~1 and not significant. Overdispersion was not an issue). Overdispersed models (also those with excess zeros) were refitted using a negative binomial model. Poisson: ear flick, tail wag and Negative binomial: headshake, head rub, lying, ruminate, neck extend, grooming.

Experimental time was fitted as a categorical variable to derive estimated at each time point, time 2 hr was used as the reference category. Treatment was also fitted as categorical variable, placebo as reference category. Two-way interaction with Treatment was forced and remained in the final model. The interpretation of the coefficients in Table 1 below is as follows:

The coefficient for Keto Trans (compared with Placebo) is −0.03, which means that, on average, the expected log ear flick count in Keto Trans was reduced by 3%, compared with Placebo group. This is equivalent to, on average, the incident risk (count) of Head Rub Count (IR) for Keto Trans was 0.97 times that of the Placebo group (Incidence Risk/count Ratio=IRR). Similarly, the highest incidence risk (count risk) of head rub was observed 4 hr after exposure, compared with the reference time (2 hr). Unfortunately, none of the treatment groups main effect were statistically significant.

Figure 20:
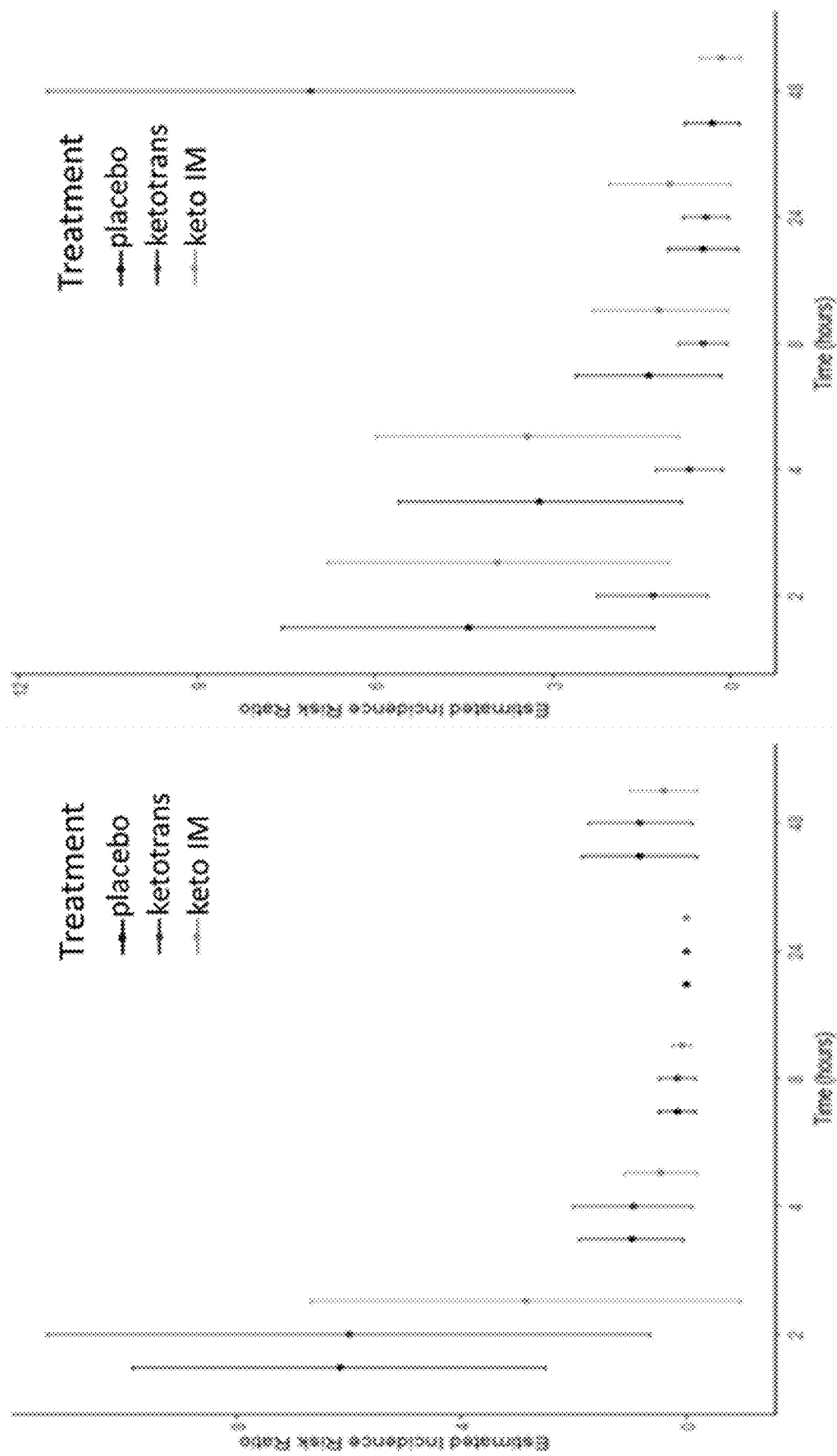
FIG. 20: Predicted marginal means and prediction intervals.
Figure 20:
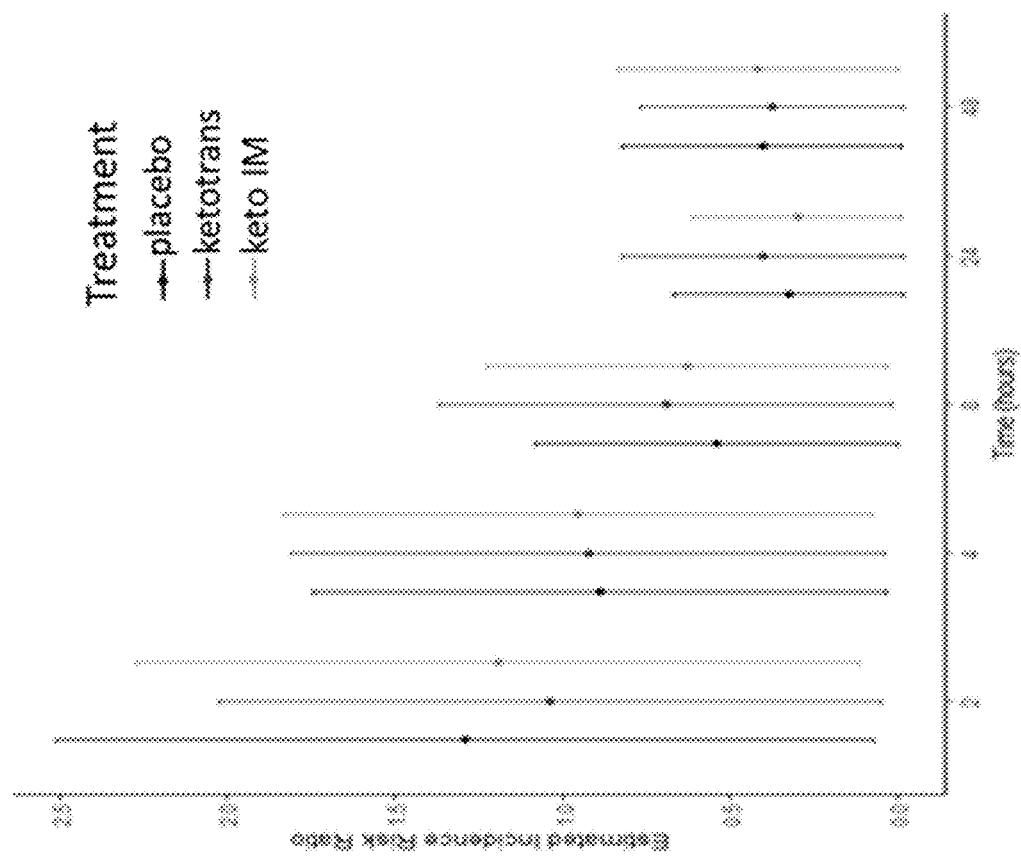
Figure 20:
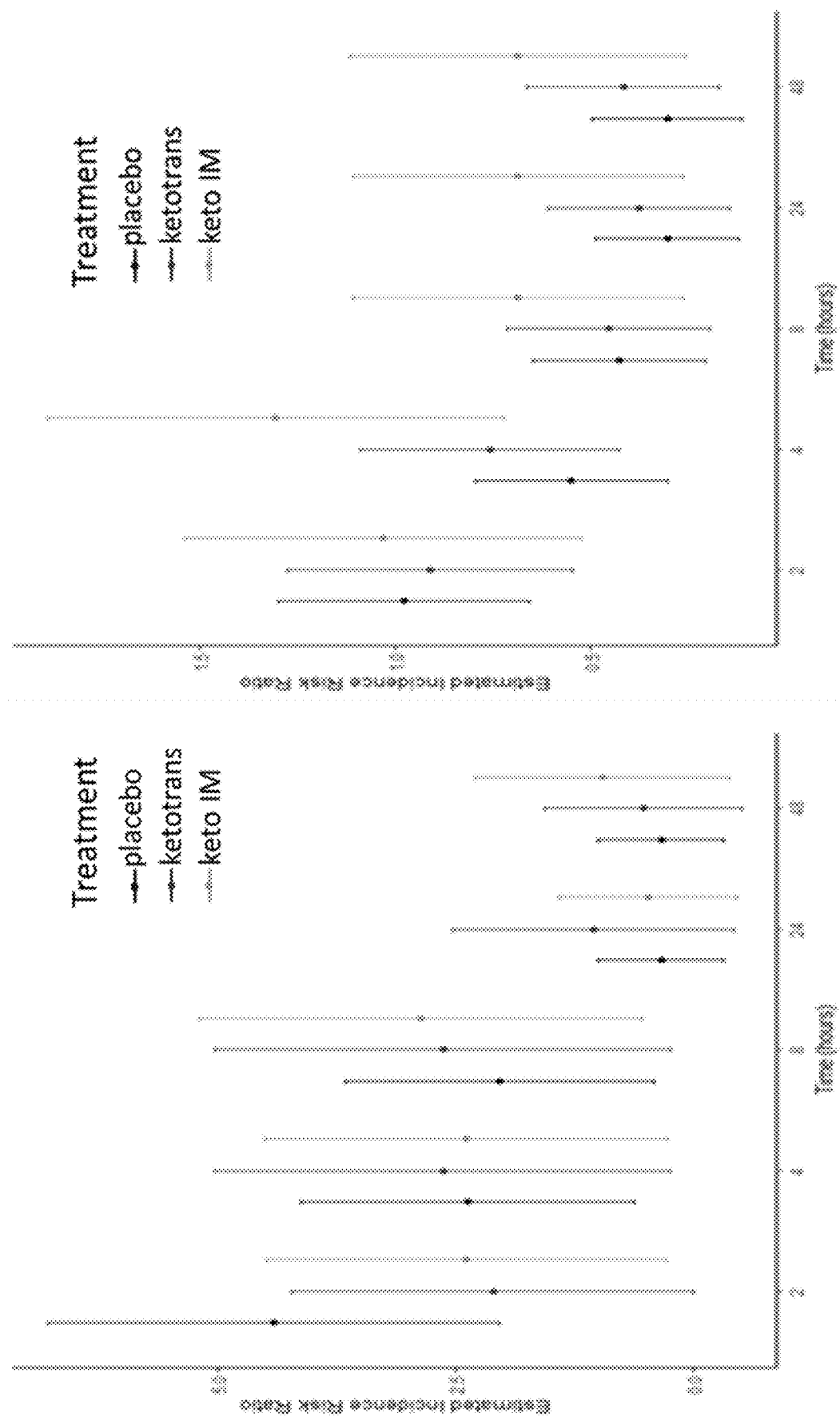
Figure 20:
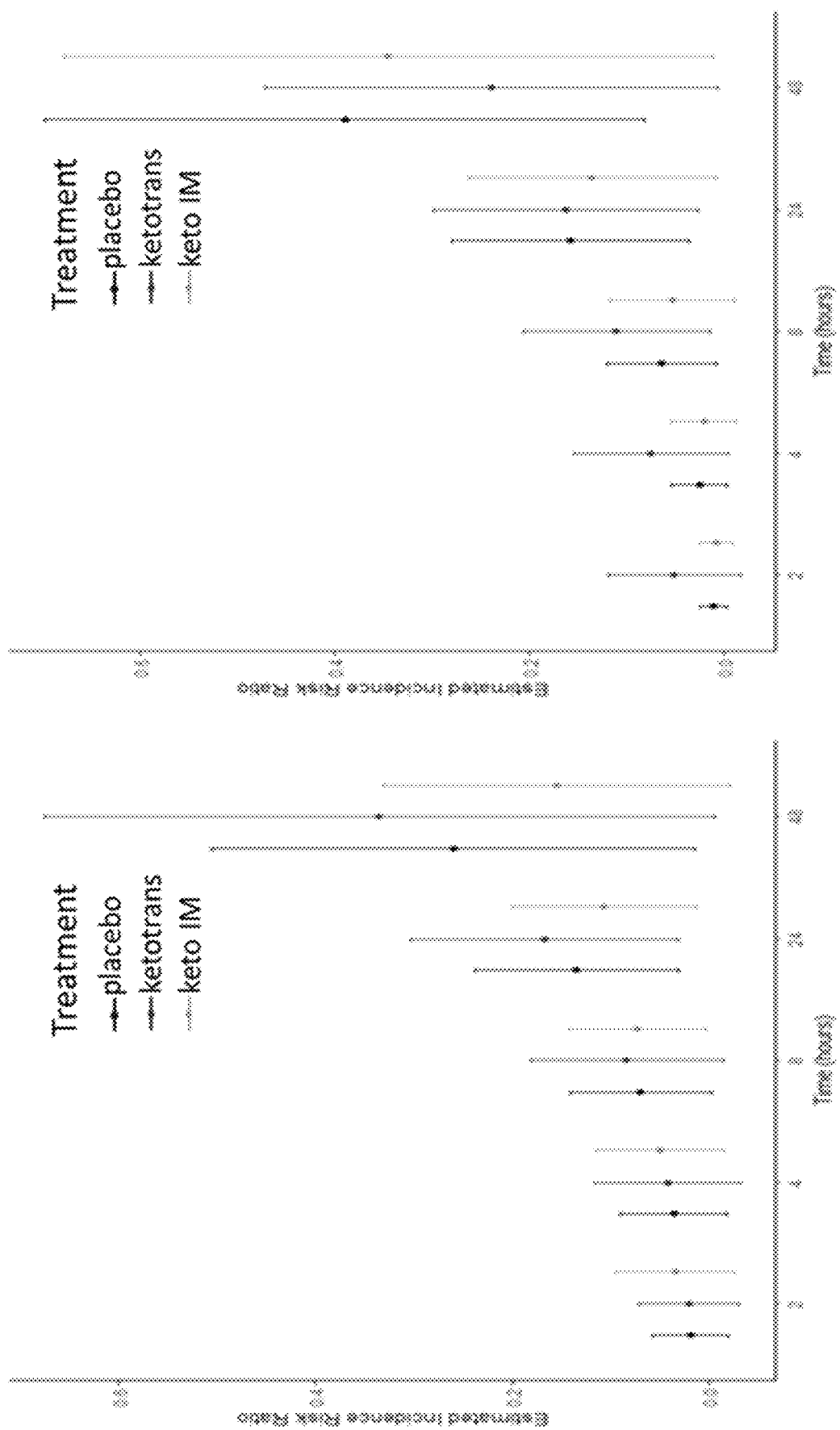

The true treatment effect is estimated using the interaction term. Hence, it was forced in the final models. In the marginal tables below (Tables 7-10) and FIG. 20, the interaction term was not significant either. The same comments about the main effect apply here too. Although no statistical differences were observed, there are numerical differences in favour of treatment.

The lack of statistical differences is related to the lack of statistical power in this study. To clarify, assuming a power of 80%, significance level percentage of 95%, balanced groups size, a probability of observing an outcome in the control group of 80%, the required sample size for this study to detect an odd ratio (or IRR) of 4 or greater is 88 animals in each group. The current study has a power of 17%.

TABLE 8

Marginal table for head rub, head shake and ear flick

| | Animal Behaviour | | | | | | | | |
|---|---|---|---|---|---|---|---|---|---|
| | Head rub | | | Head shake | | | Ear Flick | | |
| Variable | Coef (SE) | IRR 95% CI | P | Coef (SE) | IRR 95% CI | P | Coef (SE) | IRR 95% CI | P |
| Constant | −3.75 (0.98) | 0.02 (0.00 to 0.16) | <0.01 | −3.12 (0.36) | 0.04 (0.02 to 0.09) | <0.01 | −3.37 (0.17) | 0.03 (0.02 to 0.05) | <0.01 |
| Behaviour's count at Baseline (time 0) | 0.96 (0.93) | 2.61 (0.42 to 16.00) | 0.30 | −0.32 (0.52) | 0.72 (0.26 to 2.02) | 0.53 | −0.05 (0.04) | 0.95 (0.87 to 1.03) | 0.22 |
| Time | | | | | | | | | |
| 2 h | Reference | | | Reference | | | | | |
| 4 h | −1.84 (0.44) | 0.16 (0.07 to 0.38) | <0.01 | −0.32 (0.52) | 0.72 (0.26 to 2.02) | 0.53 | −0.04 (0.17) | 0.96 (0.69 to 1.33) | 0.80 |
| 8 h | −3.64 (1.01) | 0.03 (0.00 to 0.19) | <0.01 | −1.17 (0.58) | 0.31 (0.10 to 0.97) | 0.04 | −0.36 (0.18) | 0.70 (0.49 to 1.00) | 0.05 |
| 24 hrs | −2.14 (2.95) | 0.12 (0.00 to 38.00) | 0.21 | −2.27 (0.75) | 0.10 (0.02 to 0.45) | <0.01 | −1.73 (0.30) | 0.18 (0.10 to 0.32) | <0.01 |
| 48 hrs | −1.99 (0.62) | 0.14 (0.04 to 0.46) | <0.01 | −2.67 (0.85) | 0.07 (0.01 to 0.37) | <0.01 | −1.35 (0.26) | 0.26 (0.16 to 0.43) | <0.01 |
| Treatment | | | | | | | | | |
| Placebo | Reference | | | Reference | | | | | |
| Keto Trans | −0.03 (0.49) | 0.97 (0.37 to 2.55) | 0.96 | −1.22 (0.51) | 0.30 (0.11  0.81) | 0.02 | −0.07 (0.18) | 0.93 (0.65 to 1.32) | 0.68 |
| Keto IM | −0.77 (0.70) | 0.46 (0.12 to 1.83) | 0.27 | −0.12 (0.52) | 0.89 (0.32 2.45) | 0.82 | −0.10 (0.19) | 0.91 (0.62 to 1.32) | 0.60 |

TABLE 9

Marginal table for tail wag, lying and neck extending

| | Animal Behaviour | | | | | | | | |
|---|---|---|---|---|---|---|---|---|---|
| | Tail wag | | | Lying | | | Neck extended | | |
| Variable | Coef (SE) | IRR 95% CI | P | Coef (SE) | IRR 95% CI | P | Coef (SE) | IRR 95% CI | P |
| Constant | −3.13 (0.18) | 0.04 (0.03 to 0.06) | <0.01 | −2.62 (0.45) | 0.07 (0.03 to 0.18) | <0.01 | −2.42 (0.17) | 0.09 (0.06 to 0.12) | <0.01 |
| Behaviour's count at Baseline (time 0) | −0.12 (0.06) | 0.88 (0.79 to 0.99) | 0.03 | −0.51 (0.34) | 0.60 (0.31 to 1.16) | 0.13 | −0.58 (0.28) | 0.56 (0.33 to 0.97) | 0.03 |
| Time | | | | | | | | | |
| 2 hr | Reference | | | Reference | | | Reference | | |
| 4 h | −0.37 (0.23) | 0.69 (0.44 to 1.07) | 0.09 | −0.62 (0.47) | 0.54 (0.21 to 1.35) | 0.18 | −0.58 (0.28) | 0.56 (0.33 to 0.97) | 0.04 |
| 8 hr | −0.88 (0.27) | 0.42 (0.25 to 0.70) | <0.01 | −0.77 (0.49) | 0.46 (0.18 to 1.21) | 0.11 | −0.83 (0.31) | 0.44 (0.24 to 0.81) | <0.01 |
| 24 hr | −1.39 (0.32) | 0.25 (0.13 to 0.47) | <0.01 | −2.56 (1.04) | 0.08 (0.01 to 0.59) | 0.01 | −1.16 (0.34) | 0.31 (0.16 to 0.61) | <0.01 |
| 48 hr | −1.16 (0.30) | 0.31 (0.18 to 0.56) | <0.01 | −2.56 (1.04) | 0.08 (0.01 to 0.59) | 0.01 | −1.16 (0.37) | 0.31 (0.15 to 0.64) | <0.01 |
| Treatment | | | | | | | | | |
| Placebo | Reference | | | Reference | | | Reference | | |
| Keto Trans | −0.22 (0.22) | 0.80 (0.52 to 1.24) | 0.32 | −0.74 (0.58) | 0.48 (0.15 to 1.49) | 0.20 | −0.07 (0.26) | 0.93 (0.55 to 1.56) | 0.78 |
| Keto IM | −0.08 (0.22) | 0.92 (0.60 to 1.41) | 0.71 | −0.61 (0.53) | 0.54 (0.19 to 1.53) | 0.25 | 0.05 (0.30) | 1.05 (0.59 to 1.88) | 0.85 |

TABLE 10

Marginal table for grooming and ruminating

| | Animal Behaviour | | | | | |
|---|---|---|---|---|---|---|
| | Grooming | | | Ruminating | | |
| Variable | Coef (SE) | IRR 95% CI | P | Coef (SE) | IRR 95% CI | P |
| Constant | −7.15 (1.42) | 0.00 (0.00 to 0.01) | <0.01 | −11.17 (3.19) | 0.00 (0.00 to 0.01) | <0.01 |
| Behaviour count at Baseline (time 0) | 0.09 (0.26) | 1.10 (0.67 to 1.82) | 0.71 | −0.08 (0.43) | 0.93 (0.40 to 2.16) | 0.86 |
| Time (continuous variable) | 0.66 (0.32) | 1.94 (1.04 to 3.62) | 0.03 | 2.11 (1.06) | 8.22 (1.03 to 65.45) | 0.04 |
| Treatment | | | | | | |
| Placebo | Reference | | | | | |
| Keto Trans | 0.08 (2.12) | 1.08 (0.02 to 68.22) | 0.97 | 0.64 (0.77) | 1.91 (0.42 to 8.65) | 0.40 |
| Keto IM | 0.90 (1.78) | 2.46 (0.08 to 80.6) | 0.61 | −0.30 (1.10) | 0.74 (0.09 to 6.37) | 0.78 |

TABLE 11

Predicted marginal means from derived from the models above for an animal with behavioural count at baseline set to the average observed for that trait.

| | Time | | | | | | | | |
|---|---|---|---|---|---|---|---|---|---|
| | 2 hr | | | 4 hr | | | 8 hrs | | |
| Behaviour | Placebo | KteoTrans | KetoIM | Placebo | KteoTrans | KetoIM | Placebo | KteoTrans | KetoIM |
| Head rub | 6.17 | 6.00 | 2.85 | 0.98 | 0.95 | 0.45 | 0.16 | 0.16 | 0.08 |
| Head shake | 4.44 | 1.32 | 3.94 | 3.21 | 0.70 | 3.42 | 1.38 | 0.47 | 1.20 |

TABLE 11-continued

Predicted marginal means from derived from the models above for an animal with behavioural count at baseline set to the average observed for that trait.

| | | | | | | | | | |
|---|---|---|---|---|---|---|---|---|---|
| Ear flick | 2.02 | 1.88 | 1.83 | 1.94 | 1.97 | 2.09 | 1.41 | 1.34 | 1.26 |
| Tail wag | 1.29 | 1.04 | 1.19 | 0.89 | 0.92 | 0.95 | 0.54 | 0.69 | 0.63 |
| Laying | 4.60 | 2.87 | 2.91 | 2.47 | 2.18 | 2.22 | 1.33 | 1.66 | 1.69 |
| Neck extended | 0.98 | 0.91 | 1.03 | 0.55 | 0.76 | 1.31 | 0.43 | 0.46 | 0.69 |
| Grooming | 0.19 | 0.21 | 0.34 | 0.36 | 0.42 | 0.50 | 0.70 | 0.84 | 0.73 |
| Ruminating | 0.00 | 0.00 | 0.00 | 0.00 | 0.00 | 0.00 | 0.00 | 0.00 | 0.00 |

| | Time | | | | | |
|---|---|---|---|---|---|---|
| | 24 hr | | | 48 hr | | |
| Behaviour | Placebo | KteoTrans | KetoIM | Placebo | KteoTrans | KetoIM |
| Head rub | 0.00 | 0.00 | 0.00 | 0.84 | 0.82 | 0.39 |
| Head shake | 0.46 | 0.42 | 1.03 | 0.31 | 7.09 | 0.17 |
| Ear flick | 0.36 | 0.49 | 0.43 | 0.53 | 0.52 | 0.50 |
| Tail wag | 0.32 | 0.40 | 0.30 | 0.40 | 0.37 | 0.42 |
| Laying | 0.72 | 1.27 | 1.29 | 0.39 | 0.96 | 0.98 |
| Neck extended | 0.31 | 0.38 | 0.69 | 0.31 | 0.42 | 0.69 |
| Grooming | 1.36 | 1.68 | 1.07 | 2.63 | 3.39 | 1.56 |
| Ruminating | 0.02 | 0.02 | 0.02 | 0.18 | 0.15 | 0.15 |

Proteomic Assessment of Pain and Inflammation

Currently, data collection to create an expanded cattle plasma spectral library is in progress. Plasma samples from a wide range of animals (age, breed/species and health conditions) are being interrogated in order to identify as many plasma proteins as possible. Spectral library construction is an inevitable component of SWATH-MS analysis. This analysis uses information contain in a library to analyse the acquired fragment ion maps to identify and quantify the targeted peptides because all the information about fragment ion signals, their intensities and chromatographic concurrence of targeted peptide can be access from this library. If the targeted peptide is not present in the spectral library then it cannot be identified and quantified in SWATH-MS analysis of samples.

We have processed eight plasma samples from adult cattle suffering with different pathological conditions. Sample preparation was done using in solution digestion method. Desalting was performed using stage tips. After sample preparation, mass spectrometer analysis was conducted using LC-MS/MS technique on ABSciex platform. Data generated through mass spectrometer were analysed using ProteinPilot search engine against bovine protein database. Data were analysed at 1% global FDR to eliminate falsely discovered proteins. We also removed proteins with very low unused score and very low peptide number to avoid false positive results.

Currently, approximately 165 proteins, including immunoglobulins, have been identified from all of these samples. Table 1 shows proteins of interest that include acute phase proteins, oxidative stress marker and few highly abundant cytokines. This list will be expanded further using additional protein separation techniques. The list will be benchmarked to plasma protein spectral library published from human proteins.

TABLE 12

Potential Pain Biomarkers found in first few plasma sample analysis

| No | Name of Protein | Function of Protein |
|---|---|---|
| 1 | Alpha-1 acid glycoprotein | APP; anti-inflammatory properties, immune system modulation |
| 2 | Alpha-2-macroglobulin | APP; protease inhibition and clearance, inflammatory regulation |
| 3 | Alpha-2-macroglobulin variant 20 | |
| 4 | Alpha-2-macroglobulin variant 4 | |
| 5 | Alpha-2-macroglobulin variant 5 | |
| 6 | Apolipoprotein A-I | APP; reverse cholesterol transport, anti-inflammatory and anti-coagulant activities |
| 7 | Apolipoprotein A-II | |
| 8 | Apolipoprotein C-III | |
| 9 | Ceruloplasmin (ferroxidase) | APP; iron oxidation, free radical scavenging |
| 10 | Chain D, The Three-Dimensional Structure Of Bovine Platelet Factor 4 At 3.0 Angstroms Resolution | Cytokine; Neutralizes the anticoagulant effect of heparin, chemotactic for neutrophils and monocytes. Inhibits endothelial cell proliferation. |
| 11 | C-reactive protein precursor | APP; It regulate the immune system during the early stage of an infection, plays a role in destroying infectious agents, minimizing tissue damage, and facilitating tissue repair and regeneration. |

TABLE 12-continued

Potential Pain Biomarkers found in first few plasma sample analysis

| No | Name of Protein | Function of Protein |
|---|---|---|
| 12 | Fibrinogen beta chain | |
| 13 | Fibrinogen, alpha polypeptide precursor | APP; involved in blood coagulation, cellular and matrix interactions, endothelial cell proliferation, inflammatory response, angiogenesis, neoplasia. |
| 14 | Haptoglobin | APP; haemoglobin binding protein, iron elimination control, anti-oxidant/anti-inflammatory role, immunomodulation. |
| 15 | Lactoferrin | APP; iron-binding glycoprotein, anti-microbial, anti-inflammatory, anti- cancer activities, immune system modulation. |
| 16 | Lipopolysaccharide binding protein | APP; innate immune response, Pro-inflammatory activity in high concentration and anti-inflammatory activity in low concentration. |
| 17 | Paraoxonase 1 | Enzyme having antioxidant effect. It has a protective effect against oxidation of lipoproteins. |
| 18 | Plasminogen | APP; Anti-coagulant properties by fibrinolysis, cell migration enhancer, inflammatory response regulation. |
| 19 | Plasminogen precursor | |
| 20 | Regakine-1 precursor | Cytokine; Chemotactic activity for neutrophils and lymphocytes. Binds to heparin. |
| 21 | Serum amyloid A | APP; Immunomodulation, binding to cholesterol and opsonisation. |
| 22 | Transferrin | APP; Iron binding blood plasma glycoprotein. |

Cytokines and neuropeptides are very low abundance proteins and are not likely to be in concentrations detectable in plasma by SWATH-MS analysis. However, multiple reaction monitoring (MRM) is the technique that allow to detect proteins with very low concentration, such as cytokines. With SWATH-MS, few highly abundant bovine cytokines like Regakine 1, Bovine platelet factor-4 (PF4/CXCL4) and Hemofiltrate CC Chemokine-1 (HCC-1/CCL14) can be detected and we have already detected Regakine 1 and platelet factor 4(PF4/CXCL4) in cattle sample analysis for the spectral library. Regakine 1 is a naturally abundant cytokine in bovine serum (100 ng/mL).

Figure 21:
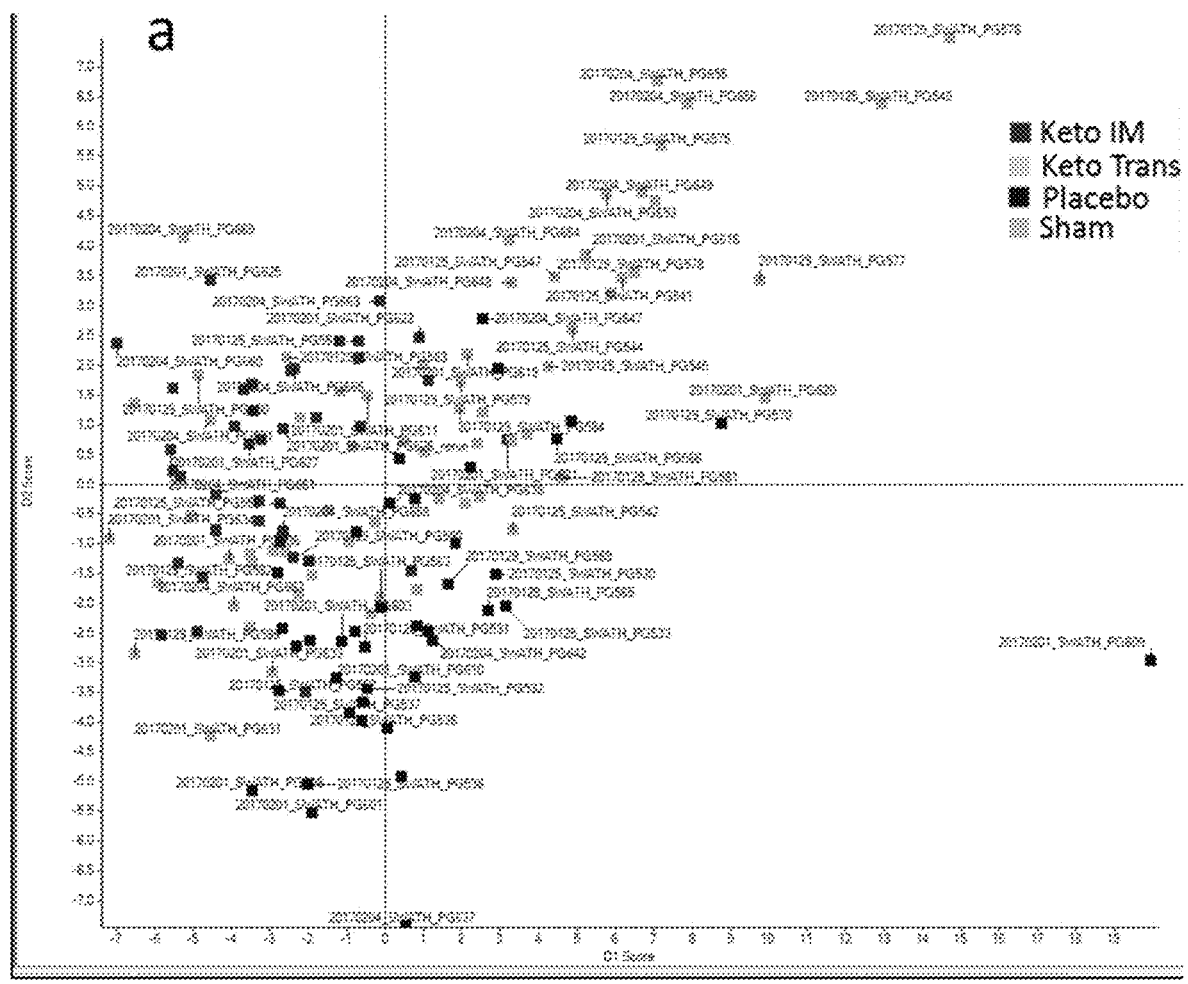
FIG. 21: Analysis of proteins measured in plasma during the clinical study.
Figure 21:
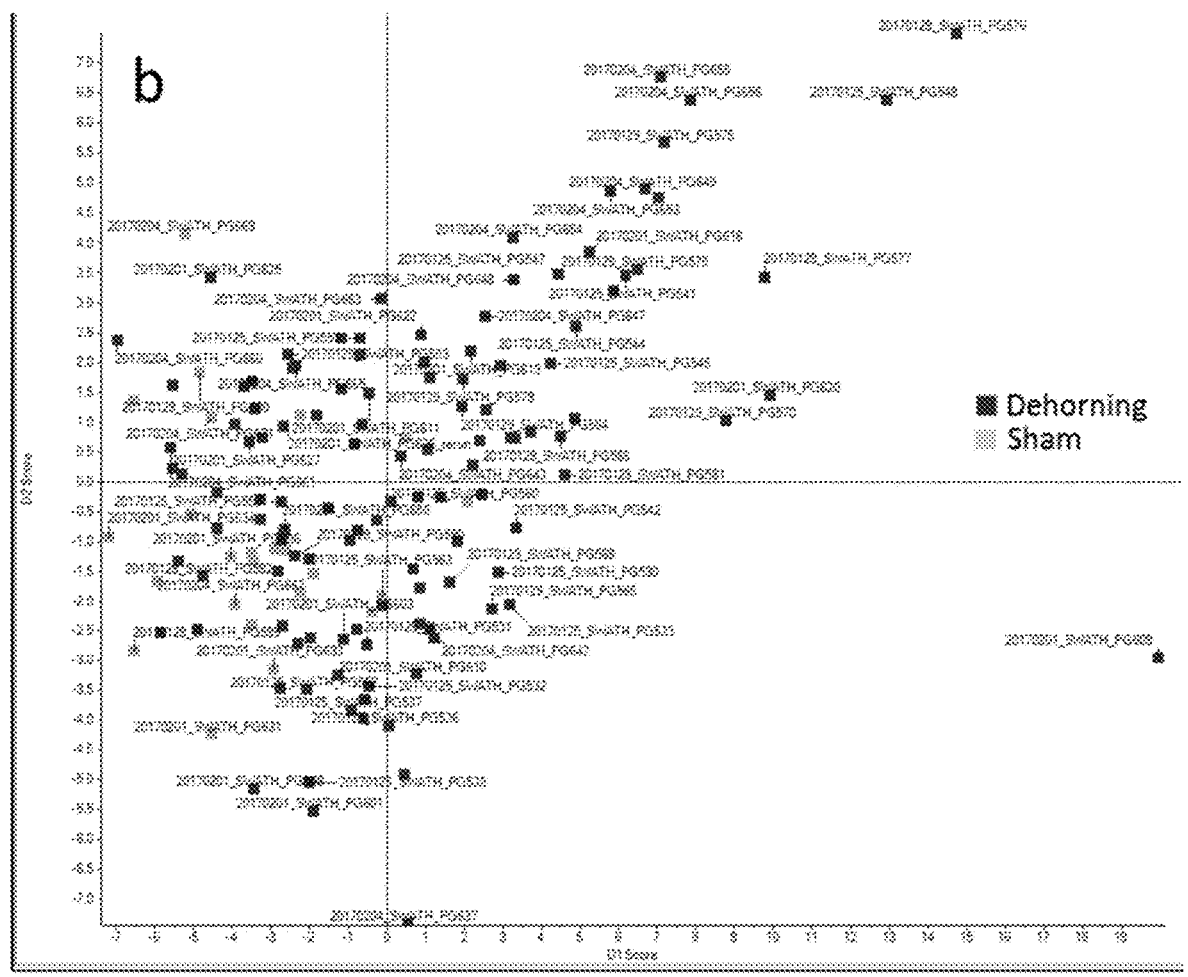
Figure 21:
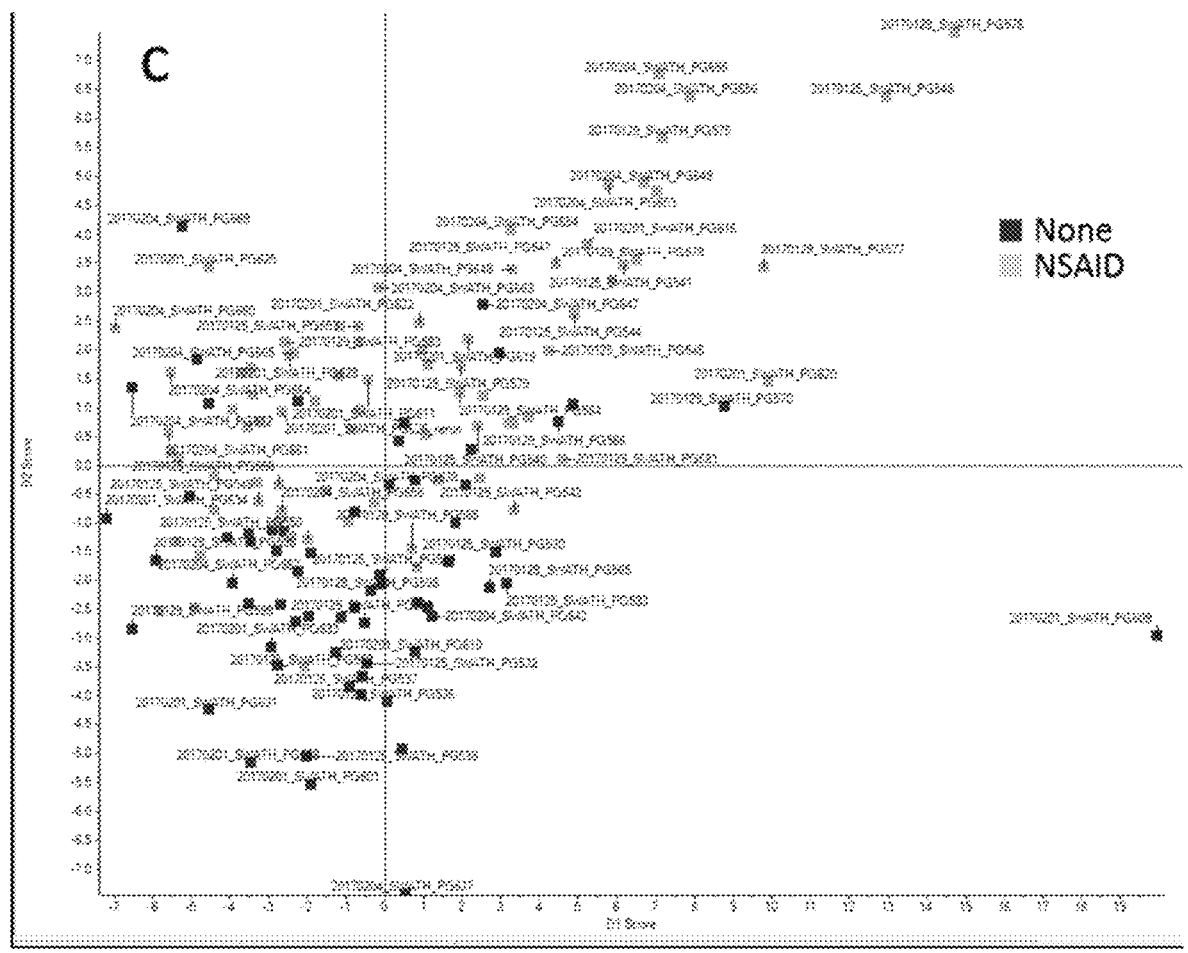

A preliminary analysis of the proteins identified was undertaken using Principal Component Analysis (PCA) within the MarkerView software package (FIG. 21). This analysis looked at a comparison of groups for all time points (FIG. 21a), a comparison of dehoming vs. sham (FIG. 21b) and a comparison of treatment vs. placebo (FIG. 21c). Although further analysis and validation is required, there appears to be clear effects of treatment and, possibly, a better outcome (efficacy) with the transdermal formulation compared to IM.

TABLE 13

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 50% | KET451 | KET31 | Ethanol | 70% EtOH | None | 0 | Menthol | 50 | NA | 0.5 | 1 | 0.01 | 0.03 |
| Ketoprofen | 50% | KET452 | KET31 | Ethanol | 70% EtOH | None | 0 | Menthol | 50 | NA | 2 | 1 | 0.005 | 0.015 |
| Ketoprofen | 50% | KET453 | KET31 | Ethanol | 70% EtOH | None | 0 | Menthol | 50 | NA | 4 | 1 | 0.01 | 0.03 |
| Ketoprofen | 50% | KET454 | KET31 | Ethanol | 70% EtOH | None | 0 | Menthol | 50 | NA | 6 | 1 | 0.005 | 0.015 |
| Ketoprofen | 50% | KET455 | KET31 | Ethanol | 70% EtOH | None | 0 | Menthol | 50 | NA | 8 | 1 | 0.005 | 0.015 |
| Ketoprofen | 50% | KET456 | KET31 | Ethanol | 70% EtOH | None | 0 | Menthol | 50 | NA | 0.5 | 2 | 0.006 | 0.018 |
| Ketoprofen | 50% | KET457 | KET31 | Ethanol | 70% EtOH | None | 0 | Menthol | 50 | NA | 2 | 2 | 0.006 | 0.018 |
| Ketoprofen | 50% | KET458 | KET31 | Ethanol | 70% EtOH | None | 0 | Menthol | 50 | NA | 4 | 2 | 0.004 | 0.012 |
| Ketoprofen | 50% | KET459 | KET31 | Ethanol | 70% EtOH | None | 0 | Menthol | 50 | NA | 6 | 2 | 0.005 | 0.015 |
| Ketoprofen | 50% | KET460 | KET31 | Ethanol | 70% EtOH | None | 0 | Menthol | 50 | NA | 8 | 2 | 0.003 | 0.009 |
| Ketoprofen | 50% | KET461 | KET31 | Ethanol | 70% EtOH | None | 0 | Menthol | 50 | NA | 0.5 | 3 | 0.006 | 0.018 |
| Ketoprofen | 50% | KET462 | KET31 | Ethanol | 70% EtOH | None | 0 | Menthol | 50 | NA | 2 | 3 | 0.006 | 0.018 |
| Ketoprofen | 50% | KET463 | KET31 | Ethanol | 70% EtOH | None | 0 | Menthol | 50 | NA | 4 | 3 | 0.003 | 0.009 |
| Ketoprofen | 50% | KET464 | KET31 | Ethanol | 70% EtOH | None | 0 | Menthol | 50 | NA | 6 | 3 | 0.003 | 0.009 |
| Ketoprofen | 50% | KET465 | KET31 | Ethanol | 70% EtOH | None | 0 | Menthol | 50 | NA | 8 | 3 | 0.004 | 0.012 |
| Ketoprofen | 50% | KET466 | KET32 | Isopropanol | 70% IPN | None | 0 | Menthol | 50 | NA | 0.5 | 1 | 0.252 | 0.756 |
| Ketoprofen | 50% | KET467 | KET32 | Isopropanol | 70% IPN | None | 0 | Menthol | 50 | NA | 2 | 1 | 0.005 | 0.015 |
| Ketoprofen | 50% | KET468 | KET32 | Isopropanol | 70% IPN | None | 0 | Menthol | 50 | NA | 4 | 1 | 0.005 | 0.015 |
| Ketoprofen | 50% | KET469 | KET32 | Isopropanol | 70% IPN | None | 0 | Menthol | 50 | NA | 6 | 1 | 0.006 | 0.018 |
| Ketoprofen | 50% | KET470 | KET32 | Isopropanol | 70% IPN | None | 0 | Menthol | 50 | NA | 8 | 1 | 0.008 | 0.024 |
| Ketoprofen | 50% | KET471 | KET32 | Isopropanol | 70% IPN | None | 0 | Menthol | 50 | NA | 0.5 | 2 | 0.004 | 0.012 |
| Ketoprofen | 50% | KET472 | KET32 | Isopropanol | 70% IPN | None | 0 | Menthol | 50 | NA | 2 | 2 | 0.017 | 0.051 |
| Ketoprofen | 50% | KET473 | KET32 | Isopropanol | 70% IPN | None | 0 | Menthol | 50 | NA | 4 | 2 | 0.004 | 0.012 |
| Ketoprofen | 50% | KET474 | KET32 | Isopropanol | 70% IPN | None | 0 | Menthol | 50 | NA | 6 | 2 | 0.004 | 0.012 |
| Ketoprofen | 50% | KET475 | KET32 | Isopropanol | 70% IPN | None | 0 | Menthol | 50 | NA | 8 | 2 | 0.004 | 0.012 |
| Ketoprofen | 50% | KET476 | KET32 | Isopropanol | 70% IPN | None | 0 | Menthol | 50 | NA | 0.5 | 3 | 0.025 | 0.075 |
| Ketoprofen | 50% | KET477 | KET32 | Isopropanol | 70% IPN | None | 0 | Menthol | 50 | NA | 2 | 3 | 0.007 | 0.021 |
| Ketoprofen | 50% | KET478 | KET32 | Isopropanol | 70% IPN | None | 0 | Menthol | 50 | NA | 4 | 3 | 0.004 | 0.012 |
| Ketoprofen | 50% | KET479 | KET32 | Isopropanol | 70% IPN | None | 0 | Menthol | 50 | NA | 6 | 3 | 0.005 | 0.015 |
| Ketoprofen | 50% | KET480 | KET32 | Isopropanol | 70% IPN | None | 0 | Menthol | 50 | NA | 8 | 3 | 0.003 | 0.009 |
| Flunixin | 50% | KET481 | KET33 | Ethanol | 70% EtOH | None | 0 | Menthol | 50 | NA | 0.5 | 1 | 0.005 | 0.015 |
| Flunixin | 50% | KET482 | KET33 | Ethanol | 70% EtOH | None | 0 | Menthol | 50 | NA | 2 | 1 | — | 0 |
| Flunixin | 50% | KET483 | KET33 | Ethanol | 70% EtOH | None | 0 | Menthol | 50 | NA | 4 | 1 | — | 0 |
| Flunixin | 50% | KET484 | KET33 | Ethanol | 70% EtOH | None | 0 | Menthol | 50 | NA | 6 | 1 | — | 0 |
| Flunixin | 50% | KET485 | KET33 | Ethanol | 70% EtOH | None | 0 | Menthol | 50 | NA | 8 | 1 | — | 0 |
| Flunixin | 50% | KET486 | KET33 | Ethanol | 70% EtOH | None | 0 | Menthol | 50 | NA | 0.5 | 2 | — | 0 |
| Flunixin | 50% | KET487 | KET33 | Ethanol | 70% EtOH | None | 0 | Menthol | 50 | NA | 2 | 2 | — | 0 |
| Flunixin | 50% | KET488 | KET33 | Ethanol | 70% EtOH | None | 0 | Menthol | 50 | NA | 4 | 2 | — | 0 |
| Flunixin | 50% | KET489 | KET33 | Ethanol | 70% EtOH | None | 0 | Menthol | 50 | NA | 6 | 2 | — | 0 |
| Flunixin | 50% | KET490 | KET33 | Ethanol | 70% EtOH | None | 0 | Menthol | 50 | NA | 8 | 2 | — | 0 |
| Flunixin | 50% | KET491 | KET33 | Ethanol | 70% EtOH | None | 0 | Menthol | 50 | NA | 0.5 | 3 | — | 0 |
| Flunixin | 50% | KET492 | KET33 | Ethanol | 70% EtOH | None | 0 | Menthol | 50 | NA | 2 | 3 | — | 0 |
| Flunixin | 50% | KET493 | KET33 | Ethanol | 70% EtOH | None | 0 | Menthol | 50 | NA | 4 | 3 | — | 0 |
| Flunixin | 50% | KET494 | KET33 | Ethanol | 70% EtOH | None | 0 | Menthol | 50 | NA | 6 | 3 | — | 0 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Flunixin | 50% | KET495 | KET33 | Ethanol | 70% EtOH | None | 0 | Menthol | 50 | NA | 8 | 3 | — | 0 |
| Tolfenamic acid | 50% | KET496 | KET34 | Ethanol | 70% EtOH | None | 0 | Menthol | 50 | NA | 0.5 | 1 | — | 0 |
| Tolfenamic acid | 50% | KET497 | KET34 | Ethanol | 70% EtOH | None | 0 | Menthol | 50 | NA | 2 | 1 | — | 0 |
| Tolfenamic acid | 50% | KET498 | KET34 | Ethanol | 70% EtOH | None | 0 | Menthol | 50 | NA | 4 | 1 | — | 0 |
| Tolfenamic acid | 50% | KET499 | KET34 | Ethanol | 70% EtOH | None | 0 | Menthol | 50 | NA | 6 | 1 | — | 0 |
| Tolfenamic acid | 50% | KET500 | KET34 | Ethanol | 70% EtOH | None | 0 | Menthol | 50 | NA | 8 | 1 | — | 0 |
| Tolfenamic acid | 50% | KET501 | KET34 | Ethanol | 70% EtOH | None | 0 | Menthol | 50 | NA | 0.5 | 2 | — | 0 |
| Tolfenamic acid | 50% | KET502 | KET34 | Ethanol | 70% EtOH | None | 0 | Menthol | 50 | NA | 2 | 2 | — | 0 |
| Tolfenamic acid | 50% | KET503 | KET34 | Ethanol | 70% EtOH | None | 0 | Menthol | 50 | NA | 4 | 2 | — | 0 |
| Tolfenamic acid | 50% | KET504 | KET34 | Ethanol | 70% EtOH | None | 0 | Menthol | 50 | NA | 6 | 2 | — | 0 |
| Tolfenamic acid | 50% | KET505 | KET34 | Ethanol | 70% EtOH | None | 0 | Menthol | 50 | NA | 8 | 2 | — | 0 |
| Tolfenamic acid | 50% | KET506 | KET34 | Ethanol | 70% EtOH | None | 0 | Menthol | 50 | NA | 0.5 | 3 | — | 0 |
| Tolfenamic acid | 50% | KET507 | KET34 | Ethanol | 70% EtOH | None | 0 | Menthol | 50 | NA | 2 | 3 | — | 0 |
| Tolfenamic acid | 50% | KET508 | KET34 | Ethanol | 70% EtOH | None | 0 | Menthol | 50 | NA | 4 | 3 | — | 0 |
| Tolfenamic acid | 50% | KET509 | KET34 | Ethanol | 70% EtOH | None | 0 | Menthol | 50 | NA | 6 | 3 | 0.004 | 0.012 |
| Tolfenamic acid | 50% | KET510 | KET34 | Ethanol | 70% EtOH | None | 0 | Menthol | 50 | NA | 8 | 3 | — | 0 |
| Ketoprofen | 10% | KET511 | KET35 | Isopropanol | 70% IPN | None | 0 | None | 0 | NA | 0.5 | 1 | 0.011 | 0.033 |
| Ketoprofen | 10% | KET512 | KET35 | Isopropanol | 70% IPN | None | 0 | None | 0 | NA | 2 | 1 | 0.005 | 0.015 |
| Ketoprofen | 10% | KET513 | KET35 | Isopropanol | 70% IPN | None | 0 | None | 0 | NA | 4 | 1 | 0.008 | 0.024 |
| Ketoprofen | 10% | KET514 | KET35 | Isopropanol | 70% IPN | None | 0 | None | 0 | NA | 6 | 1 | 0.022 | 0.066 |
| Ketoprofen | 10% | KET515 | KET35 | Isopropanol | 70% IPN | None | 0 | None | 0 | NA | 8 | 1 | 0.066 | 0.198 |
| Ketoprofen | 10% | KET516 | KET35 | Isopropanol | 70% IPN | None | 0 | None | 0 | NA | 0.5 | 2 | 0.005 | 0.015 |
| Ketoprofen | 10% | KET517 | KET35 | Isopropanol | 70% IPN | None | 0 | None | 0 | NA | 2 | 2 | 0.016 | 0.048 |
| Ketoprofen | 10% | KET518 | KET35 | Isopropanol | 70% IPN | None | 0 | None | 0 | NA | 4 | 2 | 0.005 | 0.015 |
| Ketoprofen | 10% | KET519 | KET35 | Isopropanol | 70% IPN | None | 0 | None | 0 | NA | 6 | 2 | 0.04 | 0.12 |
| Ketoprofen | 10% | KET520 | KET35 | Isopropanol | 70% IPN | None | 0 | None | 0 | NA | 8 | 2 | 0.125 | 0.375 |
| Ketoprofen | 10% | KET521 | KET35 | Isopropanol | 70% IPN | None | 0 | None | 0 | NA | 0.5 | 3 | 0.006 | 0.018 |
| Ketoprofen | 10% | KET522 | KET35 | Isopropanol | 70% IPN | None | 0 | None | 0 | NA | 2 | 3 | 0.008 | 0.024 |
| Ketoprofen | 10% | KET523 | KET35 | Isopropanol | 70% IPN | None | 0 | None | 0 | NA | 4 | 3 | 0.035 | 0.105 |
| Ketoprofen | 10% | KET524 | KET35 | Isopropanol | 70% IPN | None | 0 | None | 0 | NA | 6 | 3 | 0.141 | 0.423 |
| Ketoprofen | 10% | KET525 | KET35 | Isopropanol | 70% IPN | None | 0 | None | 0 | NA | 8 | 3 | 0.415 | 1.245 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 50% | KET526 | KET36 | Ethanol | 50% EthOH | None | 0 | Menthol | 50 | NA | 0.5 | 1 | 0.01 | 0.03 |
| Ketoprofen | 50% | KET527 | KET36 | Ethanol | 50% EthOH | None | 0 | Menthol | 50 | NA | 2 | 1 | 0.008 | 0.024 |
| Ketoprofen | 50% | KET528 | KET36 | Ethanol | 50% EthOH | None | 0 | Menthol | 50 | NA | 4 | 1 | 0.01 | 0.03 |
| Ketoprofen | 50% | KET529 | KET36 | Ethanol | 50% EthOH | None | 0 | Menthol | 50 | NA | 6 | 1 | 0.009 | 0.027 |
| Ketoprofen | 50% | KET530 | KET36 | Ethanol | 50% EthOH | None | 0 | Menthol | 50 | NA | 8 | 1 | 0.007 | 0.021 |
| Ketoprofen | 50% | KET531 | KET36 | Ethanol | 50% EthOH | None | 0 | Menthol | 50 | NA | 0.5 | 2 | 0.011 | 0.033 |
| Ketoprofen | 50% | KET532 | KET36 | Ethanol | 50% EthOH | None | 0 | Menthol | 50 | NA | 2 | 2 | 0.006 | 0.018 |
| Ketoprofen | 50% | KET533 | KET36 | Ethanol | 50% EthOH | None | 0 | Menthol | 50 | NA | 4 | 2 | 0.006 | 0.018 |
| Ketoprofen | 50% | KET534 | KET36 | Ethanol | 50% EthOH | None | 0 | Menthol | 50 | NA | 6 | 2 | 0.008 | 0.024 |
| Ketoprofen | 50% | KET535 | KET36 | Ethanol | 50% EthOH | None | 0 | Menthol | 50 | NA | 8 | 2 | 0.006 | 0.018 |
| Ketoprofen | 50% | KET536 | KET36 | Ethanol | 50% EthOH | None | 0 | Menthol | 50 | NA | 0.5 | 3 | 0.007 | 0.021 |
| Ketoprofen | 50% | KET537 | KET36 | Ethanol | 50% EthOH | None | 0 | Menthol | 50 | NA | 2 | 3 | 0.007 | 0.021 |
| Ketoprofen | 50% | KET538 | KET36 | Ethanol | 50% EthOH | None | 0 | Menthol | 50 | NA | 4 | 3 | 0.011 | 0.033 |
| Ketoprofen | 50% | KET539 | KET36 | Ethanol | 50% EthOH | None | 0 | Menthol | 50 | NA | 6 | 3 | 0.023 | 0.069 |
| Ketoprofen | 50% | KET540 | KET36 | Ethanol | 50% EthOH | None | 0 | Menthol | 50 | NA | 8 | 3 | 0.128 | 0.384 |
| Ketoprofen | 50% | KET541 | KET37 | Ethanol | 50% IPN | None | 0 | Menthol | 50 | NA | 0.5 | 1 | 0.112 | 0.336 |
| Ketoprofen | 50% | KET542 | KET37 | Ethanol | 50% IPN | None | 0 | Menthol | 50 | NA | 2 | 1 | 0.029 | 0.087 |
| Ketoprofen | 50% | KET543 | KET37 | Ethanol | 50% IPN | None | 0 | Menthol | 50 | NA | 4 | 1 | 0.009 | 0.027 |
| Ketoprofen | 50% | KET544 | KET37 | Ethanol | 50% IPN | None | 0 | Menthol | 50 | NA | 6 | 1 | 0.01 | 0.03 |
| Ketoprofen | 50% | KET545 | KET37 | Ethanol | 50% IPN | None | 0 | Menthol | 50 | NA | 8 | 1 | 0.021 | 0.063 |
| Ketoprofen | 50% | KET546 | KET37 | Ethanol | 50% IPN | None | 0 | Menthol | 50 | NA | 0.5 | 2 | 0.009 | 0.027 |
| Ketoprofen | 50% | KET547 | KET37 | Ethanol | 50% IPN | None | 0 | Menthol | 50 | NA | 2 | 2 | 0.013 | 0.039 |
| Ketoprofen | 50% | KET548 | KET37 | Ethanol | 50% IPN | None | 0 | Menthol | 50 | NA | 4 | 2 | 0.061 | 0.183 |
| Ketoprofen | 50% | KET549 | KET37 | Ethanol | 50% IPN | None | 0 | Menthol | 50 | NA | 6 | 2 | 0.143 | 0.429 |
| Ketoprofen | 50% | KET550 | KET37 | Ethanol | 50% IPN | None | 0 | Menthol | 50 | NA | 8 | 2 | 0.236 | 0.708 |
| Ketoprofen | 50% | KET551 | KET37 | Ethanol | 50% IPN | None | 0 | Menthol | 50 | NA | 0.5 | 3 | 0.013 | 0.039 |
| Ketoprofen | 50% | KET552 | KET37 | Ethanol | 50% IPN | None | 0 | Menthol | 50 | NA | 2 | 3 | 0.005 | 0.015 |
| Ketoprofen | 50% | KET553 | KET37 | Ethanol | 50% IPN | None | 0 | Menthol | 50 | NA | 4 | 3 | 0.005 | 0.015 |
| Ketoprofen | 50% | KET554 | KET37 | Ethanol | 50% IPN | None | 0 | Menthol | 50 | NA | 6 | 3 | 0.007 | 0.021 |
| Ketoprofen | 50% | KET555 | KET37 | Ethanol | 50% IPN | None | 0 | Menthol | 50 | NA | 8 | 3 | 0.005 | 0.015 |
| Flunixin | 50% | KET556 | KET38 | Ethanol | 50% EthOH | None | 0 | Menthol | 50 | NA | 0.5 | 1 | — | 0 |
| Flunixin | 50% | KET557 | KET38 | Ethanol | 50% EthOH | None | 0 | Menthol | 50 | NA | 2 | 1 | — | 0 |
| Flunixin | 50% | KET558 | KET38 | Ethanol | 50% EthOH | None | 0 | Menthol | 50 | NA | 4 | 1 | — | 0 |
| Flunixin | 50% | KET559 | KET38 | Ethanol | 50% EthOH | None | 0 | Menthol | 50 | NA | 6 | 1 | — | 0 |
| Flunixin | 50% | KET560 | KET38 | Ethanol | 50% EthOH | None | 0 | Menthol | 50 | NA | 8 | 1 | — | 0 |
| Flunixin | 50% | KET561 | KET38 | Ethanol | 50% EthOH | None | 0 | Menthol | 50 | NA | 0.5 | 2 | — | 0 |
| Flunixin | 50% | KET562 | KET38 | Ethanol | 50% EthOH | None | 0 | Menthol | 50 | NA | 2 | 2 | — | 0 |
| Flunixin | 50% | KET563 | KET38 | Ethanol | 50% EthOH | None | 0 | Menthol | 50 | NA | 4 | 2 | — | 0 |
| Flunixin | 50% | KET564 | KET38 | Ethanol | 50% EthOH | None | 0 | Menthol | 50 | NA | 6 | 2 | — | 0 |
| Flunixin | 50% | KET565 | KET38 | Ethanol | 50% EthOH | None | 0 | Menthol | 50 | NA | 8 | 2 | — | 0 |
| Flunixin | 50% | KET566 | KET38 | Ethanol | 50% EthOH | None | 0 | Menthol | 50 | NA | 0.5 | 3 | — | 0 |
| Flunixin | 50% | KET567 | KET38 | Ethanol | 50% EthOH | None | 0 | Menthol | 50 | NA | 2 | 3 | — | 0 |
| Flunixin | 50% | KET568 | KET38 | Ethanol | 50% EthOH | None | 0 | Menthol | 50 | NA | 4 | 3 | — | 0 |
| Flunixin | 50% | KET569 | KET38 | Ethanol | 50% EthOH | None | 0 | Menthol | 50 | NA | 6 | 3 | — | 0 |
| Flunixin | 50% | KET570 | KET38 | Ethanol | 50% EthOH | None | 0 | Menthol | 50 | NA | 8 | 3 | — | 0 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Tolfenamic acid | 50% | KET571 | KET39 | Ethanol | 50% EtOH | None | 0 | Menthol | 50 | NA | 0.5 | 1 | — | 0 |
| Tolfenamic acid | 50% | KET572 | KET39 | Ethanol | 50% EtOH | None | 0 | Menthol | 50 | NA | 2 | 1 | — | 0 |
| Tolfenamic acid | 50% | KET573 | KET39 | Ethanol | 50% EtOH | None | 0 | Menthol | 50 | NA | 4 | 1 | 0.004 | 0.012 |
| Tolfenamic acid | 50% | KET574 | KET39 | Ethanol | 50% EtOH | None | 0 | Menthol | 50 | NA | 6 | 1 | — | 0 |
| Tolfenamic acid | 50% | KET575 | KET39 | Ethanol | 50% EtOH | None | 0 | Menthol | 50 | NA | 8 | 1 | — | 0 |
| Tolfenamic acid | 50% | KET576 | KET39 | Ethanol | 50% EtOH | None | 0 | Menthol | 50 | NA | 0.5 | 2 | 0.006 | 0.018 |
| Tolfenamic acid | 50% | KET577 | KET39 | Ethanol | 50% EtOH | None | 0 | Menthol | 50 | NA | 2 | 2 | — | 0 |
| Tolfenamic acid | 50% | KET578 | KET39 | Ethanol | 50% EtOH | None | 0 | Menthol | 50 | NA | 4 | 2 | — | 0 |
| Tolfenamic acid | 50% | KET579 | KET39 | Ethanol | 50% EtOH | None | 0 | Menthol | 50 | NA | 6 | 2 | — | 0 |
| Tolfenamic acid | 50% | KET580 | KET39 | Ethanol | 50% EtOH | None | 0 | Menthol | 50 | NA | 8 | 2 | — | 0 |
| Tolfenamic acid | 50% | KET581 | KET39 | Ethanol | 50% EtOH | None | 0 | Menthol | 50 | NA | 0.5 | 3 | — | 0 |
| Tolfenamic acid | 50% | KET582 | KET39 | Ethanol | 50% EtOH | None | 0 | Menthol | 50 | NA | 2 | 3 | 0.009 | 0.027 |
| Tolfenamic acid | 50% | KET583 | KET39 | Ethanol | 50% EtOH | None | 0 | Menthol | 50 | NA | 4 | 3 | — | 0 |
| Tolfenamic acid | 50% | KET584 | KET39 | Ethanol | 50% EtOH | None | 0 | Menthol | 50 | NA | 6 | 3 | — | 0 |
| Tolfenamic acid | 50% | KET585 | KET39 | Ethanol | 50% EtOH | None | 0 | Menthol | 50 | NA | 8 | 3 | — | 0 |
| Ketoprofen | 10% | KET586 | KET40 | Isopropanol | 50% IPN | None | 0 | None | 0 | NA | 0.5 | 1 | 0.014 | 0.042 |
| Ketoprofen | 10% | KET587 | KET40 | Isopropanol | 50% IPN | None | 0 | None | 0 | NA | 2 | 1 | 0.011 | 0.033 |
| Ketoprofen | 10% | KET588 | KET40 | Isopropanol | 50% IPN | None | 0 | None | 0 | NA | 4 | 1 | 0.009 | 0.027 |
| Ketoprofen | 10% | KET589 | KET40 | Isopropanol | 50% IPN | None | 0 | None | 0 | NA | 6 | 1 | 0.007 | 0.021 |
| Ketoprofen | 10% | KET590 | KET40 | Isopropanol | 50% IPN | None | 0 | None | 0 | NA | 8 | 1 | 0.008 | 0.024 |
| Ketoprofen | 10% | KET591 | KET40 | Isopropanol | 50% IPN | None | 0 | None | 0 | NA | 0.5 | 2 | 0.012 | 0.036 |
| Ketoprofen | 10% | KET592 | KET40 | Isopropanol | 50% IPN | None | 0 | None | 0 | NA | 2 | 2 | 0.005 | 0.015 |
| Ketoprofen | 10% | KET593 | KET40 | Isopropanol | 50% IPN | None | 0 | None | 0 | NA | 4 | 2 | 0.009 | 0.027 |
| Ketoprofen | 10% | KET594 | KET40 | Isopropanol | 50% IPN | None | 0 | None | 0 | NA | 6 | 2 | 0.007 | 0.021 |
| Ketoprofen | 10% | KET595 | KET40 | Isopropanol | 50% IPN | None | 0 | None | 0 | NA | 8 | 2 | 0.007 | 0.021 |
| Ketoprofen | 10% | KET596 | KET40 | Isopropanol | 50% IPN | None | 0 | None | 0 | NA | 0.5 | 3 | 0.02 | 0.06 |
| Ketoprofen | 10% | KET597 | KET40 | Isopropanol | 50% IPN | None | 0 | None | 0 | NA | 2 | 3 | 0.011 | 0.033 |
| Ketoprofen | 10% | KET598 | KET40 | Isopropanol | 50% IPN | None | 0 | None | 0 | NA | 4 | 3 | 0.021 | 0.063 |
| Ketoprofen | 10% | KET599 | KET40 | Isopropanol | 50% IPN | None | 0 | None | 0 | NA | 6 | 3 | 0.013 | 0.039 |
| Ketoprofen | 10% | KET600 | KET40 | Isopropanol | 50% IPN | None | 0 | None | 0 | NA | 8 | 3 | 0.013 | 0.039 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET601 | KET41 | Ethanol | 70% EtOH | Propylene glycol | 30% PPG | None | 0 | 0.1M citrate | 6 | 1 | 0.007 | 0.021 |
| Ketoprofen | 10% | KET602 | KET41 | Ethanol | 70% EtOH | Propylene glycol | 30% PPG | None | 0 | 0.1M citrate | 0.5 | 1 | 0.007 | 0.021 |
| Ketoprofen | 10% | KET603 | KET41 | Ethanol | 70% EtOH | Propylene glycol | 30% PPG | None | 0 | 0.1M citrate | 2 | 1 | 0.083 | 0.249 |
| Ketoprofen | 10% | KET604 | KET41 | Ethanol | 70% EtOH | Propylene glycol | 30% PPG | None | 0 | 0.1M citrate | 8 | 1 | 0.161 | 0.483 |
| Ketoprofen | 10% | KET605 | KET41 | Ethanol | 70% EtOH | Propylene glycol | 30% PPG | None | 0 | 0.1M citrate | 4 | 1 | 1.396 | 4.188 |
| Ketoprofen | 10% | KET606 | KET41 | Ethanol | 70% EtOH | Propylene glycol | 30% PPG | None | 0 | 0.1M citrate | 0.5 | 2 | 0.002 | 0.006 |
| Ketoprofen | 10% | KET607 | KET41 | Ethanol | 70% EtOH | Propylene glycol | 30% PPG | None | 0 | 0.1M citrate | 2 | 2 | 0.009 | 0.027 |
| Ketoprofen | 10% | KET608 | KET41 | Ethanol | 70% EtOH | Propylene glycol | 30% PPG | None | 0 | 0.1M citrate | 4 | 2 | 0.01 | 0.03 |
| Ketoprofen | 10% | KET609 | KET41 | Ethanol | 70% EtOH | Propylene glycol | 30% PPG | None | 0 | 0.1M citrate | 8 | 2 | 0.062 | 0.186 |
| Ketoprofen | 10% | KET610 | KET41 | Ethanol | 70% EtOH | Propylene glycol | 30% PPG | None | 0 | 0.1M citrate | 6 | 2 | 0.693 | 2.079 |
| Ketoprofen | 10% | KET611 | KET41 | Ethanol | 70% EtOH | Propylene glycol | 30% PPG | None | 0 | 0.1M citrate | 0.5 | 3 | 0.001 | 0.003 |
| Ketoprofen | 10% | KET612 | KET41 | Ethanol | 70% EtOH | Propylene glycol | 30% PPG | None | 0 | 0.1M citrate | 2 | 3 | 0.002 | 0.006 |
| Ketoprofen | 10% | KET613 | KET41 | Ethanol | 70% EtOH | Propylene glycol | 30% PPG | None | 0 | 0.1M citrate | 4 | 3 | 0.019 | 0.057 |
| Ketoprofen | 10% | KET614 | KET41 | Ethanol | 70% EtOH | Propylene glycol | 30% PPG | None | 0 | 0.1M citrate | 6 | 3 | 0.245 | 0.735 |
| Ketoprofen | 10% | KET615 | KET41 | Ethanol | 70% EtOH | Propylene glycol | 30% PPG | None | 0 | 0.1M citrate | 8 | 3 | 0.687 | 2.061 |
| Ketoprofen | 10% | KET616 | KET42 | Ethanol | 70% EtOH | Propylene glycol | 30% PPG | Menthol | 50 | 0.1M citrate | 2 | 1 | 0.001 | 0.003 |
| Ketoprofen | 10% | KET617 | KET42 | Ethanol | 70% EtOH | Propylene glycol | 30% PPG | Menthol | 50 | 0.1M citrate | 4 | 1 | 0.002 | 0.006 |
| Ketoprofen | 10% | KET618 | KET42 | Ethanol | 70% EtOH | Propylene glycol | 30% PPG | Menthol | 50 | 0.1M citrate | 6 | 1 | 0.324 | 0.972 |
| Ketoprofen | 10% | KET619 | KET42 | Ethanol | 70% EtOH | Propylene glycol | 30% PPG | Menthol | 50 | 0.1M citrate | 0.5 | 1 | 0.474 | 1.422 |
| Ketoprofen | 10% | KET620 | KET42 | Ethanol | 70% EtOH | Propylene glycol | 30% PPG | Menthol | 50 | 0.1M citrate | 8 | 1 | 0.816 | 2.448 |
| Ketoprofen | 10% | KET621 | KET42 | Ethanol | 70% EtOH | Propylene glycol | 30% PPG | Menthol | 50 | 0.1M citrate | 0.5 | 2 | 0.007 | 0.021 |
| Ketoprofen | 10% | KET622 | KET42 | Ethanol | 70% EtOH | Propylene glycol | 30% PPG | Menthol | 50 | 0.1M citrate | 8 | 2 | 0.016 | 0.048 |
| Ketoprofen | 10% | KET623 | KET42 | Ethanol | 70% EtOH | Propylene glycol | 30% PPG | Menthol | 50 | 0.1M citrate | 2 | 2 | 0.017 | 0.051 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET624 | KET42 | Ethanol | 70% EtOH | Propylene glycol | 30% PPG | Menthol | 50 | 0.1M citrate | 4 | 2 | 0.365 | 1.095 |
| Ketoprofen | 10% | KET625 | KET42 | Ethanol | 70% EtOH | Propylene glycol | 30% PPG | Menthol | 50 | 0.1M citrate | 6 | 2 | 1.459 | 4.377 |
| Ketoprofen | 10% | KET626 | KET42 | Ethanol | 70% EtOH | Propylene glycol | 30% PPG | Menthol | 50 | 0.1M citrate | 0.5 | 3 | 0.003 | 0.009 |
| Ketoprofen | 10% | KET627 | KET42 | Ethanol | 70% EtOH | Propylene glycol | 30% PPG | Menthol | 50 | 0.1M citrate | 8 | 3 | 0.009 | 0.027 |
| Ketoprofen | 10% | KET628 | KET42 | Ethanol | 70% EtOH | Propylene glycol | 30% PPG | Menthol | 50 | 0.1M citrate | 6 | 3 | 0.007 | 0.021 |
| Ketoprofen | 10% | KET629 | KET42 | Ethanol | 70% EtOH | Propylene glycol | 30% PPG | Menthol | 50 | 0.1M citrate | 2 | 3 | 0.378 | 1.134 |
| Ketoprofen | 10% | KET630 | KET42 | Ethanol | 70% EtOH | Propylene glycol | 30% PPG | Menthol | 50 | 0.1M citrate | 4 | 3 | 0.513 | 1.539 |
| Ketoprofen | 10% | KET631 | KET43 | Ethanol | 70% EtOH | Oleyl alcohol | 30% OA | None | 0 | 0.1M citrate | 0.5 | 1 | 0.002 | 0.006 |
| Ketoprofen | 10% | KET632 | KET43 | Ethanol | 70% EtOH | Oleyl alcohol | 30% OA | None | 0 | 0.1M citrate | 2 | 1 | 0.003 | 0.009 |
| Ketoprofen | 10% | KET633 | KET43 | Ethanol | 70% EtOH | Oleyl alcohol | 30% OA | None | 0 | 0.1M citrate | 4 | 1 | 0.027 | 0.081 |
| Ketoprofen | 10% | KET634 | KET43 | Ethanol | 70% EtOH | Oleyl alcohol | 30% OA | None | 0 | 0.1M citrate | 6 | 1 | 0.095 | 0.285 |
| Ketoprofen | 10% | KET635 | KET43 | Ethanol | 70% EtOH | Oleyl alcohol | 30% OA | None | 0 | 0.1M citrate | 8 | 1 | 1.075 | 3.225 |
| Ketoprofen | 10% | KET636 | KET43 | Ethanol | 70% EtOH | Oleyl alcohol | 30% OA | None | 0 | 0.1M citrate | 0.5 | 2 | 0.013 | 0.039 |
| Ketoprofen | 10% | KET637 | KET43 | Ethanol | 70% EtOH | Oleyl alcohol | 30% OA | None | 0 | 0.1M citrate | 2 | 2 | 0.013 | 0.039 |
| Ketoprofen | 10% | KET638 | KET43 | Ethanol | 70% EtOH | Oleyl alcohol | 30% OA | None | 0 | 0.1M citrate | 4 | 2 | 0.142 | 0.426 |
| Ketoprofen | 10% | KET639 | KET43 | Ethanol | 70% EtOH | Oleyl alcohol | 30% OA | None | 0 | 0.1M citrate | 6 | 2 | 0.411 | 1.233 |
| Ketoprofen | 10% | KET640 | KET43 | Ethanol | 70% EtOH | Oleyl alcohol | 30% OA | None | 0 | 0.1M citrate | 8 | 2 | 0.826 | 2.478 |
| Ketoprofen | 10% | KET641 | KET43 | Ethanol | 70% EtOH | Oleyl alcohol | 30% OA | None | 0 | 0.1M citrate | 0.5 | 3 | 0.003 | 0.009 |
| Ketoprofen | 10% | KET642 | KET43 | Ethanol | 70% EtOH | Oleyl alcohol | 30% OA | None | 0 | 0.1M citrate | 8 | 3 | 0.002 | 0.006 |
| Ketoprofen | 10% | KET643 | KET43 | Ethanol | 70% EtOH | Oleyl alcohol | 30% OA | None | 0 | 0.1M citrate | 2 | 3 | 0.379 | 1.137 |
| Ketoprofen | 10% | KET644 | KET43 | Ethanol | 70% EtOH | Oleyl alcohol | 30% OA | None | 0 | 0.1M citrate | 4 | 3 | 1.119 | 3.357 |
| Ketoprofen | 10% | KET645 | KET43 | Ethanol | 70% EtOH | Oleyl alcohol | 30% OA | None | 0 | 0.1M citrate | 6 | 3 | 1.132 | 3.396 |
| Ketoprofen | 10% | KET646 | KET44 | None | None | Superfine Arlasolve | 100% SRArl | | | 0.1M citrate | 0.5 | 1 | 0.008 | 0.024 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET647 | KET44 | None | None | Superfine Arlasolve | 100% SRArl | | 0 | 0.1M citrate | 2 | 1 | 0.003 | 0.009 |
| Ketoprofen | 10% | KET648 | KET44 | None | None | Superfine Arlasolve | 100% SRArl | | 0 | 0.1M citrate | 4 | 1 | 0.012 | 0.036 |
| Ketoprofen | 10% | KET649 | KET44 | None | None | Superfine Arlasolve | 100% SRArl | | 0 | 0.1M citrate | 6 | 1 | 0.015 | 0.045 |
| Ketoprofen | 10% | KET650 | KET44 | None | None | Superfine Arlasolve | 100% SRArl | | 0 | 0.1M citrate | 8 | 1 | 0.015 | 0.045 |
| Ketoprofen | 10% | KET651 | KET44 | None | None | Superfine Arlasolve | 100% SRArl | | 0 | 0.1M citrate | 0.5 | 2 | 0.006 | 0.018 |
| Ketoprofen | 10% | KET652 | KET44 | None | None | Superfine Arlasolve | 100% SRArl | | 0 | 0.1M citrate | 2 | 2 | 0.019 | 0.057 |
| Ketoprofen | 10% | KET653 | KET44 | None | None | Superfine Arlasolve | 100% SRArl | | 0 | 0.1M citrate | 4 | 2 | 0.009 | 0.027 |
| Ketoprofen | 10% | KET654 | KET44 | None | None | Superfine Arlasolve | 100% SRArl | | 0 | 0.1M citrate | 6 | 2 | 0.02 | 0.06 |
| Ketoprofen | 10% | KET655 | KET44 | None | None | Superfine Arlasolve | 100% SRArl | | 0 | 0.1M citrate | 8 | 2 | 0.028 | 0.084 |
| Ketoprofen | 10% | KET656 | KET44 | None | None | Superfine Arlasolve | 100% SRArl | | 0 | 0.1M citrate | 8 | 3 | 0.005 | 0.015 |
| Ketoprofen | 10% | KET657 | KET44 | None | None | Superfine Arlasolve | 100% SRArl | | 0 | 0.1M citrate | 6 | 3 | 0.01 | 0.03 |
| Ketoprofen | 10% | KET658 | KET44 | None | None | Superfine Arlasolve | 100% SRArl | | 0 | 0.1M citrate | 4 | 3 | 0.005 | 0.015 |
| Ketoprofen | 10% | KET659 | KET44 | None | None | Superfine Arlasolve | 100% SRArl | | 0 | 0.1M citrate | 2 | 3 | 0.011 | 0.033 |
| Ketoprofen | 10% | KET660 | KET44 | None | None | Superfine Arlasolve | 100% SRArl | | 0 | 0.1M citrate | 0.5 | 3 | 0.002 | 0.006 |
| Ketoprofen | 10% | KET661 | KET44 | None | None | Superfine Arlasolve | 100% SRArl | | 0 | 0.1M citrate | 8 | 1 | 0.009 | 0.027 |
| Ketoprofen | 10% | KET662 | KET45 | None | None | Crodamol STS-LQ(MH) | 100% Crodamol | | 0 | 0.1M citrate | 6 | 1 | 0.006 | 0.018 |
| Ketoprofen | 10% | KET663 | KET45 | None | None | Crodamol STS-LQ(MH) | 100% Crodamol | | 0 | 0.1M citrate | 0.5 | 1 | 0.025 | 0.075 |
| Ketoprofen | 10% | KET664 | KET45 | None | None | Crodamol STS-LQ(MH) | 100% Crodamol | | 0 | 0.1M citrate | 4 | 1 | 0.052 | 0.156 |
| Ketoprofen | 10% | KET665 | KET45 | None | None | Crodamol STS-LQ(MH) | 100% Crodamol | | 0 | 0.1M citrate | 2 | 1 | 1.017 | 3.051 |
| Ketoprofen | 10% | KET666 | KET45 | None | None | Crodamol STS-LQ(MH) | 100% Crodamol | | 0 | 0.1M citrate | 4 | 2 | 0.024 | 0.072 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/EVAP | sample time (hrs) | Replicate | analysis conc | Concentration (µg/mL) |
|---|---|---|---|---|---|---|---|---|---|---|---|---|---|---|
| Ketoprofen | 10% | KET667 | KET45 | None | None | Crodamol STS-LQ(MH) | 100% Crodamol | | 0 | 0.1M citrate | 6 | 2 | 0.026 | 0.078 |
| Ketoprofen | 10% | KET668 | KET45 | None | None | Crodamol STS-LQ(MH) | 100% Crodamol | | 0 | 0.1M citrate | 0.5 | 2 | 0.645 | 1.935 |
| Ketoprofen | 10% | KET669 | KET45 | None | None | Crodamol STS-LQ(MH) | 100% Crodamol | | 0 | 0.1M citrate | 2 | 2 | 0.54 | 1.62 |
| Ketoprofen | 10% | KET670 | KET45 | None | None | Crodamol STS-LQ(MH) | 100% Crodamol | | 0 | 0.1M citrate | 8 | 2 | 0.645 | 1.935 |
| Ketoprofen | 10% | KET671 | KET45 | None | None | Crodamol STS-LQ(MH) | 100% Crodamol | | 0 | 0.1M citrate | 2 | 3 | 0.012 | 0.036 |
| Ketoprofen | 10% | KET672 | KET45 | None | None | Crodamol STS-LQ(MH) | 100% Crodamol | | 0 | 0.1M citrate | 4 | 3 | 0.01 | 0.03 |
| Ketoprofen | 10% | KET673 | KET45 | None | None | Crodamol STS-LQ(MH) | 100% Crodamol | | 0 | 0.1M citrate | 6 | 3 | 0.053 | 0.159 |
| Ketoprofen | 10% | KET674 | KET45 | None | None | Crodamol STS-LQ(MH) | 100% Crodamol | | 0 | 0.1M citrate | 8 | 3 | 0.179 | 0.537 |
| Ketoprofen | 10% | KET675 | KET45 | None | None | Crodamol STS-LQ(MH) | 100% Crodamol | | 0 | 0.1M citrate | 0.5 | 3 | 0.213 | 0.639 |
| Flunixin | 10% | KET676 | KET46 | Ethanol | 70% EtOH | Propylene glycol | 30% PPG | None | 0 | 0.1M citrate | 0.5 | 1 | 0.014 | 0.042 |
| Flunixin | 10% | KET677 | KET46 | Ethanol | 70% EtOH | Propylene glycol | 30% PPG | None | 0 | 0.1M citrate | 2 | 1 | — | 0 |
| Flunixin | 10% | KET678 | KET46 | Ethanol | 70% EtOH | Propylene glycol | 30% PPG | None | 0 | 0.1M citrate | 4 | 1 | — | 0 |
| Flunixin | 10% | KET679 | KET46 | Ethanol | 70% EtOH | Propylene glycol | 30% PPG | None | 0 | 0.1M citrate | 6 | 1 | 0.048 | 0.144 |
| Flunixin | 10% | KET680 | KET46 | Ethanol | 70% EtOH | Propylene glycol | 30% PPG | None | 0 | 0.1M citrate | 8 | 1 | — | 0 |
| Flunixin | 10% | KET681 | KET46 | Ethanol | 70% EtOH | Propylene glycol | 30% PPG | None | 0 | 0.1M citrate | 0.5 | 2 | — | 0 |
| Flunixin | 10% | KET682 | KET46 | Ethanol | 70% EtOH | Propylene glycol | 30% PPG | None | 0 | 0.1M citrate | 2 | 2 | 0.008 | 0.024 |
| Flunixin | 10% | KET683 | KET46 | Ethanol | 70% EtOH | Propylene glycol | 30% PPG | None | 0 | 0.1M citrate | 4 | 2 | 0.12 | 0.36 |
| Flunixin | 10% | KET684 | KET46 | Ethanol | 70% EtOH | Propylene glycol | 30% PPG | None | 0 | 0.1M citrate | 6 | 2 | 0.241 | 0.723 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Flunixin | 10% | KET685 | KET46 | Ethanol | 70% EtOH | Propylene glycol | 30% PPG | None | 0 | 0.1M citrate | 8 | 2 | 0.106 | 0.318 |
| Flunixin | 10% | KET686 | KET46 | Ethanol | 70% EtOH | Propylene glycol | 30% PPG | None | 0 | 0.1M citrate | 0.5 | 3 | — | 0 |
| Flunixin | 10% | KET687 | KET46 | Ethanol | 70% EtOH | Propylene glycol | 30% PPG | None | 0 | 0.1M citrate | 2 | 3 | — | 0 |
| Flunixin | 10% | KET688 | KET46 | Ethanol | 70% EtOH | Propylene glycol | 30% PPG | None | 0 | 0.1M citrate | 4 | 3 | — | 0 |
| Flunixin | 10% | KET689 | KET46 | Ethanol | 70% EtOH | Propylene glycol | 30% PPG | None | 0 | 0.1M citrate | 6 | 3 | 0.012 | 0.036 |
| Flunixin | 10% | KET690 | KET46 | Ethanol | 70% EtOH | Propylene glycol | 30% PPG | None | 0 | 0.1M citrate | 8 | 3 | 0.012 | 0.036 |
| Flunixin | 10% | KET691 | KET47 | Ethanol | 70% EtOH | Propylene glycol | 30% PPG | Menthol | 50 | 0.1M citrate | 0.5 | 1 | 0.009 | 0.027 |
| Flunixin | 10% | KET692 | KET47 | Ethanol | 70% EtOH | Propylene glycol | 30% PPG | Menthol | 50 | 0.1M citrate | 2 | 1 | 0.02 | 0.06 |
| Flunixin | 10% | KET693 | KET47 | Ethanol | 70% EtOH | Propylene glycol | 30% PPG | Menthol | 50 | 0.1M citrate | 4 | 1 | 0.013 | 0.039 |
| Flunixin | 10% | KET694 | KET47 | Ethanol | 70% EtOH | Propylene glycol | 30% PPG | Menthol | 50 | 0.1M citrate | 6 | 1 | 0.008 | 0.024 |
| Flunixin | 10% | KET695 | KET47 | Ethanol | 70% EtOH | Propylene glycol | 30% PPG | Menthol | 50 | 0.1M citrate | 8 | 1 | 0.015 | 0.045 |
| Flunixin | 10% | KET696 | KET47 | Ethanol | 70% EtOH | Propylene glycol | 30% PPG | Menthol | 50 | 0.1M citrate | 0.5 | 2 | — | 0 |
| Flunixin | 10% | KET697 | KET47 | Ethanol | 70% EtOH | Propylene glycol | 30% PPG | Menthol | 50 | 0.1M citrate | 2 | 2 | 0.039 | 0.117 |
| Flunixin | 10% | KET698 | KET47 | Ethanol | 70% EtOH | Propylene glycol | 30% PPG | Menthol | 50 | 0.1M citrate | 4 | 2 | — | 0 |
| Flunixin | 10% | KET699 | KET47 | Ethanol | 70% EtOH | Propylene glycol | 30% PPG | Menthol | 50 | 0.1M citrate | 6 | 2 | — | 0 |
| Flunixin | 10% | KET700 | KET47 | Ethanol | 70% EtOH | Propylene glycol | 30% PPG | Menthol | 50 | 0.1M citrate | 8 | 2 | 0.005 | 0.015 |
| Flunixin | 10% | KET701 | KET47 | Ethanol | 70% EtOH | Propylene glycol | 30% PPG | Menthol | 50 | 0.1M citrate | 0.5 | 3 | — | 0 |
| Flunixin | 10% | KET702 | KET47 | Ethanol | 70% EtOH | Propylene glycol | 30% PPG | Menthol | 50 | 0.1M citrate | 2 | 3 | 0.007 | 0.021 |
| Flunixin | 10% | KET703 | KET47 | Ethanol | 70% EtOH | Propylene glycol | 30% PPG | Menthol | 50 | 0.1M citrate | 4 | 3 | 0.005 | 0.015 |
| Flunixin | 10% | KET704 | KET47 | Ethanol | 70% EtOH | Propylene glycol | 30% PPG | Menthol | 50 | 0.1M citrate | 6 | 3 | — | 0 |
| Flunixin | 10% | KET705 | KET47 | Ethanol | 70% EtOH | Propylene glycol | 30% PPG | Menthol | 50 | 0.1M citrate | 8 | 3 | — | 0 |
| Flunixin | 10% | KET706 | KET48 | Ethanol | 70% EtOH | Oleyl alcohol | 30% OA | None | 0 | 0.1M citrate | 0.5 | 1 | 0.01 | 0.03 |
| Flunixin | 10% | KET707 | KET48 | Ethanol | 70% EtOH | Oleyl alcohol | 30% OA | None | 0 | 0.1M citrate | 2 | 1 | 0.007 | 0.021 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Flunixin | 10% | KET708 | KET48 | Ethanol | 70% EtOH | Oleyl alcohol | 30% OA | None | 0 | 0.1M citrate | 4 | 1 | 0.007 | 0.021 |
| Flunixin | 10% | KET709 | KET48 | Ethanol | 70% EtOH | Oleyl alcohol | 30% OA | None | 0 | 0.1M citrate | 6 | 1 | 0.005 | 0.015 |
| Flunixin | 10% | KET710 | KET48 | Ethanol | 70% EtOH | Oleyl alcohol | 30% OA | None | 0 | 0.1M citrate | 8 | 1 | 0.01 | 0.03 |
| Flunixin | 10% | KET711 | KET48 | Ethanol | 70% EtOH | Oleyl alcohol | 30% OA | None | 0 | 0.1M citrate | 0.5 | 2 | 0.008 | 0.024 |
| Flunixin | 10% | KET712 | KET48 | Ethanol | 70% EtOH | Oleyl alcohol | 30% OA | None | 0 | 0.1M citrate | 2 | 2 | 0.006 | 0.018 |
| Flunixin | 10% | KET713 | KET48 | Ethanol | 70% EtOH | Oleyl alcohol | 30% OA | None | 0 | 0.1M citrate | 4 | 2 | 0.007 | 0.021 |
| Flunixin | 10% | KET714 | KET48 | Ethanol | 70% EtOH | Oleyl alcohol | 30% OA | None | 0 | 0.1M citrate | 6 | 2 | 0.007 | 0.021 |
| Flunixin | 10% | KET715 | KET48 | Ethanol | 70% EtOH | Oleyl alcohol | 30% OA | None | 0 | 0.1M citrate | 8 | 2 | 0.007 | 0.021 |
| Flunixin | 10% | KET716 | KET48 | Ethanol | 70% EtOH | Oleyl alcohol | 30% OA | None | 0 | 0.1M citrate | 0.5 | 3 | — | 0 |
| Flunixin | 10% | KET717 | KET48 | Ethanol | 70% EtOH | Oleyl alcohol | 30% OA | None | 0 | 0.1M citrate | 2 | 3 | 0.222 | 0.666 |
| Flunixin | 10% | KET718 | KET48 | Ethanol | 70% EtOH | Oleyl alcohol | 30% OA | None | 0 | 0.1M citrate | 4 | 3 | — | 0 |
| Flunixin | 10% | KET719 | KET48 | Ethanol | 70% EtOH | Oleyl alcohol | 30% OA | None | 0 | 0.1M citrate | 6 | 3 | — | 0 |
| Flunixin | 10% | KET720 | KET48 | Ethanol | 70% EtOH | Oleyl alcohol | 30% OA | None | 0 | 0.1M citrate | 8 | 3 | 0.008 | 0.024 |
| Flunixin | 10% | KET721 | KET49 | None | None | Superfine Arlasolve | 100% SRArl | | | 0.1M citrate | 0.5 | 1 | — | 0 |
| Flunixin | 10% | KET722 | KET49 | None | None | Superfine Arlasolve | 100% SRArl | | | 0.1M citrate | 2 | 1 | 0.005 | 0.015 |
| Flunixin | 10% | KET723 | KET49 | None | None | Superfine Arlasolve | 100% SRArl | | | 0.1M citrate | 4 | 1 | 0.005 | 0.015 |
| Flunixin | 10% | KET724 | KET49 | None | None | Superfine Arlasolve | 100% SRArl | | | 0.1M citrate | 6 | 1 | 0.007 | 0.021 |
| Flunixin | 10% | KET725 | KET49 | None | None | Superfine Arlasolve | 100% SRArl | | | 0.1M citrate | 8 | 1 | 0.026 | 0.078 |
| Flunixin | 10% | KET726 | KET49 | None | None | Superfine Arlasolve | 100% SRArl | | | 0.1M citrate | 0.5 | 2 | — | 0 |
| Flunixin | 10% | KET727 | KET49 | None | None | Superfine Arlasolve | 100% SRArl | | | 0.1M citrate | 2 | 2 | — | 0 |
| Flunixin | 10% | KET728 | KET49 | None | None | Superfine Arlasolve | 100% SRArl | | | 0.1M citrate | 4 | 2 | — | 0 |
| Flunixin | 10% | KET729 | KET49 | None | None | Superfine Arlasolve | 100% SRArl | | | 0.1M citrate | 6 | 2 | 0.006 | 0.018 |
| Flunixin | 10% | KET730 | KET49 | None | None | Superfine Arlasolve | 100% SRArl | | | 0.1M citrate | 8 | 2 | — | 0 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Flunixin | 10% | KET731 | KET49 | None | None | Superfine Arlasolve | 100% SRArl | | 0 | 0.1M citrate | 0.5 | 3 | 0.007 | 0.021 |
| Flunixin | 10% | KET732 | KET49 | None | None | Superfine Arlasolve | 100% SRArl | | 0 | 0.1M citrate | 2 | 3 | — | 0 |
| Flunixin | 10% | KET733 | KET49 | None | None | Superfine Arlasolve | 100% SRArl | | 0 | 0.1M citrate | 4 | 3 | — | 0 |
| Flunixin | 10% | KET734 | KET49 | None | None | Superfine Arlasolve | 100% SRArl | | 0 | 0.1M citrate | 6 | 3 | — | 0 |
| Flunixin | 10% | KET735 | KET49 | None | None | Superfine Arlasolve | 100% SRArl | | 0 | 0.1M citrate | 8 | 3 | — | 0 |
| Flunixin | 10% | KET736 | KET50 | None | None | Crodamol STS-LQ(MH) | 100% Crodamol | | 0 | 0.1M citrate | 0.5 | 1 | 0.012 | 0.036 |
| Flunixin | 10% | KET737 | KET50 | None | None | Crodamol STS-LQ(MH) | 100% Crodamol | | 0 | 0.1M citrate | 2 | 1 | 0.011 | 0.033 |
| Flunixin | 10% | KET738 | KET50 | None | None | Crodamol STS-LQ(MH) | 100% Crodamol | | 0 | 0.1M citrate | 4 | 1 | 0.006 | 0.018 |
| Flunixin | 10% | KET739 | KET50 | None | None | Crodamol STS-LQ(MH) | 100% Crodamol | | 0 | 0.1M citrate | 6 | 1 | 0.009 | 0.027 |
| Flunixin | 10% | KET740 | KET50 | None | None | Crodamol STS-LQ(MH) | 100% Crodamol | | 0 | 0.1M citrate | 8 | 1 | 0.007 | 0.021 |
| Flunixin | 10% | KET741 | KET50 | None | None | Crodamol STS-LQ(MH) | 100% Crodamol | | 0 | 0.1M citrate | 0.5 | 2 | 0.007 | 0.021 |
| Flunixin | 10% | KET742 | KET50 | None | None | Crodamol STS-LQ(MH) | 100% Crodamol | | 0 | 0.1M citrate | 2 | 2 | 0.013 | 0.039 |
| Flunixin | 10% | KET743 | KET50 | None | None | Crodamol STS-LQ(MH) | 100% Crodamol | | 0 | 0.1M citrate | 4 | 2 | 0.006 | 0.018 |
| Flunixin | 10% | KET744 | KET50 | None | None | Crodamol STS-LQ(MH) | 100% Crodamol | | 0 | 0.1M citrate | 6 | 2 | 0.006 | 0.018 |
| Flunixin | 10% | KET745 | KET50 | None | None | Crodamol STS-LQ(MH) | 100% Crodamol | | 0 | 0.1M citrate | 8 | 2 | 0.014 | 0.042 |
| Flunixin | 10% | KET746 | KET50 | None | None | Crodamol STS-LQ(MH) | 100% Crodamol | | 0 | 0.1M citrate | 0.5 | 3 | — | 0 |
| Flunixin | 10% | KET747 | KET50 | None | None | Crodamol STS-LQ(MH) | 100% Crodamol | | 0 | 0.1M citrate | 2 | 3 | 0.008 | 0.024 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/EVAP | sample time (hrs) | Replicate | analysis conc | Concentration (μg/mL) |
|---|---|---|---|---|---|---|---|---|---|---|---|---|---|---|
| Flunixin | 10% | KET748 | KET50 | None | None | Crodamol STS-LQ(MH) | 100% Crodamol | | 0 | 0.1M citrate | 4 | 3 | 0.012 | 0.036 |
| Flunixin | 10% | KET749 | KET50 | None | None | Crodamol STS-LQ(MH) | 100% Crodamol | | 0 | 0.1M citrate | 6 | 3 | 0.019 | 0.057 |
| Flunixin | 10% | KET750 | KET50 | None | None | Crodamol STS-LQ(MH) | 100% Crodamol | | 0 | 0.1M citrate | 8 | 3 | — | 0 |
| Tolfenamic acid | 10% | KET751 | KET51 | Ethanol | 70% EtOH | Propylene glycol | 30% PPG | None | 0 | 0.1M citrate | 0.5 | 1 | 0.004 | 0.012 |
| Tolfenamic acid | 10% | KET752 | KET51 | Ethanol | 70% EtOH | Propylene glycol | 30% PPG | None | 0 | 0.1M citrate | 2 | 1 | 0.011 | 0.033 |
| Tolfenamic acid | 10% | KET753 | KET51 | Ethanol | 70% EtOH | Propylene glycol | 30% PPG | None | 0 | 0.1M citrate | 4 | 1 | — | 0 |
| Tolfenamic acid | 10% | KET754 | KET51 | Ethanol | 70% EtOH | Propylene glycol | 30% PPG | None | 0 | 0.1M citrate | 6 | 1 | 0.004 | 0.012 |
| Tolfenamic acid | 10% | KET755 | KET51 | Ethanol | 70% EtOH | Propylene glycol | 30% PPG | None | 0 | 0.1M citrate | 8 | 1 | 0.006 | 0.018 |
| Tolfenamic acid | 10% | KET756 | KET51 | Ethanol | 70% EtOH | Propylene glycol | 30% PPG | None | 0 | 0.1M citrate | 0.5 | 2 | 0.015 | 0.045 |
| Tolfenamic acid | 10% | KET757 | KET51 | Ethanol | 70% EtOH | Propylene glycol | 30% PPG | None | 0 | 0.1M citrate | 2 | 2 | 0.01 | 0.03 |
| Tolfenamic acid | 10% | KET758 | KET51 | Ethanol | 70% EtOH | Propylene glycol | 30% PPG | None | 0 | 0.1M citrate | 4 | 2 | 0.004 | 0.012 |
| Tolfenamic acid | 10% | KET759 | KET51 | Ethanol | 70% EtOH | Propylene glycol | 30% PPG | None | 0 | 0.1M citrate | 6 | 2 | 0.005 | 0.015 |
| Tolfenamic acid | 10% | KET760 | KET51 | Ethanol | 70% EtOH | Propylene glycol | 30% PPG | None | 0 | 0.1M citrate | 8 | 2 | 0.005 | 0.015 |
| Tolfenamic acid | 10% | KET761 | KET51 | Ethanol | 70% EtOH | Propylene glycol | 30% PPG | None | 0 | 0.1M citrate | 0.5 | 3 | — | 0 |
| Tolfenamic acid | 10% | KET762 | KET51 | Ethanol | 70% EtOH | Propylene glycol | 30% PPG | None | 0 | 0.1M citrate | 2 | 3 | — | 0 |
| Tolfenamic acid | 10% | KET763 | KET51 | Ethanol | 70% EtOH | Propylene glycol | 30% PPG | None | 0 | 0.1M citrate | 4 | 3 | 0.003 | 0.009 |
| Tolfenamic acid | 10% | KET764 | KET51 | Ethanol | 70% EtOH | Propylene glycol | 30% PPG | None | 0 | 0.1M citrate | 6 | 3 | 0.004 | 0.012 |
| Tolfenamic acid | 10% | KET765 | KET51 | Ethanol | 70% EtOH | Propylene glycol | 30% PPG | None | 0 | 0.1M citrate | 8 | 3 | 0.004 | 0.012 |
| Tolfenamic acid | 10% | KET766 | KET52 | Ethanol | 70% EtOH | Propylene glycol | 30% PPG | Menthol | 50 | 0.1M citrate | 0.5 | 1 | 0.003 | 0.009 |
| Tolfenamic acid | 10% | KET767 | KET52 | Ethanol | 70% EtOH | Propylene glycol | 30% PPG | Menthol | 50 | 0.1M citrate | 2 | 1 | 0.004 | 0.012 |
| Tolfenamic acid | 10% | KET768 | KET52 | Ethanol | 70% EtOH | Propylene glycol | 30% PPG | Menthol | 50 | 0.1M citrate | 4 | 1 | 0.003 | 0.009 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Tolfenamic acid | 10% | KET769 | KET52 | Ethanol | 70% EtOH | Propylene glycol | 30% PPG | Menthol | 50 | 0.1M citrate | 6 | 1 | 0.002 | 0.006 |
| Tolfenamic acid | 10% | KET770 | KET52 | Ethanol | 70% EtOH | Propylene glycol | 30% PPG | Menthol | 50 | 0.1M citrate | 8 | 1 | 0.004 | 0.012 |
| Tolfenamic acid | 10% | KET771 | KET52 | Ethanol | 70% EtOH | Propylene glycol | 30% PPG | Menthol | 50 | 0.1M citrate | 0.5 | 2 | 0.003 | 0.009 |
| Tolfenamic acid | 10% | KET772 | KET52 | Ethanol | 70% EtOH | Propylene glycol | 30% PPG | Menthol | 50 | 0.1M citrate | 2 | 2 | 0.002 | 0.006 |
| Tolfenamic acid | 10% | KET773 | KET52 | Ethanol | 70% EtOH | Propylene glycol | 30% PPG | Menthol | 50 | 0.1M citrate | 4 | 2 | 0.004 | 0.012 |
| Tolfenamic acid | 10% | KET774 | KET52 | Ethanol | 70% EtOH | Propylene glycol | 30% PPG | Menthol | 50 | 0.1M citrate | 6 | 2 | 0.003 | 0.009 |
| Tolfenamic acid | 10% | KET775 | KET52 | Ethanol | 70% EtOH | Propylene glycol | 30% PPG | Menthol | 50 | 0.1M citrate | 8 | 2 | 0.007 | 0.021 |
| Tolfenamic acid | 10% | KET776 | KET52 | Ethanol | 70% EtOH | Propylene glycol | 30% PPG | Menthol | 50 | 0.1M citrate | 0.5 | 3 | 0.002 | 0.006 |
| Tolfenamic acid | 10% | KET777 | KET52 | Ethanol | 70% EtOH | Propylene glycol | 30% PPG | Menthol | 50 | 0.1M citrate | 2 | 3 | — | 0 |
| Tolfenamic acid | 10% | KET778 | KET52 | Ethanol | 70% EtOH | Propylene glycol | 30% PPG | Menthol | 50 | 0.1M citrate | 4 | 3 | — | 0 |
| Tolfenamic acid | 10% | KET779 | KET52 | Ethanol | 70% EtOH | Propylene glycol | 30% PPG | Menthol | 50 | 0.1M citrate | 6 | 3 | — | 0 |
| Tolfenamic acid | 10% | KET780 | KET52 | Ethanol | 70% EtOH | Propylene glycol | 30% PPG | Menthol | 50 | 0.1M citrate | 8 | 3 | 0.004 | 0.012 |
| Tolfenamic acid | 10% | KET781 | KET53 | Ethanol | 70% EtOH | Oleyl alcohol | 30% OA | None | 0 | 0.1M citrate | 0.5 | 1 | 0.002 | 0.006 |
| Tolfenamic acid | 10% | KET782 | KET53 | Ethanol | 70% EtOH | Oleyl alcohol | 30% OA | None | 0 | 0.1M citrate | 2 | 1 | — | 0 |
| Tolfenamic acid | 10% | KET783 | KET53 | Ethanol | 70% EtOH | Oleyl alcohol | 30% OA | None | 0 | 0.1M citrate | 4 | 1 | 0.007 | 0.021 |
| Tolfenamic acid | 10% | KET784 | KET53 | Ethanol | 70% EtOH | Oleyl alcohol | 30% OA | None | 0 | 0.1M citrate | 6 | 1 | 0.013 | 0.039 |
| Tolfenamic acid | 10% | KET785 | KET53 | Ethanol | 70% EtOH | Oleyl alcohol | 30% OA | None | 0 | 0.1M citrate | 8 | 1 | 0.047 | 0.141 |
| Tolfenamic acid | 10% | KET786 | KET53 | Ethanol | 70% EtOH | Oleyl alcohol | 30% OA | None | 0 | 0.1M citrate | 0.5 | 2 | 0.002 | 0.006 |
| Tolfenamic acid | 10% | KET787 | KET53 | Ethanol | 70% EtOH | Oleyl alcohol | 30% OA | None | 0 | 0.1M citrate | 2 | 2 | — | 0 |
| Tolfenamic acid | 10% | KET788 | KET53 | Ethanol | 70% EtOH | Oleyl alcohol | 30% OA | None | 0 | 0.1M citrate | 4 | 2 | 0.003 | 0.009 |
| Tolfenamic acid | 10% | KET789 | KET53 | Ethanol | 70% EtOH | Oleyl alcohol | 30% OA | None | 0 | 0.1M citrate | 6 | 2 | 0.009 | 0.027 |
| Tolfenamic acid | 10% | KET790 | KET53 | Ethanol | 70% EtOH | Oleyl alcohol | 30% OA | None | 0 | 0.1M citrate | 8 | 2 | 0.08 | 0.24 |
| Tolfenamic acid | 10% | KET791 | KET53 | Ethanol | 70% EtOH | Oleyl alcohol | 30% OA | None | 0 | 0.1M citrate | 0.5 | 3 | 0.002 | 0.006 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Tolfenamic acid | 10% | KET792 | KET53 | Ethanol | 70% EtOH | Oleyl alcohol | 30% OA | None | 0 | 0.1M citrate | 2 | 3 | 0.005 | 0.015 |
| Tolfenamic acid | 10% | KET793 | KET53 | Ethanol | 70% EtOH | Oleyl alcohol | 30% OA | None | 0 | 0.1M citrate | 4 | 3 | 0.007 | 0.021 |
| Tolfenamic acid | 10% | KET794 | KET53 | Ethanol | 70% EtOH | Oleyl alcohol | 30% OA | None | 0 | 0.1M citrate | 6 | 3 | 0.034 | 0.102 |
| Tolfenamic acid | 10% | KET795 | KET53 | Ethanol | 70% EtOH | Oleyl alcohol | 30% OA | None | 0 | 0.1M citrate | 8 | 3 | 0.04 | 0.12 |
| Tolfenamic acid | 10% | KET796 | KET54 | None | None | Superfine Arlasolve | 100% SRArl | | 0 | 0.1M citrate | 0.5 | 1 | 0.002 | 0.006 |
| Tolfenamic acid | 10% | KET797 | KET54 | None | None | Superfine Arlasolve | 100% SRArl | | 0 | 0.1M citrate | 2 | 1 | — | 0 |
| Tolfenamic acid | 10% | KET798 | KET54 | None | None | Superfine Arlasolve | 100% SRArl | | 0 | 0.1M citrate | 4 | 1 | — | 0 |
| Tolfenamic acid | 10% | KET799 | KET54 | None | None | Superfine Arlasolve | 100% SRArl | | 0 | 0.1M citrate | 6 | 1 | 0.003 | 0.009 |
| Tolfenamic acid | 10% | KET800 | KET54 | None | None | Superfine Arlasolve | 100% SRArl | | 0 | 0.1M citrate | 8 | 1 | 0.038 | 0.114 |
| Tolfenamic acid | 10% | KET801 | KET54 | None | None | Superfine Arlasolve | 100% SRArl | | 0 | 0.1M citrate | 0.5 | 2 | 0.002 | 0.006 |
| Tolfenamic acid | 10% | KET802 | KET54 | None | None | Superfine Arlasolve | 100% SRArl | | 0 | 0.1M citrate | 2 | 2 | — | 0 |
| Tolfenamic acid | 10% | KET803 | KET54 | None | None | Superfine Arlasolve | 100% SRArl | | 0 | 0.1M citrate | 4 | 2 | — | 0 |
| Tolfenamic acid | 10% | KET804 | KET54 | None | None | Superfine Arlasolve | 100% SRArl | | 0 | 0.1M citrate | 6 | 2 | 0.002 | 0.006 |
| Tolfenamic acid | 10% | KET805 | KET54 | None | None | Superfine Arlasolve | 100% SRArl | | 0 | 0.1M citrate | 8 | 2 | — | 0 |
| Tolfenamic acid | 10% | KET806 | KET54 | None | None | Superfine Arlasolve | 100% SRArl | | 0 | 0.1M citrate | 0.5 | 3 | — | 0 |
| Tolfenamic acid | 10% | KET807 | KET54 | None | None | Superfine Arlasolve | 100% SRArl | | 0 | 0.1M citrate | 2 | 3 | — | 0 |
| Tolfenamic acid | 10% | KET808 | KET54 | None | None | Superfine Arlasolve | 100% SRArl | | 0 | 0.1M citrate | 4 | 3 | — | 0 |
| Tolfenamic acid | 10% | KET809 | KET54 | None | None | Superfine Arlasolve | 100% SRArl | | 0 | 0.1M citrate | 6 | 3 | 0.004 | 0.012 |
| Tolfenamic acid | 10% | KET810 | KET54 | None | None | Superfine Arlasolve | 100% SRArl | | 0 | 0.1M citrate | 8 | 3 | 0.002 | 0.006 |
| Tolfenamic acid | 10% | KET811 | KET55 | None | None | Crodamol STS-LQ(MH) | 100% Crodamol | | 0 | 0.1M citrate | 0.5 | 1 | 0.004 | 0.012 |
| Tolfenamic acid | 10% | KET812 | KET55 | None | None | Crodamol STS-LQ(MH) | 100% Crodamol | | 0 | 0.1M citrate | 2 | 1 | 0.018 | 0.054 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Tolfenamic acid | 10% | KET813 | KET55 | None | None | Crodamol STS-LQ(MH) | 100% Crodamol | | 0 | 0.1M citrate | 4 | 1 | 0.094 | 0.282 |
| Tolfenamic acid | 10% | KET814 | KET55 | None | None | Crodamol STS-LQ(MH) | 100% Crodamol | | 0 | 0.1M citrate | 6 | 1 | 0.002 | 0.006 |
| Tolfenamic acid | 10% | KET815 | KET55 | None | None | Crodamol STS-LQ(MH) | 100% Crodamol | | 0 | 0.1M citrate | 8 | 1 | 0.002 | 0.006 |
| Tolfenamic acid | 10% | KET816 | KET55 | None | None | Crodamol STS-LQ(MH) | 100% Crodamol | | 0 | 0.1M citrate | 0.5 | 2 | — | 0 |
| Tolfenamic acid | 10% | KET817 | KET55 | None | None | Crodamol STS-LQ(MH) | 100% Crodamol | | 0 | 0.1M citrate | 2 | 2 | 0.003 | 0.009 |
| Tolfenamic acid | 10% | KET818 | KET55 | None | None | Crodamol STS-LQ(MH) | 100% Crodamol | | 0 | 0.1M citrate | 4 | 2 | 0.008 | 0.024 |
| Tolfenamic acid | 10% | KET819 | KET55 | None | None | Crodamol STS-LQ(MH) | 100% Crodamol | | 0 | 0.1M citrate | 6 | 2 | 0.002 | 0.006 |
| Tolfenamic acid | 10% | KET820 | KET55 | None | None | Crodamol STS-LQ(MH) | 100% Crodamol | | 0 | 0.1M citrate | 8 | 2 | 0.002 | 0.006 |
| Tolfenamic acid | 10% | KET821 | KET55 | None | None | Crodamol STS-LQ(MH) | 100% Crodamol | | 0 | 0.1M citrate | 0.5 | 3 | — | 0 |
| Tolfenamic acid | 10% | KET822 | KET55 | None | None | Crodamol STS-LQ(MH) | 100% Crodamol | | 0 | 0.1M citrate | 2 | 3 | 0.005 | 0.015 |
| Tolfenamic acid | 10% | KET823 | KET55 | None | None | Crodamol STS-LQ(MH) | 100% Crodamol | | 0 | 0.1M citrate | 4 | 3 | — | 0 |
| Tolfenamic acid | 10% | KET824 | KET55 | None | None | Crodamol STS-LQ(MH) | 100% Crodamol | | 0 | 0.1M citrate | 6 | 3 | 0.012 | 0.036 |
| Tolfenamic acid | 10% | KET825 | KET55 | None | None | Crodamol STS-LQ(MH) | 100% Crodamol | | 0 | 0.1M citrate | 8 | 3 | — | 0 |
| Ketoprofen | 10% | KET826 | KET56 | Ethanol | 50% Ethanol | None | None | Eucalyptus oil | 21% 1,8-cineole | 0.1M citrate | 0.5 | 1 | 0.004 | 0.012 |
| Ketoprofen | 10% | KET827 | KET56 | Ethanol | 50% Ethanol | None | None | Eucalyptus oil | 21% 1,8-cineole | 0.1M citrate | 2 | 1 | 0.006 | 0.018 |
| Ketoprofen | 10% | KET828 | KET56 | Ethanol | 50% Ethanol | None | None | Eucalyptus oil | 21% 1,8-cineole | 0.1M citrate | 4 | 1 | 0.006 | 0.018 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/EVAP | sample time (hrs) | Replicate | analysis conc | Concentration (µg/mL) |
|---|---|---|---|---|---|---|---|---|---|---|---|---|---|---|
| Ketoprofen | 10% | KET829 | KET56 | Ethanol | 50% Ethanol | None | None | Eucalyptus oil | 21% 1,8 cineole | 0.1M citrate | 6 | 1 | 0.12 | 0.36 |
| Ketoprofen | 10% | KET830 | KET56 | Ethanol | 50% Ethanol | None | None | Eucalyptus oil | 21% 1,8 cineole | 0.1M citrate | 8 | 1 | 0.018 | 0.054 |
| Ketoprofen | 10% | KET831 | KET56 | Ethanol | 50% Ethanol | None | None | Eucalyptus oil | 21% 1,8 cineole | 0.1M citrate | 0.5 | 2 | 0.003 | 0.009 |
| Ketoprofen | 10% | KET832 | KET56 | Ethanol | 50% Ethanol | None | None | Eucalyptus oil | 21% 1,8 cineole | 0.1M citrate | 2 | 2 | 0.005 | 0.015 |
| Ketoprofen | 10% | KET833 | KET56 | Ethanol | 50% Ethanol | None | None | Eucalyptus oil | 21% 1,8 cineole | 0.1M citrate | 4 | 2 | 0.007 | 0.021 |
| Ketoprofen | 10% | KET834 | KET56 | Ethanol | 50% Ethanol | None | None | Eucalyptus oil | 21% 1,8 cineole | 0.1M citrate | 6 | 2 | 0.011 | 0.033 |
| Ketoprofen | 10% | KET835 | KET56 | Ethanol | 50% Ethanol | None | None | Eucalyptus oil | 21% 1,8 cineole | 0.1M citrate | 8 | 2 | 0.04 | 0.12 |
| Ketoprofen | 10% | KET836 | KET56 | Ethanol | 50% Ethanol | None | None | Eucalyptus oil | 21% 1,8 cineole | 0.1M citrate | 0.5 | 3 | 0.004 | 0.012 |
| Ketoprofen | 10% | KET837 | KET56 | Ethanol | 50% Ethanol | None | None | Eucalyptus oil | 21% 1,8 cineole | 0.1M citrate | 2 | 3 | 0.006 | 0.018 |
| Ketoprofen | 10% | KET838 | KET56 | Ethanol | 50% Ethanol | None | None | Eucalyptus oil | 21% 1,8 cineole | 0.1M citrate | 4 | 3 | 0.007 | 0.021 |
| Ketoprofen | 10% | KET839 | KET56 | Ethanol | 50% Ethanol | None | None | Eucalyptus oil | 21% 1,8 cineole | 0.1M citrate | 6 | 3 | 0.015 | 0.045 |
| Ketoprofen | 10% | KET840 | KET56 | Ethanol | 50% Ethanol | None | None | Eucalyptus oil | 21% 1,8 cineole | 0.1M citrate | 8 | 3 | 0.071 | 0.213 |
| Ketoprofen | 10% | KET841 | KET57 | None | None | None | None | Eucalyptus oil | 70% 1,8- cineole | None | 0.5 | 1 | 0.005 | 0.015 |
| Ketoprofen | 10% | KET842 | KET57 | None | None | None | None | Eucalyptus oil | 70% 1,8- cineole | None | 2 | 1 | 0.024 | 0.072 |
| Ketoprofen | 10% | KET843 | KET57 | None | None | None | None | Eucalyptus oil | 70% 1,8- cineole | None | 4 | 1 | 0.027 | 0.081 |
| Ketoprofen | 10% | KET844 | KET57 | None | None | None | None | Eucalyptus oil | 70% 1,8- cineole | None | 6 | 1 | 0.121 | 0.363 |
| Ketoprofen | 10% | KET845 | KET57 | None | None | None | None | Eucalyptus oil | 70% 1,8- cineole | None | 8 | 1 | 0.379 | 1.137 |
| Ketoprofen | 10% | KET846 | KET57 | None | None | None | None | Eucalyptus oil | 70% 1,8- cineole | None | 0.5 | 2 | 0.002 | 0.006 |
| Ketoprofen | 10% | KET847 | KET57 | None | None | None | None | Eucalyptus oil | 70% 1,8- cineole | None | 2 | 2 | 0.002 | 0.006 |
| Ketoprofen | 10% | KET848 | KET57 | None | None | None | None | Eucalyptus oil | 70% 1,8- cineole | None | 4 | 2 | 0.018 | 0.054 |
| Ketoprofen | 10% | KET849 | KET57 | None | None | None | None | Eucalyptus oil | 70% 1,8- cineole | None | 6 | 2 | 0.11 | 0.33 |
| Ketoprofen | 10% | KET850 | KET57 | None | None | None | None | Eucalyptus oil | 70% 1,8- cineole | None | 8 | 2 | 0.406 | 1.218 |
| Ketoprofen | 10% | KET851 | KET57 | None | None | None | None | Eucalyptus oil | 70% 1,8- cineole | None | 0.5 | 3 | 0.002 | 0.006 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET852 | KET57 | None | None | None | None | Eucalyptus oil | 70% 1,8-cineole | None | 2 | 3 | 0.005 | 0.015 |
| Ketoprofen | 10% | KET853 | KET57 | None | None | None | None | Eucalyptus oil | 70% 1,8-cineole | None | 4 | 3 | 0.023 | 0.069 |
| Ketoprofen | 10% | KET854 | KET57 | None | None | None | None | Eucalyptus oil | 70% 1,8-cineole | None | 6 | 3 | 0.06 | 0.18 |
| Ketoprofen | 10% | KET855 | KET57 | None | None | None | None | Eucalyptus oil | 70% 1,8-cineole | None | 8 | 3 | 0.178 | 0.534 |
| Ketoprofen | 10% | KET856 | KET58 | None | None | Propylene glycol | 100% PPG | None | None | None | 0.5 | 1 | 0.004 | 0.012 |
| Ketoprofen | 10% | KET857 | KET58 | None | None | Propylene glycol | 100% PPG | None | None | None | 2 | 1 | 0.003 | 0.009 |
| Ketoprofen | 10% | KET858 | KET58 | None | None | Propylene glycol | 100% PPG | None | None | None | 4 | 1 | 0.004 | 0.012 |
| Ketoprofen | 10% | KET859 | KET58 | None | None | Propylene glycol | 100% PPG | None | None | None | 6 | 1 | 0.005 | 0.015 |
| Ketoprofen | 10% | KET860 | KET58 | None | None | Propylene glycol | 100% PPG | None | None | None | 8 | 1 | 0.021 | 0.063 |
| Ketoprofen | 10% | KET861 | KET58 | None | None | Propylene glycol | 100% PPG | None | None | None | 0.5 | 2 | 0.01 | 0.03 |
| Ketoprofen | 10% | KET862 | KET58 | None | None | Propylene glycol | 100% PPG | None | None | None | 2 | 2 | 0.003 | 0.009 |
| Ketoprofen | 10% | KET863 | KET58 | None | None | Propylene glycol | 100% PPG | None | None | None | 4 | 2 | 0.002 | 0.006 |
| Ketoprofen | 10% | KET864 | KET58 | None | None | Propylene glycol | 100% PPG | None | None | None | 6 | 2 | 0.004 | 0.012 |
| Ketoprofen | 10% | KET865 | KET58 | None | None | Propylene glycol | 100% PPG | None | None | None | 8 | 2 | 0.019 | 0.057 |
| Ketoprofen | 10% | KET866 | KET58 | None | None | Propylene glycol | 100% PPG | None | None | None | 0.5 | 3 | 0.003 | 0.009 |
| Ketoprofen | 10% | KET867 | KET58 | None | None | Propylene glycol | 100% PPG | None | None | None | 2 | 3 | 0.002 | 0.006 |
| Ketoprofen | 10% | KET868 | KET58 | None | None | Propylene glycol | 100% PPG | None | None | None | 4 | 3 | 0.006 | 0.018 |
| Ketoprofen | 10% | KET869 | KET58 | None | None | Propylene glycol | 100% PPG | None | None | None | 6 | 3 | 0.004 | 0.012 |
| Ketoprofen | 10% | KET870 | KET58 | None | None | Propylene glycol | 100% PPG | None | None | None | 8 | 3 | 0.017 | 0.051 |
| Ketoprofen | 10% | KET871 | KET59 | None | None | Crodamol-STS-LQ | 100% PPG-3 Benzyl ether myristate | None | None | None | 0.5 | 1 | 0.003 | 0.009 |
| Ketoprofen | 10% | KET872 | KET59 | None | None | Crodamol-STS-LQ | 100% PPG-3 Benzyl ether myristate | None | None | None | 2 | 1 | 0.004 | 0.012 |
| Ketoprofen | 10% | KET873 | KET59 | None | None | Crodamol-STS-LQ | 100% PPG-3 Benzyl ether | None | None | None | 4 | 1 | 0.008 | 0.024 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET874 | KET59 | None | None | Crodamol-STS-LQ | 100% PPG-3 Benzyl ether myristate | None | None | None | 6 | 1 | 0.016 | 0.048 |
| Ketoprofen | 10% | KET875 | KET59 | None | None | Crodamol-STS-LQ | 100% PPG-3 Benzyl ether myristate | None | None | None | 8 | 1 | 0.109 | 0.327 |
| Ketoprofen | 10% | KET876 | KET59 | None | None | Crodamol-STS-LQ | 100% PPG-3 Benzyl ether myristate | None | None | None | 0.5 | 2 | 0.004 | 0.012 |
| Ketoprofen | 10% | KET877 | KET59 | None | None | Crodamol-STS-LQ | 100% PPG-3 Benzyl ether myristate | None | None | None | 2 | 2 | 0.006 | 0.018 |
| Ketoprofen | 10% | KET878 | KET59 | None | None | Crodamol-STS-LQ | 100% PPG-3 Benzyl ether myristate | None | None | None | 4 | 2 | 0.007 | 0.021 |
| Ketoprofen | 10% | KET879 | KET59 | None | None | Crodamol-STS-LQ | 100% PPG-3 Benzyl ether myristate | None | None | None | 6 | 2 | 0.015 | 0.045 |
| Ketoprofen | 10% | KET880 | KET59 | None | None | Crodamol-STS-LQ | 100% PPG-3 Benzyl ether myristate | None | None | None | 8 | 2 | 0.05 | 0.15 |
| Ketoprofen | 10% | KET881 | KET59 | None | None | Crodamol-STS-LQ | 100% PPG-3 Benzyl ether myristate | None | None | None | 0.5 | 3 | 0.004 | 0.012 |
| Ketoprofen | 10% | KET882 | KET59 | None | None | Crodamol-STS-LQ | 100% PPG-3 Benzyl ether myristate | None | None | None | 2 | 3 | 0.003 | 0.009 |
| Ketoprofen | 10% | KET883 | KET59 | None | None | Crodamol-STS-LQ | 100% PPG-3 Benzyl ether myristate | None | None | None | 4 | 3 | 0.011 | 0.033 |
| Ketoprofen | 10% | KET884 | KET59 | None | None | Crodamol-STS-LQ | 100% PPG-3 Benzyl ether myristate | None | None | None | 6 | 3 | 0.006 | 0.018 |
| Ketoprofen | 10% | KET885 | KET59 | None | None | Crodamol-STS-LQ | 100% PPG-3 Benzyl ether myristate | None | None | None | 8 | 3 | 0.025 | 0.075 |
| Ketoprofen | 10% | KET886 | KET60 | None | None | Cromollient-SCE-LQ-(MH) | 100% Di-PPG2-Myreth-10-Adipate | None | None | None | 0.5 | 1 | 0.006 | 0.018 |
| Ketoprofen | 10% | KET887 | KET60 | None | None | Cromollient-SCE-LQ-(MH) | 100% Di-PPG2-Myreth-10-Adipate | None | None | None | 2 | 1 | 0.021 | 0.063 |
| Ketoprofen | 10% | KET888 | KET60 | None | None | Cromollient-SCE-LQ-(MH) | 100% Di-PPG2-Myreth-10-Adipate | None | None | None | 4 | 1 | 0.028 | 0.084 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/EVAP | sample time (hrs) | Replicate | analysis conc | Concentration (µg/mL) |
|---|---|---|---|---|---|---|---|---|---|---|---|---|---|---|
| Ketoprofen | 10% | KET889 | KET60 | None | None | Cromollient-SCE-LQ-(MH) | 100% Di-PPG2-Myreth-10-Adipate | None | None | None | 6 | 1 | 0.037 | 0.111 |
| Ketoprofen | 10% | KET890 | KET60 | None | None | Cromollient-SCE-LQ-(MH) | 100% Di-PPG2-Myreth-10-Adipate | None | None | None | 8 | 1 | 0.06 | 0.18 |
| Ketoprofen | 10% | KET891 | KET60 | None | None | Cromollient-SCE-LQ-(MH) | 100% Di-PPG2-Myreth-10-Adipate | None | None | None | 0.5 | 2 | 0.006 | 0.018 |
| Ketoprofen | 10% | KET892 | KET60 | None | None | Cromollient-SCE-LQ-(MH) | 100% Di-PPG2-Myreth-10-Adipate | None | None | None | 2 | 2 | 0.008 | 0.024 |
| Ketoprofen | 10% | KET893 | KET60 | None | None | Cromollient-SCE-LQ-(MH) | 100% Di-PPG2-Myreth-10-Adipate | None | None | None | 4 | 2 | 0.008 | 0.024 |
| Ketoprofen | 10% | KET894 | KET60 | None | None | Cromollient-SCE-LQ-(MH) | 100% Di-PPG2-Myreth-10-Adipate | None | None | None | 6 | 2 | 0.017 | 0.051 |
| Ketoprofen | 10% | KET895 | KET60 | None | None | Cromollient-SCE-LQ-(MH) | 100% Di-PPG2-Myreth-10-Adipate | None | None | None | 8 | 2 | 0.038 | 0.114 |
| Ketoprofen | 10% | KET896 | KET60 | None | None | Cromollient-SCE-LQ-(MH) | 100% Di-PPG2-Myreth-10-Adipate | None | None | None | 0.5 | 3 | 0.006 | 0.018 |
| Ketoprofen | 10% | KET897 | KET60 | None | None | Cromollient-SCE-LQ-(MH) | 100% Di-PPG2-Myreth-10-Adipate | None | None | None | 2 | 3 | 0.005 | 0.015 |
| Ketoprofen | 10% | KET898 | KET60 | None | None | Cromollient-SCE-LQ-(MH) | 100% Di-PPG2-Myreth-10-Adipate | None | None | None | 4 | 3 | 0.007 | 0.021 |
| Ketoprofen | 10% | KET899 | KET60 | None | None | Cromollient-SCE-LQ-(MH) | 100% Di-PPG2-Myreth-10-Adipate | None | None | None | 6 | 3 | 0.011 | 0.033 |
| Ketoprofen | 10% | KET900 | KET60 | None | None | Cromollient-SCE-LQ-(MH) | 100% Di-PPG2-Myreth-10-Adipate | None | None | None | 8 | 3 | 0.018 | 0.054 |
| Flunixin | 10% | KET901 | KET61 | Ethanol | 50% Ethanol | None | None | Eucalyptus oil | 21% 1,8-cineole | 0.1M citrate | 0.5 | 1 | 0.006 | 0.018 |
| Flunixin | 10% | KET902 | KET61 | Ethanol | 50% Ethanol | None | None | Eucalyptus oil | 21% 1,8-cineole | 0.1M citrate | 2 | 1 | 0.005 | 0.015 |
| Flunixin | 10% | KET903 | KET61 | Ethanol | 50% Ethanol | None | None | Eucalyptus oil | 21% 1,8-cineole | 0.1M citrate | 4 | 1 | 0.007 | 0.021 |
| Flunixin | 10% | KET904 | KET61 | Ethanol | 50% Ethanol | None | None | Eucalyptus oil | 21% 1,8-cineole | 0.1M citrate | 6 | 1 | 0.01 | 0.03 |
| Flunixin | 10% | KET905 | KET61 | Ethanol | 50% Ethanol | None | None | Eucalyptus oil | 21% 1,8-cineole | 0.1M citrate | 8 | 1 | 0.039 | 0.117 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Flunixin | 10% | KET906 | KET61 | Ethanol | 50% Ethanol | None | None | Eucalyptus oil | 21% 1,8 cineole | 0.1M citrate | 0.5 | 2 | 0.008 | 0.024 |
| Flunixin | 10% | KET907 | KET61 | Ethanol | 50% Ethanol | None | None | Eucalyptus oil | 21% 1,8 cineole | 0.1M citrate | 2 | 2 | 0.007 | 0.021 |
| Flunixin | 10% | KET908 | KET61 | Ethanol | 50% Ethanol | None | None | Eucalyptus oil | 21% 1,8 cineole | 0.1M citrate | 4 | 2 | 0.006 | 0.018 |
| Flunixin | 10% | KET909 | KET61 | Ethanol | 50% Ethanol | None | None | Eucalyptus oil | 21% 1,8 cineole | 0.1M citrate | 8 | 2 | 0.218 | 0.654 |
| Flunixin | 10% | KET910 | KET61 | Ethanol | 50% Ethanol | None | None | Eucalyptus oil | 21% 1,8 cineole | 0.1M citrate | 6 | 2 | 0.008 | 0.024 |
| Flunixin | 10% | KET911 | KET61 | Ethanol | 50% Ethanol | None | None | Eucalyptus oil | 21% 1,8 cineole | 0.1M citrate | 4 | 3 | 0.009 | 0.027 |
| Flunixin | 10% | KET912 | KET61 | Ethanol | 50% Ethanol | None | None | Eucalyptus oil | 21% 1,8 cineole | 0.1M citrate | 0.5 | 3 | — | 0 |
| Flunixin | 10% | KET913 | KET61 | Ethanol | 50% Ethanol | None | None | Eucalyptus oil | 21% 1,8 cineole | 0.1M citrate | 2 | 3 | 0.005 | 0.015 |
| Flunixin | 10% | KET914 | KET61 | Ethanol | 50% Ethanol | None | None | Eucalyptus oil | 21% 1,8 cineole | 0.1M citrate | 6 | 3 | 0.008 | 0.024 |
| Flunixin | 10% | KET915 | KET61 | Ethanol | 50% Ethanol | None | None | Eucalyptus oil | 21% 1,8 cineole | 0.1M citrate | 8 | 3 | 0.014 | 0.042 |
| Flunixin | 10% | KET916 | KET62 | None | None | None | None | Eucalyptus oil | 70% 1,8 cineole | None | 2 | 1 | 0.005 | 0.015 |
| Flunixin | 10% | KET917 | KET62 | None | None | None | None | Eucalyptus oil | 70% 1,8 cineole | None | 4 | 1 | 0.005 | 0.015 |
| Flunixin | 10% | KET918 | KET62 | None | None | None | None | Eucalyptus oil | 70% 1,8 cineole | None | 0.5 | 1 | — | 0 |
| Flunixin | 10% | KET919 | KET62 | None | None | None | None | Eucalyptus oil | 70% 1,8 cineole | None | 6 | 1 | 0.251 | 0.753 |
| Flunixin | 10% | KET920 | KET62 | None | None | None | None | Eucalyptus oil | 70% 1,8 cineole | None | 8 | 1 | 2.775 | 8.325 |
| Flunixin | 10% | KET921 | KET62 | None | None | None | None | Eucalyptus oil | 70% 1,8 cineole | None | 2 | 2 | 0.009 | 0.027 |
| Flunixin | 10% | KET922 | KET62 | None | None | None | None | Eucalyptus oil | 70% 1,8 cineole | None | 4 | 2 | 0.017 | 0.051 |
| Flunixin | 10% | KET923 | KET62 | None | None | None | None | Eucalyptus oil | 70% 1,8 cineole | None | 0.5 | 2 | — | 0 |
| Flunixin | 10% | KET924 | KET62 | None | None | None | None | Eucalyptus oil | 70% 1,8 cineole | None | 6 | 2 | 0.044 | 0.132 |
| Flunixin | 10% | KET925 | KET62 | None | None | None | None | Eucalyptus oil | 70% 1,8 cineole | None | 8 | 2 | 1.094 | 3.282 |
| Flunixin | 10% | KET926 | KET62 | None | None | None | None | Eucalyptus oil | 70% 1,8 cineole | None | 6 | 3 | — | 0 |
| Flunixin | 10% | KET927 | KET62 | None | None | None | None | Eucalyptus oil | 70% 1,8 cineole | None | 8 | 3 | 0.056 | 0.168 |
| Flunixin | 10% | KET928 | KET62 | None | None | None | None | Eucalyptus oil | 70% 1,8 cineole | None | 4 | 3 | — | 0 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Flunixin | 10% | KET929 | KET62 | None | None | None | None | Eucalyptus oil | 70% 1,8-cineole | None | 2 | 3 | — | 0 |
| Flunixin | 10% | KET930 | KET62 | None | None | None | None | Eucalyptus oil | 70% 1,8-cineole | None | 0.5 | 3 | — | 0 |
| Flunixin | 10% | KET931 | KET63 | None | None | Propylene glycol | 100% PPG | None | None | None | 0.5 | 1 | — | 0 |
| Flunixin | 10% | KET932 | KET63 | None | None | Propylene glycol | 100% PPG | None | None | None | 8 | 1 | 0.208 | 0.624 |
| Flunixin | 10% | KET933 | KET63 | None | None | Propylene glycol | 100% PPG | None | None | None | 2 | 1 | — | 0 |
| Flunixin | 10% | KET934 | KET63 | None | None | Propylene glycol | 100% PPG | None | None | None | 4 | 1 | 0.012 | 0.036 |
| Flunixin | 10% | KET935 | KET63 | None | None | Propylene glycol | 100% PPG | None | None | None | 6 | 1 | — | 0 |
| Flunixin | 10% | KET936 | KET63 | None | None | Propylene glycol | 100% PPG | None | None | None | 6 | 2 | 0.009 | 0.027 |
| Flunixin | 10% | KET937 | KET63 | None | None | Propylene glycol | 100% PPG | None | None | None | 4 | 2 | 0.006 | 0.018 |
| Flunixin | 10% | KET938 | KET63 | None | None | Propylene glycol | 100% PPG | None | None | None | 0.5 | 2 | — | 0 |
| Flunixin | 10% | KET939 | KET63 | None | None | Propylene glycol | 100% PPG | None | None | None | 2 | 2 | 0.006 | 0.018 |
| Flunixin | 10% | KET940 | KET63 | None | None | Propylene glycol | 100% PPG | None | None | None | 8 | 2 | 0.012 | 0.036 |
| Flunixin | 10% | KET941 | KET63 | None | None | Propylene glycol | 100% PPG | None | None | None | 8 | 3 | 0.006 | 0.018 |
| Flunixin | 10% | KET942 | KET63 | None | None | Propylene glycol | 100% PPG | None | None | None | 6 | 3 | 0.009 | 0.027 |
| Flunixin | 10% | KET943 | KET63 | None | None | Propylene glycol | 100% PPG | None | None | None | 4 | 3 | 0.006 | 0.018 |
| Flunixin | 10% | KET944 | KET63 | None | None | Propylene glycol | 100% PPG | None | None | None | 2 | 3 | 0.006 | 0.018 |
| Flunixin | 10% | KET945 | KET63 | None | None | Propylene glycol | 100% PPG | None | None | None | 0.5 | 3 | — | 0 |
| Flunixin | 10% | KET946 | KET64 | None | None | Crodamol-STS-LQ | 100% PPG-3 Benzyl ether myristate | None | None | None | 8 | 1 | 0.018 | 0.054 |
| Flunixin | 10% | KET947 | KET64 | None | None | Crodamol-STS-LQ | 100% PPG-3 Benzyl ether myristate | None | None | None | 6 | 1 | 0.006 | 0.018 |
| Flunixin | 10% | KET948 | KET64 | None | None | Crodamol-STS-LQ | 100% PPG-3 Benzyl ether myristate | None | None | None | 4 | 1 | 0.005 | 0.015 |
| Flunixin | 10% | KET949 | KET64 | None | None | Crodamol-STS-LQ | 100% PPG-3 Benzyl ether myristate | None | None | None | 2 | 1 | — | 0 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/EVAP | sample time (hrs) | Replicate | analysis conc | Concentration (µg/mL) |
|---|---|---|---|---|---|---|---|---|---|---|---|---|---|---|
| Flunixin | 10% | KET950 | KET64 | None | None | Crodamol-STS-LQ | 100% PPG-3 Benzyl ether myristate | None | None | None | 0.5 | 1 | 0.006 | 0.018 |
| Flunixin | 10% | KET951 | KET64 | None | None | Crodamol-STS-LQ | 100% PPG-3 Benzyl ether myristate | None | None | None | 0.5 | 2 | 0.007 | 0.021 |
| Flunixin | 10% | KET952 | KET64 | None | None | Crodamol-STS-LQ | 100% PPG-3 Benzyl ether myristate | None | None | None | 2 | 2 | 0.005 | 0.015 |
| Flunixin | 10% | KET953 | KET64 | None | None | Crodamol-STS-LQ | 100% PPG-3 Benzyl ether myristate | None | None | None | 4 | 2 | — | 0 |
| Flunixin | 10% | KET954 | KET64 | None | None | Crodamol-STS-LQ | 100% PPG-3 Benzyl ether myristate | None | None | None | 6 | 2 | 0.006 | 0.018 |
| Flunixin | 10% | KET955 | KET64 | None | None | Crodamol-STS-LQ | 100% PPG-3 Benzyl ether myristate | None | None | None | 8 | 2 | — | 0 |
| Flunixin | 10% | KET956 | KET64 | None | None | Crodamol-STS-LQ | 100% PPG-3 Benzyl ether myristate | None | None | None | 0.5 | 3 | — | 0 |
| Flunixin | 10% | KET957 | KET64 | None | None | Crodamol-STS-LQ | 100% PPG-3 Benzyl ether myristate | None | None | None | 2 | 3 | — | 0 |
| Flunixin | 10% | KET958 | KET64 | None | None | Crodamol-STS-LQ | 100% PPG-3 Benzyl ether myristate | None | None | None | 4 | 3 | — | 0 |
| Flunixin | 10% | KET959 | KET64 | None | None | Crodamol-STS-LQ | 100% PPG-3 Benzyl ether myristate | None | None | None | 6 | 3 | 0.006 | 0.018 |
| Flunixin | 10% | KET960 | KET64 | None | None | Crodamol-STS-LQ | 100% PPG-3 Benzyl ether myristate | None | None | None | 8 | 3 | — | 0 |
| Flunixin | 10% | KET961 | KET65 | None | None | Cromollient-SCE-LQ-(MH) | 100% Di-PPG2-Myreth-10-Adipate | None | None | None | 0.5 | 1 | — | 0 |
| Flunixin | 10% | KET962 | KET65 | None | None | Cromollient-SCE-LQ-(MH) | 100% Di-PPG2-Myreth-10-Adipate | None | None | None | 2 | 1 | — | 0 |
| Flunixin | 10% | KET963 | KET65 | None | None | Cromollient-SCE-LQ-(MH) | 100% Di-PPG2-Myreth-10-Adipate | None | None | None | 6 | 1 | 0.006 | 0.018 |
| Flunixin | 10% | KET964 | KET65 | None | None | Cromollient-SCE-LQ-(MH) | 100% Di-PPG2-Myreth-10-Adipate | None | None | None | 4 | 1 | — | 0 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Flunixin | 10% | KET965 | KET65 | None | None | Cromollient-SCE-LQ-(MH) | 100% Di-PPG2-Myreth-10-Adipate | None | None | None | 8 | 1 | 0.008 | 0.024 |
| Flunixin | 10% | KET966 | KET65 | None | None | Cromollient-SCE-LQ-(MH) | 100% Di-PPG2-Myreth-10-Adipate | None | None | None | 6 | 2 | 0.007 | 0.021 |
| Flunixin | 10% | KET967 | KET65 | None | None | Cromollient-SCE-LQ-(MH) | 100% Di-PPG2-Myreth-10-Adipate | None | None | None | 2 | 2 | — | 0 |
| Flunixin | 10% | KET968 | KET65 | None | None | Cromollient-SCE-LQ-(MH) | 100% Di-PPG2-Myreth-10-Adipate | None | None | None | 8 | 2 | 0.02 | 0.06 |
| Flunixin | 10% | KET969 | KET65 | None | None | Cromollient-SCE-LQ-(MH) | 100% Di-PPG2-Myreth-10-Adipate | None | None | None | 0.5 | 2 | — | 0 |
| Flunixin | 10% | KET970 | KET65 | None | None | Cromollient-SCE-LQ-(MH) | 100% Di-PPG2-Myreth-10-Adipate | None | None | None | 4 | 2 | 0.006 | 0.018 |
| Flunixin | 10% | KET971 | KET65 | None | None | Cromollient-SCE-LQ-(MH) | 100% Di-PPG2-Myreth-10-Adipate | None | None | None | 4 | 3 | 0.005 | 0.015 |
| Flunixin | 10% | KET972 | KET65 | None | None | Cromollient-SCE-LQ-(MH) | 100% Di-PPG2-Myreth-10-Adipate | None | None | None | 6 | 3 | 0.005 | 0.015 |
| Flunixin | 10% | KET973 | KET65 | None | None | Cromollient-SCE-LQ-(MH) | 100% Di-PPG2-Myreth-10-Adipate | None | None | None | 8 | 3 | 0.006 | 0.018 |
| Flunixin | 10% | KET974 | KET65 | None | None | Cromollient-SCE-LQ-(MH) | 100% Di-PPG2-Myreth-10-Adipate | None | None | None | 2 | 3 | — | 0 |
| Flunixin | 10% | KET975 | KET65 | None | None | Cromollient-SCE-LQ-(MH) | 100% Di-PPG2-Myreth-10-Adipate | None | None | None | 0.5 | 3 | — | 0 |
| Tolfenamic acid | 10% | KET976 | KET66 | Ethanol | 50% Ethanol | None | None | Eucalyptus oil | 21% 1,8-cineole | 0.1M citrate | 0.5 | 1 | 0.004 | 0.012 |
| Tolfenamic acid | 10% | KET977 | KET66 | Ethanol | 50% Ethanol | None | None | Eucalyptus oil | 21% 1,8-cineole | 0.1M citrate | 2 | 1 | 0.009 | 0.027 |
| Tolfenamic acid | 10% | KET978 | KET66 | Ethanol | 50% Ethanol | None | None | Eucalyptus oil | 21% 1,8-cineole | 0.1M citrate | 4 | 1 | 0.01 | 0.03 |
| Tolfenamic acid | 10% | KET979 | KET66 | Ethanol | 50% Ethanol | None | None | Eucalyptus oil | 21% 1,8-cineole | 0.1M citrate | 6 | 1 | 0.015 | 0.045 |
| Tolfenamic acid | 10% | KET980 | KET66 | Ethanol | 50% Ethanol | None | None | Eucalyptus oil | 21% 1,8-cineole | 0.1M citrate | 8 | 1 | 0.006 | 0.018 |
| Tolfenamic acid | 10% | KET981 | KET66 | Ethanol | 50% Ethanol | None | None | Eucalyptus oil | 21% 1,8-cineole | 0.1M citrate | 0.5 | 2 | — | 0 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Tolfenamic acid | 10% | KET982 | KET66 | Ethanol | 50% Ethanol | None | None | Eucalyptus oil | 21% 1,8-cineole | 0.1M citrate | 2 | 2 | 0.004 | 0.012 |
| Tolfenamic acid | 10% | KET983 | KET66 | Ethanol | 50% Ethanol | None | None | Eucalyptus oil | 21% 1,8-cineole | 0.1M citrate | 4 | 2 | 0.003 | 0.009 |
| Tolfenamic acid | 10% | KET984 | KET66 | Ethanol | 50% Ethanol | None | None | Eucalyptus oil | 21% 1,8-cineole | 0.1M citrate | 6 | 2 | 0.005 | 0.015 |
| Tolfenamic acid | 10% | KET985 | KET66 | Ethanol | 50% Ethanol | None | None | Eucalyptus oil | 21% 1,8-cineole | 0.1M citrate | 8 | 2 | 0.002 | 0.006 |
| Tolfenamic acid | 10% | KET986 | KET66 | Ethanol | 50% Ethanol | None | None | Eucalyptus oil | 21% 1,8-cineole | 0.1M citrate | 0.5 | 3 | 0.004 | 0.012 |
| Tolfenamic acid | 10% | KET987 | KET66 | Ethanol | 50% Ethanol | None | None | Eucalyptus oil | 21% 1,8-cineole | 0.1M citrate | 2 | 3 | 0.004 | 0.012 |
| Tolfenamic acid | 10% | KET988 | KET66 | Ethanol | 50% Ethanol | None | None | Eucalyptus oil | 21% 1,8-cineole | 0.1M citrate | 4 | 3 | 0.009 | 0.027 |
| Tolfenamic acid | 10% | KET989 | KET66 | Ethanol | 50% Ethanol | None | None | Eucalyptus oil | 21% 1,8-cineole | 0.1M citrate | 6 | 3 | 0.005 | 0.015 |
| Tolfenamic acid | 10% | KET990 | KET66 | Ethanol | 50% Ethanol | None | None | Eucalyptus oil | 21% 1,8-cineole | 0.1M citrate | 8 | 3 | 0.003 | 0.009 |
| Tolfenamic acid | 10% | KET991 | KET67 | None | None | None | None | Eucalyptus oil | 70% 1,8-cineole | None | 0.5 | 1 | 0.005 | 0.015 |
| Tolfenamic acid | 10% | KET992 | KET67 | None | None | None | None | Eucalyptus oil | 70% 1,8-cineole | None | 2 | 1 | 0.007 | 0.021 |
| Tolfenamic acid | 10% | KET993 | KET67 | None | None | None | None | Eucalyptus oil | 70% 1,8-cineole | None | 4 | 1 | 0.01 | 0.03 |
| Tolfenamic acid | 10% | KET994 | KET67 | None | None | None | None | Eucalyptus oil | 70% 1,8-cineole | None | 6 | 1 | 0.006 | 0.018 |
| Tolfenamic acid | 10% | KET995 | KET67 | None | None | None | None | Eucalyptus oil | 70% 1,8-cineole | None | 8 | 1 | 0.006 | 0.018 |
| Tolfenamic acid | 10% | KET996 | KET67 | None | None | None | None | Eucalyptus oil | 70% 1,8-cineole | None | 0.5 | 2 | — | 0 |
| Tolfenamic acid | 10% | KET997 | KET67 | None | None | None | None | Eucalyptus oil | 70% 1,8-cineole | None | 2 | 2 | 0.003 | 0.009 |
| Tolfenamic acid | 10% | KET998 | KET67 | None | None | None | None | Eucalyptus oil | 70% 1,8-cineole | None | 4 | 2 | 0.005 | 0.015 |
| Tolfenamic acid | 10% | KET999 | KET67 | None | None | None | None | Eucalyptus oil | 70% 1,8-cineole | None | 6 | 2 | 0.005 | 0.015 |
| Tolfenamic acid | 10% | KET1000 | KET67 | None | None | None | None | Eucalyptus oil | 70% 1,8-cineole | None | 8 | 2 | 0.005 | 0.015 |
| Tolfenamic acid | 10% | KET1001 | KET67 | None | None | None | None | Eucalyptus oil | 70% 1,8-cineole | None | 0.5 | 3 | 0.003 | 0.009 |
| Tolfenamic acid | 10% | KET1002 | KET67 | None | None | None | None | Eucalyptus oil | 70% 1,8-cineole | None | 2 | 3 | 0.002 | 0.006 |
| Tolfenamic acid | 10% | KET1003 | KET67 | None | None | None | None | Eucalyptus oil | 70% 1,8-cineole | None | 4 | 3 | 0.005 | 0.015 |
| Tolfenamic acid | 10% | KET1004 | KET67 | None | None | None | None | Eucalyptus oil | 70% 1,8-cineole | None | 6 | 3 | 0.008 | 0.024 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Tolfenamic acid | 10% | KET1005 | KET67 | None | None | None | None | Eucalyptus oil | 70% 1,8-cineole | None | 8 | 3 | 0.004 | 0.012 |
| Tolfenamic acid | 10% | KET1006 | KET68 | None | None | Propylene glycol | 100% PPG | None | None | None | 0.5 | 1 | 0.002 | 0.006 |
| Tolfenamic acid | 10% | KET1007 | KET68 | None | None | Propylene glycol | 100% PPG | None | None | None | 2 | 1 | 0.005 | 0.015 |
| Tolfenamic acid | 10% | KET1008 | KET68 | None | None | Propylene glycol | 100% PPG | None | None | None | 4 | 1 | 0.007 | 0.021 |
| Tolfenamic acid | 10% | KET1009 | KET68 | None | None | Propylene glycol | 100% PPG | None | None | None | 6 | 1 | — | 0 |
| Tolfenamic acid | 10% | KET1010 | KET68 | None | None | Propylene glycol | 100% PPG | None | None | None | 8 | 1 | 0.002 | 0.006 |
| Tolfenamic acid | 10% | KET1011 | KET68 | None | None | Propylene glycol | 100% PPG | None | None | None | 0.5 | 2 | — | 0 |
| Tolfenamic acid | 10% | KET1012 | KET68 | None | None | Propylene glycol | 100% PPG | None | None | None | 2 | 2 | 0.002 | 0.006 |
| Tolfenamic acid | 10% | KET1013 | KET68 | None | None | Propylene glycol | 100% PPG | None | None | None | 4 | 2 | 0.004 | 0.012 |
| Tolfenamic acid | 10% | KET1014 | KET68 | None | None | Propylene glycol | 100% PPG | None | None | None | 6 | 2 | 0.002 | 0.006 |
| Tolfenamic acid | 10% | KET1015 | KET68 | None | None | Propylene glycol | 100% PPG | None | None | None | 8 | 2 | 0.005 | 0.015 |
| Tolfenamic acid | 10% | KET1016 | KET68 | None | None | Propylene glycol | 100% PPG | None | None | None | 0.5 | 3 | 0.005 | 0.015 |
| Tolfenamic acid | 10% | KET1017 | KET68 | None | None | Propylene glycol | 100% PPG | None | None | None | 2 | 3 | 0.012 | 0.036 |
| Tolfenamic acid | 10% | KET1018 | KET68 | None | None | Propylene glycol | 100% PPG | None | None | None | 4 | 3 | 0.006 | 0.018 |
| Tolfenamic acid | 10% | KET1019 | KET68 | None | None | Propylene glycol | 100% PPG | None | None | None | 6 | 3 | 0.008 | 0.024 |
| Tolfenamic acid | 10% | KET1020 | KET68 | None | None | Propylene glycol | 100% PPG | None | None | None | 8 | 3 | 0.002 | 0.006 |
| Tolfenamic acid | 10% | KET1021 | KET69 | None | None | Crodamol-STS-LQ | 100% PPG-3 Benzyl ether myristate | None | None | None | 0.5 | 1 | — | 0 |
| Tolfenamic acid | 10% | KET1022 | KET69 | None | None | Crodamol-STS-LQ | 100% PPG-3 Benzyl ether myristate | None | None | None | 2 | 1 | — | 0 |
| Tolfenamic acid | 10% | KET1023 | KET69 | None | None | Crodamol-STS-LQ | 100% PPG-3 Benzyl ether myristate | None | None | None | 4 | 1 | 0.006 | 0.018 |
| Tolfenamic acid | 10% | KET1024 | KET69 | None | None | Crodamol-STS-LQ | 100% PPG-3 Benzyl ether myristate | None | None | None | 6 | 1 | 0.016 | 0.048 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Tolfenamic acid | 10% | KET1025 | KET69 | None | None | Crodamol-STS-LQ | 100% PPG-3 Benzyl ether myristate | None | None | None | 8 | 1 | 0.012 | 0.036 |
| Tolfenamic acid | 10% | KET1026 | KET69 | None | None | Crodamol-STS-LQ | 100% PPG-3 Benzyl ether myristate | None | None | None | 0.5 | 2 | 0.01 | 0.03 |
| Tolfenamic acid | 10% | KET1027 | KET69 | None | None | Crodamol-STS-LQ | 100% PPG-3 Benzyl ether myristate | None | None | None | 2 | 2 | 0.017 | 0.051 |
| Tolfenamic acid | 10% | KET1028 | KET69 | None | None | Crodamol-STS-LQ | 100% PPG-3 Benzyl ether myristate | None | None | None | 4 | 2 | 0.004 | 0.012 |
| Tolfenamic acid | 10% | KET1029 | KET69 | None | None | Crodamol-STS-LQ | 100% PPG-3 Benzyl ether myristate | None | None | None | 6 | 2 | 0.005 | 0.015 |
| Tolfenamic acid | 10% | KET1030 | KET69 | None | None | Crodamol-STS-LQ | 100% PPG-3 Benzyl ether myristate | None | None | None | 8 | 2 | 0.003 | 0.009 |
| Tolfenamic acid | 10% | KET1031 | KET69 | None | None | Crodamol-STS-LQ | 100% PPG-3 Benzyl ether myristate | None | None | None | 0.5 | 3 | 0.003 | 0.009 |
| Tolfenamic acid | 10% | KET1032 | KET69 | None | None | Crodamol-STS-LQ | 100% PPG-3 Benzyl ether myristate | None | None | None | 2 | 3 | 0.002 | 0.006 |
| Tolfenamic acid | 10% | KET1033 | KET69 | None | None | Crodamol-STS-LQ | 100% PPG-3 Benzyl ether myristate | None | None | None | 4 | 3 | 0.005 | 0.015 |
| Tolfenamic acid | 10% | KET1034 | KET69 | None | None | Crodamol-STS-LQ | 100% PPG-3 Benzyl ether myristate | None | None | None | 6 | 3 | 0.003 | 0.009 |
| Tolfenamic acid | 10% | KET1035 | KET69 | None | None | Crodamol-STS-LQ | 100% PPG-3 Benzyl ether myristate | None | None | None | 8 | 3 | 0.003 | 0.009 |
| Tolfenamic acid | 10% | KET1036 | KET70 | None | None | Cromollient-SCE-LQ-(MH) | 100% Di-PPG2-Myreth-10-Adipate | None | None | None | 0.5 | 1 | 0.007 | 0.021 |
| Tolfenamic acid | 10% | KET1037 | KET70 | None | None | Cromollient-SCE-LQ-(MH) | 100% Di-PPG2-Myreth-10-Adipate | None | None | None | 2 | 1 | 0.003 | 0.009 |
| Tolfenamic acid | 10% | KET1038 | KET70 | None | None | Cromollient-SCE-LQ-(MH) | 100% Di-PPG2-Myreth-10-Adipate | None | None | None | 4 | 1 | 0.008 | 0.024 |
| Tolfenamic acid | 10% | KET1039 | KET70 | None | None | Cromollient-SCE-LQ-(MH) | 100% Di-PPG2-Myreth-10-Adipate | None | None | None | 6 | 1 | 0.004 | 0.012 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/EVAP | sample time (hrs) | Replicate | analysis conc | Concentration (μg/mL) |
|---|---|---|---|---|---|---|---|---|---|---|---|---|---|---|
| Tolfenamic acid | 10% | KET1040 | KET70 | None | None | Cromollient-SCE-LQ-(MH) | 100% Di-PPG2-Myreth-10-Adipate | None | None | None | 8 | 1 | — | 0 |
| Tolfenamic acid | 10% | KET1041 | KET70 | None | None | Cromollient-SCE-LQ-(MH) | 100% Di-PPG2-Myreth-10-Adipate | None | None | None | 0.5 | 2 | 0.004 | 0.012 |
| Tolfenamic acid | 10% | KET1042 | KET70 | None | None | Cromollient-SCE-LQ-(MH) | 100% Di-PPG2-Myreth-10-Adipate | None | None | None | 2 | 2 | 0.009 | 0.027 |
| Tolfenamic acid | 10% | KET1043 | KET70 | None | None | Cromollient-SCE-LQ-(MH) | 100% Di-PPG2-Myreth-10-Adipate | None | None | None | 4 | 2 | 0.006 | 0.018 |
| Tolfenamic acid | 10% | KET1044 | KET70 | None | None | Cromollient-SCE-LQ-(MH) | 100% Di-PPG2-Myreth-10-Adipate | None | None | None | 6 | 2 | 0.012 | 0.036 |
| Tolfenamic acid | 10% | KET1045 | KET70 | None | None | Cromollient-SCE-LQ-(MH) | 100% Di-PPG2-Myreth-10-Adipate | None | None | None | 8 | 2 | 0.008 | 0.024 |
| Tolfenamic acid | 10% | KET1046 | KET70 | None | None | Cromollient-SCE-LQ-(MH) | 100% Di-PPG2-Myreth-10-Adipate | None | None | None | 0.5 | 3 | — | 0 |
| Tolfenamic acid | 10% | KET1047 | KET70 | None | None | Cromollient-SCE-LQ-(MH) | 100% Di-PPG2-Myreth-10-Adipate | None | None | None | 2 | 3 | 0.003 | 0.009 |
| Tolfenamic acid | 10% | KET1048 | KET70 | None | None | Cromollient-SCE-LQ-(MH) | 100% Di-PPG2-Myreth-10-Adipate | None | None | None | 4 | 3 | 0.005 | 0.015 |
| Tolfenamic acid | 10% | KET1049 | KET70 | None | None | Cromollient-SCE-LQ-(MH) | 100% Di-PPG2-Myreth-10-Adipate | None | None | None | 6 | 3 | 0.003 | 0.009 |
| Tolfenamic acid | 10% | KET1050 | KET70 | None | None | Cromollient-SCE-LQ-(MH) | 100% Di-PPG2-Myreth-10-Adipate | None | None | None | 8 | 3 | 0.002 | 0.006 |
| Ketoprofen | 10% | KET1051 | KET71 | Ethanol | 50% EtOH | 1-Ethyl-2-Pyrrolidone | 45% EP | Menthol | 50 ng/mL | None | 0.5 | 1 | 0.029 | 0.087 |
| Ketoprofen | 10% | KET1052 | KET71 | Ethanol | 50% EtOH | 1-Ethyl-2-Pyrrolidone | 45% EP | Menthol | 50 ng/mL | None | 2 | 1 | 0.033 | 0.099 |
| Ketoprofen | 10% | KET1053 | KET71 | Ethanol | 50% EtOH | 1-Ethyl-2-Pyrrolidone | 45% EP | Menthol | 50 ng/mL | None | 4 | 1 | 0.007 | 0.021 |
| Ketoprofen | 10% | KET1054 | KET71 | Ethanol | 50% EtOH | 1-Ethyl-2-Pyrrolidone | 45% EP | Menthol | 50 ng/mL | None | 6 | 1 | 0.013 | 0.039 |
| Ketoprofen | 10% | KET1055 | KET71 | Ethanol | 50% EtOH | 1-Ethyl-2-Pyrrolidone | 45% EP | Menthol | 50 ng/mL | None | 8 | 1 | 0.024 | 0.072 |
| Ketoprofen | 10% | KET1056 | KET71 | Ethanol | 50% EtOH | 1-Ethyl-2-Pyrrolidone | 45% EP | Menthol | 50 ng/mL | None | 0.5 | 2 | 0.025 | 0.075 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 10% | KET1057 | KET71 | Ethanol | 50% EtOH | 1-Ethyl-2-Pyrrolidone | 45% EP | Menthol | 50 ng/mL | None | 2 | 2 | 0.023 | 0.069 |
| Ketoprofen | 10% | KET1058 | KET71 | Ethanol | 50% EtOH | 1-Ethyl-2-Pyrrolidone | 45% EP | Menthol | 50 ng/mL | None | 4 | 2 | 0.007 | 0.021 |
| Ketoprofen | 10% | KET1059 | KET71 | Ethanol | 50% EtOH | 1-Ethyl-2-Pyrrolidone | 45% EP | Menthol | 50 ng/mL | None | 6 | 2 | 0.007 | 0.021 |
| Ketoprofen | 10% | KET1060 | KET71 | Ethanol | 50% EtOH | 1-Ethyl-2-Pyrrolidone | 45% EP | Menthol | 50 ng/mL | None | 8 | 2 | 0.01 | 0.03 |
| Ketoprofen | 10% | KET1061 | KET71 | Ethanol | 50% EtOH | 1-Ethyl-2-Pyrrolidone | 45% EP | Menthol | 50 ng/mL | None | 0.5 | 3 | 0.022 | 0.066 |
| Ketoprofen | 10% | KET1062 | KET71 | Ethanol | 50% EtOH | 1-Ethyl-2-Pyrrolidone | 45% EP | Menthol | 50 ng/mL | None | 2 | 3 | 0.057 | 0.171 |
| Ketoprofen | 10% | KET1063 | KET71 | Ethanol | 50% EtOH | 1-Ethyl-2-Pyrrolidone | 45% EP | Menthol | 50 ng/mL | None | 4 | 3 | 0.016 | 0.048 |
| Ketoprofen | 10% | KET1064 | KET71 | Ethanol | 50% EtOH | 1-Ethyl-2-Pyrrolidone | 45% EP | Menthol | 50 ng/mL | None | 6 | 3 | 0.011 | 0.033 |
| Ketoprofen | 10% | KET1065 | KET71 | Ethanol | 50% EtOH | 1-Ethyl-2-Pyrrolidone | 45% EP | Menthol | 50 ng/mL | None | 8 | 3 | 0.059 | 0.177 |
| Ketoprofen | 10% | KET1066 | KET72 | Ethanol | 50% EtOH | Propylene glycol | 45% PPG | Menthol | 50 ng/mL | None | 0.5 | 1 | 0.009 | 0.027 |
| Ketoprofen | 10% | KET1067 | KET72 | Ethanol | 50% EtOH | Propylene glycol | 45% PPG | Menthol | 50 ng/mL | None | 2 | 1 | 0.007 | 0.021 |
| Ketoprofen | 10% | KET1068 | KET72 | Ethanol | 50% EtOH | Propylene glycol | 45% PPG | Menthol | 50 ng/mL | None | 4 | 1 | 0.017 | 0.051 |
| Ketoprofen | 10% | KET1069 | KET72 | Ethanol | 50% EtOH | Propylene glycol | 45% PPG | Menthol | 50 ng/mL | None | 6 | 1 | 0.034 | 0.102 |
| Ketoprofen | 10% | KET1070 | KET72 | Ethanol | 50% EtOH | Propylene glycol | 45% PPG | Menthol | 50 ng/mL | None | 8 | 1 | 0.033 | 0.099 |
| Ketoprofen | 10% | KET1071 | KET72 | Ethanol | 50% EtOH | Propylene glycol | 45% PPG | Menthol | 50 ng/mL | None | 0.5 | 2 | 0.013 | 0.039 |
| Ketoprofen | 10% | KET1072 | KET72 | Ethanol | 50% EtOH | Propylene glycol | 45% PPG | Menthol | 50 ng/mL | None | 2 | 2 | 0.045 | 0.135 |
| Ketoprofen | 10% | KET1073 | KET72 | Ethanol | 50% EtOH | Propylene glycol | 45% PPG | Menthol | 50 ng/mL | None | 4 | 2 | 0.047 | 0.141 |
| Ketoprofen | 10% | KET1074 | KET72 | Ethanol | 50% EtOH | Propylene glycol | 45% PPG | Menthol | 50 ng/mL | None | 6 | 2 | 0.053 | 0.159 |
| Ketoprofen | 10% | KET1075 | KET72 | Ethanol | 50% EtOH | Propylene glycol | 45% PPG | Menthol | 50 ng/mL | None | 8 | 2 | 0.086 | 0.258 |
| Ketoprofen | 10% | KET1076 | KET72 | Ethanol | 50% EtOH | Propylene glycol | 45% PPG | Menthol | 50 ng/mL | None | 0.5 | 3 | 0.017 | 0.051 |
| Ketoprofen | 10% | KET1077 | KET72 | Ethanol | 50% EtOH | Propylene glycol | 45% PPG | Menthol | 50 ng/mL | None | 2 | 3 | 0.075 | 0.225 |
| Ketoprofen | 10% | KET1078 | KET72 | Ethanol | 50% EtOH | Propylene glycol | 45% PPG | Menthol | 50 ng/mL | None | 4 | 3 | 0.083 | 0.249 |
| Ketoprofen | 10% | KET1079 | KET72 | Ethanol | 50% EtOH | Propylene glycol | 45% PPG | Menthol | 50 ng/mL | None | 6 | 3 | 0.089 | 0.267 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET1080 | KET72 | Ethanol | 50% EtOH | Propylene glycol | 45% PPG | Menthol | 50 ng/mL | None | 8 | 3 | 0.107 | 0.321 |
| Ketoprofen | 10% | KET1081 | KET73 | Ethanol | 50% EtOH | Isomyristate | 45% ISOMYR | Menthol | 50 ng/mL | None | 0.5 | 1 | 0.035 | 0.105 |
| Ketoprofen | 10% | KET1082 | KET73 | Ethanol | 50% EtOH | Isomyristate | 45% ISOMYR | Menthol | 50 ng/mL | None | 2 | 1 | 0.042 | 0.126 |
| Ketoprofen | 10% | KET1083 | KET73 | Ethanol | 50% EtOH | Isomyristate | 45% ISOMYR | Menthol | 50 ng/mL | None | 4 | 1 | 0.04 | 0.12 |
| Ketoprofen | 10% | KET1084 | KET73 | Ethanol | 50% EtOH | Isomyristate | 45% ISOMYR | Menthol | 50 ng/mL | None | 6 | 1 | 0.051 | 0.153 |
| Ketoprofen | 10% | KET1085 | KET73 | Ethanol | 50% EtOH | Isomyristate | 45% ISOMYR | Menthol | 50 ng/mL | None | 8 | 1 | 0.048 | 0.144 |
| Ketoprofen | 10% | KET1086 | KET73 | Ethanol | 50% EtOH | Isomyristate | 45% ISOMYR | Menthol | 50 ng/mL | None | 0.5 | 2 | 0.029 | 0.087 |
| Ketoprofen | 10% | KET1087 | KET73 | Ethanol | 50% EtOH | Isomyristate | 45% ISOMYR | Menthol | 50 ng/mL | None | 2 | 2 | 0.024 | 0.072 |
| Ketoprofen | 10% | KET1088 | KET73 | Ethanol | 50% EtOH | Isomyristate | 45% ISOMYR | Menthol | 50 ng/mL | None | 4 | 2 | 0.032 | 0.096 |
| Ketoprofen | 10% | KET1089 | KET73 | Ethanol | 50% EtOH | Isomyristate | 45% ISOMYR | Menthol | 50 ng/mL | None | 6 | 2 | 0.034 | 0.102 |
| Ketoprofen | 10% | KET1090 | KET73 | Ethanol | 50% EtOH | Isomyristate | 45% ISOMYR | Menthol | 50 ng/mL | None | 8 | 2 | 0.062 | 0.186 |
| Ketoprofen | 10% | KET1091 | KET73 | Ethanol | 50% EtOH | Isomyristate | 45% ISOMYR | Menthol | 50 ng/mL | None | 0.5 | 3 | 0.018 | 0.054 |
| Ketoprofen | 10% | KET1092 | KET73 | Ethanol | 50% EtOH | Isomyristate | 45% ISOMYR | Menthol | 50 ng/mL | None | 2 | 3 | 0.025 | 0.075 |
| Ketoprofen | 10% | KET1093 | KET73 | Ethanol | 50% EtOH | Isomyristate | 45% ISOMYR | Menthol | 50 ng/mL | None | 4 | 3 | 0.025 | 0.075 |
| Ketoprofen | 10% | KET1094 | KET73 | Ethanol | 50% EtOH | Isomyristate | 45% ISOMYR | Menthol | 50 ng/mL | None | 6 | 3 | 0.057 | 0.171 |
| Ketoprofen | 10% | KET1095 | KET73 | Ethanol | 50% EtOH | Isomyristate | 45% ISOMYR | Menthol | 50 ng/mL | None | 8 | 3 | 0.874 | 2.622 |
| Ketoprofen | 10% | KET1096 | KET74 | Ethanol | 50% EtOH | Oleyl alcohol | 45% OA | Menthol | 50 ng/mL | None | 0.5 | 1 | 0.006 | 0.018 |
| Ketoprofen | 10% | KET1097 | KET74 | Ethanol | 50% EtOH | Oleyl alcohol | 45% OA | Menthol | 50 ng/mL | None | 2 | 1 | 0.026 | 0.078 |
| Ketoprofen | 10% | KET1098 | KET74 | Ethanol | 50% EtOH | Oleyl alcohol | 45% OA | Menthol | 50 ng/mL | None | 4 | 1 | 0.032 | 0.096 |
| Ketoprofen | 10% | KET1099 | KET74 | Ethanol | 50% EtOH | Oleyl alcohol | 45% OA | Menthol | 50 ng/mL | None | 6 | 1 | 0.031 | 0.093 |
| Ketoprofen | 10% | KET1100 | KET74 | Ethanol | 50% EtOH | Oleyl alcohol | 45% OA | Menthol | 50 ng/mL | None | 8 | 1 | 0.037 | 0.111 |
| Ketoprofen | 10% | KET1101 | KET74 | Ethanol | 50% EtOH | Oleyl alcohol | 45% OA | Menthol | 50 ng/mL | None | 0.5 | 2 | 0.025 | 0.075 |
| Ketoprofen | 10% | KET1102 | KET74 | Ethanol | 50% EtOH | Oleyl alcohol | 45% OA | Menthol | 50 ng/mL | None | 2 | 2 | 0.029 | 0.087 |
| Ketoprofen | 10% | KET1103 | KET74 | Ethanol | 50% EtOH | Oleyl alcohol | 45% OA | Menthol | 50 ng/mL | None | 4 | 2 | 0.033 | 0.099 |
| Ketoprofen | 10% | KET1104 | KET74 | Ethanol | 50% EtOH | Oleyl alcohol | 45% OA | Menthol | 50 ng/mL | None | 6 | 2 | 0.038 | 0.114 |
| Ketoprofen | 10% | KET1105 | KET74 | Ethanol | 50% EtOH | Oleyl alcohol | 45% OA | Menthol | 50 ng/mL | None | 8 | 2 | 0.057 | 0.171 |
| Ketoprofen | 10% | KET1106 | KET74 | Ethanol | 50% EtOH | Oleyl alcohol | 45% OA | Menthol | 50 ng/mL | None | 0.5 | 3 | 0.015 | 0.045 |
| Ketoprofen | 10% | KET1107 | KET74 | Ethanol | 50% EtOH | Oleyl alcohol | 45% OA | Menthol | 50 ng/mL | None | 2 | 3 | 0.018 | 0.054 |
| Ketoprofen | 10% | KET1108 | KET74 | Ethanol | 50% EtOH | Oleyl alcohol | 45% OA | Menthol | 50 ng/mL | None | 4 | 3 | 0.54 | 1.62 |
| Ketoprofen | 10% | KET1109 | KET74 | Ethanol | 50% EtOH | Oleyl alcohol | 45% OA | Menthol | 50 ng/mL | None | 6 | 3 | 1.309 | 3.927 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Rep- licate | analysis conc | Concen- tration (µg/mL) |
|---|---|---|---|---|---|---|---|---|---|---|---|---|---|---|
| Ketoprofen | 10% | KET1110 | KET74 | Ethanol | 50% EthOH | Oleyl alcohol | 45% OA | Menthol | 50 ng/mL | None | 8 | 3 | 3.433 | 10.299 |
| Ketoprofen | 10% | KET1111 | KET75 | Isopronanol | 50% IPN | Oleyl alcohol | 45% OA | Menthol | 50 ng/mL | None | 0.5 | 1 | 0.015 | 0.045 |
| Ketoprofen | 10% | KET1112 | KET75 | Isopronanol | 50% IPN | Oleyl alcohol | 45% OA | Menthol | 50 ng/mL | None | 2 | 1 | 0.033 | 0.099 |
| Ketoprofen | 10% | KET1113 | KET75 | Isopronanol | 50% IPN | Oleyl alcohol | 45% OA | Menthol | 50 ng/mL | None | 4 | 1 | 0.033 | 0.099 |
| Ketoprofen | 10% | KET1114 | KET75 | Isopronanol | 50% IPN | Oleyl alcohol | 45% OA | Menthol | 50 ng/mL | None | 6 | 1 | 0.052 | 0.156 |
| Ketoprofen | 10% | KET1115 | KET75 | Isopronanol | 50% IPN | Oleyl alcohol | 45% OA | Menthol | 50 ng/mL | None | 8 | 1 | 0.051 | 0.153 |
| Ketoprofen | 10% | KET1116 | KET75 | Isopronanol | 50% IPN | Oleyl alcohol | 45% OA | Menthol | 50 ng/mL | None | 0.5 | 2 | 0.041 | 0.123 |
| Ketoprofen | 10% | KET1117 | KET75 | Isopronanol | 50% IPN | Oleyl alcohol | 45% OA | Menthol | 50 ng/mL | None | 2 | 2 | 0.037 | 0.111 |
| Ketoprofen | 10% | KET1118 | KET75 | Isopronanol | 50% IPN | Oleyl alcohol | 45% OA | Menthol | 50 ng/mL | None | 4 | 2 | 0.037 | 0.111 |
| Ketoprofen | 10% | KET1119 | KET75 | Isopronanol | 50% IPN | Oleyl alcohol | 45% OA | Menthol | 50 ng/mL | None | 6 | 2 | 0.042 | 0.126 |
| Ketoprofen | 10% | KET1120 | KET75 | Isopronanol | 50% IPN | Oleyl alcohol | 45% OA | Menthol | 50 ng/mL | None | 8 | 2 | 0.041 | 0.123 |
| Ketoprofen | 10% | KET1121 | KET75 | Isopronanol | 50% IPN | Oleyl alcohol | 45% OA | Menthol | 50 ng/mL | None | 0.5 | 3 | 0.036 | 0.108 |
| Ketoprofen | 10% | KET1122 | KET75 | Isopronanol | 50% IPN | Oleyl alcohol | 45% OA | Menthol | 50 ng/mL | None | 2 | 3 | 0.032 | 0.096 |
| Ketoprofen | 10% | KET1123 | KET75 | Isopronanol | 50% IPN | Oleyl alcohol | 45% OA | Menthol | 50 ng/mL | None | 4 | 3 | 0.062 | 0.186 |
| Ketoprofen | 10% | KET1124 | KET75 | Isopronanol | 50% IPN | Oleyl alcohol | 45% OA | Menthol | 50 ng/mL | None | 6 | 3 | 0.159 | 0.477 |
| Ketoprofen | 10% | KET1125 | KET75 | Isopronanol | 50% IPN | Oleyl alcohol | 45% OA | Menthol | 50 ng/mL | None | 8 | 3 | 0.315 | 0.945 |
| Ketoprofen | 10% | KET1126 | KET76 | Ethanol | 50% EthOH | 1-Ethyl-2-Pyrrolidone | 45% EP | Eucalyptus oil | 3.5% 1,8-cineole | None | 0.5 | 1 | 0.033 | 0.099 |
| Ketoprofen | 10% | KET1127 | KET76 | Ethanol | 50% EthOH | 1-Ethyl-2-Pyrrolidone | 45% EP | Eucalyptus oil | 3.5% 1,8-cineole | None | 2 | 1 | 0.038 | 0.114 |
| Ketoprofen | 10% | KET1128 | KET76 | Ethanol | 50% EthOH | 1-Ethyl-2-Pyrrolidone | 45% EP | Eucalyptus oil | 3.5% 1,8-cineole | None | 4 | 1 | 0.044 | 0.132 |
| Ketoprofen | 10% | KET1129 | KET76 | Ethanol | 50% EthOH | 1-Ethyl-2-Pyrrolidone | 45% EP | Eucalyptus oil | 3.5% 1,8-cineole | None | 6 | 1 | 0.241 | 0.723 |
| Ketoprofen | 10% | KET1130 | KET76 | Ethanol | 50% EthOH | 1-Ethyl-2-Pyrrolidone | 45% EP | Eucalyptus oil | 3.5% 1,8-cineole | None | 8 | 1 | 0.597 | 1.791 |
| Ketoprofen | 10% | KET1131 | KET76 | Ethanol | 50% EthOH | 1-Ethyl-2-Pyrrolidone | 45% EP | Eucalyptus oil | 3.5% 1,8-cineole | None | 0.5 | 2 | 0.021 | 0.063 |
| Ketoprofen | 10% | KET1132 | KET76 | Ethanol | 50% EthOH | 1-Ethyl-2-Pyrrolidone | 45% EP | Eucalyptus oil | 3.5% 1,8-cineole | None | 2 | 2 | 0.072 | 0.216 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 10% | KET1133 | KET76 | Ethanol | 50% EtOH | 1-Ethyl-2-Pyrrolidone | 45% EP | Eucalyptus oil | 3.5% 1,8-cineole | None | 4 | 2 | 0.09 | 0.27 |
| Ketoprofen | 10% | KET1134 | KET76 | Ethanol | 50% EtOH | 1-Ethyl-2-Pyrrolidone | 45% EP | Eucalyptus oil | 3.5% 1,8-cineole | None | 6 | 2 | 0.092 | 0.276 |
| Ketoprofen | 10% | KET1135 | KET76 | Ethanol | 50% EtOH | 1-Ethyl-2-Pyrrolidone | 45% EP | Eucalyptus oil | 3.5% 1,8-cineole | None | 8 | 2 | 0.099 | 0.297 |
| Ketoprofen | 10% | KET1136 | KET76 | Ethanol | 50% EtOH | 1-Ethyl-2-Pyrrolidone | 45% EP | Eucalyptus oil | 3.5% 1,8-cineole | None | 0.5 | 3 | 0.041 | 0.123 |
| Ketoprofen | 10% | KET1137 | KET76 | Ethanol | 50% EtOH | 1-Ethyl-2-Pyrrolidone | 45% EP | Eucalyptus oil | 3.5% 1,8-cineole | None | 2 | 3 | 0.034 | 0.102 |
| Ketoprofen | 10% | KET1138 | KET76 | Ethanol | 50% EtOH | 1-Ethyl-2-Pyrrolidone | 45% EP | Eucalyptus oil | 3.5% 1,8-cineole | None | 4 | 3 | 0.679 | 2.037 |
| Ketoprofen | 10% | KET1139 | KET76 | Ethanol | 50% EtOH | 1-Ethyl-2-Pyrrolidone | 45% EP | Eucalyptus oil | 3.5% 1,8-cineole | None | 6 | 3 | 4.982 | 14.946 |
| Ketoprofen | 10% | KET1140 | KET76 | Ethanol | 50% EtOH | 1-Ethyl-2-Pyrrolidone | 45% EP | Eucalyptus oil | 3.5% 1,8-cineole | None | 8 | 3 | 10.669 | 32.007 |
| Ketoprofen | 10% | KET1141 | KET77 | Ethanol | 50% EtOH | Propylene glycol | 45% PPG | Eucalyptus oil | 3.5% 1,8-cineole | None | 0.5 | 1 | 0.085 | 0.255 |
| Ketoprofen | 10% | KET1142 | KET77 | Ethanol | 50% EtOH | Propylene glycol | 45% PPG | Eucalyptus oil | 3.5% 1,8-cineole | None | 2 | 1 | 0.1 | 0.3 |
| Ketoprofen | 10% | KET1143 | KET77 | Ethanol | 50% EtOH | Propylene glycol | 45% PPG | Eucalyptus oil | 3.5% 1,8-cineole | None | 4 | 1 | 0.12 | 0.36 |
| Ketoprofen | 10% | KET1144 | KET77 | Ethanol | 50% EtOH | Propylene glycol | 45% PPG | Eucalyptus oil | 3.5% 1,8-cineole | None | 6 | 1 | 0.069 | 0.207 |
| Ketoprofen | 10% | KET1145 | KET77 | Ethanol | 50% EtOH | Propylene glycol | 45% PPG | Eucalyptus oil | 3.5% 1,8-cineole | None | 8 | 1 | 0.085 | 0.255 |
| Ketoprofen | 10% | KET1146 | KET77 | Ethanol | 50% EtOH | Propylene glycol | 45% PPG | Eucalyptus oil | 3.5% 1,8-cineole | None | 0.5 | 2 | 0.008 | 0.024 |
| Ketoprofen | 10% | KET1147 | KET77 | Ethanol | 50% EtOH | Propylene glycol | 45% PPG | Eucalyptus oil | 3.5% 1,8-cineole | None | 2 | 2 | 0.046 | 0.138 |
| Ketoprofen | 10% | KET1148 | KET77 | Ethanol | 50% EtOH | Propylene glycol | 45% PPG | Eucalyptus oil | 3.5% 1,8-cineole | None | 4 | 2 | 1.005 | 3.015 |
| Ketoprofen | 10% | KET1149 | KET77 | Ethanol | 50% EtOH | Propylene glycol | 45% PPG | Eucalyptus oil | 3.5% 1,8-cineole | None | 6 | 2 | 4.796 | 14.388 |
| Ketoprofen | 10% | KET1150 | KET77 | Ethanol | 50% EtOH | Propylene glycol | 45% PPG | Eucalyptus oil | 3.5% 1,8-cineole | None | 8 | 2 | 7.932 | 23.796 |
| Ketoprofen | 10% | KET1151 | KET77 | Ethanol | 50% EtOH | Propylene glycol | 45% PPG | Eucalyptus oil | 3.5% 1,8-cineole | None | 0.5 | 3 | 0.074 | 0.222 |
| Ketoprofen | 10% | KET1152 | KET77 | Ethanol | 50% EtOH | Propylene glycol | 45% PPG | Eucalyptus oil | 3.5% 1,8-cineole | None | 2 | 3 | 0.076 | 0.228 |
| Ketoprofen | 10% | KET1153 | KET77 | Ethanol | 50% EtOH | Propylene glycol | 45% PPG | Eucalyptus oil | 3.5% 1,8-cineole | None | 4 | 3 | 0.14 | 0.42 |
| Ketoprofen | 10% | KET1154 | KET77 | Ethanol | 50% EtOH | Propylene glycol | 45% PPG | Eucalyptus oil | 3.5% 1,8-cineole | None | 6 | 3 | 0.949 | 2.847 |
| Ketoprofen | 10% | KET1155 | KET77 | Ethanol | 50% EtOH | Propylene glycol | 45% PPG | Eucalyptus oil | 3.5% 1,8-cineole | None | 8 | 3 | 2.319 | 6.957 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET1156 | KET78 | Ethanol | 50% EtOH | Isomyristate | 45% ISOMYR | Eucalyptus oil | 3.5% 1,8-cineole | None | 0.5 | 1 | 0.052 | 0.156 |
| Ketoprofen | 10% | KET1157 | KET78 | Ethanol | 50% EtOH | Isomyristate | 45% ISOMYR | Eucalyptus oil | 3.5% 1,8-cineole | None | 2 | 1 | 0.044 | 0.132 |
| Ketoprofen | 10% | KET1158 | KET78 | Ethanol | 50% EtOH | Isomyristate | 45% ISOMYR | Eucalyptus oil | 3.5% 1,8-cineole | None | 4 | 1 | 0.015 | 0.045 |
| Ketoprofen | 10% | KET1159 | KET78 | Ethanol | 50% EtOH | Isomyristate | 45% ISOMYR | Eucalyptus oil | 3.5% 1,8-cineole | None | 6 | 1 | 0.378 | 1.134 |
| Ketoprofen | 10% | KET1160 | KET78 | Ethanol | 50% EtOH | Isomyristate | 45% ISOMYR | Eucalyptus oil | 3.5% 1,8-cineole | None | 8 | 1 | 1.624 | 4.872 |
| Ketoprofen | 10% | KET1161 | KET78 | Ethanol | 50% EtOH | Isomyristate | 45% ISOMYR | Eucalyptus oil | 3.5% 1,8-cineole | None | 0.5 | 2 | 0.014 | 0.042 |
| Ketoprofen | 10% | KET1162 | KET78 | Ethanol | 50% EtOH | Isomyristate | 45% ISOMYR | Eucalyptus oil | 3.5% 1,8-cineole | None | 2 | 2 | 0.016 | 0.048 |
| Ketoprofen | 10% | KET1163 | KET78 | Ethanol | 50% EtOH | Isomyristate | 45% ISOMYR | Eucalyptus oil | 3.5% 1,8-cineole | None | 4 | 2 | 0.039 | 0.117 |
| Ketoprofen | 10% | KET1164 | KET78 | Ethanol | 50% EtOH | Isomyristate | 45% ISOMYR | Eucalyptus oil | 3.5% 1,8-cineole | None | 6 | 2 | 0.053 | 0.159 |
| Ketoprofen | 10% | KET1165 | KET78 | Ethanol | 50% EtOH | Isomyristate | 45% ISOMYR | Eucalyptus oil | 3.5% 1,8-cineole | None | 8 | 2 | 0.367 | 1.101 |
| Ketoprofen | 10% | KET1166 | KET78 | Ethanol | 50% EtOH | Isomyristate | 45% ISOMYR | Eucalyptus oil | 3.5% 1,8-cineole | None | 0.5 | 3 | 0.054 | 0.162 |
| Ketoprofen | 10% | KET1167 | KET78 | Ethanol | 50% EtOH | Isomyristate | 45% ISOMYR | Eucalyptus oil | 3.5% 1,8-cineole | None | 2 | 3 | 0.015 | 0.045 |
| Ketoprofen | 10% | KET1168 | KET78 | Ethanol | 50% EtOH | Isomyristate | 45% ISOMYR | Eucalyptus oil | 3.5% 1,8-cineole | None | 4 | 3 | 0.009 | 0.027 |
| Ketoprofen | 10% | KET1169 | KET78 | Ethanol | 50% EtOH | Isomyristate | 45% ISOMYR | Eucalyptus oil | 3.5% 1,8-cineole | None | 6 | 3 | 0.799 | 2.397 |
| Ketoprofen | 10% | KET1170 | KET78 | Ethanol | 50% EtOH | Isomyristate | 45% ISOMYR | Eucalyptus oil | 3.5% 1,8-cineole | None | 8 | 3 | 1.725 | 5.175 |
| Ketoprofen | 10% | KET1171 | KET79 | Ethanol | 50% EtOH | Oleyl alcohol | 45% OA | Eucalyptus oil | 3.5% 1,8-cineole | None | 0.5 | 1 | 0.012 | 0.036 |
| Ketoprofen | 10% | KET1172 | KET79 | Ethanol | 50% EtOH | Oleyl alcohol | 45% OA | Eucalyptus oil | 3.5% 1,8-cineole | None | 2 | 1 | 0.013 | 0.039 |
| Ketoprofen | 10% | KET1173 | KET79 | Ethanol | 50% EtOH | Oleyl alcohol | 45% OA | Eucalyptus oil | 3.5% 1,8-cineole | None | 4 | 1 | 0.038 | 0.114 |
| Ketoprofen | 10% | KET1174 | KET79 | Ethanol | 50% EtOH | Oleyl alcohol | 45% OA | Eucalyptus oil | 3.5% 1,8-cineole | None | 6 | 1 | 0.194 | 0.582 |
| Ketoprofen | 10% | KET1175 | KET79 | Ethanol | 50% EtOH | Oleyl alcohol | 45% OA | Eucalyptus oil | 3.5% 1,8-cineole | None | 8 | 1 | 0.534 | 1.602 |
| Ketoprofen | 10% | KET1176 | KET79 | Ethanol | 50% EtOH | Oleyl alcohol | 45% OA | Eucalyptus oil | 3.5% 1,8-cineole | None | 0.5 | 2 | 0.045 | 0.135 |
| Ketoprofen | 10% | KET1177 | KET79 | Ethanol | 50% EtOH | Oleyl alcohol | 45% OA | Eucalyptus oil | 3.5% 1,8-cineole | None | 2 | 2 | 0.049 | 0.147 |
| Ketoprofen | 10% | KET1178 | KET79 | Ethanol | 50% EtOH | Oleyl alcohol | 45% OA | Eucalyptus oil | 3.5% 1,8-cineole | None | 4 | 2 | 0.074 | 0.222 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET1179 | KET79 | Ethanol | 50% EthOH | Oleyl alcohol | 45% OA | Eucalyptus oil | 3.5% 1,8-cineole | None | 6 | 2 | 0.197 | 0.591 |
| Ketoprofen | 10% | KET1180 | KET79 | Ethanol | 50% EthOH | Oleyl alcohol | 45% OA | Eucalyptus oil | 3.5% 1,8-cineole | None | 8 | 2 | 0.387 | 1.161 |
| Ketoprofen | 10% | KET1181 | KET79 | Ethanol | 50% EthOH | Oleyl alcohol | 45% OA | Eucalyptus oil | 3.5% 1,8-cineole | None | 0.5 | 3 | 0.09 | 0.27 |
| Ketoprofen | 10% | KET1182 | KET79 | Ethanol | 50% EthOH | Oleyl alcohol | 45% OA | Eucalyptus oil | 3.5% 1,8-cineole | None | 2 | 3 | 0.049 | 0.147 |
| Ketoprofen | 10% | KET1183 | KET79 | Ethanol | 50% EthOH | Oleyl alcohol | 45% OA | Eucalyptus oil | 3.5% 1,8-cineole | None | 4 | 3 | 0.048 | 0.144 |
| Ketoprofen | 10% | KET1184 | KET79 | Ethanol | 50% EthOH | Oleyl alcohol | 45% OA | Eucalyptus oil | 3.5% 1,8-cineole | None | 6 | 3 | 0.055 | 0.165 |
| Ketoprofen | 10% | KET1185 | KET79 | Ethanol | 50% EthOH | Oleyl alcohol | 45% OA | Eucalyptus oil | 3.5% 1,8-cineole | None | 8 | 3 | 0.17 | 0.51 |
| Ketoprofen | 10% | KET1186 | KET80 | Isopropanol | 50% IPN | Oleyl alcohol | 45% OA | Eucalyptus oil | 3.5% 1,8-cineole | None | 0.5 | 1 | 0.059 | 0.177 |
| Ketoprofen | 10% | KET1187 | KET80 | Isopropanol | 50% IPN | Oleyl alcohol | 45% OA | Eucalyptus oil | 3.5% 1,8-cineole | None | 2 | 1 | 0.066 | 0.198 |
| Ketoprofen | 10% | KET1188 | KET80 | Isopropanol | 50% IPN | Oleyl alcohol | 45% OA | Eucalyptus oil | 3.5% 1,8-cineole | None | 4 | 1 | 0.079 | 0.237 |
| Ketoprofen | 10% | KET1189 | KET80 | Isopropanol | 50% IPN | Oleyl alcohol | 45% OA | Eucalyptus oil | 3.5% 1,8-cineole | None | 6 | 1 | 0.086 | 0.258 |
| Ketoprofen | 10% | KET1190 | KET80 | Isopropanol | 50% IPN | Oleyl alcohol | 45% OA | Eucalyptus oil | 3.5% 1,8-cineole | None | 8 | 1 | 0.298 | 0.894 |
| Ketoprofen | 10% | KET1191 | KET80 | Isopropanol | 50% IPN | Oleyl alcohol | 45% OA | Eucalyptus oil | 3.5% 1,8-cineole | None | 0.5 | 2 | 0.057 | 0.171 |
| Ketoprofen | 10% | KET1192 | KET80 | Isopropanol | 50% IPN | Oleyl alcohol | 45% OA | Eucalyptus oil | 3.5% 1,8-cineole | None | 2 | 2 | 0.067 | 0.201 |
| Ketoprofen | 10% | KET1193 | KET80 | Isopropanol | 50% IPN | Oleyl alcohol | 45% OA | Eucalyptus oil | 3.5% 1,8-cineole | None | 4 | 2 | 0.067 | 0.201 |
| Ketoprofen | 10% | KET1194 | KET80 | Isopropanol | 50% IPN | Oleyl alcohol | 45% OA | Eucalyptus oil | 3.5% 1,8-cineole | None | 6 | 2 | 0.079 | 0.237 |
| Ketoprofen | 10% | KET1195 | KET80 | Isopropanol | 50% IPN | Oleyl alcohol | 45% OA | Eucalyptus oil | 3.5% 1,8-cineole | None | 8 | 2 | 0.118 | 0.354 |
| Ketoprofen | 10% | KET1196 | KET80 | Isopropanol | 50% IPN | Oleyl alcohol | 45% OA | Eucalyptus oil | 3.5% 1,8-cineole | None | 0.5 | 3 | 0.07 | 0.21 |
| Ketoprofen | 10% | KET1197 | KET80 | Isopropanol | 50% IPN | Oleyl alcohol | 45% OA | Eucalyptus oil | 3.5% 1,8-cineole | None | 2 | 3 | 0.005 | 0.015 |
| Ketoprofen | 10% | KET1198 | KET80 | Isopropanol | 50% IPN | Oleyl alcohol | 45% OA | Eucalyptus oil | 3.5% 1,8-cineole | None | 4 | 3 | 0.005 | 0.015 |
| Ketoprofen | 10% | KET1199 | KET80 | Isopropanol | 50% IPN | Oleyl alcohol | 45% OA | Eucalyptus oil | 3.5% 1,8-cineole | None | 6 | 3 | 0.006 | 0.018 |
| Ketoprofen | 10% | KET1200 | KET80 | Isopropanol | 50% IPN | Oleyl alcohol | 45% OA | Eucalyptus oil | 3.5% 1,8-cineole | None | 8 | 3 | 0.087 | 0.261 |
| Flunixin | 10% | KET1201 | KET81 | Ethanol | 50% EthOH | 1-Ethyl-2-Pyrrolidone | 45% EP | Menthol | 50 ng/mL | None | 0.5 | 1 | 0.005 | 0.015 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Flunixin | 10% | KET1202 | KET81 | Ethanol | 50% EtOH | 1-Ethyl-2-Pyrrolidone | 45% EP | Menthol | 50 ng/mL | None | 2 | 1 | 0.006 | 0.018 |
| Flunixin | 10% | KET1203 | KET81 | Ethanol | 50% EtOH | 1-Ethyl-2-Pyrrolidone | 45% EP | Menthol | 50 ng/mL | None | 4 | 1 | 0.008 | 0.024 |
| Flunixin | 10% | KET1204 | KET81 | Ethanol | 50% EtOH | 1-Ethyl-2-Pyrrolidone | 45% EP | Menthol | 50 ng/mL | None | 6 | 1 | 0.01 | 0.03 |
| Flunixin | 10% | KET1205 | KET81 | Ethanol | 50% EtOH | 1-Ethyl-2-Pyrrolidone | 45% EP | Menthol | 50 ng/mL | None | 8 | 1 | 0.061 | 0.183 |
| Flunixin | 10% | KET1206 | KET81 | Ethanol | 50% EtOH | 1-Ethyl-2-Pyrrolidone | 45% EP | Menthol | 50 ng/mL | None | 0.5 | 2 | 0.051 | 0.153 |
| Flunixin | 10% | KET1207 | KET81 | Ethanol | 50% EtOH | 1-Ethyl-2-Pyrrolidone | 45% EP | Menthol | 50 ng/mL | None | 2 | 2 | 0.077 | 0.231 |
| Flunixin | 10% | KET1208 | KET81 | Ethanol | 50% EtOH | 1-Ethyl-2-Pyrrolidone | 45% EP | Menthol | 50 ng/mL | None | 4 | 2 | 0.081 | 0.243 |
| Flunixin | 10% | KET1209 | KET81 | Ethanol | 50% EtOH | 1-Ethyl-2-Pyrrolidone | 45% EP | Menthol | 50 ng/mL | None | 6 | 2 | 0.099 | 0.297 |
| Flunixin | 10% | KET1210 | KET81 | Ethanol | 50% EtOH | 1-Ethyl-2-Pyrrolidone | 45% EP | Menthol | 50 ng/mL | None | 8 | 2 | 0.111 | 0.333 |
| Flunixin | 10% | KET1211 | KET81 | Ethanol | 50% EtOH | 1-Ethyl-2-Pyrrolidone | 45% EP | Menthol | 50 ng/mL | None | 0.5 | 3 | — | 0 |
| Flunixin | 10% | KET1212 | KET81 | Ethanol | 50% EtOH | 1-Ethyl-2-Pyrrolidone | 45% EP | Menthol | 50 ng/mL | None | 2 | 3 | 0.005 | 0.015 |
| Flunixin | 10% | KET1213 | KET81 | Ethanol | 50% EtOH | 1-Ethyl-2-Pyrrolidone | 45% EP | Menthol | 50 ng/mL | None | 4 | 3 | 0.008 | 0.024 |
| Flunixin | 10% | KET1214 | KET81 | Ethanol | 50% EtOH | 1-Ethyl-2-Pyrrolidone | 45% EP | Menthol | 50 ng/mL | None | 6 | 3 | 0.009 | 0.027 |
| Flunixin | 10% | KET1215 | KET81 | Ethanol | 50% EtOH | 1-Ethyl-2-Pyrrolidone | 45% EP | Menthol | 50 ng/mL | None | 8 | 3 | 0.045 | 0.135 |
| Flunixin | 10% | KET1216 | KET82 | Ethanol | 50% EtOH | Propylene glycol | 45% PPG | Eucalyptus oil | 3.5% 1,8-cineole | None | 0.5 | 1 | 0.005 | 0.015 |
| Flunixin | 10% | KET1217 | KET82 | Ethanol | 50% EtOH | Propylene glycol | 45% PPG | Eucalyptus oil | 3.5% 1,8-cineole | None | 2 | 1 | 0.006 | 0.018 |
| Flunixin | 10% | KET1218 | KET82 | Ethanol | 50% EtOH | Propylene glycol | 45% PPG | Eucalyptus oil | 3.5% 1,8-cineole | None | 4 | 1 | 0.006 | 0.018 |
| Flunixin | 10% | KET1219 | KET82 | Ethanol | 50% EtOH | Propylene glycol | 45% PPG | Eucalyptus oil | 3.5% 1,8-cineole | None | 6 | 1 | 0.009 | 0.027 |
| Flunixin | 10% | KET1220 | KET82 | Ethanol | 50% EtOH | Propylene glycol | 45% PPG | Eucalyptus oil | 3.5% 1,8-cineole | None | 8 | 1 | 0.024 | 0.072 |
| Flunixin | 10% | KET1221 | KET82 | Ethanol | 50% EtOH | Propylene glycol | 45% PPG | Eucalyptus oil | 3.5% 1,8-cineole | None | 0.5 | 2 | 0.01 | 0.03 |
| Flunixin | 10% | KET1222 | KET82 | Ethanol | 50% EtOH | Propylene glycol | 45% PPG | Eucalyptus oil | 3.5% 1,8-cineole | None | 2 | 2 | 0.01 | 0.03 |
| Flunixin | 10% | KET1223 | KET82 | Ethanol | 50% EtOH | Propylene glycol | 45% PPG | Eucalyptus oil | 3.5% 1,8-cineole | None | 4 | 2 | 0.011 | 0.033 |
| Flunixin | 10% | KET1224 | KET82 | Ethanol | 50% EtOH | Propylene glycol | 45% PPG | Eucalyptus oil | 3.5% 1,8-cineole | None | 6 | 2 | 0.011 | 0.033 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Flunixin | 10% | KET1225 | KET82 | Ethanol | 50% EtOH | Propylene glycol | 45% PPG | Eucalyptus oil | 3.5% 1,8-cineole | None | 8 | 2 | 0.024 | 0.072 |
| Flunixin | 10% | KET1226 | KET82 | Ethanol | 50% EtOH | Propylene glycol | 45% PPG | Eucalyptus oil | 3.5% 1,8-cineole | None | 0.5 | 3 | — | 0 |
| Flunixin | 10% | KET1227 | KET82 | Ethanol | 50% EtOH | Propylene glycol | 45% PPG | Eucalyptus oil | 3.5% 1,8-cineole | None | 2 | 3 | — | 0 |
| Flunixin | 10% | KET1228 | KET82 | Ethanol | 50% EtOH | Propylene glycol | 45% PPG | Eucalyptus oil | 3.5% 1,8-cineole | None | 4 | 3 | 0.007 | 0.021 |
| Flunixin | 10% | KET1229 | KET82 | Ethanol | 50% EtOH | Propylene glycol | 45% PPG | Eucalyptus oil | 3.5% 1,8-cineole | None | 6 | 3 | 0.006 | 0.018 |
| Flunixin | 10% | KET1230 | KET82 | Ethanol | 50% EtOH | Propylene glycol | 45% PPG | Eucalyptus oil | 3.5% 1,8-cineole | None | 8 | 3 | 0.007 | 0.021 |
| Flunixin | 10% | KET1231 | KET83 | Ethanol | 50% EtOH | 1-Ethyl-2-Pyrrolidone | 45% EP | Menthol | 50 ng/mL | None | 0.5 | 1 | 0.008 | 0.024 |
| Flunixin | 10% | KET1232 | KET83 | Ethanol | 50% EtOH | 1-Ethyl-2-Pyrrolidone | 45% EP | Menthol | 50 ng/mL | None | 2 | 1 | 0.009 | 0.027 |
| Flunixin | 10% | KET1233 | KET83 | Ethanol | 50% EtOH | 1-Ethyl-2-Pyrrolidone | 45% EP | Menthol | 50 ng/mL | None | 4 | 1 | 0.008 | 0.024 |
| Flunixin | 10% | KET1234 | KET83 | Ethanol | 50% EtOH | 1-Ethyl-2-Pyrrolidone | 45% EP | Menthol | 50 ng/mL | None | 6 | 1 | 0.008 | 0.024 |
| Flunixin | 10% | KET1235 | KET83 | Ethanol | 50% EtOH | 1-Ethyl-2-Pyrrolidone | 45% EP | Menthol | 50 ng/mL | None | 8 | 1 | 0.351 | 1.053 |
| Flunixin | 10% | KET1236 | KET83 | Ethanol | 50% EtOH | 1-Ethyl-2-Pyrrolidone | 45% EP | Menthol | 50 ng/mL | None | 0.5 | 2 | 0.007 | 0.021 |
| Flunixin | 10% | KET1237 | KET83 | Ethanol | 50% EtOH | 1-Ethyl-2-Pyrrolidone | 45% EP | Menthol | 50 ng/mL | None | 2 | 2 | — | 0 |
| Flunixin | 10% | KET1238 | KET83 | Ethanol | 50% EtOH | 1-Ethyl-2-Pyrrolidone | 45% EP | Menthol | 50 ng/mL | None | 4 | 2 | — | 0 |
| Flunixin | 10% | KET1239 | KET83 | Ethanol | 50% EtOH | 1-Ethyl-2-Pyrrolidone | 45% EP | Menthol | 50 ng/mL | None | 6 | 2 | 0.008 | 0.024 |
| Flunixin | 10% | KET1240 | KET83 | Ethanol | 50% EtOH | 1-Ethyl-2-Pyrrolidone | 45% EP | Menthol | 50 ng/mL | None | 8 | 2 | 0.012 | 0.036 |
| Flunixin | 10% | KET1241 | KET83 | Ethanol | 50% EtOH | 1-Ethyl-2-Pyrrolidone | 45% EP | Menthol | 50 ng/mL | None | 0.5 | 3 | — | 0 |
| Flunixin | 10% | KET1242 | KET83 | Ethanol | 50% EtOH | 1-Ethyl-2-Pyrrolidone | 45% EP | Menthol | 50 ng/mL | None | 2 | 3 | — | 0 |
| Flunixin | 10% | KET1243 | KET83 | Ethanol | 50% EtOH | 1-Ethyl-2-Pyrrolidone | 45% EP | Menthol | 50 ng/mL | None | 4 | 3 | 0.007 | 0.021 |
| Flunixin | 10% | KET1244 | KET83 | Ethanol | 50% EtOH | 1-Ethyl-2-Pyrrolidone | 45% EP | Menthol | 50 ng/mL | None | 6 | 3 | 0.006 | 0.018 |
| Flunixin | 10% | KET1245 | KET83 | Ethanol | 50% EtOH | 1-Ethyl-2-Pyrrolidone | 45% EP | Menthol | 50 ng/mL | None | 8 | 3 | 0.035 | 0.105 |
| Flunixin | 10% | KET1246 | KET84 | Ethanol | 50% EtOH | Propylene glycol | 45% PPG | Eucalyptus oil | 3.5% 1,8-cineole | None | 0.5 | 1 | 0.005 | 0.015 |
| Flunixin | 10% | KET1247 | KET84 | Ethanol | 50% EtOH | Propylene glycol | 45% PPG | Eucalyptus oil | 3.5% 1,8-cineole | None | 2 | 1 | 0.006 | 0.018 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Flunixin | 10% | KET1248 | KET84 | Ethanol | 50% EtOH | Propylene glycol | 45% PPG | Eucalyptus oil | 3.5% 1,8-cineole | None | 4 | 1 | 0.006 | 0.018 |
| Flunixin | 10% | KET1249 | KET84 | Ethanol | 50% EtOH | Propylene glycol | 45% PPG | Eucalyptus oil | 3.5% 1,8-cineole | None | 6 | 1 | 0.006 | 0.018 |
| Flunixin | 10% | KET1250 | KET84 | Ethanol | 50% EtOH | Propylene glycol | 45% PPG | Eucalyptus oil | 3.5% 1,8-cineole | None | 8 | 1 | 0.017 | 0.051 |
| Flunixin | 10% | KET1251 | KET84 | Ethanol | 50% EtOH | Propylene glycol | 45% PPG | Eucalyptus oil | 3.5% 1,8-cineole | None | 0.5 | 2 | 9.98 | 29.94 |
| Flunixin | 10% | KET1252 | KET84 | Ethanol | 50% EtOH | Propylene glycol | 45% PPG | Eucalyptus oil | 3.5% 1,8-cineole | None | 2 | 2 | 10.843 | 32.529 |
| Flunixin | 10% | KET1253 | KET84 | Ethanol | 50% EtOH | Propylene glycol | 45% PPG | Eucalyptus oil | 3.5% 1,8-cineole | None | 4 | 2 | 12.381 | 37.143 |
| Flunixin | 10% | KET1254 | KET84 | Ethanol | 50% EtOH | Propylene glycol | 45% PPG | Eucalyptus oil | 3.5% 1,8-cineole | None | 6 | 2 | 13.123 | 39.369 |
| Flunixin | 10% | KET1255 | KET84 | Ethanol | 50% EtOH | Propylene glycol | 45% PPG | Eucalyptus oil | 3.5% 1,8-cineole | None | 8 | 2 | 13.487 | 40.461 |
| Flunixin | 10% | KET1256 | KET84 | Ethanol | 50% EtOH | Propylene glycol | 45% PPG | Eucalyptus oil | 3.5% 1,8-cineole | None | 0.5 | 3 | 1.005 | 3.015 |
| Flunixin | 10% | KET1257 | KET84 | Ethanol | 50% EtOH | Propylene glycol | 45% PPG | Eucalyptus oil | 3.5% 1,8-cineole | None | 2 | 3 | 1.165 | 3.495 |
| Flunixin | 10% | KET1258 | KET84 | Ethanol | 50% EtOH | Propylene glycol | 45% PPG | Eucalyptus oil | 3.5% 1,8-cineole | None | 4 | 3 | 1.513 | 4.539 |
| Flunixin | 10% | KET1259 | KET84 | Ethanol | 50% EtOH | Propylene glycol | 45% PPG | Eucalyptus oil | 3.5% 1,8-cineole | None | 6 | 3 | 1.552 | 4.656 |
| Flunixin | 10% | KET1260 | KET84 | Ethanol | 50% EtOH | Propylene glycol | 45% PPG | Eucalyptus oil | 3.5% 1,8-cineole | None | 8 | 3 | 1.78 | 5.34 |
| Ketoprofen | 10% | KET1261 | KET85 | Isopropanol | 50% IPN | 1-Ethyl-2-Pyrrolidone | 45% EP | Menthol | 50 ng/mL | None | 0.5 | 1 | 0.033 | 0.099 |
| Ketoprofen | 10% | KET1262 | KET85 | Isopropanol | 50% IPN | 1-Ethyl-2-Pyrrolidone | 45% EP | Menthol | 50 ng/mL | None | 2 | 1 | 0.039 | 0.117 |
| Ketoprofen | 10% | KET1263 | KET85 | Isopropanol | 50% IPN | 1-Ethyl-2-Pyrrolidone | 45% EP | Menthol | 50 ng/mL | None | 4 | 1 | 0.047 | 0.141 |
| Ketoprofen | 10% | KET1264 | KET85 | Isopropanol | 50% IPN | 1-Ethyl-2-Pyrrolidone | 45% EP | Menthol | 50 ng/mL | None | 6 | 1 | 0.062 | 0.186 |
| Ketoprofen | 10% | KET1265 | KET85 | Isopropanol | 50% IPN | 1-Ethyl-2-Pyrrolidone | 45% EP | Menthol | 50 ng/mL | None | 8 | 1 | 0.068 | 0.204 |
| Ketoprofen | 10% | KET1266 | KET85 | Isopropanol | 50% IPN | 1-Ethyl-2-Pyrrolidone | 45% EP | Menthol | 50 ng/mL | None | 0.5 | 2 | 0.019 | 0.057 |
| Ketoprofen | 10% | KET1267 | KET85 | Isopropanol | 50% IPN | 1-Ethyl-2-Pyrrolidone | 45% EP | Menthol | 50 ng/mL | None | 2 | 2 | 0.054 | 0.162 |
| Ketoprofen | 10% | KET1268 | KET85 | Isopropanol | 50% IPN | 1-Ethyl-2-Pyrrolidone | 45% EP | Menthol | 50 ng/mL | None | 4 | 2 | 0.059 | 0.177 |
| Ketoprofen | 10% | KET1269 | KET85 | Isopropanol | 50% IPN | 1-Ethyl-2-Pyrrolidone | 45% EP | Menthol | 50 ng/mL | None | 6 | 2 | 0.058 | 0.174 |
| Ketoprofen | 10% | KET1270 | KET85 | Isopropanol | 50% IPN | 1-Ethyl-2-Pyrrolidone | 45% EP | Menthol | 50 ng/mL | None | 8 | 2 | 0.059 | 0.177 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 10% | KET1271 | KET85 | Isopropanol | 50% IPN | 1-Ethyl-2-Pyrrolidone | 45% EP | Menthol | 50 ng/mL | None | 0.5 | 3 | 0.008 | 0.024 |
| Ketoprofen | 10% | KET1272 | KET85 | Isopropanol | 50% IPN | 1-Ethyl-2-Pyrrolidone | 45% EP | Menthol | 50 ng/mL | None | 2 | 3 | 0.013 | 0.039 |
| Ketoprofen | 10% | KET1273 | KET85 | Isopropanol | 50% IPN | 1-Ethyl-2-Pyrrolidone | 45% EP | Menthol | 50 ng/mL | None | 4 | 3 | 0.024 | 0.072 |
| Ketoprofen | 10% | KET1274 | KET85 | Isopropanol | 50% IPN | 1-Ethyl-2-Pyrrolidone | 45% EP | Menthol | 50 ng/mL | None | 6 | 3 | 0.053 | 0.159 |
| Ketoprofen | 10% | KET1275 | KET85 | Isopropanol | 50% IPN | 1-Ethyl-2-Pyrrolidone | 45% EP | Menthol | 50 ng/mL | None | 8 | 3 | 0.06 | 0.18 |
| Ketoprofen | 10% | KET1276 | KET86 | Isopropanol | 50% IPN | Propylene glycol | 45% PPG | Menthol | 50 ng/mL | None | 0.5 | 1 | 0.061 | 0.183 |
| Ketoprofen | 10% | KET1277 | KET86 | Isopropanol | 50% IPN | Propylene glycol | 45% PPG | Menthol | 50 ng/mL | None | 2 | 1 | 0.142 | 0.426 |
| Ketoprofen | 10% | KET1278 | KET86 | Isopropanol | 50% IPN | Propylene glycol | 45% PPG | Menthol | 50 ng/mL | None | 4 | 1 | 0.283 | 0.849 |
| Ketoprofen | 10% | KET1279 | KET86 | Isopropanol | 50% IPN | Propylene glycol | 45% PPG | Menthol | 50 ng/mL | None | 6 | 1 | 0.322 | 0.966 |
| Ketoprofen | 10% | KET1280 | KET86 | Isopropanol | 50% IPN | Propylene glycol | 45% PPG | Menthol | 50 ng/mL | None | 8 | 1 | 0.356 | 1.068 |
| Ketoprofen | 10% | KET1281 | KET86 | Isopropanol | 50% IPN | Propylene glycol | 45% PPG | Menthol | 50 ng/mL | None | 0.5 | 2 | 0.014 | 0.042 |
| Ketoprofen | 10% | KET1282 | KET86 | Isopropanol | 50% IPN | Propylene glycol | 45% PPG | Menthol | 50 ng/mL | None | 2 | 2 | 0.017 | 0.051 |
| Ketoprofen | 10% | KET1283 | KET86 | Isopropanol | 50% IPN | Propylene glycol | 45% PPG | Menthol | 50 ng/mL | None | 4 | 2 | 0.027 | 0.081 |
| Ketoprofen | 10% | KET1284 | KET86 | Isopropanol | 50% IPN | Propylene glycol | 45% PPG | Menthol | 50 ng/mL | None | 6 | 2 | 0.049 | 0.147 |
| Ketoprofen | 10% | KET1285 | KET86 | Isopropanol | 50% IPN | Propylene glycol | 45% PPG | Menthol | 50 ng/mL | None | 8 | 2 | 0.043 | 0.129 |
| Ketoprofen | 10% | KET1286 | KET86 | Isopropanol | 50% IPN | Propylene glycol | 45% PPG | Menthol | 50 ng/mL | None | 0.5 | 3 | 0.048 | 0.144 |
| Ketoprofen | 10% | KET1287 | KET86 | Isopropanol | 50% IPN | Propylene glycol | 45% PPG | Menthol | 50 ng/mL | None | 2 | 3 | 0.045 | 0.135 |
| Ketoprofen | 10% | KET1288 | KET86 | Isopropanol | 50% IPN | Propylene glycol | 45% PPG | Menthol | 50 ng/mL | None | 4 | 3 | 0.045 | 0.135 |
| Ketoprofen | 10% | KET1289 | KET86 | Isopropanol | 50% IPN | Propylene glycol | 45% PPG | Menthol | 50 ng/mL | None | 6 | 3 | 0.053 | 0.159 |
| Ketoprofen | 10% | KET1290 | KET86 | Isopropanol | 50% IPN | Propylene glycol | 45% PPG | Menthol | 50 ng/mL | None | 8 | 3 | 0.057 | 0.171 |
| Ketoprofen | 10% | KET1291 | KET87 | Isopropanol | 50% IPN | Isomyristate | 45% ISOMYR | Menthol | 50 ng/mL | None | 0.5 | 1 | 0.018 | 0.054 |
| Ketoprofen | 10% | KET1292 | KET87 | Isopropanol | 50% IPN | Isomyristate | 45% ISOMYR | Menthol | 50 ng/mL | None | 2 | 1 | 0.028 | 0.084 |
| Ketoprofen | 10% | KET1293 | KET87 | Isopropanol | 50% IPN | Isomyristate | 45% ISOMYR | Menthol | 50 ng/mL | None | 4 | 1 | 0.071 | 0.213 |
| Ketoprofen | 10% | KET1294 | KET87 | Isopropanol | 50% IPN | Isomyristate | 45% ISOMYR | Menthol | 50 ng/mL | None | 6 | 1 | 0.073 | 0.219 |
| Ketoprofen | 10% | KET1295 | KET87 | Isopropanol | 50% IPN | Isomyristate | 45% ISOMYR | Menthol | 50 ng/mL | None | 8 | 1 | 0.081 | 0.243 |
| Ketoprofen | 10% | KET1296 | KET87 | Isopropanol | 50% IPN | Isomyristate | 45% ISOMYR | Menthol | 50 ng/mL | None | 0.5 | 2 | 0.045 | 0.135 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 10% | KET1297 | KET87 | Isopronanol | 50% IPN | Isomyristate | 45% ISOMYR | Menthol | 50 ng/mL | None | 2 | 2 | 0.038 | 0.114 |
| Ketoprofen | 10% | KET1298 | KET87 | Isopronanol | 50% IPN | Isomyristate | 45% ISOMYR | Menthol | 50 ng/mL | None | 4 | 2 | 0.072 | 0.216 |
| Ketoprofen | 10% | KET1299 | KET87 | Isopronanol | 50% IPN | Isomyristate | 45% ISOMYR | Menthol | 50 ng/mL | None | 6 | 2 | 0.455 | 1.365 |
| Ketoprofen | 10% | KET1300 | KET87 | Isopronanol | 50% IPN | Isomyristate | 45% ISOMYR | Menthol | 50 ng/mL | None | 8 | 2 | 0.476 | 1.428 |
| Ketoprofen | 10% | KET1301 | KET87 | Isopronanol | 50% IPN | Isomyristate | 45% ISOMYR | Menthol | 50 ng/mL | None | 0.5 | 3 | 0.009 | 0.027 |
| Ketoprofen | 10% | KET1302 | KET87 | Isopronanol | 50% IPN | Isomyristate | 45% ISOMYR | Menthol | 50 ng/mL | None | 2 | 3 | 0.03 | 0.09 |
| Ketoprofen | 10% | KET1303 | KET87 | Isopronanol | 50% IPN | Isomyristate | 45% ISOMYR | Menthol | 50 ng/mL | None | 4 | 3 | 0.03 | 0.09 |
| Ketoprofen | 10% | KET1304 | KET87 | Isopronanol | 50% IPN | Isomyristate | 45% ISOMYR | Menthol | 50 ng/mL | None | 6 | 3 | 0.129 | 0.387 |
| Ketoprofen | 10% | KET1305 | KET87 | Isopronanol | 50% IPN | Isomyristate | 45% ISOMYR | Menthol | 50 ng/mL | None | 8 | 3 | 0.233 | 0.699 |
| Ketoprofen | 10% | KET1306 | KET88 | Ethanol | 50% EthOH | Oleyl alcohol | 45% OA | Menthol | 50 ng/mL | 0.1M citrate | 0.5 | 1 | 0.01 | 0.03 |
| Ketoprofen | 10% | KET1307 | KET88 | Ethanol | 50% EthOH | Oleyl alcohol | 45% OA | Menthol | 50 ng/mL | 0.1M citrate | 2 | 1 | 0.013 | 0.039 |
| Ketoprofen | 10% | KET1308 | KET88 | Ethanol | 50% EthOH | Oleyl alcohol | 45% OA | Menthol | 50 ng/mL | 0.1M citrate | 4 | 1 | 0.012 | 0.036 |
| Ketoprofen | 10% | KET1309 | KET88 | Ethanol | 50% EthOH | Oleyl alcohol | 45% OA | Menthol | 50 ng/mL | 0.1M citrate | 6 | 1 | 0.018 | 0.054 |
| Ketoprofen | 10% | KET1310 | KET88 | Ethanol | 50% EthOH | Oleyl alcohol | 45% OA | Menthol | 50 ng/mL | 0.1M citrate | 8 | 1 | 0.026 | 0.078 |
| Ketoprofen | 10% | KET1311 | KET88 | Ethanol | 50% EthOH | Oleyl alcohol | 45% OA | Menthol | 50 ng/mL | 0.1M citrate | 0.5 | 2 | 0.007 | 0.021 |
| Ketoprofen | 10% | KET1312 | KET88 | Ethanol | 50% EthOH | Oleyl alcohol | 45% OA | Menthol | 50 ng/mL | 0.1M citrate | 2 | 2 | 0.009 | 0.027 |
| Ketoprofen | 10% | KET1313 | KET88 | Ethanol | 50% EthOH | Oleyl alcohol | 45% OA | Menthol | 50 ng/mL | 0.1M citrate | 4 | 2 | 0.034 | 0.102 |
| Ketoprofen | 10% | KET1314 | KET88 | Ethanol | 50% EthOH | Oleyl alcohol | 45% OA | Menthol | 50 ng/mL | 0.1M citrate | 6 | 2 | 0.047 | 0.141 |
| Ketoprofen | 10% | KET1315 | KET88 | Ethanol | 50% EthOH | Oleyl alcohol | 45% OA | Menthol | 50 ng/mL | 0.1M citrate | 8 | 2 | 0.315 | 0.945 |
| Ketoprofen | 10% | KET1316 | KET88 | Ethanol | 50% EthOH | Oleyl alcohol | 45% OA | Menthol | 50 ng/mL | 0.1M citrate | 0.5 | 3 | 0.049 | 0.147 |
| Ketoprofen | 10% | KET1317 | KET88 | Ethanol | 50% EthOH | Oleyl alcohol | 45% OA | Menthol | 50 ng/mL | 0.1M citrate | 2 | 3 | 0.045 | 0.135 |
| Ketoprofen | 10% | KET1318 | KET88 | Ethanol | 50% EthOH | Oleyl alcohol | 45% OA | Menthol | 50 ng/mL | 0.1M citrate | 4 | 3 | 0.047 | 0.141 |
| Ketoprofen | 10% | KET1319 | KET88 | Ethanol | 50% EthOH | Oleyl alcohol | 45% OA | Menthol | 50 ng/mL | 0.1M citrate | 6 | 3 | 0.047 | 0.141 |
| Ketoprofen | 10% | KET1320 | KET88 | Ethanol | 50% EthOH | Oleyl alcohol | 45% OA | Menthol | 50 ng/mL | 0.1M citrate | 8 | 3 | 0.03 | 0.09 |
| Ketoprofen | 10% | KET1321 | KET89 | Isopronanol | 50% IPN | 1-Ethyl-2-Pyrrolidone | 45% EP | Eucalyptus oil | 3.5% 1,8-cineole | None | 0.5 | 1 | 0.008 | 0.024 |
| Ketoprofen | 10% | KET1322 | KET89 | Isopronanol | 50% IPN | 1-Ethyl-2-Pyrrolidone | 45% EP | Eucalyptus oil | 3.5% 1,8-cineole | None | 2 | 1 | 0.009 | 0.027 |
| Ketoprofen | 10% | KET1323 | KET89 | Isopronanol | 50% IPN | 1-Ethyl-2-Pyrrolidone | 45% EP | Eucalyptus oil | 3.5% 1,8-cineole | None | 4 | 1 | 0.013 | 0.039 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 10% | KET1324 | KET89 | Isopronanol | 50% IPN | 1-Ethyl-2-Pyrrolidone | 45% EP | Eucalyptus oil | 3.5% 1,8-cineole | None | 6 | 1 | 0.009 | 0.027 |
| Ketoprofen | 10% | KET1325 | KET89 | Isopronanol | 50% IPN | 1-Ethyl-2-Pyrrolidone | 45% EP | Eucalyptus oil | 3.5% 1,8-cineole | None | 8 | 1 | 0.038 | 0.114 |
| Ketoprofen | 10% | KET1326 | KET89 | Isopronanol | 50% IPN | 1-Ethyl-2-Pyrrolidone | 45% EP | Eucalyptus oil | 3.5% 1,8-cineole | None | 0.5 | 2 | 0.027 | 0.081 |
| Ketoprofen | 10% | KET1327 | KET89 | Isopronanol | 50% IPN | 1-Ethyl-2-Pyrrolidone | 45% EP | Eucalyptus oil | 3.5% 1,8-cineole | None | 2 | 2 | 0.029 | 0.087 |
| Ketoprofen | 10% | KET1328 | KET89 | Isopronanol | 50% IPN | 1-Ethyl-2-Pyrrolidone | 45% EP | Eucalyptus oil | 3.5% 1,8-cineole | None | 4 | 2 | 0.023 | 0.069 |
| Ketoprofen | 10% | KET1329 | KET89 | Isopronanol | 50% IPN | 1-Ethyl-2-Pyrrolidone | 45% EP | Eucalyptus oil | 3.5% 1,8-cineole | None | 6 | 2 | 0.033 | 0.099 |
| Ketoprofen | 10% | KET1330 | KET89 | Isopronanol | 50% IPN | 1-Ethyl-2-Pyrrolidone | 45% EP | Eucalyptus oil | 3.5% 1,8-cineole | None | 8 | 2 | 0.035 | 0.105 |
| Ketoprofen | 10% | KET1331 | KET89 | Isopronanol | 50% IPN | 1-Ethyl-2-Pyrrolidone | 45% EP | Eucalyptus oil | 3.5% 1,8-cineole | None | 0.5 | 3 | 0.023 | 0.069 |
| Ketoprofen | 10% | KET1332 | KET89 | Isopronanol | 50% IPN | 1-Ethyl-2-Pyrrolidone | 45% EP | Eucalyptus oil | 3.5% 1,8-cineole | None | 2 | 3 | 0.023 | 0.069 |
| Ketoprofen | 10% | KET1333 | KET89 | Isopronanol | 50% IPN | 1-Ethyl-2-Pyrrolidone | 45% EP | Eucalyptus oil | 3.5% 1,8-cineole | None | 4 | 3 | 0.03 | 0.09 |
| Ketoprofen | 10% | KET1334 | KET89 | Isopronanol | 50% IPN | 1-Ethyl-2-Pyrrolidone | 45% EP | Eucalyptus oil | 3.5% 1,8-cineole | None | 6 | 3 | 0.036 | 0.108 |
| Ketoprofen | 10% | KET1335 | KET89 | Isopronanol | 50% IPN | 1-Ethyl-2-Pyrrolidone | 45% EP | Eucalyptus oil | 3.5% 1,8-cineole | None | 8 | 3 | 0.113 | 0.339 |
| Ketoprofen | 10% | KET1336 | KET90 | Isopronanol | 50% IPN | Propylene glycol | 45% PPG | Eucalyptus oil | 3.5% 1,8-cineole | None | 0.5 | 1 | 0.01 | 0.03 |
| Ketoprofen | 10% | KET1337 | KET90 | Isopronanol | 50% IPN | Propylene glycol | 45% PPG | Eucalyptus oil | 3.5% 1,8-cineole | None | 2 | 1 | 0.007 | 0.021 |
| Ketoprofen | 10% | KET1338 | KET90 | Isopronanol | 50% IPN | Propylene glycol | 45% PPG | Eucalyptus oil | 3.5% 1,8-cineole | None | 4 | 1 | 0.003 | 0.009 |
| Ketoprofen | 10% | KET1339 | KET90 | Isopronanol | 50% IPN | Propylene glycol | 45% PPG | Eucalyptus oil | 3.5% 1,8-cineole | None | 6 | 1 | 0.009 | 0.027 |
| Ketoprofen | 10% | KET1340 | KET90 | Isopronanol | 50% IPN | Propylene glycol | 45% PPG | Eucalyptus oil | 3.5% 1,8-cineole | None | 8 | 1 | 0.007 | 0.021 |
| Ketoprofen | 10% | KET1341 | KET90 | Isopronanol | 50% IPN | Propylene glycol | 45% PPG | Eucalyptus oil | 3.5% 1,8-cineole | None | 0.5 | 2 | 0.007 | 0.021 |
| Ketoprofen | 10% | KET1342 | KET90 | Isopronanol | 50% IPN | Propylene glycol | 45% PPG | Eucalyptus oil | 3.5% 1,8-cineole | None | 2 | 2 | 0.029 | 0.087 |
| Ketoprofen | 10% | KET1343 | KET90 | Isopronanol | 50% IPN | Propylene glycol | 45% PPG | Eucalyptus oil | 3.5% 1,8-cineole | None | 4 | 2 | 0.008 | 0.024 |
| Ketoprofen | 10% | KET1344 | KET90 | Isopronanol | 50% IPN | Propylene glycol | 45% PPG | Eucalyptus oil | 3.5% 1,8-cineole | None | 6 | 2 | 0.031 | 0.093 |
| Ketoprofen | 10% | KET1345 | KET90 | Isopronanol | 50% IPN | Propylene glycol | 45% PPG | Eucalyptus oil | 3.5% 1,8-cineole | None | 8 | 2 | 0.047 | 0.141 |
| Ketoprofen | 10% | KET1346 | KET90 | Isopronanol | 50% IPN | Propylene glycol | 45% PPG | Eucalyptus oil | 3.5% 1,8-cineole | None | 0.5 | 3 | 0.037 | 0.111 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 10% | KET1347 | KET90 | Isopronanol | 50% IPN | Propylene glycol | 45% PPG | Eucalyptus oil | 3.5% 1,8-cineole | None | 2 | 3 | 0.033 | 0.099 |
| Ketoprofen | 10% | KET1348 | KET90 | Isopronanol | 50% IPN | Propylene glycol | 45% PPG | Eucalyptus oil | 3.5% 1,8-cineole | None | 4 | 3 | 0.032 | 0.096 |
| Ketoprofen | 10% | KET1349 | KET90 | Isopronanol | 50% IPN | Propylene glycol | 45% PPG | Eucalyptus oil | 3.5% 1,8-cineole | None | 6 | 3 | 0.011 | 0.033 |
| Ketoprofen | 10% | KET1350 | KET90 | Isopronanol | 50% IPN | Propylene glycol | 45% PPG | Eucalyptus oil | 3.5% 1,8-cineole | None | 8 | 3 | 0.006 | 0.018 |
| Ketoprofen | 10% | KET1351 | KET91 | Isopronanol | 50% IPN | Isomyristate | 45% ISOMYR | Eucalyptus oil | 3.5% 1,8-cineole | None | 0.5 | 1 | 0.011 | 0.033 |
| Ketoprofen | 10% | KET1352 | KET91 | Isopronanol | 50% IPN | Isomyristate | 45% ISOMYR | Eucalyptus oil | 3.5% 1,8-cineole | None | 2 | 1 | 0.007 | 0.021 |
| Ketoprofen | 10% | KET1353 | KET91 | Isopronanol | 50% IPN | Isomyristate | 45% ISOMYR | Eucalyptus oil | 3.5% 1,8-cineole | None | 4 | 1 | 0.008 | 0.024 |
| Ketoprofen | 10% | KET1354 | KET91 | Isopronanol | 50% IPN | Isomyristate | 45% ISOMYR | Eucalyptus oil | 3.5% 1,8-cineole | None | 6 | 1 | 0.024 | 0.072 |
| Ketoprofen | 10% | KET1355 | KET91 | Isopronanol | 50% IPN | Isomyristate | 45% ISOMYR | Eucalyptus oil | 3.5% 1,8-cineole | None | 8 | 1 | 0.069 | 0.207 |
| Ketoprofen | 10% | KET1356 | KET91 | Isopronanol | 50% IPN | Isomyristate | 45% ISOMYR | Eucalyptus oil | 3.5% 1,8-cineole | None | 0.5 | 2 | 0.032 | 0.096 |
| Ketoprofen | 10% | KET1357 | KET91 | Isopronanol | 50% IPN | Isomyristate | 45% ISOMYR | Eucalyptus oil | 3.5% 1,8-cineole | None | 2 | 2 | 0.026 | 0.078 |
| Ketoprofen | 10% | KET1358 | KET91 | Isopronanol | 50% IPN | Isomyristate | 45% ISOMYR | Eucalyptus oil | 3.5% 1,8-cineole | None | 4 | 2 | 0.023 | 0.069 |
| Ketoprofen | 10% | KET1359 | KET91 | Isopronanol | 50% IPN | Isomyristate | 45% ISOMYR | Eucalyptus oil | 3.5% 1,8-cineole | None | 6 | 2 | 0.007 | 0.021 |
| Ketoprofen | 10% | KET1360 | KET91 | Isopronanol | 50% IPN | Isomyristate | 45% ISOMYR | Eucalyptus oil | 3.5% 1,8-cineole | None | 8 | 2 | 0.009 | 0.027 |
| Ketoprofen | 10% | KET1361 | KET91 | Isopronanol | 50% IPN | Isomyristate | 45% ISOMYR | Eucalyptus oil | 3.5% 1,8-cineole | None | 0.5 | 3 | 0.006 | 0.018 |
| Ketoprofen | 10% | KET1362 | KET91 | Isopronanol | 50% IPN | Isomyristate | 45% ISOMYR | Eucalyptus oil | 3.5% 1,8-cineole | None | 2 | 3 | 0.027 | 0.081 |
| Ketoprofen | 10% | KET1363 | KET91 | Isopronanol | 50% IPN | Isomyristate | 45% ISOMYR | Eucalyptus oil | 3.5% 1,8-cineole | None | 4 | 3 | 0.008 | 0.024 |
| Ketoprofen | 10% | KET1364 | KET91 | Isopronanol | 50% IPN | Isomyristate | 45% ISOMYR | Eucalyptus oil | 3.5% 1,8-cineole | None | 6 | 3 | 0.02 | 0.06 |
| Ketoprofen | 10% | KET1365 | KET91 | Isopronanol | 50% IPN | Isomyristate | 45% ISOMYR | Eucalyptus oil | 3.5% 1,8-cineole | None | 8 | 3 | 0.009 | 0.027 |
| Ketoprofen | 10% | KET1366 | KET92 | Ethanol | 50% EtOH | Oleyl alcohol | 45% OA | Eucalyptus oil | 3.5% 1,8-cineole | 0.1M citrate | 0.5 | 1 | 0.042 | 0.126 |
| Ketoprofen | 10% | KET1367 | KET92 | Ethanol | 50% EtOH | Oleyl alcohol | 45% OA | Eucalyptus oil | 3.5% 1,8-cineole | 0.1M citrate | 2 | 1 | 0.042 | 0.126 |
| Ketoprofen | 10% | KET1368 | KET92 | Ethanol | 50% EtOH | Oleyl alcohol | 45% OA | Eucalyptus oil | 3.5% 1,8-cineole | 0.1M citrate | 4 | 1 | 0.016 | 0.048 |
| Ketoprofen | 10% | KET1369 | KET92 | Ethanol | 50% EtOH | Oleyl alcohol | 45% OA | Eucalyptus oil | 3.5% 1,8-cineole | 0.1M citrate | 6 | 1 | 0.007 | 0.021 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 10% | KET1370 | KET92 | Ethanol | 50% EthOH | Oleyl alcohol | 45% OA | Eucalyptus oil | 3.5% 1,8-cineole | 0.1M citrate | 8 | 1 | 0.098 | 0.294 |
| Ketoprofen | 10% | KET1371 | KET92 | Ethanol | 50% EthOH | Oleyl alcohol | 45% OA | Eucalyptus oil | 3.5% 1,8-cineole | 0.1M citrate | 0.5 | 2 | 0.049 | 0.147 |
| Ketoprofen | 10% | KET1372 | KET92 | Ethanol | 50% EthOH | Oleyl alcohol | 45% OA | Eucalyptus oil | 3.5% 1,8-cineole | 0.1M citrate | 2 | 2 | 0.008 | 0.024 |
| Ketoprofen | 10% | KET1373 | KET92 | Ethanol | 50% EthOH | Oleyl alcohol | 45% OA | Eucalyptus oil | 3.5% 1,8-cineole | 0.1M citrate | 4 | 2 | 0.041 | 0.123 |
| Ketoprofen | 10% | KET1374 | KET92 | Ethanol | 50% EthOH | Oleyl alcohol | 45% OA | Eucalyptus oil | 3.5% 1,8-cineole | 0.1M citrate | 6 | 2 | 0.053 | 0.159 |
| Ketoprofen | 10% | KET1375 | KET92 | Ethanol | 50% EthOH | Oleyl alcohol | 45% OA | Eucalyptus oil | 3.5% 1,8-cineole | 0.1M citrate | 8 | 2 | 0.014 | 0.042 |
| Ketoprofen | 10% | KET1376 | KET92 | Ethanol | 50% EthOH | Oleyl alcohol | 45% OA | Eucalyptus oil | 3.5% 1,8-cineole | 0.1M citrate | 0.5 | 3 | 0.011 | 0.033 |
| Ketoprofen | 10% | KET1377 | KET92 | Ethanol | 50% EthOH | Oleyl alcohol | 45% OA | Eucalyptus oil | 3.5% 1,8-cineole | 0.1M citrate | 2 | 3 | 0.046 | 0.138 |
| Ketoprofen | 10% | KET1378 | KET92 | Ethanol | 50% EthOH | Oleyl alcohol | 45% OA | Eucalyptus oil | 3.5% 1,8-cineole | 0.1M citrate | 4 | 3 | 0.039 | 0.117 |
| Ketoprofen | 10% | KET1379 | KET92 | Ethanol | 50% EthOH | Oleyl alcohol | 45% OA | Eucalyptus oil | 3.5% 1,8-cineole | 0.1M citrate | 6 | 3 | 0.023 | 0.069 |
| Ketoprofen | 10% | KET1380 | KET92 | Ethanol | 50% EthOH | Oleyl alcohol | 45% OA | Eucalyptus oil | 3.5% 1,8-cineole | 0.1M citrate | 8 | 3 | 0.016 | 0.048 |
| Flunixin | 10% | KET1381 | KET93 | Isopronanol | 50% IPN | 1-Ethyl-2-Pyrrolidone | 45% EP | Menthol | 50 ng/mL | None | 0.5 | 1 | 0.348 | 1.044 |
| Flunixin | 10% | KET1382 | KET93 | Isopronanol | 50% IPN | 1-Ethyl-2-Pyrrolidone | 45% EP | Menthol | 50 ng/mL | None | 2 | 1 | 0.363 | 1.089 |
| Flunixin | 10% | KET1383 | KET93 | Isopronanol | 50% IPN | 1-Ethyl-2-Pyrrolidone | 45% EP | Menthol | 50 ng/mL | None | 4 | 1 | 0.369 | 1.107 |
| Flunixin | 10% | KET1384 | KET93 | Isopronanol | 50% IPN | 1-Ethyl-2-Pyrrolidone | 45% EP | Menthol | 50 ng/mL | None | 6 | 1 | 0.395 | 1.185 |
| Flunixin | 10% | KET1385 | KET93 | Isopronanol | 50% IPN | 1-Ethyl-2-Pyrrolidone | 45% EP | Menthol | 50 ng/mL | None | 8 | 1 | 0.458 | 1.374 |
| Flunixin | 10% | KET1386 | KET93 | Isopronanol | 50% IPN | 1-Ethyl-2-Pyrrolidone | 45% EP | Menthol | 50 ng/mL | None | 0.5 | 2 | 0.008 | 0.024 |
| Flunixin | 10% | KET1387 | KET93 | Isopronanol | 50% IPN | 1-Ethyl-2-Pyrrolidone | 45% EP | Menthol | 50 ng/mL | None | 2 | 2 | 0.022 | 0.066 |
| Flunixin | 10% | KET1388 | KET93 | Isopronanol | 50% IPN | 1-Ethyl-2-Pyrrolidone | 45% EP | Menthol | 50 ng/mL | None | 4 | 2 | 0.051 | 0.153 |
| Flunixin | 10% | KET1389 | KET93 | Isopronanol | 50% IPN | 1-Ethyl-2-Pyrrolidone | 45% EP | Menthol | 50 ng/mL | None | 6 | 2 | 0.057 | 0.171 |
| Flunixin | 10% | KET1390 | KET93 | Isopronanol | 50% IPN | 1-Ethyl-2-Pyrrolidone | 45% EP | Menthol | 50 ng/mL | None | 8 | 2 | 0.089 | 0.267 |
| Flunixin | 10% | KET1391 | KET93 | Isopronanol | 50% IPN | 1-Ethyl-2-Pyrrolidone | 45% EP | Menthol | 50 ng/mL | None | 0.5 | 3 | 0.032 | 0.096 |
| Flunixin | 10% | KET1392 | KET93 | Isopronanol | 50% IPN | 1-Ethyl-2-Pyrrolidone | 45% EP | Menthol | 50 ng/mL | None | 2 | 3 | 0.034 | 0.102 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Flunixin | 10% | KET1393 | KET93 | Isopropanol | 50% IPN | 1-Ethyl-2-Pyrrolidone | 45% EP | Menthol | 50 ng/mL | None | 4 | 3 | 0.181 | 0.543 |
| Flunixin | 10% | KET1394 | KET93 | Isopropanol | 50% IPN | 1-Ethyl-2-Pyrrolidone | 45% EP | Menthol | 50 ng/mL | None | 6 | 3 | 0.193 | 0.579 |
| Flunixin | 10% | KET1395 | KET93 | Isopropanol | 50% IPN | 1-Ethyl-2-Pyrrolidone | 45% EP | Menthol | 50 ng/mL | None | 8 | 3 | 0.201 | 0.603 |
| Flunixin | 10% | KET1396 | KET94 | Isopropanol | 50% IPN | Propylene glycol | 45% PPG | Eucalyptus oil | 3.5% 1,8-cineole | None | 0.5 | 1 | 0.009 | 0.027 |
| Flunixin | 10% | KET1397 | KET94 | Isopropanol | 50% IPN | Propylene glycol | 45% PPG | Eucalyptus oil | 3.5% 1,8-cineole | None | 2 | 1 | 0.045 | 0.135 |
| Flunixin | 10% | KET1398 | KET94 | Isopropanol | 50% IPN | Propylene glycol | 45% PPG | Eucalyptus oil | 3.5% 1,8-cineole | None | 4 | 1 | 0.048 | 0.144 |
| Flunixin | 10% | KET1399 | KET94 | Isopropanol | 50% IPN | Propylene glycol | 45% PPG | Eucalyptus oil | 3.5% 1,8-cineole | None | 6 | 1 | 0.051 | 0.153 |
| Flunixin | 10% | KET1400 | KET94 | Isopropanol | 50% IPN | Propylene glycol | 45% PPG | Eucalyptus oil | 3.5% 1,8-cineole | None | 8 | 1 | 0.056 | 0.168 |
| Flunixin | 10% | KET1401 | KET94 | Isopropanol | 50% IPN | Propylene glycol | 45% PPG | Eucalyptus oil | 3.5% 1,8-cineole | None | 0.5 | 2 | 0.036 | 0.108 |
| Flunixin | 10% | KET1402 | KET94 | Isopropanol | 50% IPN | Propylene glycol | 45% PPG | Eucalyptus oil | 3.5% 1,8-cineole | None | 2 | 2 | 0.041 | 0.123 |
| Flunixin | 10% | KET1403 | KET94 | Isopropanol | 50% IPN | Propylene glycol | 45% PPG | Eucalyptus oil | 3.5% 1,8-cineole | None | 4 | 2 | 0.042 | 0.126 |
| Flunixin | 10% | KET1404 | KET94 | Isopropanol | 50% IPN | Propylene glycol | 45% PPG | Eucalyptus oil | 3.5% 1,8-cineole | None | 6 | 2 | 0.042 | 0.126 |
| Flunixin | 10% | KET1405 | KET94 | Isopropanol | 50% IPN | Propylene glycol | 45% PPG | Eucalyptus oil | 3.5% 1,8-cineole | None | 8 | 2 | 0.076 | 0.228 |
| Flunixin | 10% | KET1406 | KET94 | Isopropanol | 50% IPN | Propylene glycol | 45% PPG | Eucalyptus oil | 3.5% 1,8-cineole | None | 0.5 | 3 | 0.035 | 0.105 |
| Flunixin | 10% | KET1407 | KET94 | Isopropanol | 50% IPN | Propylene glycol | 45% PPG | Eucalyptus oil | 3.5% 1,8-cineole | None | 2 | 3 | 0.045 | 0.135 |
| Flunixin | 10% | KET1408 | KET94 | Isopropanol | 50% IPN | Propylene glycol | 45% PPG | Eucalyptus oil | 3.5% 1,8-cineole | None | 4 | 3 | 0.051 | 0.153 |
| Flunixin | 10% | KET1409 | KET94 | Isopropanol | 50% IPN | Propylene glycol | 45% PPG | Eucalyptus oil | 3.5% 1,8-cineole | None | 6 | 3 | 0.052 | 0.156 |
| Flunixin | 10% | KET1410 | KET94 | Isopropanol | 50% IPN | Propylene glycol | 45% PPG | Eucalyptus oil | 3.5% 1,8-cineole | None | 8 | 3 | 0.068 | 0.204 |
| Flunixin | 10% | KET1411 | KET95 | Isopropanol | 50% IPN | 1-Ethyl-2-Pyrrolidone | 45% EP | Menthol | 50 ng/mL | None | 0.5 | 1 | 0.053 | 0.159 |
| Flunixin | 10% | KET1412 | KET95 | Isopropanol | 50% IPN | 1-Ethyl-2-Pyrrolidone | 45% EP | Menthol | 50 ng/mL | None | 2 | 1 | 0.055 | 0.165 |
| Flunixin | 10% | KET1413 | KET95 | Isopropanol | 50% IPN | 1-Ethyl-2-Pyrrolidone | 45% EP | Menthol | 50 ng/mL | None | 4 | 1 | 0.062 | 0.186 |
| Flunixin | 10% | KET1414 | KET95 | Isopropanol | 50% IPN | 1-Ethyl-2-Pyrrolidone | 45% EP | Menthol | 50 ng/mL | None | 6 | 1 | 0.062 | 0.186 |
| Flunixin | 10% | KET1415 | KET95 | Isopropanol | 50% IPN | 1-Ethyl-2-Pyrrolidone | 45% EP | Menthol | 50 ng/mL | None | 8 | 1 | 0.066 | 0.198 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Flunixin | 10% | KET1416 | KET95 | Isopropanol | 50% IPN | 1-Ethyl-2-Pyrrolidone | 45% EP | Menthol | 50 ng/mL | None | 0.5 | 2 | 0.079 | 0.237 |
| Flunixin | 10% | KET1417 | KET95 | Isopropanol | 50% IPN | 1-Ethyl-2-Pyrrolidone | 45% EP | Menthol | 50 ng/mL | None | 2 | 2 | 0.082 | 0.246 |
| Flunixin | 10% | KET1418 | KET95 | Isopropanol | 50% IPN | 1-Ethyl-2-Pyrrolidone | 45% EP | Menthol | 50 ng/mL | None | 4 | 2 | 0.095 | 0.285 |
| Flunixin | 10% | KET1419 | KET95 | Isopropanol | 50% IPN | 1-Ethyl-2-Pyrrolidone | 45% EP | Menthol | 50 ng/mL | None | 6 | 2 | 0.136 | 0.408 |
| Flunixin | 10% | KET1420 | KET95 | Isopropanol | 50% IPN | 1-Ethyl-2-Pyrrolidone | 45% EP | Menthol | 50 ng/mL | None | 8 | 2 | 0.165 | 0.495 |
| Flunixin | 10% | KET1421 | KET95 | Isopropanol | 50% IPN | 1-Ethyl-2-Pyrrolidone | 45% EP | Menthol | 50 ng/mL | None | 0.2 | 3 | 0.038 | 0.114 |
| Flunixin | 10% | KET1422 | KET95 | Isopropanol | 50% IPN | 1-Ethyl-2-Pyrrolidone | 45% EP | Menthol | 50 ng/mL | None | 2 | 3 | 0.044 | 0.132 |
| Flunixin | 10% | KET1423 | KET95 | Isopropanol | 50% IPN | 1-Ethyl-2-Pyrrolidone | 45% EP | Menthol | 50 ng/mL | None | 4 | 3 | 0.049 | 0.147 |
| Flunixin | 10% | KET1424 | KET95 | Isopropanol | 50% IPN | 1-Ethyl-2-Pyrrolidone | 45% EP | Menthol | 50 ng/mL | None | 6 | 3 | 0.064 | 0.192 |
| Flunixin | 10% | KET1425 | KET95 | Isopropanol | 50% IPN | 1-Ethyl-2-Pyrrolidone | 45% EP | Menthol | 50 ng/mL | None | 8 | 3 | 0.155 | 0.465 |
| Flunixin | 10% | KET1426 | KET96 | Isopropanol | 50% IPN | Propylene glycol | 45% PPG | Eucalyptus oil | 3.5% 1,8-cineole | None | 0.5 | 1 | — | 0 |
| Flunixin | 10% | KET1427 | KET96 | Isopropanol | 50% IPN | Propylene glycol | 45% PPG | Eucalyptus oil | 3.5% 1,8-cineole | None | 2 | 1 | 0.007 | 0.021 |
| Flunixin | 10% | KET1428 | KET96 | Isopropanol | 50% IPN | Propylene glycol | 45% PPG | Eucalyptus oil | 3.5% 1,8-cineole | None | 4 | 1 | 0.031 | 0.093 |
| Flunixin | 10% | KET1429 | KET96 | Isopropanol | 50% IPN | Propylene glycol | 45% PPG | Eucalyptus oil | 3.5% 1,8-cineole | None | 6 | 1 | 0.032 | 0.096 |
| Flunixin | 10% | KET1430 | KET96 | Isopropanol | 50% IPN | Propylene glycol | 45% PPG | Eucalyptus oil | 3.5% 1,8-cineole | None | 8 | 1 | 0.02 | 0.06 |
| Flunixin | 10% | KET1431 | KET96 | Isopropanol | 50% IPN | Propylene glycol | 45% PPG | Eucalyptus oil | 3.5% 1,8-cineole | None | 0.5 | 2 | 0.005 | 0.015 |
| Flunixin | 10% | KET1432 | KET96 | Isopropanol | 50% IPN | Propylene glycol | 45% PPG | Eucalyptus oil | 3.5% 1,8-cineole | None | 2 | 2 | 0.037 | 0.111 |
| Flunixin | 10% | KET1433 | KET96 | Isopropanol | 50% IPN | Propylene glycol | 45% PPG | Eucalyptus oil | 3.5% 1,8-cineole | None | 4 | 2 | 0.044 | 0.132 |
| Flunixin | 10% | KET1434 | KET96 | Isopropanol | 50% IPN | Propylene glycol | 45% PPG | Eucalyptus oil | 3.5% 1,8-cineole | None | 6 | 2 | 0.05 | 0.15 |
| Flunixin | 10% | KET1435 | KET96 | Isopropanol | 50% IPN | Propylene glycol | 45% PPG | Eucalyptus oil | 3.5% 1,8-cineole | None | 8 | 2 | 0.056 | 0.168 |
| Flunixin | 10% | KET1436 | KET96 | Isopropanol | 50% IPN | Propylene glycol | 45% PPG | Eucalyptus oil | 3.5% 1,8-cineole | None | 0.5 | 3 | 0.01 | 0.03 |
| Flunixin | 10% | KET1437 | KET96 | Isopropanol | 50% IPN | Propylene glycol | 45% PPG | Eucalyptus oil | 3.5% 1,8-cineole | None | 2 | 3 | 0.011 | 0.033 |
| Flunixin | 10% | KET1438 | KET96 | Isopropanol | 50% IPN | Propylene glycol | 45% PPG | Eucalyptus oil | 3.5% 1,8-cineole | None | 4 | 3 | 0.025 | 0.075 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Flunixin | 10% | KET1439 | KET96 | Isopronanol | 50% IPN | Propylene glycol | 45% PPG | Eucalyptus oil | 3.5% 1,8-cineole | None | 6 | 3 | 0.025 | 0.075 |
| Flunixin | 10% | KET1440 | KET96 | Isopronanol | 50% IPN | Propylene glycol | 45% PPG | Eucalyptus oil | 3.5% 1,8-cineole | None | 8 | 3 | 0.033 | 0.099 |
| Ketoprofen | 10% | KET1441 | KET97 | Ethanol | 50% EtOH | 1-Ethyl-2-Pyrrolidinone | 45% | Eucalyptus oil | 3.5% 1,8-cineole | NA | 0.5 | 1 | 0.006 | 0.018 |
| Ketoprofen | 10% | KET1442 | KET97 | Ethanol | 50% EtOH | 1-Ethyl-2-Pyrrolidinone | 45% | Eucalyptus oil | 3.5% 1,8-cineole | NA | 2 | 1 | 0.017 | 0.051 |
| Ketoprofen | 10% | KET1443 | KET97 | Ethanol | 50% EtOH | 1-Ethyl-2-Pyrrolidinone | 45% | Eucalyptus oil | 3.5% 1,8-cineole | NA | 4 | 1 | 0.197 | 0.591 |
| Ketoprofen | 10% | KET1444 | KET97 | Ethanol | 50% EtOH | 1-Ethyl-2-Pyrrolidinone | 45% | Eucalyptus oil | 3.5% 1,8-cineole | NA | 6 | 1 | 0.76 | 2.28 |
| Ketoprofen | 10% | KET1445 | KET97 | Ethanol | 50% EtOH | 1-Ethyl-2-Pyrrolidinone | 45% | Eucalyptus oil | 3.5% 1,8-cineole | NA | 8 | 1 | 2.17 | 6.51 |
| Ketoprofen | 10% | KET1446 | KET97 | Ethanol | 50% EtOH | 1-Ethyl-2-Pyrrolidinone | 45% | Eucalyptus oil | 3.5% 1,8-cineole | NA | 0.5 | 2 | 0.011 | 0.033 |
| Ketoprofen | 10% | KET1447 | KET97 | Ethanol | 50% EtOH | 1-Ethyl-2-Pyrrolidinone | 45% | Eucalyptus oil | 3.5% 1,8-cineole | NA | 2 | 2 | 0.053 | 0.159 |
| Ketoprofen | 10% | KET1448 | KET97 | Ethanol | 50% EtOH | 1-Ethyl-2-Pyrrolidinone | 45% | Eucalyptus oil | 3.5% 1,8-cineole | NA | 4 | 2 | 0.08 | 0.24 |
| Ketoprofen | 10% | KET1449 | KET97 | Ethanol | 50% EtOH | 1-Ethyl-2-Pyrrolidinone | 45% | Eucalyptus oil | 3.5% 1,8-cineole | NA | 6 | 2 | 0.532 | 1.596 |
| Ketoprofen | 10% | KET1450 | KET97 | Ethanol | 50% EtOH | 1-Ethyl-2-Pyrrolidinone | 45% | Eucalyptus oil | 3.5% 1,8-cineole | NA | 8 | 2 | 1.778 | 5.334 |
| Ketoprofen | 10% | KET1451 | KET97 | Ethanol | 50% EtOH | 1-Ethyl-2-Pyrrolidinone | 45% | Eucalyptus oil | 3.5% 1,8-cineole | NA | 0.5 | 3 | 0.014 | 0.042 |
| Ketoprofen | 10% | KET1452 | KET97 | Ethanol | 50% EtOH | 1-Ethyl-2-Pyrrolidinone | 45% | Eucalyptus oil | 3.5% 1,8-cineole | NA | 2 | 3 | 0.008 | 0.024 |
| Ketoprofen | 10% | KET1453 | KET97 | Ethanol | 50% EtOH | 1-Ethyl-2-Pyrrolidinone | 45% | Eucalyptus oil | 3.5% 1,8-cineole | NA | 4 | 3 | 0.119 | 0.357 |
| Ketoprofen | 10% | KET1454 | KET97 | Ethanol | 50% EtOH | 1-Ethyl-2-Pyrrolidinone | 45% | Eucalyptus oil | 3.5% 1,8-cineole | NA | 6 | 3 | 1.089 | 3.267 |
| Ketoprofen | 10% | KET1455 | KET97 | Ethanol | 50% EtOH | 1-Ethyl-2-Pyrrolidinone | 45% | Eucalyptus oil | 3.5% 1,8-cineole | NA | 8 | 3 | 3.325 | 9.975 |
| Ketoprofen | 10% | KET1456 | KET98 | Ethanol | 50% EtOH | 1-Ethyl-2-Pyrrolidinone | 45% | Eucalyptol | 5% 1,8-cineole | NA | 0.5 | 1 | 0.006 | 0.018 |
| Ketoprofen | 10% | KET1457 | KET98 | Ethanol | 50% EtOH | 1-Ethyl-2-Pyrrolidinone | 45% | Eucalyptol | 5% 1,8-cineole | NA | 2 | 1 | 0.026 | 0.078 |
| Ketoprofen | 10% | KET1458 | KET98 | Ethanol | 50% EtOH | 1-Ethyl-2-Pyrrolidinone | 45% | Eucalyptol | 5% 1,8-cineole | NA | 4 | 1 | 0.063 | 0.189 |
| Ketoprofen | 10% | KET1459 | KET98 | Ethanol | 50% EtOH | 1-Ethyl-2-Pyrrolidinone | 45% | Eucalyptol | 5% 1,8-cineole | NA | 6 | 1 | 0.187 | 0.561 |
| Ketoprofen | 10% | KET1460 | KET98 | Ethanol | 50% EtOH | 1-Ethyl-2-Pyrrolidinone | 45% | Eucalyptol | 5% 1,8-cineole | NA | 8 | 1 | 2.145 | 6.435 |
| Ketoprofen | 10% | KET1461 | KET98 | Ethanol | 50% EtOH | 1-Ethyl-2-Pyrrolidinone | 45% | Eucalyptol | 5% 1,8-cineole | NA | 0.5 | 2 | 0.016 | 0.048 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 10% | KET1462 | KET98 | Ethanol | 50% EtOH | 1-Ethyl-2-Pyrrolidinone | 45% | Eucalyptol | 5% 1,8-cineole | NA | 2 | 2 | 0.011 | 0.033 |
| Ketoprofen | 10% | KET1463 | KET98 | Ethanol | 50% EtOH | 1-Ethyl-2-Pyrrolidinone | 45% | Eucalyptol | 5% 1,8-cineole | NA | 4 | 2 | 0.735 | 2.205 |
| Ketoprofen | 10% | KET1464 | KET98 | Ethanol | 50% EtOH | 1-Ethyl-2-Pyrrolidinone | 45% | Eucalyptol | 5% 1,8-cineole | NA | 6 | 2 | 3.096 | 9.288 |
| Ketoprofen | 10% | KET1465 | KET98 | Ethanol | 50% EtOH | 1-Ethyl-2-Pyrrolidinone | 45% | Eucalyptol | 5% 1,8-cineole | NA | 8 | 2 | 13.125 | 39.375 |
| Ketoprofen | 10% | KET1466 | KET98 | Ethanol | 50% EtOH | 1-Ethyl-2-Pyrrolidinone | 45% | Eucalyptol | 5% 1,8-cineole | NA | 0.5 | 3 | 0.007 | 0.021 |
| Ketoprofen | 10% | KET1467 | KET98 | Ethanol | 50% EtOH | 1-Ethyl-2-Pyrrolidinone | 45% | Eucalyptol | 5% 1,8-cineole | NA | 2 | 3 | 0.031 | 0.093 |
| Ketoprofen | 10% | KET1468 | KET98 | Ethanol | 50% EtOH | 1-Ethyl-2-Pyrrolidinone | 45% | Eucalyptol | 5% 1,8-cineole | NA | 4 | 3 | 0.058 | 0.174 |
| Ketoprofen | 10% | KET1469 | KET98 | Ethanol | 50% EtOH | 1-Ethyl-2-Pyrrolidinone | 45% | Eucalyptol | 5% 1,8-cineole | NA | 6 | 3 | 0.615 | 1.845 |
| Ketoprofen | 10% | KET1470 | KET98 | Ethanol | 50% EtOH | 1-Ethyl-2-Pyrrolidinone | 45% | Eucalyptol | 5% 1,8-cineole | NA | 8 | 3 | 0.946 | 2.838 |
| Ketoprofen | 10% | KET1471 | KET99 | Ethanol | 45% EtOH | 1-Ethyl-2-Pyrrolidinone | 45% | Eucalyptol | 10% 1,8-cineole | NA | 0.5 | 1 | 0.07 | 0.21 |
| Ketoprofen | 10% | KET1472 | KET99 | Ethanol | 45% EtOH | 1-Ethyl-2-Pyrrolidinone | 45% | Eucalyptol | 10% 1,8-cineole | NA | 2 | 1 | 0.018 | 0.054 |
| Ketoprofen | 10% | KET1473 | KET99 | Ethanol | 45% EtOH | 1-Ethyl-2-Pyrrolidinone | 45% | Eucalyptol | 10% 1,8-cineole | NA | 4 | 1 | 0.027 | 0.081 |
| Ketoprofen | 10% | KET1474 | KET99 | Ethanol | 45% EtOH | 1-Ethyl-2-Pyrrolidinone | 45% | Eucalyptol | 10% 1,8-cineole | NA | 6 | 1 | 0.216 | 0.648 |
| Ketoprofen | 10% | KET1475 | KET99 | Ethanol | 45% EtOH | 1-Ethyl-2-Pyrrolidinone | 45% | Eucalyptol | 10% 1,8-cineole | NA | 8 | 1 | 2.211 | 6.633 |
| Ketoprofen | 10% | KET1476 | KET99 | Ethanol | 45% EtOH | 1-Ethyl-2-Pyrrolidinone | 45% | Eucalyptol | 10% 1,8-cineole | NA | 0.5 | 2 | 0.007 | 0.021 |
| Ketoprofen | 10% | KET1477 | KET99 | Ethanol | 45% EtOH | 1-Ethyl-2-Pyrrolidinone | 45% | Eucalyptol | 10% 1,8-cineole | NA | 2 | 2 | 0.01 | 0.03 |
| Ketoprofen | 10% | KET1478 | KET99 | Ethanol | 45% EtOH | 1-Ethyl-2-Pyrrolidinone | 45% | Eucalyptol | 10% 1,8-cineole | NA | 4 | 2 | 0.044 | 0.132 |
| Ketoprofen | 10% | KET1479 | KET99 | Ethanol | 45% EtOH | 1-Ethyl-2-Pyrrolidinone | 45% | Eucalyptol | 10% 1,8-cineole | NA | 6 | 2 | 0.571 | 1.713 |
| Ketoprofen | 10% | KET1480 | KET99 | Ethanol | 45% EtOH | 1-Ethyl-2-Pyrrolidinone | 45% | Eucalyptol | 10% 1,8-cineole | NA | 8 | 2 | 2.014 | 6.042 |
| Ketoprofen | 10% | KET1481 | KET99 | Ethanol | 45% EtOH | 1-Ethyl-2-Pyrrolidinone | 45% | Eucalyptol | 10% 1,8-cineole | NA | 0.2 | 3 | 0.016 | 0.048 |
| Ketoprofen | 10% | KET1482 | KET99 | Ethanol | 45% EtOH | 1-Ethyl-2-Pyrrolidinone | 45% | Eucalyptol | 10% 1,8-cineole | NA | 2 | 3 | 0.017 | 0.051 |
| Ketoprofen | 10% | KET1483 | KET99 | Ethanol | 45% EtOH | 1-Ethyl-2-Pyrrolidinone | 45% | Eucalyptol | 10% 1,8-cineole | NA | 4 | 3 | 0.041 | 0.123 |
| Ketoprofen | 10% | KET1484 | KET99 | Ethanol | 45% EtOH | 1-Ethyl-2-Pyrrolidinone | 45% | Eucalyptol | 10% 1,8-cineole | NA | 6 | 3 | 0.658 | 1.974 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/EVAP | sample time (hrs) | Replicate | analysis conc | Concentration (µg/mL) |
|---|---|---|---|---|---|---|---|---|---|---|---|---|---|---|
| Ketoprofen | 10% | KET1485 | KET99 | Ethanol | 45% EtOH | 1-Ethyl-2-Pyrrolidinone | 45% | Eucalyptol | 10% 1,8-cineole | NA | 8 | 3 | 2.793 | 8.379 |
| Ketoprofen | 10% | KET1486 | KET100 | Ethanol | 50% EtOH | Propylene glycol | 45% | Eucalyptus oil | 3.5% 1,8-cineole | NA | 0.5 | 1 | 0.007 | 0.021 |
| Ketoprofen | 10% | KET1487 | KET100 | Ethanol | 50% EtOH | Propylene glycol | 45% | Eucalyptus oil | 3.5% 1,8-cineole | NA | 2 | 1 | 0.036 | 0.108 |
| Ketoprofen | 10% | KET1488 | KET100 | Ethanol | 50% EtOH | Propylene glycol | 45% | Eucalyptus oil | 3.5% 1,8-cineole | NA | 4 | 1 | 1.648 | 4.944 |
| Ketoprofen | 10% | KET1489 | KET100 | Ethanol | 50% EtOH | Propylene glycol | 45% | Eucalyptus oil | 3.5% 1,8-cineole | NA | 6 | 1 | 5.855 | 17.565 |
| Ketoprofen | 10% | KET1490 | KET100 | Ethanol | 50% EtOH | Propylene glycol | 45% | Eucalyptus oil | 3.5% 1,8-cineole | NA | | 1 | 8.245 | 24.735 |
| Ketoprofen | 10% | KET1491 | KET100 | Ethanol | 50% EtOH | Propylene glycol | 45% | Eucalyptus oil | 3.5% 1,8-cineole | NA | 0.5 | 2 | 0.008 | 0.024 |
| Ketoprofen | 10% | KET1492 | KET100 | Ethanol | 50% EtOH | Propylene glycol | 45% | Eucalyptus oil | 3.5% 1,8-cineole | NA | 2 | 2 | 0.058 | 0.174 |
| Ketoprofen | 10% | KET1493 | KET100 | Ethanol | 50% EtOH | Propylene glycol | 45% | Eucalyptus oil | 3.5% 1,8-cineole | NA | 4 | 2 | 0.061 | 0.183 |
| Ketoprofen | 10% | KET1494 | KET100 | Ethanol | 50% EtOH | Propylene glycol | 45% | Eucalyptus oil | 3.5% 1,8-cineole | NA | 6 | 2 | 0.386 | 1.158 |
| Ketoprofen | 10% | KET1495 | KET100 | Ethanol | 50% EtOH | Propylene glycol | 45% | Eucalyptus oil | 3.5% 1,8-cineole | NA | 8 | 2 | 1.636 | 4.908 |
| Ketoprofen | 10% | KET1496 | KET100 | Ethanol | 50% EtOH | Propylene glycol | 45% | Eucalyptus oil | 3.5% 1,8-cineole | NA | 0.5 | 3 | 0.007 | 0.021 |
| Ketoprofen | 10% | KET1497 | KET100 | Ethanol | 50% EtOH | Propylene glycol | 45% | Eucalyptus oil | 3.5% 1,8-cineole | NA | 2 | 3 | 0.01 | 0.03 |
| Ketoprofen | 10% | KET1498 | KET100 | Ethanol | 50% EtOH | Propylene glycol | 45% | Eucalyptus oil | 3.5% 1,8-cineole | NA | 4 | 3 | 0.528 | 1.584 |
| Ketoprofen | 10% | KET1499 | KET100 | Ethanol | 50% EtOH | Propylene glycol | 45% | Eucalyptus oil | 3.5% 1,8-cineole | NA | 6 | 3 | 1.779 | 5.337 |
| Ketoprofen | 10% | KET1500 | KET100 | Ethanol | 50% EtOH | Propylene glycol | 45% | Eucalyptus oil | 3.5% 1,8-cineole | NA | 8 | 3 | 3.593 | 10.779 |
| Ketoprofen | 10% | KET1501 | KET101 | Ethanol | 50% EtOH | Propylene glycol | 45% | Eucalyptol | 5% 1,8-cineole | NA | 0.5 | 1 | 0.009 | 0.027 |
| Ketoprofen | 10% | KET1502 | KET101 | Ethanol | 50% EtOH | Propylene glycol | 45% | Eucalyptol | 5% 1,8-cineole | NA | 2 | 1 | 0.011 | 0.033 |
| Ketoprofen | 10% | KET1503 | KET101 | Ethanol | 50% EtOH | Propylene glycol | 45% | Eucalyptol | 5% 1,8-cineole | NA | 4 | 1 | 0.024 | 0.072 |
| Ketoprofen | 10% | KET1504 | KET101 | Ethanol | 50% EtOH | Propylene glycol | 45% | Eucalyptol | 5% 1,8-cineole | NA | 6 | 1 | 0.073 | 0.219 |
| Ketoprofen | 10% | KET1505 | KET101 | Ethanol | 50% EtOH | Propylene glycol | 45% | Eucalyptol | 5% 1,8-cineole | NA | 8 | 1 | 0.076 | 0.228 |
| Ketoprofen | 10% | KET1506 | KET101 | Ethanol | 50% EtOH | Propylene glycol | 45% | Eucalyptol | 5% 1,8-cineole | NA | 0.5 | 2 | 0.016 | 0.048 |
| Ketoprofen | 10% | KET1507 | KET101 | Ethanol | 50% EtOH | Propylene glycol | 45% | Eucalyptol | 5% 1,8-cineole | NA | 2 | 2 | 0.015 | 0.045 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/EVAP | sample time (hrs) | Replicate | analysis conc | Concentration (μg/mL) |
|---|---|---|---|---|---|---|---|---|---|---|---|---|---|---|
| Ketoprofen | 10% | KET1508 | KET101 | Ethanol | 50% EtOH | Propylene glycol | 45% | Eucalyptol | 5% 1,8-cineole | NA | 4 | 2 | 0.071 | 0.213 |
| Ketoprofen | 10% | KET1509 | KET101 | Ethanol | 50% EtOH | Propylene glycol | 45% | Eucalyptol | 5% 1,8-cineole | NA | 6 | 2 | 0.406 | 1.218 |
| Ketoprofen | 10% | KET1510 | KET101 | Ethanol | 50% EtOH | Propylene glycol | 45% | Eucalyptol | 5% 1,8-cineole | NA | 8 | 2 | 0.927 | 2.781 |
| Ketoprofen | 10% | KET1511 | KET101 | Ethanol | 50% EtOH | Propylene glycol | 45% | Eucalyptol | 5% 1,8-cineole | NA | 0.5 | 3 | 0.008 | 0.024 |
| Ketoprofen | 10% | KET1512 | KET101 | Ethanol | 50% EtOH | Propylene glycol | 45% | Eucalyptol | 5% 1,8-cineole | NA | 2 | 3 | 0.009 | 0.027 |
| Ketoprofen | 10% | KET1513 | KET101 | Ethanol | 50% EtOH | Propylene glycol | 45% | Eucalyptol | 5% 1,8-cineole | NA | 4 | 3 | 0.012 | 0.036 |
| Ketoprofen | 10% | KET1514 | KET101 | Ethanol | 50% EtOH | Propylene glycol | 45% | Eucalyptol | 5% 1,8-cineole | NA | 6 | 3 | 0.022 | 0.066 |
| Ketoprofen | 10% | KET1515 | KET101 | Ethanol | 50% EtOH | Propylene glycol | 45% | Eucalyptol | 5% 1,8-cineole | NA | 8 | 3 | 0.067 | 0.201 |
| Ketoprofen | 10% | KET1516 | KET102 | Ethanol | 45% EtOH | Propylene glycol | 45% | Eucalyptol | 10% 1,8-cineole | NA | 0.5 | 1 | 0.02 | 0.06 |
| Ketoprofen | 10% | KET1517 | KET102 | Ethanol | 45% EtOH | Propylene glycol | 45% | Eucalyptol | 10% 1,8-cineole | NA | 2 | 1 | 0.009 | 0.027 |
| Ketoprofen | 10% | KET1518 | KET102 | Ethanol | 45% EtOH | Propylene glycol | 45% | Eucalyptol | 10% 1,8-cineole | NA | 4 | 1 | 0.01 | 0.03 |
| Ketoprofen | 10% | KET1519 | KET102 | Ethanol | 45% EtOH | Propylene glycol | 45% | Eucalyptol | 10% 1,8-cineole | NA | 6 | 1 | 0.035 | 0.105 |
| Ketoprofen | 10% | KET1520 | KET102 | Ethanol | 45% EtOH | Propylene glycol | 45% | Eucalyptol | 10% 1,8-cineole | NA | 8 | 1 | 0.232 | 0.696 |
| Ketoprofen | 10% | KET1521 | KET102 | Ethanol | 45% EtOH | Propylene glycol | 45% | Eucalyptol | 10% 1,8-cineole | NA | 0.5 | 2 | 0.017 | 0.051 |
| Ketoprofen | 10% | KET1522 | KET102 | Ethanol | 45% EtOH | Propylene glycol | 45% | Eucalyptol | 10% 1,8-cineole | NA | 2 | 2 | 0.01 | 0.03 |
| Ketoprofen | 10% | KET1523 | KET102 | Ethanol | 45% EtOH | Propylene glycol | 45% | Eucalyptol | 10% 1,8-cineole | NA | 4 | 2 | 1.039 | 3.117 |
| Ketoprofen | 10% | KET1524 | KET102 | Ethanol | 45% EtOH | Propylene glycol | 45% | Eucalyptol | 10% 1,8-cineole | NA | 6 | 2 | 3.834 | 11.502 |
| Ketoprofen | 10% | KET1525 | KET102 | Ethanol | 45% EtOH | Propylene glycol | 45% | Eucalyptol | 10% 1,8-cineole | NA | 8 | 2 | 5.482 | 16.446 |
| Ketoprofen | 10% | KET1526 | KET102 | Ethanol | 45% EtOH | Propylene glycol | 45% | Eucalyptol | 10% 1,8-cineole | NA | 0.5 | 3 | 0.012 | 0.036 |
| Ketoprofen | 10% | KET1527 | KET102 | Ethanol | 45% EtOH | Propylene glycol | 45% | Eucalyptol | 10% 1,8-cineole | NA | 2 | 3 | 0.007 | 0.021 |
| Ketoprofen | 10% | KET1528 | KET102 | Ethanol | 45% EtOH | Propylene glycol | 45% | Eucalyptol | 10% 1,8-cineole | NA | 4 | 3 | 0.073 | 0.219 |
| Ketoprofen | 10% | KET1529 | KET102 | Ethanol | 45% EtOH | Propylene glycol | 45% | Eucalyptol | 10% 1,8-cineole | NA | 6 | 3 | 0.387 | 1.161 |
| Ketoprofen | 10% | KET1530 | KET102 | Ethanol | 45% EtOH | Propylene glycol | 45% | Eucalyptol | 10% 1,8-cineole | NA | 8 | 3 | 2.96 | 8.88 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 10% | KET1531 | KET103 | Ethanol | 50% EtOH | Isopropyl myristate | 45% | Eucalyptus oil | 3.5% 1,8-cineole | NA | 0.5 | 1 | 0.006 | 0.018 |
| Ketoprofen | 10% | KET1532 | KET103 | Ethanol | 50% EtOH | Isopropyl myristate | 45% | Eucalyptus oil | 3.5% 1,8-cineole | NA | 2 | 1 | 0.024 | 0.072 |
| Ketoprofen | 10% | KET1533 | KET103 | Ethanol | 50% EtOH | Isopropyl myristate | 45% | Eucalyptus oil | 3.5% 1,8-cineole | NA | 4 | 1 | 0.056 | 0.168 |
| Ketoprofen | 10% | KET1534 | KET103 | Ethanol | 50% EtOH | Isopropyl myristate | 45% | Eucalyptus oil | 3.5% 1,8-cineole | NA | 6 | 1 | 1.446 | 4.338 |
| Ketoprofen | 10% | KET1535 | KET103 | Ethanol | 50% EtOH | Isopropyl myristate | 45% | Eucalyptus oil | 3.5% 1,8-cineole | NA | 8 | 1 | 7.744 | 23.232 |
| Ketoprofen | 10% | KET1536 | KET103 | Ethanol | 50% EtOH | Isopropyl myristate | 45% | Eucalyptus oil | 3.5% 1,8-cineole | NA | 0.5 | 2 | 0.016 | 0.048 |
| Ketoprofen | 10% | KET1537 | KET103 | Ethanol | 50% EtOH | Isopropyl myristate | 45% | Eucalyptus oil | 3.5% 1,8-cineole | NA | 2 | 2 | 0.027 | 0.081 |
| Ketoprofen | 10% | KET1538 | KET103 | Ethanol | 50% EtOH | Isopropyl myristate | 45% | Eucalyptus oil | 3.5% 1,8-cineole | NA | 4 | 2 | 0.098 | 0.294 |
| Ketoprofen | 10% | KET1539 | KET103 | Ethanol | 50% EtOH | Isopropyl myristate | 45% | Eucalyptus oil | 3.5% 1,8-cineole | NA | 6 | 2 | 1.245 | 3.735 |
| Ketoprofen | 10% | KET1540 | KET103 | Ethanol | 50% EtOH | Isopropyl myristate | 45% | Eucalyptus oil | 3.5% 1,8-cineole | NA | 8 | 2 | 4.178 | 12.534 |
| Ketoprofen | 10% | KET1541 | KET103 | Ethanol | 50% EtOH | Isopropyl myristate | 45% | Eucalyptus oil | 3.5% 1,8-cineole | NA | 0.2 | 3 | 0.012 | 0.036 |
| Ketoprofen | 10% | KET1542 | KET103 | Ethanol | 50% EtOH | Isopropyl myristate | 45% | Eucalyptus oil | 3.5% 1,8-cineole | NA | 2 | 3 | 0.013 | 0.039 |
| Ketoprofen | 10% | KET1543 | KET103 | Ethanol | 50% EtOH | Isopropyl myristate | 45% | Eucalyptus oil | 3.5% 1,8-cineole | NA | 4 | 3 | 0.371 | 1.113 |
| Ketoprofen | 10% | KET1544 | KET103 | Ethanol | 50% EtOH | Isopropyl myristate | 45% | Eucalyptus oil | 3.5% 1,8-cineole | NA | 6 | 3 | 1.317 | 3.951 |
| Ketoprofen | 10% | KET1545 | KET103 | Ethanol | 50% EtOH | Isopropyl myristate | 45% | Eucalyptus oil | 3.5% 1,8-cineole | NA | 8 | 3 | 2.867 | 8.601 |
| Ketoprofen | 10% | KET1546 | KET104 | Ethanol | 50% EtOH | Isopropyl myristate | 45% | Eucalyptol | 5% 1,8-cineole | NA | 0.5 | 1 | 0.009 | 0.027 |
| Ketoprofen | 10% | KET1547 | KET104 | Ethanol | 50% EtOH | Isopropyl myristate | 45% | Eucalyptol | 5% 1,8-cineole | NA | 2 | 1 | 0.008 | 0.024 |
| Ketoprofen | 10% | KET1548 | KET104 | Ethanol | 50% EtOH | Isopropyl myristate | 45% | Eucalyptol | 5% 1,8-cineole | NA | 4 | 1 | 0.013 | 0.039 |
| Ketoprofen | 10% | KET1549 | KET104 | Ethanol | 50% EtOH | Isopropyl myristate | 45% | Eucalyptol | 5% 1,8-cineole | NA | 6 | 1 | 0.083 | 0.249 |
| Ketoprofen | 10% | KET1550 | KET104 | Ethanol | 50% EtOH | Isopropyl myristate | 45% | Eucalyptol | 5% 1,8-cineole | NA |  | 1 | 0.759 | 2.277 |
| Ketoprofen | 10% | KET1551 | KET104 | Ethanol | 50% EtOH | Isopropyl myristate | 45% | Eucalyptol | 5% 1,8-cineole | NA | 0.5 | 2 | 0.013 | 0.039 |
| Ketoprofen | 10% | KET1552 | KET104 | Ethanol | 50% EtOH | Isopropyl myristate | 45% | Eucalyptol | 5% 1,8-cineole | NA | 2 | 2 | 0.014 | 0.042 |
| Ketoprofen | 10% | KET1553 | KET104 | Ethanol | 50% EtOH | Isopropyl myristate | 45% | Eucalyptol | 5% 1,8-cineole | NA | 4 | 2 | 0.031 | 0.093 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET1554 | KET104 | Ethanol | 50% EtOH | Isopropyl myristate | 45% | Eucalyptol | 5% 1,8-cineole | NA | 6 | 2 | 0.573 | 1.719 |
| Ketoprofen | 10% | KET1555 | KET104 | Ethanol | 50% EtOH | Isopropyl myristate | 45% | Eucalyptol | 5% 1,8-cineole | NA | 8 | 2 | 2.519 | 7.557 |
| Ketoprofen | 10% | KET1556 | KET104 | Ethanol | 50% EtOH | Isopropyl myristate | 45% | Eucalyptol | 5% 1,8-cineole | NA | 0.5 | 3 | 0.012 | 0.036 |
| Ketoprofen | 10% | KET1557 | KET104 | Ethanol | 50% EtOH | Isopropyl myristate | 45% | Eucalyptol | 5% 1,8-cineole | NA | 2 | 3 | 0.023 | 0.069 |
| Ketoprofen | 10% | KET1558 | KET104 | Ethanol | 50% EtOH | Isopropyl myristate | 45% | Eucalyptol | 5% 1,8-cineole | NA | 4 | 3 | 0.077 | 0.231 |
| Ketoprofen | 10% | KET1559 | KET104 | Ethanol | 50% EtOH | Isopropyl myristate | 45% | Eucalyptol | 5% 1,8-cineole | NA | 6 | 3 | 0.097 | 0.291 |
| Ketoprofen | 10% | KET1560 | KET104 | Ethanol | 50% EtOH | Isopropyl myristate | 45% | Eucalyptol | 5% 1,8-cineole | NA | 8 | 3 | 0.442 | 1.326 |
| Ketoprofen | 10% | KET1561 | KET105 | Ethanol | 45% EtOH | Isopropyl myristate | 45% | Eucalyptol | 10% 1,8-cineole | NA | 0.5 | 1 | 0.012 | 0.036 |
| Ketoprofen | 10% | KET1562 | KET105 | Ethanol | 45% EtOH | Isopropyl myristate | 45% | Eucalyptol | 10% 1,8-cineole | NA | 2 | 1 | 0.012 | 0.036 |
| Ketoprofen | 10% | KET1563 | KET105 | Ethanol | 45% EtOH | Isopropyl myristate | 45% | Eucalyptol | 10% 1,8-cineole | NA | 4 | 1 | 0.096 | 0.288 |
| Ketoprofen | 10% | KET1564 | KET105 | Ethanol | 45% EtOH | Isopropyl myristate | 45% | Eucalyptol | 10% 1,8-cineole | NA | 6 | 1 | 1.331 | 3.993 |
| Ketoprofen | 10% | KET1565 | KET105 | Ethanol | 45% EtOH | Isopropyl myristate | 45% | Eucalyptol | 10% 1,8-cineole | NA | 8 | 1 | 1.527 | 4.581 |
| Ketoprofen | 10% | KET1566 | KET105 | Ethanol | 45% EtOH | Isopropyl myristate | 45% | Eucalyptol | 10% 1,8-cineole | NA | 0.5 | 2 | 0.009 | 0.027 |
| Ketoprofen | 10% | KET1567 | KET105 | Ethanol | 45% EtOH | Isopropyl myristate | 45% | Eucalyptol | 10% 1,8-cineole | NA | 2 | 2 | 0.017 | 0.051 |
| Ketoprofen | 10% | KET1568 | KET105 | Ethanol | 45% EtOH | Isopropyl myristate | 45% | Eucalyptol | 10% 1,8-cineole | NA | 4 | 2 | 0.017 | 0.051 |
| Ketoprofen | 10% | KET1569 | KET105 | Ethanol | 45% EtOH | Isopropyl myristate | 45% | Eucalyptol | 10% 1,8-cineole | NA | 6 | 2 | 0.084 | 0.252 |
| Ketoprofen | 10% | KET1570 | KET105 | Ethanol | 45% EtOH | Isopropyl myristate | 45% | Eucalyptol | 10% 1,8-cineole | NA | 8 | 2 | 0.423 | 1.269 |
| Ketoprofen | 10% | KET1571 | KET105 | Ethanol | 45% EtOH | Isopropyl myristate | 45% | Eucalyptol | 10% 1,8-cineole | NA | 0.5 | 3 | 0.008 | 0.024 |
| Ketoprofen | 10% | KET1572 | KET105 | Ethanol | 45% EtOH | Isopropyl myristate | 45% | Eucalyptol | 10% 1,8-cineole | NA | 2 | 3 | 0.013 | 0.039 |
| Ketoprofen | 10% | KET1573 | KET105 | Ethanol | 45% EtOH | Isopropyl myristate | 45% | Eucalyptol | 10% 1,8-cineole | NA | 4 | 3 | 0.015 | 0.045 |
| Ketoprofen | 10% | KET1574 | KET105 | Ethanol | 45% EtOH | Isopropyl myristate | 45% | Eucalyptol | 10% 1,8-cineole | NA | 6 | 3 | 0.12 | 0.36 |
| Ketoprofen | 10% | KET1575 | KET105 | Ethanol | 45% EtOH | Isopropyl myristate | 45% | Eucalyptol | 10% 1,8-cineole | NA | 8 | 3 | 0.479 | 1.437 |
| Ketoprofen | 10% | KET1576 | KET106 | Ethanol | 50% EtOH | Oleyl alcohol | 50% | Menthol | 50 mg/mL | NA | 0.5 | 1 | 0.014 | 0.042 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 10% | KET1577 | KET106 | Ethanol | 50% EtOH | Oleyl alcohol | 50% | Menthol | 50 mg/mL | NA | 2 | 1 | 0.014 | 0.042 |
| Ketoprofen | 10% | KET1578 | KET106 | Ethanol | 50% EtOH | Oleyl alcohol | 50% | Menthol | 50 mg/mL | NA | 4 | 1 | 0.086 | 0.258 |
| Ketoprofen | 10% | KET1579 | KET106 | Ethanol | 50% EtOH | Oleyl alcohol | 50% | Menthol | 50 mg/mL | NA | 6 | 1 | 0.411 | 1.233 |
| Ketoprofen | 10% | KET1580 | KET106 | Ethanol | 50% EtOH | Oleyl alcohol | 50% | Menthol | 50 mg/mL | NA | 8 | 1 | 1.24 | 3.72 |
| Ketoprofen | 10% | KET1581 | KET106 | Ethanol | 50% EtOH | Oleyl alcohol | 50% | Menthol | 50 mg/mL | NA | 0.5 | 2 | 0.018 | 0.054 |
| Ketoprofen | 10% | KET1582 | KET106 | Ethanol | 50% EtOH | Oleyl alcohol | 50% | Menthol | 50 mg/mL | NA | 2 | 2 | 0.024 | 0.072 |
| Ketoprofen | 10% | KET1583 | KET106 | Ethanol | 50% EtOH | Oleyl alcohol | 50% | Menthol | 50 mg/mL | NA | 4 | 2 | 0.04 | 0.12 |
| Ketoprofen | 10% | KET1584 | KET106 | Ethanol | 50% EtOH | Oleyl alcohol | 50% | Menthol | 50 mg/mL | NA | 6 | 2 | 0.539 | 1.617 |
| Ketoprofen | 10% | KET1585 | KET106 | Ethanol | 50% EtOH | Oleyl alcohol | 50% | Menthol | 50 mg/mL | NA | 8 | 2 | 1.232 | 3.696 |
| Ketoprofen | 10% | KET1586 | KET106 | Ethanol | 50% EtOH | Oleyl alcohol | 50% | Menthol | 50 mg/mL | NA | 0.5 | 3 | 0.008 | 0.024 |
| Ketoprofen | 10% | KET1587 | KET106 | Ethanol | 50% EtOH | Oleyl alcohol | 50% | Menthol | 50 mg/mL | NA | 2 | 3 | 0.018 | 0.054 |
| Ketoprofen | 10% | KET1588 | KET106 | Ethanol | 50% EtOH | Oleyl alcohol | 50% | Menthol | 50 mg/mL | NA | 4 | 3 | 0.066 | 0.198 |
| Ketoprofen | 10% | KET1589 | KET106 | Ethanol | 50% EtOH | Oleyl alcohol | 50% | Menthol | 50 mg/mL | NA | 6 | 3 | 0.285 | 0.855 |
| Ketoprofen | 10% | KET1590 | KET106 | Ethanol | 50% EtOH | Oleyl alcohol | 50% | Menthol | 50 mg/mL | NA | 8 | 3 | 0.706 | 2.118 |
| Ketoprofen | 10% | KET1591 | KET107 | Ethanol | 50% EtOH | Oleyl alcohol | 45% | Eucalyptus oil | 3.5% 1,8-cineole | NA | 0.5 | 1 | 0.01 | 0.03 |
| Ketoprofen | 10% | KET1592 | KET107 | Ethanol | 50% EtOH | Oleyl alcohol | 45% | Eucalyptus oil | 3.5% 1,8-cineole | NA | 2 | 1 | 0.018 | 0.054 |
| Ketoprofen | 10% | KET1593 | KET107 | Ethanol | 50% EtOH | Oleyl alcohol | 45% | Eucalyptus oil | 3.5% 1,8-cineole | NA | 4 | 1 | 0.015 | 0.045 |
| Ketoprofen | 10% | KET1594 | KET107 | Ethanol | 50% EtOH | Oleyl alcohol | 45% | Eucalyptus oil | 3.5% 1,8-cineole | NA | 6 | 1 | 0.027 | 0.081 |
| Ketoprofen | 10% | KET1595 | KET107 | Ethanol | 50% EtOH | Oleyl alcohol | 45% | Eucalyptus oil | 3.5% 1,8-cineole | NA | 8 | 1 | 2.993 | 8.979 |
| Ketoprofen | 10% | KET1596 | KET107 | Ethanol | 50% EtOH | Oleyl alcohol | 45% | Eucalyptus oil | 3.5% 1,8-cineole | NA | 0.5 | 2 | 0.006 | 0.018 |
| Ketoprofen | 10% | KET1597 | KET107 | Ethanol | 50% EtOH | Oleyl alcohol | 45% | Eucalyptus oil | 3.5% 1,8-cineole | NA | 2 | 2 | 0.011 | 0.033 |
| Ketoprofen | 10% | KET1598 | KET107 | Ethanol | 50% EtOH | Oleyl alcohol | 45% | Eucalyptus oil | 3.5% 1,8-cineole | NA | 4 | 2 | 0.014 | 0.042 |
| Ketoprofen | 10% | KET1599 | KET107 | Ethanol | 50% EtOH | Oleyl alcohol | 45% | Eucalyptus oil | 3.5% 1,8-cineole | NA | 6 | 2 | 0.018 | 0.054 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 10% | KET1600 | KET107 | Ethanol | 50% EtOH | Oleyl alcohol | 45% | Eucalyptus oil | 3.5% 1,8-cineole | NA | 8 | 2 | 11.722 | 35.166 |
| Ketoprofen | 10% | KET1601 | KET107 | Ethanol | 50% EtOH | Oleyl alcohol | 45% | Eucalyptus oil | 3.5% 1,8-cineole | NA | 0.2 | 3 | 0.009 | 0.027 |
| Ketoprofen | 10% | KET1602 | KET107 | Ethanol | 50% EtOH | Oleyl alcohol | 45% | Eucalyptus oil | 3.5% 1,8-cineole | NA | 2 | 3 | 0.012 | 0.036 |
| Ketoprofen | 10% | KET1603 | KET107 | Ethanol | 50% EtOH | Oleyl alcohol | 45% | Eucalyptus oil | 3.5% 1,8-cineole | NA | 4 | 3 | 0.014 | 0.042 |
| Ketoprofen | 10% | KET1604 | KET107 | Ethanol | 50% EtOH | Oleyl alcohol | 45% | Eucalyptus oil | 3.5% 1,8-cineole | NA | 6 | 3 | 0.012 | 0.036 |
| Ketoprofen | 10% | KET1605 | KET107 | Ethanol | 50% EtOH | Oleyl alcohol | 45% | Eucalyptus oil | 3.5% 1,8-cineole | NA | 8 | 3 | 1.94 | 5.82 |
| Ketoprofen | 10% | KET1606 | KET107 | Ethanol | 50% EtOH | Oleyl alcohol | 45% | Eucalyptol | 5% 1,8-cineole | NA | 0.5 | 1 | 0.009 | 0.027 |
| Ketoprofen | 10% | KET1607 | KET108 | Ethanol | 50% EtOH | Oleyl alcohol | 45% | Eucalyptol | 5% 1,8-cineole | NA | 2 | 1 | 0.008 | 0.024 |
| Ketoprofen | 10% | KET1608 | KET108 | Ethanol | 50% EtOH | Oleyl alcohol | 45% | Eucalyptol | 5% 1,8-cineole | NA | 4 | 1 | 0.01 | 0.03 |
| Ketoprofen | 10% | KET1609 | KET108 | Ethanol | 50% EtOH | Oleyl alcohol | 45% | Eucalyptol | 5% 1,8-cineole | NA | 6 | 1 | 0.02 | 0.06 |
| Ketoprofen | 10% | KET1610 | KET108 | Ethanol | 50% EtOH | Oleyl alcohol | 45% | Eucalyptol | 5% 1,8-cineole | NA | | 1 | 3.517 | 10.551 |
| Ketoprofen | 10% | KET1611 | KET108 | Ethanol | 50% EtOH | Oleyl alcohol | 45% | Eucalyptol | 5% 1,8-cineole | NA | 0.5 | 2 | 0.009 | 0.027 |
| Ketoprofen | 10% | KET1612 | KET108 | Ethanol | 50% EtOH | Oleyl alcohol | 45% | Eucalyptol | 5% 1,8-cineole | NA | 2 | 2 | 0.011 | 0.033 |
| Ketoprofen | 10% | KET1613 | KET108 | Ethanol | 50% EtOH | Oleyl alcohol | 45% | Eucalyptol | 5% 1,8-cineole | NA | 4 | 2 | 0.01 | 0.03 |
| Ketoprofen | 10% | KET1614 | KET108 | Ethanol | 50% EtOH | Oleyl alcohol | 45% | Eucalyptol | 5% 1,8-cineole | NA | 6 | 2 | 0.011 | 0.033 |
| Ketoprofen | 10% | KET1615 | KET108 | Ethanol | 50% EtOH | Oleyl alcohol | 45% | Eucalyptol | 5% 1,8-cineole | NA | 8 | 2 | 0.475 | 1.425 |
| Ketoprofen | 10% | KET1616 | KET108 | Ethanol | 50% EtOH | Oleyl alcohol | 45% | Eucalyptol | 5% 1,8-cineole | NA | 0.5 | 3 | 0.008 | 0.024 |
| Ketoprofen | 10% | KET1617 | KET108 | Ethanol | 50% EtOH | Oleyl alcohol | 45% | Eucalyptol | 5% 1,8-cineole | NA | 2 | 3 | 0.009 | 0.027 |
| Ketoprofen | 10% | KET1618 | KET108 | Ethanol | 50% EtOH | Oleyl alcohol | 45% | Eucalyptol | 5% 1,8-cineole | NA | 4 | 3 | 0.009 | 0.027 |
| Ketoprofen | 10% | KET1619 | KET108 | Ethanol | 50% EtOH | Oleyl alcohol | 45% | Eucalyptol | 5% 1,8-cineole | NA | 6 | 3 | 0.006 | 0.018 |
| Ketoprofen | 10% | KET1620 | KET108 | Ethanol | 50% EtOH | Oleyl alcohol | 45% | Eucalyptus oil | 5% 1,8-cineole | NA | 8 | 3 | 0.988 | 2.964 |
| Flunixin | 10% | KET1621 | KET109 | Ethanol | 50% EtOH | Propylene glycol | 45% PPG | Eucalyptus oil | 3.5% 1,8-cineole | NA | 0.5 | 1 | 0.032 | 0.096 |
| Flunixin | 10% | KET1622 | KET109 | Ethanol | 50% EtOH | Propylene glycol | 45% PPG | Eucalyptus oil | 3.5% 1,8-cineole | NA | 2 | 1 | 0.03 | 0.09 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Flunixin | 10% | KET1623 | KET109 | Ethanol | 50% EtOH | Propylene glycol | 45% PPG | Eucalyptus oil | 3.5% 1,8-cineole | NA | 4 | 1 | 0.044 | 0.132 |
| Flunixin | 10% | KET1624 | KET109 | Ethanol | 50% EtOH | Propylene glycol | 45% PPG | Eucalyptus oil | 3.5% 1,8-cineole | NA | 6 | 1 | 0.156 | 0.468 |
| Flunixin | 10% | KET1625 | KET109 | Ethanol | 50% EtOH | Propylene glycol | 45% PPG | Eucalyptus oil | 3.5% 1,8-cineole | NA | 8 | 1 | 2.307 | 6.921 |
| Flunixin | 10% | KET1626 | KET109 | Ethanol | 50% EtOH | Propylene glycol | 45% PPG | Eucalyptus oil | 3.5% 1,8-cineole | NA | 0.5 | 2 | 0.032 | 0.096 |
| Flunixin | 10% | KET1627 | KET109 | Ethanol | 50% EtOH | Propylene glycol | 45% PPG | Eucalyptus oil | 3.5% 1,8-cineole | NA | 2 | 2 | 0.029 | 0.087 |
| Flunixin | 10% | KET1628 | KET109 | Ethanol | 50% EtOH | Propylene glycol | 45% PPG | Eucalyptus oil | 3.5% 1,8-cineole | NA | 4 | 2 | 0.021 | 0.063 |
| Flunixin | 10% | KET1629 | KET109 | Ethanol | 50% EtOH | Propylene glycol | 45% PPG | Eucalyptus oil | 3.5% 1,8-cineole | NA | 6 | 2 | 0.09 | 0.27 |
| Flunixin | 10% | KET1630 | KET109 | Ethanol | 50% EtOH | Propylene glycol | 45% PPG | Eucalyptus oil | 3.5% 1,8-cineole | NA | 8 | 2 | 0.196 | 0.588 |
| Flunixin | 10% | KET1631 | KET109 | Ethanol | 50% EtOH | Propylene glycol | 45% PPG | Eucalyptus oil | 3.5% 1,8-cineole | NA | 0.5 | 3 | 0.032 | 0.096 |
| Flunixin | 10% | KET1632 | KET109 | Ethanol | 50% EtOH | Propylene glycol | 45% PPG | Eucalyptus oil | 3.5% 1,8-cineole | NA | 2 | 3 | 0.123 | 0.369 |
| Flunixin | 10% | KET1633 | KET109 | Ethanol | 50% EtOH | Propylene glycol | 45% PPG | Eucalyptus oil | 3.5% 1,8-cineole | NA | 4 | 3 | 0.189 | 0.567 |
| Flunixin | 10% | KET1634 | KET109 | Ethanol | 50% EtOH | Propylene glycol | 45% PPG | Eucalyptus oil | 3.5% 1,8-cineole | NA | 6 | 3 | 0.355 | 1.065 |
| Flunixin | 10% | KET1635 | KET109 | Ethanol | 50% EtOH | Propylene glycol | 45% PPG | Eucalyptus oil | 3.5% 1,8-cineole | NA | 8 | 3 | 0.933 | 2.799 |
| Flunixin | 10% | KET1636 | KET110 | Ethanol | 50% EtOH | Propylene glycol | 45% PPG | Eucalyptol | 5% 1,8-cineole | NA | 0.5 | 1 | 0.028 | 0.084 |
| Flunixin | 10% | KET1637 | KET110 | Ethanol | 50% EtOH | Propylene glycol | 45% PPG | Eucalyptol | 5% 1,8-cineole | NA | 2 | 1 | 0.022 | 0.066 |
| Flunixin | 10% | KET1638 | KET110 | Ethanol | 50% EtOH | Propylene glycol | 45% PPG | Eucalyptol | 5% 1,8-cineole | NA | 4 | 1 | 0.02 | 0.06 |
| Flunixin | 10% | KET1639 | KET110 | Ethanol | 50% EtOH | Propylene glycol | 45% PPG | Eucalyptol | 5% 1,8-cineole | NA | 6 | 1 | 0.035 | 0.105 |
| Flunixin | 10% | KET1640 | KET110 | Ethanol | 50% EtOH | Propylene glycol | 45% PPG | Eucalyptol | 5% 1,8-cineole | NA | 8 | 1 | 0.035 | 0.105 |
| Flunixin | 10% | KET1641 | KET110 | Ethanol | 50% EtOH | Propylene glycol | 45% PPG | Eucalyptol | 5% 1,8-cineole | NA | 0.5 | 2 | 0.019 | 0.057 |
| Flunixin | 10% | KET1642 | KET110 | Ethanol | 50% EtOH | Propylene glycol | 45% PPG | Eucalyptol | 5% 1,8-cineole | NA | 2 | 2 | 0.019 | 0.057 |
| Flunixin | 10% | KET1643 | KET110 | Ethanol | 50% EtOH | Propylene glycol | 45% PPG | Eucalyptol | 5% 1,8-cineole | NA | 4 | 2 | 0.025 | 0.075 |
| Flunixin | 10% | KET1644 | KET110 | Ethanol | 50% EtOH | Propylene glycol | 45% PPG | Eucalyptol | 5% 1,8-cineole | NA | 6 | 2 | 0.034 | 0.102 |
| Flunixin | 10% | KET1645 | KET110 | Ethanol | 50% EtOH | Propylene glycol | 45% PPG | Eucalyptol | 5% 1,8-cineole | NA | 8 | 2 | 0.184 | 0.552 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Flunixin | 10% | KET1646 | KET110 | Ethanol | 50% EtOH | Propylene glycol | 45% PPG | Eucalyptol | 5% 1,8-cineole | NA | 0.5 | 3 | 0.022 | 0.066 |
| Flunixin | 10% | KET1647 | KET110 | Ethanol | 50% EtOH | Propylene glycol | 45% PPG | Eucalyptol | 5% 1,8-cineole | NA | 2 | 3 | 0.039 | 0.117 |
| Flunixin | 10% | KET1648 | KET110 | Ethanol | 50% EtOH | Propylene glycol | 45% PPG | Eucalyptol | 5% 1,8-cineole | NA | 4 | 3 | 0.037 | 0.111 |
| Flunixin | 10% | KET1649 | KET110 | Ethanol | 50% EtOH | Propylene glycol | 45% PPG | Eucalyptol | 5% 1,8-cineole | NA | 6 | 3 | 0.042 | 0.126 |
| Flunixin | 10% | KET1650 | KET110 | Ethanol | 50% EtOH | Propylene glycol | 45% PPG | Eucalyptol | 5% 1,8-cineole | NA | 8 | 3 | 0.076 | 0.228 |
| Flunixin | 10% | KET1651 | KET111 | Ethanol | 50% EtOH | Propylene glycol | 45% PPG | Eucalyptol | 10% 1,8-cineole | NA | 0.5 | 1 | 0.42 | 1.26 |
| Flunixin | 10% | KET1652 | KET111 | Ethanol | 50% EtOH | Propylene glycol | 45% PPG | Eucalyptol | 10% 1,8-cineole | NA | 2 | 1 | 0.402 | 1.206 |
| Flunixin | 10% | KET1653 | KET111 | Ethanol | 50% EtOH | Propylene glycol | 45% PPG | Eucalyptol | 10% 1,8-cineole | NA | 4 | 1 | 0.406 | 1.218 |
| Flunixin | 10% | KET1654 | KET111 | Ethanol | 50% EtOH | Propylene glycol | 45% PPG | Eucalyptol | 10% 1,8-cineole | NA | 6 | 1 | 0.806 | 2.418 |
| Flunixin | 10% | KET1655 | KET111 | Ethanol | 50% EtOH | Propylene glycol | 45% PPG | Eucalyptol | 10% 1,8-cineole | NA | 8 | 1 | 1.345 | 4.035 |
| Flunixin | 10% | KET1656 | KET111 | Ethanol | 50% EtOH | Propylene glycol | 45% PPG | Eucalyptol | 10% 1,8-cineole | NA | 0.5 | 2 | 0.038 | 0.114 |
| Flunixin | 10% | KET1657 | KET111 | Ethanol | 50% EtOH | Propylene glycol | 45% PPG | Eucalyptol | 10% 1,8-cineole | NA | 2 | 2 | 0.045 | 0.135 |
| Flunixin | 10% | KET1658 | KET111 | Ethanol | 50% EtOH | Propylene glycol | 45% PPG | Eucalyptol | 10% 1,8-cineole | NA | 4 | 2 | 0.046 | 0.138 |
| Flunixin | 10% | KET1659 | KET111 | Ethanol | 50% EtOH | Propylene glycol | 45% PPG | Eucalyptol | 10% 1,8-cineole | NA | 6 | 2 | 0.082 | 0.246 |
| Flunixin | 10% | KET1660 | KET111 | Ethanol | 50% EtOH | Propylene glycol | 45% PPG | Eucalyptol | 10% 1,8-cineole | NA | 8 | 2 | 0.141 | 0.423 |
| Flunixin | 10% | KET1661 | KET111 | Ethanol | 50% EtOH | Propylene glycol | 45% PPG | Eucalyptol | 10% 1,8-cineole | NA | 0.2 | 3 | 0.063 | 0.189 |
| Flunixin | 10% | KET1662 | KET111 | Ethanol | 50% EtOH | Propylene glycol | 45% PPG | Eucalyptol | 10% 1,8-cineole | NA | 2 | 3 | 0.044 | 0.132 |
| Flunixin | 10% | KET1663 | KET111 | Ethanol | 50% EtOH | Propylene glycol | 45% PPG | Eucalyptol | 10% 1,8-cineole | NA | 4 | 3 | 0.028 | 0.084 |
| Flunixin | 10% | KET1664 | KET111 | Ethanol | 50% EtOH | Propylene glycol | 45% PPG | Eucalyptol | 10% 1,8-cineole | NA | 6 | 3 | 0.041 | 0.123 |
| Flunixin | 10% | KET1665 | KET111 | Ethanol | 50% EtOH | Propylene glycol | 45% PPG | Eucalyptol | 10% 1,8-cineole | NA | 8 | 3 | 0.633 | 1.899 |
| Ketoprofen | 10% | KET1701 | KET112 | Ethanol | Propylene glycol 30:70 | Eucalyptus oil | | 3.5% 1,8-cineole | | No | 0.5 | 1 | 0.04 | 0.12 |
| Ketoprofen | 10% | KET1702 | KET112 | Ethanol | Propylene glycol 30:70 | Eucalyptus oil | | 3.5% 1,8-cineole | | No | 2 | 1 | 0.018 | 0.054 |
| Ketoprofen | 10% | KET1703 | KET112 | Ethanol | Propylene glycol 30:70 | Eucalyptus oil | | 3.5% 1,8-cineole | | No | 4 | 1 | 0.264 | 0.792 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Rep-licate | analysis conc | Concentration (μg/mL) |
|---|---|---|---|---|---|---|---|---|---|---|---|---|---|---|
| Ketoprofen | 10% | KET1704 | KETH2 | Ethanol | Propylene glycol | 30:70 | Eucalyptus oil | 3.5% 1,8-cineole | | No | 6 | 1 | 1.666 | 4.998 |
| Ketoprofen | 10% | KET1705 | KET112 | Ethanol | Propylene glycol | 30:70 | Eucalyptus oil | 3.5% 1,8-cineole | | No | 8 | 1 | 8.688 | 26.064 |
| Ketoprofen | 10% | KET1706 | KET112 | Ethanol | Propylene glycol | 30:70 | Eucalyptus oil | 3.5% 1,8-cineole | | No | 0.5 | 2 | 0.1 | 0.3 |
| Ketoprofen | 10% | KET1707 | KET112 | Ethanol | Propylene glycol | 30:70 | Eucalyptus oil | 3.5% 1,8-cineole | | No | 2 | 2 | 0.045 | 0.135 |
| Ketoprofen | 10% | KET1708 | KET112 | Ethanol | Propylene glycol | 30:70 | Eucalyptus oil | 3.5% 1,8-cineole | | No | 4 | 2 | 0.048 | 0.144 |
| Ketoprofen | 10% | KET1709 | KET112 | Ethanol | Propylene glycol | 30:70 | Eucalyptus oil | 3.5% 1,8-cineole | | No | 6 | 2 | 0.084 | 0.252 |
| Ketoprofen | 10% | KET1710 | KET112 | Ethanol | Propylene glycol | 30:70 | Eucalyptus oil | 3.5% 1,8-cineole | | No | 8 | 2 | 0.805 | 2.415 |
| Ketoprofen | 10% | KET1711 | KET112 | Ethanol | Propylene glycol | 30:70 | Eucalyptus oil | 3.5% 1,8-cineole | | No | 0.5 | 3 | 0.059 | 0.177 |
| Ketoprofen | 10% | KET1712 | KET112 | Ethanol | Propylene glycol | 30:70 | Eucalyptus oil | 3.5% 1,8-cineole | | No | 2 | 3 | 0.023 | 0.069 |
| Ketoprofen | 10% | KET1713 | KET112 | Ethanol | Propylene glycol | 30:70 | Eucalyptus oil | 3.5% 1,8-cineole | | No | 4 | 3 | 0.041 | 0.123 |
| Ketoprofen | 10% | KET1714 | KET112 | Ethanol | Propylene glycol | 30:70 | Eucalyptus oil | 3.5% 1,8-cineole | | No | 6 | 3 | 0.096 | 0.288 |
| Ketoprofen | 10% | KET1715 | KET112 | Ethanol | Propylene glycol | 30:70 | Eucalyptus oil | 3.5% 1,8-cineole | | No | 8 | 3 | 0.323 | 0.969 |
| Ketoprofen | 10% | KET1716 | KET113 | Ethanol | Propylene glycol | 30:70 | Eucalyptus oil | 3.5% 1,8-cineole | | Yes | 0.5 | 1 | 0.094 | 0.282 |
| Ketoprofen | 10% | KET1717 | KET113 | Ethanol | Propylene glycol | 30:70 | Eucalyptus oil | 3.5% 1,8-cineole | | Yes | 2 | 1 | 0.031 | 0.093 |
| Ketoprofen | 10% | KET1718 | KET113 | Ethanol | Propylene glycol | 30:70 | Eucalyptus oil | 3.5% 1,8-cineole | | Yes | 4 | 1 | 0.041 | 0.123 |
| Ketoprofen | 10% | KET1719 | KET113 | Ethanol | Propylene glycol | 30:70 | Eucalyptus oil | 3.5% 1,8-cineole | | Yes | 6 | 1 | 0.027 | 0.081 |
| Ketoprofen | 10% | KET1720 | KET113 | Ethanol | Propylene glycol | 30:70 | Eucalyptus oil | 3.5% 1,8-cineole | | Yes | 8 | 1 | 0.106 | 0.318 |
| Ketoprofen | 10% | KET1721 | KET113 | Ethanol | Propylene glycol | 30:70 | Eucalyptus oil | 3.5% 1,8-cineole | | Yes | 0.5 | 2 | 0.067 | 0.201 |
| Ketoprofen | 10% | KET1722 | KET113 | Ethanol | Propylene glycol | 30:70 | Eucalyptus oil | 3.5% 1,8-cineole | | Yes | 2 | 2 | 0.029 | 0.087 |
| Ketoprofen | 10% | KET1723 | KET113 | Ethanol | Propylene glycol | 30:70 | Eucalyptus oil | 3.5% 1,8-cineole | | Yes | 4 | 2 | 0.02 | 0.06 |
| Ketoprofen | 10% | KET1724 | KET113 | Ethanol | Propylene glycol | 30:70 | Eucalyptus oil | 3.5% 1,8-cineole | | Yes | 6 | 2 | 0.052 | 0.156 |
| Ketoprofen | 10% | KET1725 | KET113 | Ethanol | Propylene glycol | 30:70 | Eucalyptus oil | 3.5% 1,8-cineole | | Yes | 8 | 2 | 0.054 | 0.162 |
| Ketoprofen | 10% | KET1726 | KET113 | Ethanol | Propylene glycol | 30:70 | Eucalyptus oil | 3.5% 1,8-cineole | | Yes | 0.5 | 3 | 0.088 | 0.264 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET1727 | KET113 | Ethanol | Propylene glycol | 30:70 | Eucalyptus oil | 3.5% 1,8-cineole | | Yes | 2 | 3 | 0.023 | 0.069 |
| Ketoprofen | 10% | KET1728 | KET113 | Ethanol | Propylene glycol | 30:70 | Eucalyptus oil | 3.5% 1,8-cineole | | Yes | 4 | 3 | 0.022 | 0.066 |
| Ketoprofen | 10% | KET1729 | KET113 | Ethanol | Propylene glycol | 30:70 | Eucalyptus oil | 3.5% 1,8-cineole | | Yes | 6 | 3 | 0.016 | 0.048 |
| Ketoprofen | 10% | KET1730 | KET113 | Ethanol | Propylene glycol | 30:70 | Eucalyptus oil | 3.5% 1,8-cineole | | Yes | 8 | 3 | 0.021 | 0.063 |
| Ketoprofen | 10% | KET1731 | KETH4 | Ethanol | Propylene glycol | 30:70 | Eucalyptus oil | 3.5% 1,8-cineole | | No | 0.5 | 1 | 0.291 | 0.873 |
| Ketoprofen | 10% | KET1732 | KET114 | Ethanol | Propylene glycol | 50:50 | Eucalyptus oil | 3.5% 1,8-cineole | | No | 2 | 1 | 0.03 | 0.09 |
| Ketoprofen | 10% | KET1733 | KET114 | Ethanol | Propylene glycol | 50:50 | Eucalyptus oil | 3.5% 1,8-cineole | | No | 4 | 1 | 0.05 | 0.15 |
| Ketoprofen | 10% | KET1734 | KET114 | Ethanol | Propylene glycol | 50:50 | Eucalyptus oil | 3.5% 1,8-cineole | | No | 6 | 1 | 0.052 | 0.156 |
| Ketoprofen | 10% | KET1735 | KET114 | Ethanol | Propylene glycol | 50:50 | Eucalyptus oil | 3.5% 1,8-cineole | | No | 8 | 1 | 0.655 | 1.965 |
| Ketoprofen | 10% | KET1736 | KET114 | Ethanol | Propylene glycol | 50:50 | Eucalyptus oil | 3.5% 1,8-cineole | | No | 0.5 | 2 | 0.029 | 0.087 |
| Ketoprofen | 10% | KET1737 | KET114 | Ethanol | Propylene glycol | 50:50 | Eucalyptus oil | 3.5% 1,8-cineole | | No | 2 | 2 | 0.109 | 0.327 |
| Ketoprofen | 10% | KET1738 | KET114 | Ethanol | Propylene glycol | 50:50 | Eucalyptus oil | 3.5% 1,8-cineole | | No | 4 | 2 | 0.088 | 0.264 |
| Ketoprofen | 10% | KET1739 | KET114 | Ethanol | Propylene glycol | 50:50 | Eucalyptus oil | 3.5% 1,8-cineole | | No | 6 | 2 | 0.175 | 0.525 |
| Ketoprofen | 10% | KET1740 | KET114 | Ethanol | Propylene glycol | 50:50 | Eucalyptus oil | 3.5% 1,8-cineole | | No | 8 | 2 | 0.589 | 1.767 |
| Ketoprofen | 10% | KET1741 | KET114 | Ethanol | Propylene glycol | 50:50 | Eucalyptus oil | 3.5% 1,8-cineole | | No | 0.5 | 3 | 0.037 | 0.111 |
| Ketoprofen | 10% | KET1742 | KET114 | Ethanol | Propylene glycol | 50:50 | Eucalyptus oil | 3.5% 1,8-cineole | | No | 2 | 3 | 0.043 | 0.129 |
| Ketoprofen | 10% | KET1743 | KET114 | Ethanol | Propylene glycol | 50:50 | Eucalyptus oil | 3.5% 1,8-cineole | | No | 4 | 3 | 0.142 | 0.426 |
| Ketoprofen | 10% | KET1744 | KET114 | Ethanol | Propylene glycol | 50:50 | Eucalyptus oil | 3.5% 1,8-cineole | | No | 6 | 3 | 1.23 | 3.69 |
| Ketoprofen | 10% | KET1745 | KET114 | Ethanol | Propylene glycol | 50:50 | Eucalyptus oil | 3.5% 1,8-cineole | | No | 8 | 3 | 2.713 | 8.139 |
| Ketoprofen | 10% | KET1746 | KET115 | Ethanol | Propylene glycol | 50:50 | Eucalyptus oil | 3.5% 1,8-cineole | | Yes | 0.5 | 1 | 0.204 | 0.612 |
| Ketoprofen | 10% | KET1747 | KET115 | Ethanol | Propylene glycol | 50:50 | Eucalyptus oil | 3.5% 1,8-cineole | | Yes | 2 | 1 | 0.127 | 0.381 |
| Ketoprofen | 10% | KET1748 | KET115 | Ethanol | Propylene glycol | 50:50 | Eucalyptus oil | 3.5% 1,8-cineole | | Yes | 4 | 1 | 0.042 | 0.126 |
| Ketoprofen | 10% | KET1749 | KET115 | Ethanol | Propylene glycol | 50:50 | Eucalyptus oil | 3.5% 1,8-cineole | | Yes | 6 | 1 | 0.089 | 0.267 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET1750 | KET115 | Ethanol | Propylene glycol | 50:50 | Eucalyptus oil | 3.5% 1,8-cineole | | Yes | 8 | 1 | 0.138 | 0.414 |
| Ketoprofen | 10% | KET1751 | KET115 | Ethanol | Propylene glycol | 50:50 | Eucalyptus oil | 3.5% 1,8-cineole | | Yes | 0.5 | 2 | 0.128 | 0.384 |
| Ketoprofen | 10% | KET1752 | KET115 | Ethanol | Propylene glycol | 50:50 | Eucalyptus oil | 3.5% 1,8-cineole | | Yes | 2 | 2 | 0.094 | 0.282 |
| Ketoprofen | 10% | KET1753 | KET115 | Ethanol | Propylene glycol | 50:50 | Eucalyptus oil | 3.5% 1,8-cineole | | Yes | 4 | 2 | 0.067 | 0.201 |
| Ketoprofen | 10% | KET1754 | KET115 | Ethanol | Propylene glycol | 50:50 | Eucalyptus oil | 3.5% 1,8-cineole | | Yes | 6 | 2 | 0.051 | 0.153 |
| Ketoprofen | 10% | KET1755 | KET115 | Ethanol | Propylene glycol | 50:50 | Eucalyptus oil | 3.5% 1,8-cineole | | Yes | 8 | 2 | 0.218 | 0.654 |
| Ketoprofen | 10% | KET1756 | KET115 | Ethanol | Propylene glycol | 50:50 | Eucalyptus oil | 3.5% 1,8-cineole | | Yes | 0.5 | 3 | 0.024 | 0.072 |
| Ketoprofen | 10% | KET1757 | KET115 | Ethanol | Propylene glycol | 50:50 | Eucalyptus oil | 3.5% 1,8-cineole | | Yes | 2 | 3 | 0.036 | 0.108 |
| Ketoprofen | 10% | KET1758 | KETH5 | Ethanol | Propylene glycol | 50:50 | Eucalyptus oil | 3.5% 1,8-cineole | | Yes | 4 | 3 | 0.023 | 0.069 |
| Ketoprofen | 10% | KET1759 | KET115 | Ethanol | Propylene glycol | 50:50 | Eucalyptus oil | 3.5% 1,8-cineole | | Yes | 6 | 3 | 0.03 | 0.09 |
| Ketoprofen | 10% | KET1760 | KET115 | Ethanol | Propylene glycol | 50:50 | Eucalyptus oil | 3.5% 1,8-cineole | | Yes | 8 | 3 | 0.58 | 1.74 |
| Ketoprofen | 10% | KET1761 | KET116 | Ethanol | Propylene glycol | 70:30 | Eucalyptus oil | 3.5% 1,8-cineole | | No | 0.5 | 1 | 0.093 | 0.279 |
| Ketoprofen | 10% | KET1762 | KET116 | Ethanol | Propylene glycol | 70:30 | Eucalyptus oil | 3.5% 1,8-cineole | | No | 2 | 1 | 0.836 | 2.508 |
| Ketoprofen | 10% | KET1763 | KET116 | Ethanol | Propylene glycol | 70:30 | Eucalyptus oil | 3.5% 1,8-cineole | | No | 4 | 1 | 12.264 | 36.792 |
| Ketoprofen | 10% | KET1764 | KET116 | Ethanol | Propylene glycol | 70:30 | Eucalyptus oil | 3.5% 1,8-cineole | | No | 6 | 1 | 16.074 | 48.222 |
| Ketoprofen | 10% | KET1765 | KET116 | Ethanol | Propylene glycol | 70:30 | Eucalyptus oil | 3.5% 1,8-cineole | | No | 8 | 1 | 17.972 | 53.916 |
| Ketoprofen | 10% | KET1766 | KET116 | Ethanol | Propylene glycol | 70:30 | Eucalyptus oil | 3.5% 1,8-cineole | | No | 0.5 | 2 | 0.021 | 0.063 |
| Ketoprofen | 10% | KET1767 | KET116 | Ethanol | Propylene glycol | 70:30 | Eucalyptus oil | 3.5% 1,8-cineole | | No | 2 | 2 | 0.077 | 0.231 |
| Ketoprofen | 10% | KET1768 | KET116 | Ethanol | Propylene glycol | 70:30 | Eucalyptus oil | 3.5% 1,8-cineole | | No | 4 | 2 | 0.264 | 0.792 |
| Ketoprofen | 10% | KET1769 | KET116 | Ethanol | Propylene glycol | 70:30 | Eucalyptus oil | 3.5% 1,8-cineole | | No | 6 | 2 | 0.665 | 1.995 |
| Ketoprofen | 10% | KET1770 | KET116 | Ethanol | Propylene glycol | 70:30 | Eucalyptus oil | 3.5% 1,8-cineole | | No | 8 | 2 | 1.635 | 4.905 |
| Ketoprofen | 10% | KET1771 | KET116 | Ethanol | Propylene glycol | 70:30 | Eucalyptus oil | 3.5% 1,8-cineole | | No | 0.5 | 3 | 0.026 | 0.078 |
| Ketoprofen | 10% | KET1772 | KET116 | Ethanol | Propylene glycol | 70:30 | Eucalyptus oil | 3.5% 1,8-cineole | | No | 2 | 3 | 0.042 | 0.126 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET1773 | KET116 | Ethanol | Propylene glycol | 70:30 | Eucalyptus oil | 3.5% 1,8-cineole | | No | 4 | 3 | 0.48 | 1.44 |
| Ketoprofen | 10% | KET1774 | KET116 | Ethanol | Propylene glycol | 70:30 | Eucalyptus oil | 3.5% 1,8-cineole | | No | 6 | 3 | 2.102 | 6.306 |
| Ketoprofen | 10% | KET1775 | KET116 | Ethanol | Propylene glycol | 70:30 | Eucalyptus oil | 3.5% 1,8-cineole | | No | 8 | 3 | 4.722 | 14.166 |
| Ketoprofen | 20% | KET1776 | KET117 | Ethanol | Propylene glycol | 30:70 | Eucalyptus oil | 3.5% 1,8-cineole | | No | 0.5 | 1 | 0.027 | 0.081 |
| Ketoprofen | 20% | KET1777 | KET117 | Ethanol | Propylene glycol | 30:70 | Eucalyptus oil | 3.5% 1,8-cineole | | No | 2 | 1 | 0.029 | 0.087 |
| Ketoprofen | 20% | KET1778 | KET117 | Ethanol | Propylene glycol | 30:70 | Eucalyptus oil | 3.5% 1,8-cineole | | No | 4 | 1 | 0.046 | 0.138 |
| Ketoprofen | 20% | KET1779 | KET117 | Ethanol | Propylene glycol | 30:70 | Eucalyptus oil | 3.5% 1,8-cineole | | No | 6 | 1 | 0.12 | 0.36 |
| Ketoprofen | 20% | KET1780 | KET117 | Ethanol | Propylene glycol | 30:70 | Eucalyptus oil | 3.5% 1,8-cineole | | No | 8 | 1 | 0.364 | 1.092 |
| Ketoprofen | 20% | KET1781 | KET117 | Ethanol | Propylene glycol | 30:70 | Eucalyptus oil | 3.5% 1,8-cineole | | No | 0.5 | 2 | 0.029 | 0.087 |
| Ketoprofen | 20% | KET1782 | KET117 | Ethanol | Propylene glycol | 30:70 | Eucalyptus oil | 3.5% 1,8-cineole | | No | 2 | 2 | 0.02 | 0.06 |
| Ketoprofen | 20% | KET1783 | KET117 | Ethanol | Propylene glycol | 30:70 | Eucalyptus oil | 3.5% 1,8-cineole | | No | 4 | 2 | 0.024 | 0.072 |
| Ketoprofen | 20% | KET1784 | KET117 | Ethanol | Propylene glycol | 30:70 | Eucalyptus oil | 3.5% 1,8-cineole | | No | 6 | 2 | 0.063 | 0.189 |
| Ketoprofen | 20% | KET1785 | KETH7 | Ethanol | Propylene glycol | 30:70 | Eucalyptus oil | 3.5% 1,8-cineole | | No | 8 | 2 | 0.498 | 1.494 |
| Ketoprofen | 20% | KET1786 | KET117 | Ethanol | Propylene glycol | 30:70 | Eucalyptus oil | 3.5% 1,8-cineole | | No | 0.5 | 3 | 0.024 | 0.072 |
| Ketoprofen | 20% | KET1787 | KET117 | Ethanol | Propylene glycol | 30:70 | Eucalyptus oil | 3.5% 1,8-cineole | | No | 2 | 3 | 0.035 | 0.105 |
| Ketoprofen | 20% | KET1788 | KET117 | Ethanol | Propylene glycol | 30:70 | Eucalyptus oil | 3.5% 1,8-cineole | | No | 4 | 3 | 0.095 | 0.285 |
| Ketoprofen | 20% | KET1789 | KET117 | Ethanol | Propylene glycol | 30:70 | Eucalyptus oil | 3.5% 1,8-cineole | | No | 6 | 3 | 0.581 | 1.743 |
| Ketoprofen | 20% | KET1790 | KET117 | Ethanol | Propylene glycol | 30:70 | Eucalyptus oil | 3.5% 1,8-cineole | | No | 8 | 3 | 1.776 | 5.328 |
| Ketoprofen | 20% | KET1791 | KET118 | Ethanol | Propylene glycol | 30:70 | Eucalyptus oil | 3.5% 1,8-cineole | | Yes | 0.5 | 1 | 0.032 | 0.096 |
| Ketoprofen | 20% | KET1792 | KET118 | Ethanol | Propylene glycol | 30:70 | Eucalyptus oil | 3.5% 1,8-cineole | | Yes | 2 | 1 | 0.016 | 0.048 |
| Ketoprofen | 20% | KET1793 | KET118 | Ethanol | Propylene glycol | 30:70 | Eucalyptus oil | 3.5% 1,8-cineole | | Yes | 4 | 1 | 0.02 | 0.06 |
| Ketoprofen | 20% | KET1794 | KET118 | Ethanol | Propylene glycol | 30:70 | Eucalyptus oil | 3.5% 1,8-cineole | | Yes | 6 | 1 | 0.251 | 0.753 |
| Ketoprofen | 20% | KET1795 | KET118 | Ethanol | Propylene glycol | 30:70 | Eucalyptus oil | 3.5% 1,8-cineole | | Yes | 8 | 1 | 1.298 | 3.894 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Rep- licate | analysis conc | Concen- tration (μg/mL) |
|---|---|---|---|---|---|---|---|---|---|---|---|---|---|---|
| Ketoprofen | 20% | KET1796 | KET118 | Ethanol | Propylene glycol | 30:70 | Eucalyptus oil | 3.5% 1,8-cineole | | Yes | 0.5 | 2 | 0.022 | 0.066 |
| Ketoprofen | 20% | KET1797 | KET118 | Ethanol | Propylene glycol | 30:70 | Eucalyptus oil | 3.5% 1,8-cineole | | Yes | 2 | 2 | 0.022 | 0.066 |
| Ketoprofen | 20% | KET1798 | KET118 | Ethanol | Propylene glycol | 30:70 | Eucalyptus oil | 3.5% 1,8-cineole | | Yes | 4 | 2 | 0.017 | 0.051 |
| Ketoprofen | 20% | KET1799 | KET118 | Ethanol | Propylene glycol | 30:70 | Eucalyptus oil | 3.5% 1,8-cineole | | Yes | 6 | 2 | 0.028 | 0.084 |
| Ketoprofen | 20% | KET1800 | KET118 | Ethanol | Propylene glycol | 30:70 | Eucalyptus oil | 3.5% 1,8-cineole | | Yes | 8 | 2 | 0.587 | 1.761 |
| Ketoprofen | 20% | KET1801 | KET118 | Ethanol | Propylene glycol | 30:70 | Eucalyptus oil | 3.5% 1,8-cineole | | Yes | 0.5 | 3 | 0.042 | 0.126 |
| Ketoprofen | 20% | KET1802 | KET118 | Ethanol | Propylene glycol | 30:70 | Eucalyptus oil | 3.5% 1,8-cineole | | Yes | 2 | 3 | 0.039 | 0.117 |
| Ketoprofen | 20% | KET1803 | KET118 | Ethanol | Propylene glycol | 30:70 | Eucalyptus oil | 3.5% 1,8-cineole | | Yes | 4 | 3 | 0.042 | 0.126 |
| Ketoprofen | 20% | KET1804 | KET118 | Ethanol | Propylene glycol | 30:70 | Eucalyptus oil | 3.5% 1,8-cineole | | Yes | 6 | 3 | 0.045 | 0.135 |
| Ketoprofen | 20% | KET1805 | KET118 | Ethanol | Propylene glycol | 30:70 | Eucalyptus oil | 3.5% 1,8-cineole | | Yes | 8 | 3 | 0.157 | 0.471 |
| Ketoprofen | 20% | KET1806 | KET119 | Ethanol | Propylene glycol | 50:50 | Eucalyptus oil | 3.5% 1,8-cineole | | No | 0.5 | 1 | 0.035 | 0.105 |
| Ketoprofen | 20% | KET1807 | KET119 | Ethanol | Propylene glycol | 50:50 | Eucalyptus oil | 3.5% 1,8-cineole | | No | 2 | 1 | 0.169 | 0.507 |
| Ketoprofen | 20% | KET1808 | KET119 | Ethanol | Propylene glycol | 50:50 | Eucalyptus oil | 3.5% 1,8-cineole | | No | 4 | 1 | 0.676 | 2.028 |
| Ketoprofen | 20% | KET1809 | KET119 | Ethanol | Propylene glycol | 50:50 | Eucalyptus oil | 3.5% 1,8-cineole | | No | 6 | 1 | 2.562 | 7.686 |
| Ketoprofen | 20% | KET1810 | KET119 | Ethanol | Propylene glycol | 50:50 | Eucalyptus oil | 3.5% 1,8-cineole | | No | 8 | 1 | 6.732 | 20.196 |
| Ketoprofen | 20% | KET1811 | KET119 | Ethanol | Propylene glycol | 50:50 | Eucalyptus oil | 3.5% 1,8-cineole | | No | 0.5 | 2 | 0.031 | 0.093 |
| Ketoprofen | 20% | KET1812 | KETH9 | Ethanol | Propylene glycol | 50:50 | Eucalyptus oil | 3.5% 1,8-cineole | | No | 2 | 2 | 0.027 | 0.081 |
| Ketoprofen | 20% | KET1813 | KET119 | Ethanol | Propylene glycol | 50:50 | Eucalyptus oil | 3.5% 1,8-cineole | | No | 4 | 2 | 0.051 | 0.153 |
| Ketoprofen | 20% | KET1814 | KET119 | Ethanol | Propylene glycol | 50:50 | Eucalyptus oil | 3.5% 1,8-cineole | | No | 6 | 2 | 0.154 | 0.462 |
| Ketoprofen | 20% | KET1815 | KET119 | Ethanol | Propylene glycol | 50:50 | Eucalyptus oil | 3.5% 1,8-cineole | | No | 8 | 2 | 0.591 | 1.773 |
| Ketoprofen | 20% | KET1816 | KET119 | Ethanol | Propylene glycol | 50:50 | Eucalyptus oil | 3.5% 1,8-cineole | | No | 0.5 | 3 | 0.024 | 0.072 |
| Ketoprofen | 20% | KET1817 | KET119 | Ethanol | Propylene glycol | 50:50 | Eucalyptus oil | 3.5% 1,8-cineole | | No | 2 | 3 | 0.031 | 0.093 |
| Ketoprofen | 20% | KET1818 | KET119 | Ethanol | Propylene glycol | 50:50 | Eucalyptus oil | 3.5% 1,8-cineole | | No | 4 | 3 | 0.027 | 0.081 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 20% | KET1819 | KET119 | Ethanol | Propylene glycol | 50:50 | Eucalyptus oil | 3.5% 1,8-cineole | | No | 6 | 3 | 0.055 | 0.165 |
| Ketoprofen | 20% | KET1820 | KET119 | Ethanol | Propylene glycol | 50:50 | Eucalyptus oil | 3.5% 1,8-cineole | | No | 8 | 3 | 0.245 | 0.735 |
| Ketoprofen | 20% | KET1821 | KET120 | Ethanol | Propylene glycol | 50:50 | Eucalyptus oil | 3.5% 1,8-cineole | | Yes | 0.5 | 1 | 0.026 | 0.078 |
| Ketoprofen | 20% | KET1822 | KET120 | Ethanol | Propylene glycol | 50:50 | Eucalyptus oil | 3.5% 1,8-cineole | | Yes | 2 | 1 | 0.025 | 0.075 |
| Ketoprofen | 20% | KET1823 | KET120 | Ethanol | Propylene glycol | 50:50 | Eucalyptus oil | 3.5% 1,8-cineole | | Yes | 4 | 1 | 0.019 | 0.057 |
| Ketoprofen | 20% | KET1824 | KET120 | Ethanol | Propylene glycol | 50:50 | Eucalyptus oil | 3.5% 1,8-cineole | | Yes | 6 | 1 | 0.035 | 0.105 |
| Ketoprofen | 20% | KET1825 | KET120 | Ethanol | Propylene glycol | 50:50 | Eucalyptus oil | 3.5% 1,8-cineole | | Yes | 8 | 1 | 0.079 | 0.237 |
| Ketoprofen | 20% | KET1826 | KET120 | Ethanol | Propylene glycol | 50:50 | Eucalyptus oil | 3.5% 1,8-cineole | | Yes | 0.5 | 2 | 0.041 | 0.123 |
| Ketoprofen | 20% | KET1827 | KET120 | Ethanol | Propylene glycol | 50:50 | Eucalyptus oil | 3.5% 1,8-cineole | | Yes | 2 | 2 | 0.031 | 0.093 |
| Ketoprofen | 20% | KET1828 | KET120 | Ethanol | Propylene glycol | 50:50 | Eucalyptus oil | 3.5% 1,8-cineole | | Yes | 4 | 2 | 0.039 | 0.117 |
| Ketoprofen | 20% | KET1829 | KET120 | Ethanol | Propylene glycol | 50:50 | Eucalyptus oil | 3.5% 1,8-cineole | | Yes | 6 | 2 | 0.024 | 0.072 |
| Ketoprofen | 20% | KET1830 | KET120 | Ethanol | Propylene glycol | 50:50 | Eucalyptus oil | 3.5% 1,8-cineole | | Yes | 8 | 2 | 0.067 | 0.201 |
| Ketoprofen | 20% | KET1831 | KET120 | Ethanol | Propylene glycol | 50:50 | Eucalyptus oil | 3.5% 1,8-cineole | | Yes | 0.5 | 3 | 0.029 | 0.087 |
| Ketoprofen | 20% | KET1832 | KET120 | Ethanol | Propylene glycol | 50:50 | Eucalyptus oil | 3.5% 1,8-cineole | | Yes | 2 | 3 | 0.025 | 0.075 |
| Ketoprofen | 20% | KET1833 | KET120 | Ethanol | Propylene glycol | 50:50 | Eucalyptus oil | 3.5% 1,8-cineole | | Yes | 4 | 3 | 0.027 | 0.081 |
| Ketoprofen | 20% | KET1834 | KET120 | Ethanol | Propylene glycol | 50:50 | Eucalyptus oil | 3.5% 1,8-cineole | | Yes | 6 | 3 | 0.022 | 0.066 |
| Ketoprofen | 20% | KET1835 | KET120 | Ethanol | Propylene glycol | 50:50 | Eucalyptus oil | 3.5% 1,8-cineole | | Yes | 8 | 3 | 0.106 | 0.318 |
| Ketoprofen | 20% | KET1836 | KET121 | Ethanol | Propylene glycol | 70:30 | Eucalyptus oil | 3.5% 1,8-cineole | | No | 0.5 | 1 | — | 0.117 |
| Ketoprofen | 20% | KET1837 | KET121 | Ethanol | Propylene glycol | 70:30 | Eucalyptus oil | 3.5% 1,8-cineole | | No | 2 | 1 | — | 0.06 |
| Ketoprofen | 20% | KET1838 | KET121 | Ethanol | Propylene glycol | 70:30 | Eucalyptus oil | 3.5% 1,8-cineole | | No | 4 | 1 | — | 0.279 |
| Ketoprofen | 20% | KET1839 | KET121 | Ethanol | Propylene glycol | 70:30 | Eucalyptus oil | 3.5% 1,8-cineole | | No | 6 | 1 | — | 2.091 |
| Ketoprofen | 20% | KET1840 | KET121 | Ethanol | Propylene glycol | 70:30 | Eucalyptus oil | 3.5% 1,8-cineole | | No | 8 | 1 | — | 10.968 |
| Ketoprofen | 20% | KET1841 | KET121 | Ethanol | Propylene glycol | 70:30 | Eucalyptus oil | 3.5% 1,8-cineole | | No | 0.5 | 2 | — | 0.135 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 20% | KET1842 | KET121 | Ethanol | Propylene glycol | 70:30 | Eucalyptus oil | 3.5% 1,8-cineole | | No | 2 | 2 | — | 0.108 |
| Ketoprofen | 20% | KET1843 | KET121 | Ethanol | Propylene glycol | 70:30 | Eucalyptus oil | 3.5% 1,8-cineole | | No | 4 | 2 | — | 0.219 |
| Ketoprofen | 20% | KET1844 | KET121 | Ethanol | Propylene glycol | 70:30 | Eucalyptus oil | 3.5% 1,8-cineole | | No | 6 | 2 | — | 1.458 |
| Ketoprofen | 20% | KET1845 | KET121 | Ethanol | Propylene glycol | 70:30 | Eucalyptus oil | 3.5% 1,8-cineole | | No | 8 | 2 | — | 7.125 |
| Ketoprofen | 20% | KET1846 | KET121 | Ethanol | Propylene glycol | 70:30 | Eucalyptus oil | 3.5% 1,8-cineole | | No | 0.5 | 3 | — | 0.117 |
| Ketoprofen | 20% | KET1847 | KET121 | Ethanol | Propylene glycol | 70:30 | Eucalyptus oil | 3.5% 1,8-cineole | | No | 2 | 3 | — | 0.168 |
| Ketoprofen | 20% | KET1848 | KET121 | Ethanol | Propylene glycol | 70:30 | Eucalyptus oil | 3.5% 1,8-cineole | | No | 4 | 3 | — | 1.236 |
| Ketoprofen | 20% | KET1849 | KET121 | Ethanol | Propylene glycol | 70:30 | Eucalyptus oil | 3.5% 1,8-cineole | | No | 6 | 3 | — | 6.642 |
| Ketoprofen | 20% | KET1850 | KET121 | Ethanol | Propylene glycol | 70:30 | Eucalyptus oil | 3.5% 1,8-cineole | | No | 8 | 3 | — | 11.982 |
| Ketoprofen | 30% | KET1851 | KET122 | Ethanol | Propylene glycol | 30:70 | Eucalyptus oil | 3.5% 1,8-cineole | | No | 0.5 | 1 | 0.034 | 0.102 |
| Ketoprofen | 30% | KET1852 | KET122 | Ethanol | Propylene glycol | 30:70 | Eucalyptus oil | 3.5% 1,8-cineole | | No | 2 | 1 | 0.015 | 0.045 |
| Ketoprofen | 30% | KET1853 | KET122 | Ethanol | Propylene glycol | 30:70 | Eucalyptus oil | 3.5% 1,8-cineole | | No | 4 | 1 | 0.031 | 0.093 |
| Ketoprofen | 30% | KET1854 | KET122 | Ethanol | Propylene glycol | 30:70 | Eucalyptus oil | 3.5% 1,8-cineole | | No | 6 | 1 | 0.036 | 0.108 |
| Ketoprofen | 30% | KET1855 | KET122 | Ethanol | Propylene glycol | 30:70 | Eucalyptus oil | 3.5% 1,8-cineole | | No | 8 | 1 | 0.653 | 1.959 |
| Ketoprofen | 30% | KET1856 | KET122 | Ethanol | Propylene glycol | 30:70 | Eucalyptus oil | 3.5% 1,8-cineole | | No | 0.5 | 2 | 0.032 | 0.096 |
| Ketoprofen | 30% | KET1857 | KET122 | Ethanol | Propylene glycol | 30:70 | Eucalyptus oil | 3.5% 1,8-cineole | | No | 2 | 2 | 0.032 | 0.096 |
| Ketoprofen | 30% | KET1858 | KET122 | Ethanol | Propylene glycol | 30:70 | Eucalyptus oil | 3.5% 1,8-cineole | | No | 4 | 2 | 0.099 | 0.297 |
| Ketoprofen | 30% | KET1859 | KET122 | Ethanol | Propylene glycol | 30:70 | Eucalyptus oil | 3.5% 1,8-cineole | | No | 6 | 2 | 0.017 | 0.051 |
| Ketoprofen | 30% | KET1860 | KET122 | Ethanol | Propylene glycol | 30:70 | Eucalyptus oil | 3.5% 1,8-cineole | | No | 8 | 2 | 0.082 | 0.246 |
| Ketoprofen | 30% | KET1861 | KET122 | Ethanol | Propylene glycol | 30:70 | Eucalyptus oil | 3.5% 1,8-cineole | | No | 0.5 | 3 | 0.044 | 0.132 |
| Ketoprofen | 30% | KET1862 | KET122 | Ethanol | Propylene glycol | 30:70 | Eucalyptus oil | 3.5% 1,8-cineole | | No | 2 | 3 | 0.018 | 0.054 |
| Ketoprofen | 30% | KET1863 | KET122 | Ethanol | Propylene glycol | 30:70 | Eucalyptus oil | 3.5% 1,8-cineole | | No | 4 | 3 | 0.026 | 0.078 |
| Ketoprofen | 30% | KET1864 | KET122 | Ethanol | Propylene glycol | 30:70 | Eucalyptus oil | 3.5% 1,8-cineole | | No | 6 | 3 | 0.019 | 0.057 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 30% | KET1865 | KET122 | Ethanol | Propylene glycol | 30:70 | Eucalyptus oil | 3.5% 1,8-cineole | | No | 8 | 3 | 0.083 | 0.249 |
| Ketoprofen | 30% | KET1866 | KET123 | Ethanol | Propylene glycol | 30:70 | Eucalyptus oil | 3.5% 1,8-cineole | | Yes | 0.5 | 1 | 0.031 | 0.093 |
| Ketoprofen | 30% | KET1867 | KET123 | Ethanol | Propylene glycol | 30:70 | Eucalyptus oil | 3.5% 1,8-cineole | | Yes | 2 | 1 | 0.017 | 0.051 |
| Ketoprofen | 30% | KET1868 | KET123 | Ethanol | Propylene glycol | 30:70 | Eucalyptus oil | 3.5% 1,8-cineole | | Yes | 4 | 1 | 0.027 | 0.081 |
| Ketoprofen | 30% | KET1869 | KET123 | Ethanol | Propylene glycol | 30:70 | Eucalyptus oil | 3.5% 1,8-cineole | | Yes | 6 | 1 | 0.029 | 0.087 |
| Ketoprofen | 30% | KET1870 | KET123 | Ethanol | Propylene glycol | 30:70 | Eucalyptus oil | 3.5% 1,8-cineole | | Yes | 8 | 1 | 0.122 | 0.366 |
| Ketoprofen | 30% | KET1871 | KET123 | Ethanol | Propylene glycol | 30:70 | Eucalyptus oil | 3.5% 1,8-cineole | | Yes | 0.5 | 2 | 0.046 | 0.138 |
| Ketoprofen | 30% | KET1872 | KET123 | Ethanol | Propylene glycol | 30:70 | Eucalyptus oil | 3.5% 1,8-cineole | | Yes | 2 | 2 | 0.021 | 0.063 |
| Ketoprofen | 30% | KET1873 | KET123 | Ethanol | Propylene glycol | 30:70 | Eucalyptus oil | 3.5% 1,8-cineole | | Yes | 4 | 2 | 0.023 | 0.069 |
| Ketoprofen | 30% | KET1874 | KET123 | Ethanol | Propylene glycol | 30:70 | Eucalyptus oil | 3.5% 1,8-cineole | | Yes | 6 | 2 | 0.019 | 0.057 |
| Ketoprofen | 30% | KET1875 | KET123 | Ethanol | Propylene glycol | 30:70 | Eucalyptus oil | 3.5% 1,8-cineole | | Yes | 8 | 2 | 0.028 | 0.084 |
| Ketoprofen | 30% | KET1876 | KET123 | Ethanol | Propylene glycol | 30:70 | Eucalyptus oil | 3.5% 1,8-cineole | | Yes | 0.5 | 3 | 0.022 | 0.066 |
| Ketoprofen | 30% | KET1877 | KET123 | Ethanol | Propylene glycol | 30:70 | Eucalyptus oil | 3.5% 1,8-cineole | | Yes | 2 | 3 | 0.02 | 0.06 |
| Ketoprofen | 30% | KET1878 | KET123 | Ethanol | Propylene glycol | 30:70 | Eucalyptus oil | 3.5% 1,8-cineole | | Yes | 4 | 3 | 0.018 | 0.054 |
| Ketoprofen | 30% | KET1879 | KET123 | Ethanol | Propylene glycol | 30:70 | Eucalyptus oil | 3.5% 1,8-cineole | | Yes | 6 | 3 | 0.02 | 0.06 |
| Ketoprofen | 30% | KET1880 | KET123 | Ethanol | Propylene glycol | 30:70 | Eucalyptus oil | 3.5% 1,8-cineole | | Yes | 8 | 3 | 0.097 | 0.291 |
| Ketoprofen | 30% | KET1881 | KET124 | Ethanol | Propylene glycol | 50:50 | Eucalyptus oil | 3.5% 1,8-cineole | | No | 0.5 | 1 | 0.021 | 0.063 |
| Ketoprofen | 30% | KET1882 | KET124 | Ethanol | Propylene glycol | 50:50 | Eucalyptus oil | 3.5% 1,8-cineole | | No | 2 | 1 | 0.035 | 0.105 |
| Ketoprofen | 30% | KET1883 | KET124 | Ethanol | Propylene glycol | 50:50 | Eucalyptus oil | 3.5% 1,8-cineole | | No | 4 | 1 | 0.023 | 0.069 |
| Ketoprofen | 30% | KET1884 | KET124 | Ethanol | Propylene glycol | 50:50 | Eucalyptus oil | 3.5% 1,8-cineole | | No | 6 | 1 | 0.087 | 0.261 |
| Ketoprofen | 30% | KET1885 | KET124 | Ethanol | Propylene glycol | 50:50 | Eucalyptus oil | 3.5% 1,8-cineole | | No | 8 | 1 | 1.363 | 4.089 |
| Ketoprofen | 30% | KET1886 | KET124 | Ethanol | Propylene glycol | 50:50 | Eucalyptus oil | 3.5% 1,8-cineole | | No | 0.5 | 2 | 0.04 | 0.12 |
| Ketoprofen | 30% | KET1887 | KET124 | Ethanol | Propylene glycol | 50:50 | Eucalyptus oil | 3.5% 1,8-cineole | | No | 2 | 2 | 0.025 | 0.075 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 30% | KET1888 | KET124 | Ethanol | Propylene glycol | 50:50 | Eucalyptus oil | 3.5% 1,8-cineole | | No | 4 | 2 | 0.023 | 0.069 |
| Ketoprofen | 30% | KET1889 | KET124 | Ethanol | Propylene glycol | 50:50 | Eucalyptus oil | 3.5% 1,8-cineole | | No | 6 | 2 | 0.086 | 0.258 |
| Ketoprofen | 30% | KET1890 | KET124 | Ethanol | Propylene glycol | 50:50 | Eucalyptus oil | 3.5% 1,8-cineole | | No | 8 | 2 | 0.527 | 1.581 |
| Ketoprofen | 30% | KET1891 | KET124 | Ethanol | Propylene glycol | 50:50 | Eucalyptus oil | 3.5% 1,8-cineole | | No | 0.5 | 3 | 0.028 | 0.084 |
| Ketoprofen | 30% | KET1892 | KET124 | Ethanol | Propylene glycol | 50:50 | Eucalyptus oil | 3.5% 1,8-cineole | | No | 2 | 3 | 0.024 | 0.072 |
| Ketoprofen | 30% | KET1893 | KET124 | Ethanol | Propylene glycol | 50:50 | Eucalyptus oil | 3.5% 1,8-cineole | | No | 4 | 3 | 0.026 | 0.078 |
| Ketoprofen | 30% | KET1894 | KET124 | Ethanol | Propylene glycol | 50:50 | Eucalyptus oil | 3.5% 1,8-cineole | | No | 6 | 3 | 0.071 | 0.213 |
| Ketoprofen | 30% | KET1895 | KET124 | Ethanol | Propylene glycol | 50:50 | Eucalyptus oil | 3.5% 1,8-cineole | | No | 8 | 3 | 0.877 | 2.631 |
| Ketoprofen | 30% | KET1896 | KET125 | Ethanol | Propylene glycol | 50:50 | Eucalyptus oil | 3.5% 1,8-cineole | | Yes | 0.5 | 1 | 0.028 | 0.084 |
| Ketoprofen | 30% | KET1897 | KET125 | Ethanol | Propylene glycol | 50:50 | Eucalyptus oil | 3.5% 1,8-cineole | | Yes | 2 | 1 | 0.028 | 0.084 |
| Ketoprofen | 30% | KET1898 | KET125 | Ethanol | Propylene glycol | 50:50 | Eucalyptus oil | 3.5% 1,8-cineole | | Yes | 4 | 1 | 0.02 | 0.06 |
| Ketoprofen | 30% | KET1899 | KET125 | Ethanol | Propylene glycol | 50:50 | Eucalyptus oil | 3.5% 1,8-cineole | | Yes | 6 | 1 | 0.039 | 0.117 |
| Ketoprofen | 30% | KET1900 | KET125 | Ethanol | Propylene glycol | 50:50 | Eucalyptus oil | 3.5% 1,8-cineole | | Yes | 8 | 1 | 0.251 | 0.753 |
| Ketoprofen | 30% | KET1901 | KET125 | Ethanol | Propylene glycol | 50:50 | Eucalyptus oil | 3.5% 1,8-cineole | | Yes | 0.5 | 2 | 0.025 | 0.075 |
| Ketoprofen | 30% | KET1902 | KET125 | Ethanol | Propylene glycol | 50:50 | Eucalyptus oil | 3.5% 1,8-cineole | | Yes | 2 | 2 | 0.178 | 0.534 |
| Ketoprofen | 30% | KET1903 | KET125 | Ethanol | Propylene glycol | 50:50 | Eucalyptus oil | 3.5% 1,8-cineole | | Yes | 4 | 2 | 0.017 | 0.051 |
| Ketoprofen | 30% | KET1904 | KET125 | Ethanol | Propylene glycol | 50:50 | Eucalyptus oil | 3.5% 1,8-cineole | | Yes | 6 | 2 | 0.026 | 0.078 |
| Ketoprofen | 30% | KET1905 | KET125 | Ethanol | Propylene glycol | 50:50 | Eucalyptus oil | 3.5% 1,8-cineole | | Yes | 8 | 2 | 0.474 | 1.422 |
| Ketoprofen | 30% | KET1906 | KET125 | Ethanol | Propylene glycol | 50:50 | Eucalyptus oil | 3.5% 1,8-cineole | | Yes | 0.5 | 3 | 0.02 | 0.06 |
| Ketoprofen | 30% | KET1907 | KET125 | Ethanol | Propylene glycol | 50:50 | Eucalyptus oil | 3.5% 1,8-cineole | | Yes | 2 | 3 | 0.035 | 0.105 |
| Ketoprofen | 30% | KET1908 | KET125 | Ethanol | Propylene glycol | 50:50 | Eucalyptus oil | 3.5% 1,8-cineole | | Yes | 4 | 3 | 0.02 | 0.06 |
| Ketoprofen | 30% | KET1909 | KET125 | Ethanol | Propylene glycol | 50:50 | Eucalyptus oil | 3.5% 1,8-cineole | | Yes | 6 | 3 | 0.023 | 0.069 |
| Ketoprofen | 30% | KET1910 | KET125 | Ethanol | Propylene glycol | 50:50 | Eucalyptus oil | 3.5% 1,8-cineole | | Yes | 8 | 3 | 0.255 | 0.765 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 30% | KET1911 | KET126 | Ethanol | Propylene glycol | 70:30 | Eucalyptus oil | 3.5% 1,8-cineole | | No | 0.5 | 1 | 0.026 | 0.078 |
| Ketoprofen | 30% | KET1912 | KET126 | Ethanol | Propylene glycol | 70:30 | Eucalyptus oil | 3.5% 1,8-cineole | | No | 2 | 1 | 0.028 | 0.084 |
| Ketoprofen | 30% | KET1913 | KET126 | Ethanol | Propylene glycol | 70:30 | Eucalyptus oil | 3.5% 1,8-cineole | | No | 4 | 1 | 0.047 | 0.141 |
| Ketoprofen | 30% | KET1914 | KET126 | Ethanol | Propylene glycol | 70:30 | Eucalyptus oil | 3.5% 1,8-cineole | | No | 6 | 1 | 0.967 | 2.901 |
| Ketoprofen | 30% | KET1915 | KET126 | Ethanol | Propylene glycol | 70:30 | Eucalyptus oil | 3.5% 1,8-cineole | | No | 8 | 1 | 3.753 | 11.259 |
| Ketoprofen | 30% | KET1916 | KET126 | Ethanol | Propylene glycol | 70:30 | Eucalyptus oil | 3.5% 1,8-cineole | | No | 0.5 | 2 | 0.03 | 0.09 |
| Ketoprofen | 30% | KET1917 | KET126 | Ethanol | Propylene glycol | 70:30 | Eucalyptus oil | 3.5% 1,8-cineole | | No | 2 | 2 | 0.046 | 0.138 |
| Ketoprofen | 30% | KET1918 | KET126 | Ethanol | Propylene glycol | 70:30 | Eucalyptus oil | 3.5% 1,8-cineole | | No | 4 | 2 | 0.031 | 0.093 |
| Ketoprofen | 30% | KET1919 | KET126 | Ethanol | Propylene glycol | 70:30 | Eucalyptus oil | 3.5% 1,8-cineole | | No | 6 | 2 | 0.047 | 0.141 |
| Ketoprofen | 30% | KET1920 | KET126 | Ethanol | Propylene glycol | 70:30 | Eucalyptus oil | 3.5% 1,8-cineole | | No | 8 | 2 | 0.217 | 0.651 |
| Ketoprofen | 30% | KET1921 | KET126 | Ethanol | Propylene glycol | 70:30 | Eucalyptus oil | 3.5% 1,8-cineole | | No | 0.5 | 3 | 0.05 | 0.15 |
| Ketoprofen | 30% | KET1922 | KET126 | Ethanol | Propylene glycol | 70:30 | Eucalyptus oil | 3.5% 1,8-cineole | | No | 2 | 3 | 0.027 | 0.081 |
| Ketoprofen | 30% | KET1923 | KET126 | Ethanol | Propylene glycol | 70:30 | Eucalyptus oil | 3.5% 1,8-cineole | | No | 4 | 3 | 0.032 | 0.096 |
| Ketoprofen | 30% | KET1924 | KET126 | Ethanol | Propylene glycol | 70:30 | Eucalyptus oil | 3.5% 1,8-cineole | | No | 6 | 3 | 0.09 | 0.27 |
| Ketoprofen | 30% | KET1925 | KET126 | Ethanol | Propylene glycol | 70:30 | Eucalyptus oil | 3.5% 1,8-cineole | | No | 8 | 3 | 1.329 | 3.987 |
| Ketoprofen | 10% | KET1926 | KET127 | Ethanol | Propylene glycol | 70:30 | Eucalyptus oil | 3.5% 1,8-cineole | | Yes | 0.5 | 1 | 0.013 | 0.039 |
| Ketoprofen | 10% | KET1927 | KET127 | Ethanol | Propylene glycol | 70:30 | Eucalyptus oil | 3.5% 1,8-cineole | | Yes | 2 | 1 | 0.012 | 0.036 |
| Ketoprofen | 10% | KET1928 | KET127 | Ethanol | Propylene glycol | 70:30 | Eucalyptus oil | 3.5% 1,8-cineole | | Yes | 4 | 1 | 0.053 | 0.159 |
| Ketoprofen | 10% | KET1929 | KET127 | Ethanol | Propylene glycol | 70:30 | Eucalyptus oil | 3.5% 1,8-cineole | | Yes | 6 | 1 | 0.307 | 0.921 |
| Ketoprofen | 10% | KET1930 | KET127 | Ethanol | Propylene glycol | 70:30 | Eucalyptus oil | 3.5% 1,8-cineole | | Yes | 8 | 1 | 1.71 | 5.13 |
| Ketoprofen | 10% | KET1931 | KET127 | Ethanol | Propylene glycol | 70:30 | Eucalyptus oil | 3.5% 1,8-cineole | | Yes | 0.5 | 2 | 0.024 | 0.072 |
| Ketoprofen | 10% | KET1932 | KET127 | Ethanol | Propylene glycol | 70:30 | Eucalyptus oil | 3.5% 1,8-cineole | | Yes | 2 | 2 | 0.469 | 1.407 |
| Ketoprofen | 10% | KET1933 | KET127 | Ethanol | Propylene glycol | 70:30 | Eucalyptus oil | 3.5% 1,8-cineole | | Yes | 4 | 2 | 1.367 | 4.101 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 10% | KET1934 | KET127 | Ethanol | Propylene glycol | 70:30 | Eucalyptus oil | 3.5% 1,8-cineole | | Yes | 6 | 2 | 4.517 | 13.551 |
| Ketoprofen | 10% | KET1935 | KET127 | Ethanol | Propylene glycol | 70:30 | Eucalyptus oil | 3.5% 1,8-cineole | | Yes | 8 | 2 | 6.107 | 18.321 |
| Ketoprofen | 10% | KET1936 | KET127 | Ethanol | Propylene glycol | 70:30 | Eucalyptus oil | 3.5% 1,8-cineole | | Yes | 0.5 | 3 | 0.008 | 0.024 |
| Ketoprofen | 10% | KET1937 | KET127 | Ethanol | Propylene glycol | 70:30 | Eucalyptus oil | 3.5% 1,8-cineole | | Yes | 2 | 3 | 0.024 | 0.072 |
| Ketoprofen | 10% | KET1938 | KET127 | Ethanol | Propylene glycol | 70:30 | Eucalyptus oil | 3.5% 1,8-cineole | | Yes | 4 | 3 | 0.056 | 0.168 |
| Ketoprofen | 10% | KET1939 | KET127 | Ethanol | Propylene glycol | 70:30 | Eucalyptus oil | 3.5% 1,8-cineole | | Yes | 6 | 3 | 0.395 | 1.185 |
| Ketoprofen | 10% | KET1940 | KET127 | Ethanol | Propylene glycol | 70:30 | Eucalyptus oil | 3.5% 1,8-cineole | | Yes | 8 | 3 | 1.323 | 3.969 |
| Ketoprofen | 10% | KET1941 | KET128 | Ethanol | Isopropyl myristate | 30:70 | Eucalyptus oil | 3.5% 1,8-cineole | | No | 0.5 | 1 | 0.028 | 0.084 |
| Ketoprofen | 10% | KET1942 | KET128 | Ethanol | Isopropyl myristate | 30:70 | Eucalyptus oil | 3.5% 1,8-cineole | | No | 2 | 1 | 0.103 | 0.309 |
| Ketoprofen | 10% | KET1943 | KET128 | Ethanol | Isopropyl myristate | 30:70 | Eucalyptus oil | 3.5% 1,8-cineole | | No | 4 | 1 | 0.064 | 0.192 |
| Ketoprofen | 10% | KET1944 | KET128 | Ethanol | Isopropyl myristate | 30:70 | Eucalyptus oil | 3.5% 1,8-cineole | | No | 6 | 1 | 0.088 | 0.264 |
| Ketoprofen | 10% | KET1945 | KET128 | Ethanol | Isopropyl myristate | 30:70 | Eucalyptus oil | 3.5% 1,8-cineole | | No | 8 | 1 | 0.569 | 1.707 |
| Ketoprofen | 10% | KET1946 | KET128 | Ethanol | Isopropyl myristate | 30:70 | Eucalyptus oil | 3.5% 1,8-cineole | | No | 0.5 | 2 | 0.284 | 0.852 |
| Ketoprofen | 10% | KET1947 | KET128 | Ethanol | Isopropyl myristate | 30:70 | Eucalyptus oil | 3.5% 1,8-cineole | | No | 2 | 2 | 2.64 | 7.92 |
| Ketoprofen | 10% | KET1948 | KET128 | Ethanol | Isopropyl myristate | 30:70 | Eucalyptus oil | 3.5% 1,8-cineole | | No | 4 | 2 | 8.094 | 24.282 |
| Ketoprofen | 10% | KET1949 | KET128 | Ethanol | Isopropyl myristate | 30:70 | Eucalyptus oil | 3.5% 1,8-cineole | | No | 6 | 2 | 12.799 | 38.397 |
| Ketoprofen | 10% | KET1950 | KET128 | Ethanol | Isopropyl myristate | 30:70 | Eucalyptus oil | 3.5% 1,8-cineole | | No | 8 | 2 | 17.165 | 51.495 |
| Ketoprofen | 10% | KET1951 | KET128 | Ethanol | Isopropyl myristate | 30:70 | Eucalyptus oil | 3.5% 1,8-cineole | | No | 0.5 | 3 | 0.069 | 0.207 |
| Ketoprofen | 10% | KET1952 | KET128 | Ethanol | Isopropyl myristate | 30:70 | Eucalyptus oil | 3.5% 1,8-cineole | | No | 2 | 3 | 0.206 | 0.618 |
| Ketoprofen | 10% | KET1953 | KET128 | Ethanol | Isopropyl myristate | 30:70 | Eucalyptus oil | 3.5% 1,8-cineole | | No | 4 | 3 | 0.484 | 1.452 |
| Ketoprofen | 10% | KET1954 | KET128 | Ethanol | Isopropyl myristate | 30:70 | Eucalyptus oil | 3.5% 1,8-cineole | | No | 6 | 3 | 0.957 | 2.871 |
| Ketoprofen | 10% | KET1955 | KET128 | Ethanol | Isopropyl myristate | 30:70 | Eucalyptus oil | 3.5% 1,8-cineole | | No | 8 | 3 | 1.397 | 4.191 |
| Ketoprofen | 10% | KET1956 | KET129 | Ethanol | Isopropyl myristate | 30:70 | Eucalyptus oil | 3.5% 1,8-cineole | | Yes | 0.5 | 1 | 0.043 | 0.129 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/EVAP | sample time (hrs) | Replicate | analysis conc | Concentration (µg/mL) |
|---|---|---|---|---|---|---|---|---|---|---|---|---|---|---|
| Ketoprofen | 10% | KET1957 | KET129 | Ethanol | Isopropyl myristate | 30:70 | Eucalyptus oil | 3.5% 1,8-cineole | | Yes | 2 | 1 | 0.265 | 0.795 |
| Ketoprofen | 10% | KET1958 | KET129 | Ethanol | Isopropyl myristate | 30:70 | Eucalyptus oil | 3.5% 1,8-cineole | | Yes | 4 | 1 | 1.159 | 3.477 |
| Ketoprofen | 10% | KET1959 | KET129 | Ethanol | Isopropyl myristate | 30:70 | Eucalyptus oil | 3.5% 1,8-cineole | | Yes | 6 | 1 | 2.383 | 7.149 |
| Ketoprofen | 10% | KET1960 | KET129 | Ethanol | Isopropyl myristate | 30:70 | Eucalyptus oil | 3.5% 1,8-cineole | | Yes | 8 | 1 | 3.841 | 11.523 |
| Ketoprofen | 10% | KET1961 | KET129 | Ethanol | Isopropyl myristate | 30:70 | Eucalyptus oil | 3.5% 1,8-cineole | | Yes | 0.5 | 2 | 0.027 | 0.081 |
| Ketoprofen | 10% | KET1962 | KET129 | Ethanol | Isopropyl myristate | 30:70 | Eucalyptus oil | 3.5% 1,8-cineole | | Yes | 2 | 2 | 4.539 | 13.617 |
| Ketoprofen | 10% | KET1963 | KET129 | Ethanol | Isopropyl myristate | 30:70 | Eucalyptus oil | 3.5% 1,8-cineole | | Yes | 4 | 2 | 8.846 | 26.538 |
| Ketoprofen | 10% | KET1964 | KET129 | Ethanol | Isopropyl myristate | 30:70 | Eucalyptus oil | 3.5% 1,8-cineole | | Yes | 6 | 2 | 12.655 | 37.965 |
| Ketoprofen | 10% | KET1965 | KET129 | Ethanol | Isopropyl myristate | 30:70 | Eucalyptus oil | 3.5% 1,8-cineole | | Yes | 8 | 2 | 14.733 | 44.199 |
| Ketoprofen | 10% | KET1966 | KET129 | Ethanol | Isopropyl myristate | 30:70 | Eucalyptus oil | 3.5% 1,8-cineole | | Yes | 0.5 | 3 | 0.035 | 0.105 |
| Ketoprofen | 10% | KET1967 | KET129 | Ethanol | Isopropyl myristate | 30:70 | Eucalyptus oil | 3.5% 1,8-cineole | | Yes | 2 | 3 | 0.277 | 0.831 |
| Ketoprofen | 10% | KET1968 | KET129 | Ethanol | Isopropyl myristate | 30:70 | Eucalyptus oil | 3.5% 1,8-cineole | | Yes | 4 | 3 | 0.519 | 1.557 |
| Ketoprofen | 10% | KET1969 | KET129 | Ethanol | Isopropyl myristate | 30:70 | Eucalyptus oil | 3.5% 1,8-cineole | | Yes | 6 | 3 | 1.001 | 3.003 |
| Ketoprofen | 10% | KET1970 | KET129 | Ethanol | Isopropyl myristate | 30:70 | Eucalyptus oil | 3.5% 1,8-cineole | | Yes | 8 | 3 | 1.352 | 4.056 |
| Ketoprofen | 10% | KET1971 | KET130 | Ethanol | Isopropyl myristate | 50:50 | Eucalyptus oil | 3.5% 1,8-cineole | | No | 0.5 | 1 | 0.035 | 0.105 |
| Ketoprofen | 10% | KET1972 | KET130 | Ethanol | Isopropyl myristate | 50:50 | Eucalyptus oil | 3.5% 1,8-cineole | | No | 2 | 1 | 0.111 | 0.333 |
| Ketoprofen | 10% | KET1973 | KET130 | Ethanol | Isopropyl myristate | 50:50 | Eucalyptus oil | 3.5% 1,8-cineole | | No | 4 | 1 | 0.2 | 0.6 |
| Ketoprofen | 10% | KET1974 | KET130 | Ethanol | Isopropyl myristate | 50:50 | Eucalyptus oil | 3.5% 1,8-cineole | | No | 6 | 1 | 0.259 | 0.777 |
| Ketoprofen | 10% | KET1975 | KET130 | Ethanol | Isopropyl myristate | 50:50 | Eucalyptus oil | 3.5% 1,8-cineole | | No | 8 | 1 | 1.024 | 3.072 |
| Ketoprofen | 10% | KET1976 | KET130 | Ethanol | Isopropyl myristate | 50:50 | Eucalyptus oil | 3.5% 1,8-cineole | | No | 0.5 | 2 | 0.156 | 0.468 |
| Ketoprofen | 10% | KET1977 | KET130 | Ethanol | Isopropyl myristate | 50:50 | Eucalyptus oil | 3.5% 1,8-cineole | | No | 2 | 2 | 0.267 | 0.801 |
| Ketoprofen | 10% | KET1978 | KET130 | Ethanol | Isopropyl myristate | 50:50 | Eucalyptus oil | 3.5% 1,8-cineole | | No | 4 | 2 | 0.187 | 0.561 |
| Ketoprofen | 10% | KET1979 | KET130 | Ethanol | Isopropyl myristate | 50:50 | Eucalyptus oil | 3.5% 1,8-cineole | | No | 6 | 2 | 3.136 | 9.408 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 10% | KET1980 | KET130 | Ethanol | Isopropyl myristate | 50:50 | Eucalyptus oil | 3.5% 1,8-cineole | | No | 8 | 2 | 0.384 | 1.152 |
| Ketoprofen | 10% | KET1981 | KET130 | Ethanol | Isopropyl myristate | 50:50 | Eucalyptus oil | 3.5% 1,8-cineole | | No | 0.5 | 3 | 0.067 | 0.201 |
| Ketoprofen | 10% | KET1982 | KET130 | Ethanol | Isopropyl myristate | 50:50 | Eucalyptus oil | 3.5% 1,8-cineole | | No | 2 | 3 | 0.1 | 0.3 |
| Ketoprofen | 10% | KET1983 | KET130 | Ethanol | Isopropyl myristate | 50:50 | Eucalyptus oil | 3.5% 1,8-cineole | | No | 4 | 3 | 0.077 | 0.231 |
| Ketoprofen | 10% | KET1984 | KET130 | Ethanol | Isopropyl myristate | 50:50 | Eucalyptus oil | 3.5% 1,8-cineole | | No | 6 | 3 | 3.288 | 9.864 |
| Ketoprofen | 10% | KET1985 | KET130 | Ethanol | Isopropyl myristate | 50:50 | Eucalyptus oil | 3.5% 1,8-cineole | | No | 8 | 3 | 0.76 | 2.28 |
| Ketoprofen | 10% | KET1986 | KET131 | Ethanol | Isopropyl myristate | 50:50 | Eucalyptus oil | 3.5% 1,8-cineole | | Yes | 0.5 | 1 | 0.043 | 0.129 |
| Ketoprofen | 10% | KET1987 | KET131 | Ethanol | Isopropyl myristate | 50:50 | Eucalyptus oil | 3.5% 1,8-cineole | | Yes | 2 | 1 | 0.052 | 0.156 |
| Ketoprofen | 10% | KET1988 | KET131 | Ethanol | Isopropyl myristate | 50:50 | Eucalyptus oil | 3.5% 1,8-cineole | | Yes | 4 | 1 | 0.072 | 0.216 |
| Ketoprofen | 10% | KET1989 | KET131 | Ethanol | Isopropyl myristate | 50:50 | Eucalyptus oil | 3.5% 1,8-cineole | | Yes | 6 | 1 | 1.252 | 3.756 |
| Ketoprofen | 10% | KET1990 | KET131 | Ethanol | Isopropyl myristate | 50:50 | Eucalyptus oil | 3.5% 1,8-cineole | | Yes | 8 | 1 | 0.467 | 1.401 |
| Ketoprofen | 10% | KET1991 | KET131 | Ethanol | Isopropyl myristate | 50:50 | Eucalyptus oil | 3.5% 1,8-cineole | | Yes | 0.5 | 2 | 0.031 | 0.093 |
| Ketoprofen | 10% | KET1992 | KET131 | Ethanol | Isopropyl myristate | 50:50 | Eucalyptus oil | 3.5% 1,8-cineole | | Yes | 2 | 2 | 0.907 | 2.721 |
| Ketoprofen | 10% | KET1993 | KET131 | Ethanol | Isopropyl myristate | 50:50 | Eucalyptus oil | 3.5% 1,8-cineole | | Yes | 4 | 2 | 1.581 | 4.743 |
| Ketoprofen | 10% | KET1994 | KET131 | Ethanol | Isopropyl myristate | 50:50 | Eucalyptus oil | 3.5% 1,8-cineole | | Yes | 6 | 2 | 2.151 | 6.453 |
| Ketoprofen | 10% | KET1995 | KET131 | Ethanol | Isopropyl myristate | 50:50 | Eucalyptus oil | 3.5% 1,8-cineole | | Yes | 8 | 2 | 5.121 | 15.363 |
| Ketoprofen | 10% | KET1996 | KET131 | Ethanol | Isopropyl myristate | 50:50 | Eucalyptus oil | 3.5% 1,8-cineole | | Yes | 0.5 | 3 | 0.039 | 0.117 |
| Ketoprofen | 10% | KET1997 | KET131 | Ethanol | Isopropyl myristate | 50:50 | Eucalyptus oil | 3.5% 1,8-cineole | | Yes | 2 | 3 | 0.077 | 0.231 |
| Ketoprofen | 10% | KET1998 | KET131 | Ethanol | Isopropyl myristate | 50:50 | Eucalyptus oil | 3.5% 1,8-cineole | | Yes | 4 | 3 | 2.376 | 7.128 |
| Ketoprofen | 10% | KET1999 | KET131 | Ethanol | Isopropyl myristate | 50:50 | Eucalyptus oil | 3.5% 1,8-cineole | | Yes | 6 | 3 | 0.179 | 0.537 |
| Ketoprofen | 10% | KET2000 | KET131 | Ethanol | Isopropyl myristate | 50:50 | Eucalyptus oil | 3.5% 1,8-cineole | | Yes | 8 | 3 | 3.418 | 10.254 |
| Ketoprofen | 20% | KET2001 | KET132 | Ethanol | Propylene glycol | 70:30 | Eucalyptus oil | 3.5% 1,8-cineole | | No | 0.5 | 1 | 0.026 | 0.078 |
| Ketoprofen | 20% | KET2002 | KET132 | Ethanol | Propylene glycol | 70:30 | Eucalyptus oil | 3.5% 1,8-cineole | | No | 2 | 1 | 0.01 | 0.03 |

TABLE 13-continued

NSAID and vehicle screening data

| NSAID | Drug conc | Sample # | Vehicle ID | Alcohol solvent Solvent | Solvent conc | Co-solvent conc | Co-solvent | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 20% | KET2003 | KET132 | Ethanol | Propylene glycol | 70:30 | Eucalyptus oil | 3.5% 1,8-cineole | | No | 4 | 1 | 0.096 | 0.288 |
| Ketoprofen | 20% | KET2004 | KET132 | Ethanol | Propylene glycol | 70:30 | Eucalyptus oil | 3.5% 1,8-cineole | | No | 6 | 1 | 0.072 | 0.216 |
| Ketoprofen | 20% | KET2005 | KET132 | Ethanol | Propylene glycol | 70:30 | Eucalyptus oil | 3.5% 1,8-cineole | | No | 8 | 1 | 1.178 | 3.534 |
| Ketoprofen | 20% | KET2006 | KET132 | Ethanol | Propylene glycol | 70:30 | Eucalyptus oil | 3.5% 1,8-cineole | | No | 0.5 | 2 | 0.013 | 0.039 |
| Ketoprofen | 20% | KET2007 | KET132 | Ethanol | Propylene glycol | 70:30 | Eucalyptus oil | 3.5% 1,8-cineole | | No | 2 | 2 | 0.03 | 0.09 |
| Ketoprofen | 20% | KET2008 | KET132 | Ethanol | Propylene glycol | 70:30 | Eucalyptus oil | 3.5% 1,8-cineole | | No | 4 | 2 | 0.249 | 0.747 |
| Ketoprofen | 20% | KET2009 | KET132 | Ethanol | Propylene glycol | 70:30 | Eucalyptus oil | 3.5% 1,8-cineole | | No | 6 | 2 | 0.184 | 0.552 |
| Ketoprofen | 20% | KET2010 | KET132 | Ethanol | Propylene glycol | 70:30 | Eucalyptus oil | 3.5% 1,8-cineole | | No | 8 | 2 | 1.384 | 4.152 |
| Ketoprofen | 20% | KET2011 | KET132 | Ethanol | Propylene glycol | 70:30 | Eucalyptus oil | 3.5% 1,8-cineole | | No | 0.5 | 3 | 0.03 | 0.09 |
| Ketoprofen | 20% | KET2012 | KET132 | Ethanol | Propylene glycol | 70:30 | Eucalyptus oil | 3.5% 1,8-cineole | | No | 2 | 3 | 0.01 | 0.03 |
| Ketoprofen | 20% | KET2013 | KET132 | Ethanol | Propylene glycol | 70:30 | Eucalyptus oil | 3.5% 1,8-cineole | | No | 4 | 3 | 0.475 | 1.425 |
| Ketoprofen | 20% | KET2014 | KET132 | Ethanol | Propylene glycol | 70:30 | Eucalyptus oil | 3.5% 1,8-cineole | | No | 6 | 3 | 0.48 | 1.44 |
| Ketoprofen | 20% | KET2015 | KET132 | Ethanol | Propylene glycol | 70:30 | Eucalyptus oil | 3.5% 1,8-cineole | | No | 8 | 3 | 1.557 | 4.671 |
| Ketoprofen | 20% | KET2016 | KET133 | Ethanol | Isopropyl myristate | 30:70 | Eucalyptus oil | 3.5% 1,8-cineole | | No | 0.5 | 1 | 0.053 | 0.159 |
| Ketoprofen | 20% | KET2017 | KET133 | Ethanol | Isopropyl myristate | 30:70 | Eucalyptus oil | 3.5% 1,8-cineole | | No | 2 | 1 | 0.054 | 0.162 |
| Ketoprofen | 20% | KET2018 | KET133 | Ethanol | Isopropyl myristate | 30:70 | Eucalyptus oil | 3.5% 1,8-cineole | | No | 4 | 1 | 0.183 | 0.549 |
| Ketoprofen | 20% | KET2019 | KET133 | Ethanol | Isopropyl myristate | 30:70 | Eucalyptus oil | 3.5% 1,8-cineole | | No | 6 | 1 | 0.558 | 1.674 |
| Ketoprofen | 20% | KET2020 | KET133 | Ethanol | Isopropyl myristate | 30:70 | Eucalyptus oil | 3.5% 1,8-cineole | | No | 8 | 1 | 1.459 | 4.377 |
| Ketoprofen | 20% | KET2021 | KET133 | Ethanol | Isopropyl myristate | 30:70 | Eucalyptus oil | 3.5% 1,8-cineole | | No | 0.5 | 2 | 0.029 | 0.087 |
| Ketoprofen | 20% | KET2022 | KET133 | Ethanol | Isopropyl myristate | 30:70 | Eucalyptus oil | 3.5% 1,8-cineole | | No | 2 | 2 | 0.069 | 0.207 |
| Ketoprofen | 20% | KET2023 | KET133 | Ethanol | Isopropyl myristate | 30:70 | Eucalyptus oil | 3.5% 1,8-cineole | | No | 4 | 2 | 0.022 | 0.066 |
| Ketoprofen | 20% | KET2024 | KET133 | Ethanol | Isopropyl myristate | 30:70 | Eucalyptus oil | 3.5% 1,8-cineole | | No | 6 | 2 | 0.228 | 0.684 |
| Ketoprofen | 20% | KET2025 | KET133 | Ethanol | Isopropyl myristate | 30:70 | Eucalyptus oil | 3.5% 1,8-cineole | | No | 8 | 2 | 0.596 | 1.788 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 20% | KET2026 | KET133 | Ethanol | Isopropyl myristate | 30:70 | Eucalyptus oil | 3.5% 1,8-cineole | | No | 0.5 | 3 | 0.043 | 0.129 |
| Ketoprofen | 20% | KET2027 | KET133 | Ethanol | Isopropyl myristate | 30:70 | Eucalyptus oil | 3.5% 1,8-cineole | | No | 2 | 3 | 0.262 | 0.786 |
| Ketoprofen | 20% | KET2028 | KET133 | Ethanol | Isopropyl myristate | 30:70 | Eucalyptus oil | 3.5% 1,8-cineole | | No | 4 | 3 | 0.086 | 0.258 |
| Ketoprofen | 20% | KET2029 | KET133 | Ethanol | Isopropyl myristate | 30:70 | Eucalyptus oil | 3.5% 1,8-cineole | | No | 6 | 3 | 5.51 | 16.53 |
| Ketoprofen | 20% | KET2030 | KET133 | Ethanol | Isopropyl myristate | 30:70 | Eucalyptus oil | 3.5% 1,8-cineole | | No | 8 | 3 | 11.718 | 35.154 |
| Ketoprofen | 20% | KET2031 | KET134 | Ethanol | Isopropyl myristate | 30:70 | Eucalyptus oil | 3.5% 1,8-cineole | | Yes | 0.5 | 1 | 0.057 | 0.171 |
| Ketoprofen | 20% | KET2032 | KET134 | Ethanol | Isopropyl myristate | 30:70 | Eucalyptus oil | 3.5% 1,8-cineole | | Yes | 2 | 1 | 0.119 | 0.357 |
| Ketoprofen | 20% | KET2033 | KET134 | Ethanol | Isopropyl myristate | 30:70 | Eucalyptus oil | 3.5% 1,8-cineole | | Yes | 4 | 1 | 1.608 | 4.824 |
| Ketoprofen | 20% | KET2034 | KET134 | Ethanol | Isopropyl myristate | 30:70 | Eucalyptus oil | 3.5% 1,8-cineole | | Yes | 6 | 1 | 0.517 | 1.551 |
| Ketoprofen | 20% | KET2035 | KET134 | Ethanol | Isopropyl myristate | 30:70 | Eucalyptus oil | 3.5% 1,8-cineole | | Yes | 8 | 1 | 1.164 | 3.492 |
| Ketoprofen | 20% | KET2036 | KET134 | Ethanol | Isopropyl myristate | 30:70 | Eucalyptus oil | 3.5% 1,8-cineole | | Yes | 0.5 | 2 | 0.05 | 0.15 |
| Ketoprofen | 20% | KET2037 | KET134 | Ethanol | Isopropyl myristate | 30:70 | Eucalyptus oil | 3.5% 1,8-cineole | | Yes | 2 | 2 | 0.109 | 0.327 |
| Ketoprofen | 20% | KET2038 | KET134 | Ethanol | Isopropyl myristate | 30:70 | Eucalyptus oil | 3.5% 1,8-cineole | | Yes | 4 | 2 | 0.208 | 0.624 |
| Ketoprofen | 20% | KET2039 | KET134 | Ethanol | Isopropyl myristate | 30:70 | Eucalyptus oil | 3.5% 1,8-cineole | | Yes | 6 | 2 | 0.719 | 2.157 |
| Ketoprofen | 20% | KET2040 | KET134 | Ethanol | Isopropyl myristate | 30:70 | Eucalyptus oil | 3.5% 1,8-cineole | | Yes | 8 | 2 | 1.958 | 5.874 |
| Ketoprofen | 20% | KET2041 | KET134 | Ethanol | Isopropyl myristate | 30:70 | Eucalyptus oil | 3.5% 1,8-cineole | | Yes | 0.5 | 3 | 0.076 | 0.228 |
| Ketoprofen | 20% | KET2042 | KET134 | Ethanol | Isopropyl myristate | 30:70 | Eucalyptus oil | 3.5% 1,8-cineole | | Yes | 2 | 3 | 0.058 | 0.174 |
| Ketoprofen | 20% | KET2043 | KET134 | Ethanol | Isopropyl myristate | 30:70 | Eucalyptus oil | 3.5% 1,8-cineole | | Yes | 4 | 3 | 0.195 | 0.585 |
| Ketoprofen | 20% | KET2044 | KET134 | Ethanol | Isopropyl myristate | 30:70 | Eucalyptus oil | 3.5% 1,8-cineole | | Yes | 6 | 3 | 1.544 | 4.632 |
| Ketoprofen | 20% | KET2045 | KET134 | Ethanol | Isopropyl myristate | 30:70 | Eucalyptus oil | 3.5% 1,8-cineole | | Yes | 8 | 3 | 4.13 | 12.39 |
| Ketoprofen | 20% | KET2046 | KET135 | Ethanol | Isopropyl myristate | 50:50 | Eucalyptus oil | 3.5% 1,8-cineole | | No | 0.5 | 1 | 0.053 | 0.159 |
| Ketoprofen | 20% | KET2047 | KET135 | Ethanol | Isopropyl myristate | 50:50 | Eucalyptus oil | 3.5% 1,8-cineole | | No | 2 | 1 | 0.054 | 0.162 |
| Ketoprofen | 20% | KET2048 | KET135 | Ethanol | Isopropyl myristate | 50:50 | Eucalyptus oil | 3.5% 1,8-cineole | | No | 4 | 1 | 0.183 | 0.549 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 20% | KET2049 | KET135 | Ethanol | Isopropyl myristate | 50:50 | Eucalyptus oil | 3.5% 1,8-cineole | | No | 6 | 1 | 0.558 | 1.674 |
| Ketoprofen | 20% | KET2050 | KET135 | Ethanol | Isopropyl myristate | 50:50 | Eucalyptus oil | 3.5% 1,8-cineole | | No | 8 | 1 | 1.459 | 4.377 |
| Ketoprofen | 20% | KET2051 | KET135 | Ethanol | Isopropyl myristate | 50:50 | Eucalyptus oil | 3.5% 1,8-cineole | | No | 0.5 | 2 | 0.029 | 0.087 |
| Ketoprofen | 20% | KET2052 | KET135 | Ethanol | Isopropyl myristate | 50:50 | Eucalyptus oil | 3.5% 1,8-cineole | | No | 2 | 2 | 0.069 | 0.207 |
| Ketoprofen | 20% | KET2053 | KET135 | Ethanol | Isopropyl myristate | 50:50 | Eucalyptus oil | 3.5% 1,8-cineole | | No | 4 | 2 | 0.022 | 0.066 |
| Ketoprofen | 20% | KET2054 | KET135 | Ethanol | Isopropyl myristate | 50:50 | Eucalyptus oil | 3.5% 1,8-cineole | | No | 6 | 2 | 0.228 | 0.684 |
| Ketoprofen | 20% | KET2055 | KET135 | Ethanol | Isopropyl myristate | 50:50 | Eucalyptus oil | 3.5% 1,8-cineole | | No | 8 | 2 | 0.596 | 1.788 |
| Ketoprofen | 20% | KET2056 | KET135 | Ethanol | Isopropyl myristate | 50:50 | Eucalyptus oil | 3.5% 1,8-cineole | | No | 0.5 | 3 | 0.043 | 0.129 |
| Ketoprofen | 20% | KET2057 | KET135 | Ethanol | Isopropyl myristate | 50:50 | Eucalyptus oil | 3.5% 1,8-cineole | | No | 2 | 3 | 0.262 | 0.786 |
| Ketoprofen | 20% | KET2058 | KET135 | Ethanol | Isopropyl myristate | 50:50 | Eucalyptus oil | 3.5% 1,8-cineole | | No | 4 | 3 | 0.086 | 0.258 |
| Ketoprofen | 20% | KET2059 | KET135 | Ethanol | Isopropyl myristate | 50:50 | Eucalyptus oil | 3.5% 1,8-cineole | | No | 6 | 3 | 5.51 | 16.53 |
| Ketoprofen | 20% | KET2060 | KET135 | Ethanol | Isopropyl myristate | 50:50 | Eucalyptus oil | 3.5% 1,8-cineole | | No | 8 | 3 | 11.718 | 35.154 |
| Ketoprofen | 20% | KET2061 | KET136 | Ethanol | Isopropyl myristate | 50:50 | Eucalyptus oil | 3.5% 1,8-cineole | | Yes | 0.5 | 1 | 0.057 | 0.171 |
| Ketoprofen | 20% | KET2062 | KET136 | Ethanol | Isopropyl myristate | 50:50 | Eucalyptus oil | 3.5% 1,8-cineole | | Yes | 2 | 1 | 0.119 | 0.357 |
| Ketoprofen | 20% | KET2063 | KET136 | Ethanol | Isopropyl myristate | 50:50 | Eucalyptus oil | 3.5% 1,8-cineole | | Yes | 4 | 1 | 1.608 | 4.824 |
| Ketoprofen | 20% | KET2064 | KET136 | Ethanol | Isopropyl myristate | 50:50 | Eucalyptus oil | 3.5% 1,8-cineole | | Yes | 6 | 1 | 0.517 | 1.551 |
| Ketoprofen | 20% | KET2065 | KET136 | Ethanol | Isopropyl myristate | 50:50 | Eucalyptus oil | 3.5% 1,8-cineole | | Yes | 8 | 1 | 1.164 | 3.492 |
| Ketoprofen | 20% | KET2066 | KET136 | Ethanol | Isopropyl myristate | 50:50 | Eucalyptus oil | 3.5% 1,8-cineole | | Yes | 0.5 | 2 | 0.05 | 0.15 |
| Ketoprofen | 20% | KET2067 | KET136 | Ethanol | Isopropyl myristate | 50:50 | Eucalyptus oil | 3.5% 1,8-cineole | | Yes | 2 | 2 | 0.109 | 0.327 |
| Ketoprofen | 20% | KET2068 | KET136 | Ethanol | Isopropyl myristate | 50:50 | Eucalyptus oil | 3.5% 1,8-cineole | | Yes | 4 | 2 | 0.208 | 0.624 |
| Ketoprofen | 20% | KET2069 | KET136 | Ethanol | Isopropyl myristate | 50:50 | Eucalyptus oil | 3.5% 1,8-cineole | | Yes | 6 | 2 | 0.719 | 2.157 |
| Ketoprofen | 20% | KET2070 | KET136 | Ethanol | Isopropyl myristate | 50:50 | Eucalyptus oil | 3.5% 1,8-cineole | | Yes | 8 | 2 | 1.958 | 5.874 |
| Ketoprofen | 20% | KET2071 | KET136 | Ethanol | Isopropyl myristate | 50:50 | Eucalyptus oil | 3.5% 1,8-cineole | | Yes | 0.5 | 3 | 0.076 | 0.228 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/EVAP | sample time (hrs) | Replicate | analysis conc | Concentration (μg/mL) |
|---|---|---|---|---|---|---|---|---|---|---|---|---|---|---|
| Ketoprofen | 20% | KET2072 | KET136 | Ethanol | Isopropyl myristate | 50:50 | Eucalyptus oil | 3.5% 1,8-cineole | | Yes | 2 | 3 | 0.058 | 0.174 |
| Ketoprofen | 20% | KET2073 | KET136 | Ethanol | Isopropyl myristate | 50:50 | Eucalyptus oil | 3.5% 1,8-cineole | | Yes | 4 | 3 | 0.195 | 0.585 |
| Ketoprofen | 20% | KET2074 | KET136 | Ethanol | Isopropyl myristate | 50:50 | Eucalyptus oil | 3.5% 1,8-cineole | | Yes | 6 | 3 | 1.544 | 4.632 |
| Ketoprofen | 20% | KET2075 | KET136 | Ethanol | Isopropyl myristate | 50:50 | Eucalyptus oil | 3.5% 1,8-cineole | | Yes | 8 | 3 | 4.13 | 12.39 |
| Ketoprofen | 30% | KET2076 | KET137 | Ethanol | Propylene glycol | 70:30 | Eucalyptus oil | 3.5% 1,8-cineole | | No | 0.5 | 1 | 0.043 | 0.129 |
| Ketoprofen | 30% | KET2077 | KET137 | Ethanol | Propylene glycol | 70:30 | Eucalyptus oil | 3.5% 1,8-cineole | | No | 2 | 1 | 0.013 | 0.039 |
| Ketoprofen | 30% | KET2078 | KET137 | Ethanol | Propylene glycol | 70:30 | Eucalyptus oil | 3.5% 1,8-cineole | | No | 4 | 1 | 0.124 | 0.372 |
| Ketoprofen | 30% | KET2079 | KET137 | Ethanol | Propylene glycol | 70:30 | Eucalyptus oil | 3.5% 1,8-cineole | | No | 6 | 1 | 0.233 | 0.699 |
| Ketoprofen | 30% | KET2080 | KET137 | Ethanol | Propylene glycol | 70:30 | Eucalyptus oil | 3.5% 1,8-cineole | | No | 8 | 1 | 3.101 | 9.303 |
| Ketoprofen | 30% | KET2081 | KET137 | Ethanol | Propylene glycol | 70:30 | Eucalyptus oil | 3.5% 1,8-cineole | | No | 0.5 | 2 | 0.012 | 0.036 |
| Ketoprofen | 30% | KET2082 | KET137 | Ethanol | Propylene glycol | 70:30 | Eucalyptus oil | 3.5% 1,8-cineole | | No | 2 | 2 | 0.01 | 0.03 |
| Ketoprofen | 30% | KET2083 | KET137 | Ethanol | Propylene glycol | 70:30 | Eucalyptus oil | 3.5% 1,8-cineole | | No | 4 | 2 | 0.499 | 1.497 |
| Ketoprofen | 30% | KET2084 | KET137 | Ethanol | Propylene glycol | 70:30 | Eucalyptus oil | 3.5% 1,8-cineole | | No | 6 | 2 | 0.585 | 1.755 |
| Ketoprofen | 30% | KET2085 | KET137 | Ethanol | Propylene glycol | 70:30 | Eucalyptus oil | 3.5% 1,8-cineole | | No | 8 | 2 | 1.719 | 5.157 |
| Ketoprofen | 30% | KET2086 | KET137 | Ethanol | Propylene glycol | 70:30 | Eucalyptus oil | 3.5% 1,8-cineole | | No | 0.5 | 3 | 0.017 | 0.051 |
| Ketoprofen | 30% | KET2087 | KET137 | Ethanol | Propylene glycol | 70:30 | Eucalyptus oil | 3.5% 1,8-cineole | | No | 2 | 3 | 0.008 | 0.024 |
| Ketoprofen | 30% | KET2088 | KET137 | Ethanol | Propylene glycol | 70:30 | Eucalyptus oil | 3.5% 1,8-cineole | | No | 4 | 3 | 0.243 | 0.729 |
| Ketoprofen | 30% | KET2089 | KET137 | Ethanol | Propylene glycol | 70:30 | Eucalyptus oil | 3.5% 1,8-cineole | | No | 6 | 3 | 0.448 | 1.344 |
| Ketoprofen | 30% | KET2090 | KET137 | Ethanol | Propylene glycol | 70:30 | Eucalyptus oil | 3.5% 1,8-cineole | | No | 8 | 3 | 2.38 | 7.14 |
| Ketoprofen | 30% | KET2091 | KET138 | Ethanol | Isopropyl myristate | 30:70 | Eucalyptus oil | 3.5% 1,8-cineole | | No | 0.5 | 1 | 0.065 | 0.195 |
| Ketoprofen | 30% | KET2092 | KET138 | Ethanol | Isopropyl myristate | 30:70 | Eucalyptus oil | 3.5% 1,8-cineole | | No | 2 | 1 | 0.049 | 0.147 |
| Ketoprofen | 30% | KET2093 | KET138 | Ethanol | Isopropyl myristate | 30:70 | Eucalyptus oil | 3.5% 1,8-cineole | | No | 4 | 1 | 0.075 | 0.225 |
| Ketoprofen | 30% | KET2094 | KET138 | Ethanol | Isopropyl myristate | 30:70 | Eucalyptus oil | 3.5% 1,8-cineole | | No | 6 | 1 | 0.146 | 0.438 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 30% | KET2095 | KET138 | Ethanol | Isopropyl myristate | 30:70 | Eucalyptus oil | 3.5% 1,8-cineole | | No | 8 | 1 | 0.475 | 1.425 |
| Ketoprofen | 30% | KET2096 | KET138 | Ethanol | Isopropyl myristate | 30:70 | Eucalyptus oil | 3.5% 1,8-cineole | | No | 0.5 | 2 | 0.039 | 0.117 |
| Ketoprofen | 30% | KET2097 | KET138 | Ethanol | Isopropyl myristate | 30:70 | Eucalyptus oil | 3.5% 1,8-cineole | | No | 2 | 2 | 0.054 | 0.162 |
| Ketoprofen | 30% | KET2098 | KET138 | Ethanol | Isopropyl myristate | 30:70 | Eucalyptus oil | 3.5% 1,8-cineole | | No | 4 | 2 | 0.06 | 0.18 |
| Ketoprofen | 30% | KET2099 | KET138 | Ethanol | Isopropyl myristate | 30:70 | Eucalyptus oil | 3.5% 1,8-cineole | | No | 6 | 2 | 0.166 | 0.498 |
| Ketoprofen | 30% | KET2100 | KET138 | Ethanol | Isopropyl myristate | 30:70 | Eucalyptus oil | 3.5% 1,8-cineole | | No | 8 | 2 | 0.638 | 1.914 |
| Ketoprofen | 30% | KET2101 | KET138 | Ethanol | Isopropyl myristate | 30:70 | Eucalyptus oil | 3.5% 1,8-cineole | | No | 0.5 | 3 | 0.039 | 0.117 |
| Ketoprofen | 30% | KET2102 | KET138 | Ethanol | Isopropyl myristate | 30:70 | Eucalyptus oil | 3.5% 1,8-cineole | | No | 2 | 3 | 0.042 | 0.126 |
| Ketoprofen | 30% | KET2103 | KET138 | Ethanol | Isopropyl myristate | 30:70 | Eucalyptus oil | 3.5% 1,8-cineole | | No | 4 | 3 | 0.126 | 0.378 |
| Ketoprofen | 30% | KET2104 | KET138 | Ethanol | Isopropyl myristate | 30:70 | Eucalyptus oil | 3.5% 1,8-cineole | | No | 6 | 3 | 1.522 | 4.566 |
| Ketoprofen | 30% | KET2105 | KET138 | Ethanol | Isopropyl myristate | 30:70 | Eucalyptus oil | 3.5% 1,8-cineole | | No | 8 | 3 | 6.056 | 18.168 |
| Ketoprofen | 30% | KET2106 | KET139 | Ethanol | Isopropyl myristate | 30:70 | Eucalyptus oil | 3.5% 1,8-cineole | | Yes | 0.5 | 1 | 0.034 | 0.102 |
| Ketoprofen | 30% | KET2107 | KET139 | Ethanol | Isopropyl myristate | 30:70 | Eucalyptus oil | 3.5% 1,8-cineole | | Yes | 2 | 1 | 3.448 | 10.344 |
| Ketoprofen | 30% | KET2108 | KET139 | Ethanol | Isopropyl myristate | 30:70 | Eucalyptus oil | 3.5% 1,8-cineole | | Yes | 4 | 1 | 12.099 | 36.297 |
| Ketoprofen | 30% | KET2109 | KET139 | Ethanol | Isopropyl myristate | 30:70 | Eucalyptus oil | 3.5% 1,8-cineole | | Yes | 6 | 1 | 17.446 | 52.338 |
| Ketoprofen | 30% | KET2110 | KET139 | Ethanol | Isopropyl myristate | 30:70 | Eucalyptus oil | 3.5% 1,8-cineole | | Yes | 8 | 1 | 25.973 | 77.919 |
| Ketoprofen | 30% | KET2111 | KET139 | Ethanol | Isopropyl myristate | 30:70 | Eucalyptus oil | 3.5% 1,8-cineole | | Yes | 0.5 | 2 | 0.027 | 0.081 |
| Ketoprofen | 30% | KET2112 | KET139 | Ethanol | Isopropyl myristate | 30:70 | Eucalyptus oil | 3.5% 1,8-cineole | | Yes | 2 | 2 | 0.217 | 0.651 |
| Ketoprofen | 30% | KET2113 | KET139 | Ethanol | Isopropyl myristate | 30:70 | Eucalyptus oil | 3.5% 1,8-cineole | | Yes | 4 | 2 | 0.867 | 2.601 |
| Ketoprofen | 30% | KET2114 | KET139 | Ethanol | Isopropyl myristate | 30:70 | Eucalyptus oil | 3.5% 1,8-cineole | | Yes | 6 | 2 | 1.673 | 5.019 |
| Ketoprofen | 30% | KET2115 | KET139 | Ethanol | Isopropyl myristate | 30:70 | Eucalyptus oil | 3.5% 1,8-cineole | | Yes | 8 | 2 | 1.99 | 5.97 |
| Ketoprofen | 30% | KET2116 | KET139 | Ethanol | Isopropyl myristate | 30:70 | Eucalyptus oil | 3.5% 1,8-cineole | | Yes | 0.5 | 3 | 0.042 | 0.126 |
| Ketoprofen | 30% | KET2117 | KET139 | Ethanol | Isopropyl myristate | 30:70 | Eucalyptus oil | 3.5% 1,8-cineole | | Yes | 2 | 3 | 0.083 | 0.249 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 30% | KET2118 | KET139 | Ethanol | Isopropyl myristate | 30:70 | Eucalyptus oil | 3.5% 1,8-cineole | | Yes | 4 | 3 | 0.276 | 0.828 |
| Ketoprofen | 30% | KET2119 | KET139 | Ethanol | Isopropyl myristate | 30:70 | Eucalyptus oil | 3.5% 1,8-cineole | | Yes | 6 | 3 | 0.816 | 2.448 |
| Ketoprofen | 30% | KET2120 | KET139 | Ethanol | Isopropyl myristate | 30:70 | Eucalyptus oil | 3.5% 1,8-cineole | | Yes | 8 | 3 | 2.438 | 7.314 |
| Ketoprofen | 30% | KET2121 | KET140 | Ethanol | Isopropyl myristate | 50:50 | Eucalyptus oil | 3.5% 1,8-cineole | | No | 0.5 | 1 | 0.036 | 0.108 |
| Ketoprofen | 30% | KET2122 | KET140 | Ethanol | Isopropyl myristate | 50:50 | Eucalyptus oil | 3.5% 1,8-cineole | | No | 2 | 1 | 3.761 | 11.283 |
| Ketoprofen | 30% | KET2123 | KET140 | Ethanol | Isopropyl myristate | 50:50 | Eucalyptus oil | 3.5% 1,8-cineole | | No | 4 | 1 | 11.055 | 33.165 |
| Ketoprofen | 30% | KET2124 | KET140 | Ethanol | Isopropyl myristate | 50:50 | Eucalyptus oil | 3.5% 1,8-cineole | | No | 6 | 1 | 24.874 | 74.622 |
| Ketoprofen | 30% | KET2125 | KET140 | Ethanol | Isopropyl myristate | 50:50 | Eucalyptus oil | 3.5% 1,8-cineole | | No | 8 | 1 | 39.875 | 119.625 |
| Ketoprofen | 30% | KET2126 | KET140 | Ethanol | Isopropyl myristate | 50:50 | Eucalyptus oil | 3.5% 1,8-cineole | | No | 0.5 | 2 | 0.043 | 0.129 |
| Ketoprofen | 30% | KET2127 | KET140 | Ethanol | Isopropyl myristate | 50:50 | Eucalyptus oil | 3.5% 1,8-cineole | | No | 2 | 2 | 0.242 | 0.726 |
| Ketoprofen | 30% | KET2128 | KET140 | Ethanol | Isopropyl myristate | 50:50 | Eucalyptus oil | 3.5% 1,8-cineole | | No | 4 | 2 | 1.335 | 4.005 |
| Ketoprofen | 30% | KET2129 | KET140 | Ethanol | Isopropyl myristate | 50:50 | Eucalyptus oil | 3.5% 1,8-cineole | | No | 6 | 2 | 4.696 | 14.088 |
| Ketoprofen | 30% | KET2130 | KET140 | Ethanol | Isopropyl myristate | 50:50 | Eucalyptus oil | 3.5% 1,8-cineole | | No | 8 | 2 | 10.407 | 31.221 |
| Ketoprofen | 30% | KET2131 | KET140 | Ethanol | Isopropyl myristate | 50:50 | Eucalyptus oil | 3.5% 1,8-cineole | | No | 0.5 | 3 | 0.097 | 0.291 |
| Ketoprofen | 30% | KET2132 | KET140 | Ethanol | Isopropyl myristate | 50:50 | Eucalyptus oil | 3.5% 1,8-cineole | | No | 2 | 3 | 0.201 | 0.603 |
| Ketoprofen | 30% | KET2133 | KET140 | Ethanol | Isopropyl myristate | 50:50 | Eucalyptus oil | 3.5% 1,8-cineole | | No | 4 | 3 | 0.41 | 1.23 |
| Ketoprofen | 30% | KET2134 | KET140 | Ethanol | Isopropyl myristate | 50:50 | Eucalyptus oil | 3.5% 1,8-cineole | | No | 6 | 3 | 2.04 | 6.12 |
| Ketoprofen | 30% | KET2135 | KET140 | Ethanol | Isopropyl myristate | 50:50 | Eucalyptus oil | 3.5% 1,8-cineole | | No | 8 | 3 | 6.345 | 19.035 |
| Ketoprofen | 30% | KET2136 | KET141 | Ethanol | Isopropyl myristate | 50:50 | Eucalyptus oil | 3.5% 1,8-cineole | | Yes | 0.5 | 1 | 0.065 | 0.195 |
| Ketoprofen | 30% | KET2137 | KET141 | Ethanol | Isopropyl myristate | 50:50 | Eucalyptus oil | 3.5% 1,8-cineole | | Yes | 2 | 1 | 0.062 | 0.186 |
| Ketoprofen | 30% | KET2138 | KET141 | Ethanol | Isopropyl myristate | 50:50 | Eucalyptus oil | 3.5% 1,8-cineole | | Yes | 4 | 1 | 0.143 | 0.429 |
| Ketoprofen | 30% | KET2139 | KET141 | Ethanol | Isopropyl myristate | 50:50 | Eucalyptus oil | 3.5% 1,8-cineole | | Yes | 6 | 1 | 0.55 | 1.65 |
| Ketoprofen | 30% | KET2140 | KET141 | Ethanol | Isopropyl myristate | 50:50 | Eucalyptus oil | 3.5% 1,8-cineole | | Yes | 8 | 1 | 1.574 | 4.722 |

TABLE 13-continued

NSAID and vehicle screening data

| NSAID | Drug conc | Sample # | Vehicle ID | Alcohol solvent Solvent | Solvent conc | Co-solvent conc | Co-solvent | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 30% | KET2141 | KET141 | Ethanol | Isopropyl myristate | 50:50 | Eucalyptus oil | 3.5% 1,8-cineole | | Yes | 0.5 | 2 | 0.042 | 0.126 |
| Ketoprofen | 30% | KET2142 | KET141 | Ethanol | Isopropyl myristate | 50:50 | Eucalyptus oil | 3.5% 1,8-cineole | | Yes | 2 | 2 | 0.052 | 0.156 |
| Ketoprofen | 30% | KET2143 | KET141 | Ethanol | Isopropyl myristate | 50:50 | Eucalyptus oil | 3.5% 1,8-cineole | | Yes | 4 | 2 | 0.263 | 0.789 |
| Ketoprofen | 30% | KET2144 | KET141 | Ethanol | Isopropyl myristate | 50:50 | Eucalyptus oil | 3.5% 1,8-cineole | | Yes | 6 | 2 | 1.754 | 5.262 |
| Ketoprofen | 30% | KET2145 | KET141 | Ethanol | Isopropyl myristate | 50:50 | Eucalyptus oil | 3.5% 1,8-cineole | | Yes | 8 | 2 | 5.928 | 17.784 |
| Ketoprofen | 30% | KET2146 | KET141 | Ethanol | Isopropyl myristate | 50:50 | Eucalyptus oil | 3.5% 1,8-cineole | | Yes | 0.5 | 3 | 0.039 | 0.117 |
| Ketoprofen | 30% | KET2147 | KET141 | Ethanol | Isopropyl myristate | 50:50 | Eucalyptus oil | 3.5% 1,8-cineole | | Yes | 2 | 3 | 0.049 | 0.147 |
| Ketoprofen | 30% | KET2148 | KET141 | Ethanol | Isopropyl myristate | 50:50 | Eucalyptus oil | 3.5% 1,8-cineole | | Yes | 4 | 3 | 0.086 | 0.258 |
| Ketoprofen | 30% | KET2149 | KET141 | Ethanol | Isopropyl myristate | 50:50 | Eucalyptus oil | 3.5% 1,8-cineole | | Yes | 6 | 3 | 0.506 | 1.518 |
| Ketoprofen | 30% | KET2150 | KET141 | Ethanol | Isopropyl myristate | 50:50 | Eucalyptus oil | 3.5% 1,8-cineole | | Yes | 8 | 3 | 2.241 | 6.723 |
| Ketoprofen | 10% | KET2151 | KET142 | Ethanol | Isopropyl myristate | 70:30 | Eucalyptus oil | 3.5% 1,8-cineole | | No | 0.5 | 1 | 0.052 | 0.156 |
| Ketoprofen | 10% | KET2152 | KET142 | Ethanol | Isopropyl myristate | 70:30 | Eucalyptus oil | 3.5% 1,8-cineole | | No | 2 | 1 | 1.741 | 5.223 |
| Ketoprofen | 10% | KET2153 | KET142 | Ethanol | Isopropyl myristate | 70:30 | Eucalyptus oil | 3.5% 1,8-cineole | | No | 4 | 1 | 1.169 | 3.507 |
| Ketoprofen | 10% | KET2154 | KET142 | Ethanol | Isopropyl myristate | 70:30 | Eucalyptus oil | 3.5% 1,8-cineole | | No | 6 | 1 | 1.245 | 3.735 |
| Ketoprofen | 10% | KET2155 | KET142 | Ethanol | Isopropyl myristate | 70:30 | Eucalyptus oil | 3.5% 1,8-cineole | | No | 8 | 1 | 1.22 | 3.66 |
| Ketoprofen | 10% | KET2156 | KET142 | Ethanol | Isopropyl myristate | 70:30 | Eucalyptus oil | 3.5% 1,8-cineole | | No | 0.5 | 2 | 0.133 | 0.399 |
| Ketoprofen | 10% | KET2157 | KET142 | Ethanol | Isopropyl myristate | 70:30 | Eucalyptus oil | 3.5% 1,8-cineole | | No | 2 | 2 | 0.206 | 0.618 |
| Ketoprofen | 10% | KET2158 | KET142 | Ethanol | Isopropyl myristate | 70:30 | Eucalyptus oil | 3.5% 1,8-cineole | | No | 4 | 2 | 0.514 | 1.542 |
| Ketoprofen | 10% | KET2159 | KET142 | Ethanol | Isopropyl myristate | 70:30 | Eucalyptus oil | 3.5% 1,8-cineole | | No | 6 | 2 | 0.161 | 0.483 |
| Ketoprofen | 10% | KET2160 | KET142 | Ethanol | Isopropyl myristate | 70:30 | Eucalyptus oil | 3.5% 1,8-cineole | | No | 8 | 2 | 3.91 | 11.73 |
| Ketoprofen | 10% | KET2161 | KET142 | Ethanol | Isopropyl myristate | 70:30 | Eucalyptus oil | 3.5% 1,8-cineole | | No | 0.5 | 3 | 1.535 | 4.605 |
| Ketoprofen | 10% | KET2162 | KET142 | Ethanol | Isopropyl myristate | 70:30 | Eucalyptus oil | 3.5% 1,8-cineole | | No | 2 | 3 | 0.063 | 0.189 |
| Ketoprofen | 10% | KET2163 | KET142 | Ethanol | Isopropyl myristate | 70:30 | Eucalyptus oil | 3.5% 1,8-cineole | | No | 4 | 3 | 0.083 | 0.249 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET2164 | KET142 | Ethanol | Isopropyl myristate | 70:30 | Eucalyptus oil | 3.5% 1,8-cineole | | No | 6 | 3 | 1.223 | 3.669 |
| Ketoprofen | 10% | KET2165 | KET142 | Ethanol | Isopropyl myristate | 70:30 | Eucalyptus oil | 3.5% 1,8-cineole | | No | 8 | 3 | 0.363 | 1.089 |
| Ketoprofen | 10% | KET2166 | KET143 | Ethanol | Isopropyl myristate | 70:30 | Eucalyptus oil | 3.5% 1,8-cineole | | Yes | 0.5 | 1 | 0.048 | 0.144 |
| Ketoprofen | 10% | KET2167 | KET143 | Ethanol | Isopropyl myristate | 70:30 | Eucalyptus oil | 3.5% 1,8-cineole | | Yes | 2 | 1 | 0.249 | 0.747 |
| Ketoprofen | 10% | KET2168 | KET143 | Ethanol | Isopropyl myristate | 70:30 | Eucalyptus oil | 3.5% 1,8-cineole | | Yes | 4 | 1 | 0.709 | 2.127 |
| Ketoprofen | 10% | KET2169 | KET143 | Ethanol | Isopropyl myristate | 70:30 | Eucalyptus oil | 3.5% 1,8-cineole | | Yes | 6 | 1 | 1.007 | 3.021 |
| Ketoprofen | 10% | KET2170 | KET143 | Ethanol | Isopropyl myristate | 70:30 | Eucalyptus oil | 3.5% 1,8-cineole | | Yes | 8 | 1 | 1.719 | 5.157 |
| Ketoprofen | 10% | KET2171 | KET143 | Ethanol | Isopropyl myristate | 70:30 | Eucalyptus oil | 3.5% 1,8-cineole | | Yes | 0.5 | 2 | 0.061 | 0.183 |
| Ketoprofen | 10% | KET2172 | KET143 | Ethanol | Isopropyl myristate | 70:30 | Eucalyptus oil | 3.5% 1,8-cineole | | Yes | 2 | 2 | 0.235 | 0.705 |
| Ketoprofen | 10% | KET2173 | KET143 | Ethanol | Isopropyl myristate | 70:30 | Eucalyptus oil | 3.5% 1,8-cineole | | Yes | 4 | 2 | 1.562 | 4.686 |
| Ketoprofen | 10% | KET2174 | KET143 | Ethanol | Isopropyl myristate | 70:30 | Eucalyptus oil | 3.5% 1,8-cineole | | Yes | 6 | 2 | 2.804 | 8.412 |
| Ketoprofen | 10% | KET2175 | KET143 | Ethanol | Isopropyl myristate | 70:30 | Eucalyptus oil | 3.5% 1,8-cineole | | Yes | 8 | 2 | 4.219 | 12.657 |
| Ketoprofen | 10% | KET2176 | KET143 | Ethanol | Isopropyl myristate | 70:30 | Eucalyptus oil | 3.5% 1,8-cineole | | Yes | 0.5 | 3 | 0.056 | 0.168 |
| Ketoprofen | 10% | KET2177 | KET143 | Ethanol | Isopropyl myristate | 70:30 | Eucalyptus oil | 3.5% 1,8-cineole | | Yes | 2 | 3 | 0.767 | 2.301 |
| Ketoprofen | 10% | KET2178 | KET143 | Ethanol | Isopropyl myristate | 70:30 | Eucalyptus oil | 3.5% 1,8-cineole | | Yes | 4 | 3 | 0.088 | 0.264 |
| Ketoprofen | 10% | KET2179 | KET143 | Ethanol | Isopropyl myristate | 70:30 | Eucalyptus oil | 3.5% 1,8-cineole | | Yes | 6 | 3 | 2.793 | 8.379 |
| Ketoprofen | 10% | KET2180 | KET143 | Ethanol | Isopropyl myristate | 70:30 | Eucalyptus oil | 3.5% 1,8-cineole | | Yes | 8 | 3 | 4.272 | 12.816 |
| Ketoprofen | 10% | KET2181 | KET144 | Ethanol | Propylene glycol | 30:70 | Eucalyptus oil | 7.0% 1,8-cineole | | No | 0.5 | 1 | 1.347 | 4.041 |
| Ketoprofen | 10% | KET2182 | KET144 | Ethanol | Propylene glycol | 30:70 | Eucalyptus oil | 7.0% 1,8-cineole | | No | 2 | 1 | 1.532 | 4.596 |
| Ketoprofen | 10% | KET2183 | KET144 | Ethanol | Propylene glycol | 30:70 | Eucalyptus oil | 7.0% 1,8-cineole | | No | 4 | 1 | 1.375 | 4.125 |
| Ketoprofen | 10% | KET2184 | KET144 | Ethanol | Propylene glycol | 30:70 | Eucalyptus oil | 7.0% 1,8-cineole | | No | 6 | 1 | 2.095 | 6.285 |
| Ketoprofen | 10% | KET2185 | KET144 | Ethanol | Propylene glycol | 30:70 | Eucalyptus oil | 7.0% 1,8-cineole | | No | 8 | 1 | 6.049 | 18.147 |
| Ketoprofen | 10% | KET2186 | KET144 | Ethanol | Propylene glycol | 30:70 | Eucalyptus oil | 7.0% 1,8-cineole | | No | 0.5 | 2 | 0.079 | 0.237 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/EVAP | sample time (hrs) | Replicate | analysis conc | Concentration (μg/mL) |
|---|---|---|---|---|---|---|---|---|---|---|---|---|---|---|
| Ketoprofen | 10% | KET2187 | KET144 | Ethanol | Propylene glycol | 30:70 | Eucalyptus oil | 7.0% 1,8-cineole | | No | 2 | 2 | 0.077 | 0.231 |
| Ketoprofen | 10% | KET2188 | KET144 | Ethanol | Propylene glycol | 30:70 | Eucalyptus oil | 7.0% 1,8-cineole | | No | 4 | 2 | 0.073 | 0.219 |
| Ketoprofen | 10% | KET2189 | KET144 | Ethanol | Propylene glycol | 30:70 | Eucalyptus oil | 7.0% 1,8-cineole | | No | 6 | 2 | 0.095 | 0.285 |
| Ketoprofen | 10% | KET2190 | KET144 | Ethanol | Propylene glycol | 30:70 | Eucalyptus oil | 7.0% 1,8-cineole | | No | 8 | 2 | 0.986 | 2.958 |
| Ketoprofen | 10% | KET2191 | KET144 | Ethanol | Propylene glycol | 30:70 | Eucalyptus oil | 7.0% 1,8-cineole | | No | 0.5 | 3 | 0.074 | 0.222 |
| Ketoprofen | 10% | KET2192 | KET144 | Ethanol | Propylene glycol | 30:70 | Eucalyptus oil | 7.0% 1,8-cineole | | No | 2 | 3 | 0.074 | 0.222 |
| Ketoprofen | 10% | KET2193 | KET144 | Ethanol | Propylene glycol | 30:70 | Eucalyptus oil | 7.0% 1,8-cineole | | No | 4 | 3 | 0.083 | 0.249 |
| Ketoprofen | 10% | KET2194 | KET144 | Ethanol | Propylene glycol | 30:70 | Eucalyptus oil | 7.0% 1,8-cineole | | No | 6 | 3 | 0.161 | 0.483 |
| Ketoprofen | 10% | KET2195 | KET144 | Ethanol | Propylene glycol | 30:70 | Eucalyptus oil | 7.0% 1,8-cineole | | No | 8 | 3 | 2.161 | 6.483 |
| Ketoprofen | 10% | KET2196 | KET145 | Ethanol | Isopropyl myristate | 30:70 | Eucalyptus oil | 7.0% 1,8-cineole | | No | 0.5 | 1 | 0.043 | 0.129 |
| Ketoprofen | 10% | KET2197 | KET145 | Ethanol | Isopropyl myristate | 30:70 | Eucalyptus oil | 7.0% 1,8-cineole | | No | 2 | 1 | 0.34 | 1.02 |
| Ketoprofen | 10% | KET2198 | KET145 | Ethanol | Isopropyl myristate | 30:70 | Eucalyptus oil | 7.0% 1,8-cineole | | No | 4 | 1 | 0.356 | 1.068 |
| Ketoprofen | 10% | KET2199 | KET145 | Ethanol | Isopropyl myristate | 30:70 | Eucalyptus oil | 7.0% 1,8-cineole | | No | 6 | 1 | 2.57 | 7.71 |
| Ketoprofen | 10% | KET2200 | KET145 | Ethanol | Isopropyl myristate | 30:70 | Eucalyptus oil | 7.0% 1,8-cineole | | No | 8 | 1 | 3.6 | 10.8 |
| Ketoprofen | 10% | KET2201 | KET145 | Ethanol | Isopropyl myristate | 30:70 | Eucalyptus oil | 7.0% 1,8-cineole | | No | 0.5 | 2 | 0.047 | 0.141 |
| Ketoprofen | 10% | KET2202 | KET145 | Ethanol | Isopropyl myristate | 30:70 | Eucalyptus oil | 7.0% 1,8-cineole | | No | 2 | 2 | 0.224 | 0.672 |
| Ketoprofen | 10% | KET2203 | KET145 | Ethanol | Isopropyl myristate | 30:70 | Eucalyptus oil | 7.0% 1,8-cineole | | No | 4 | 2 | 0.121 | 0.363 |
| Ketoprofen | 10% | KET2204 | KET145 | Ethanol | Isopropyl myristate | 30:70 | Eucalyptus oil | 7.0% 1,8-cineole | | No | 6 | 2 | 1.846 | 5.538 |
| Ketoprofen | 10% | KET2205 | KET145 | Ethanol | Isopropyl myristate | 30:70 | Eucalyptus oil | 7.0% 1,8-cineole | | No | 8 | 2 | 3.144 | 9.432 |
| Ketoprofen | 10% | KET2206 | KET145 | Ethanol | Isopropyl myristate | 30:70 | Eucalyptus oil | 7.0% 1,8-cineole | | No | 0.5 | 3 | 0.087 | 0.261 |
| Ketoprofen | 10% | KET2207 | KET145 | Ethanol | Isopropyl myristate | 30:70 | Eucalyptus oil | 7.0% 1,8-cineole | | No | 2 | 3 | 0.271 | 0.813 |
| Ketoprofen | 10% | KET2208 | KET145 | Ethanol | Isopropyl myristate | 30:70 | Eucalyptus oil | 7.0% 1,8-cineole | | No | 4 | 3 | 1.639 | 4.917 |
| Ketoprofen | 10% | KET2209 | KET145 | Ethanol | Isopropyl myristate | 30:70 | Eucalyptus oil | 7.0% 1,8-cineole | | No | 6 | 3 | 0.621 | 1.863 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET2210 | KET145 | Ethanol | Isopropyl myristate | 30:70 | Eucalyptus oil | 7.0% 1,8-cineole | | No | 8 | 3 | 1.443 | 4.329 |
| Ketoprofen | 10% | KET2211 | KET146 | Ethanol | Propylene glycol | 30:70 | Eucalyptus oil | 7.0% 1,8-cineole | | Yes | 0.5 | 1 | 0.047 | 0.141 |
| Ketoprofen | 10% | KET2212 | KET146 | Ethanol | Propylene glycol | 30:70 | Eucalyptus oil | 7.0% 1,8-cineole | | Yes | 2 | 1 | 0.011 | 0.033 |
| Ketoprofen | 10% | KET2213 | KET146 | Ethanol | Propylene glycol | 30:70 | Eucalyptus oil | 7.0% 1,8-cineole | | Yes | 4 | 1 | 0.022 | 0.066 |
| Ketoprofen | 10% | KET2214 | KET146 | Ethanol | Propylene glycol | 30:70 | Eucalyptus oil | 7.0% 1,8-cineole | | Yes | 6 | 1 | 0.025 | 0.075 |
| Ketoprofen | 10% | KET2215 | KET146 | Ethanol | Propylene glycol | 30:70 | Eucalyptus oil | 7.0% 1,8-cineole | | Yes | 8 | 1 | 0.168 | 0.504 |
| Ketoprofen | 10% | KET2216 | KET146 | Ethanol | Propylene glycol | 30:70 | Eucalyptus oil | 7.0% 1,8-cineole | | Yes | 0.5 | 2 | 0.053 | 0.159 |
| Ketoprofen | 10% | KET2217 | KET146 | Ethanol | Propylene glycol | 30:70 | Eucalyptus oil | 7.0% 1,8-cineole | | Yes | 2 | 2 | 0.008 | 0.024 |
| Ketoprofen | 10% | KET2218 | KET146 | Ethanol | Propylene glycol | 30:70 | Eucalyptus oil | 7.0% 1,8-cineole | | Yes | 4 | 2 | 0.012 | 0.036 |
| Ketoprofen | 10% | KET2219 | KET146 | Ethanol | Propylene glycol | 30:70 | Eucalyptus oil | 7.0% 1,8-cineole | | Yes | 6 | 2 | 0.021 | 0.063 |
| Ketoprofen | 10% | KET2220 | KET146 | Ethanol | Propylene glycol | 30:70 | Eucalyptus oil | 7.0% 1,8-cineole | | Yes | 8 | 2 | 0.399 | 1.197 |
| Ketoprofen | 10% | KET2221 | KET146 | Ethanol | Propylene glycol | 30:70 | Eucalyptus oil | 7.0% 1,8-cineole | | Yes | 0.5 | 3 | 0.015 | 0.045 |
| Ketoprofen | 10% | KET2222 | KET146 | Ethanol | Propylene glycol | 30:70 | Eucalyptus oil | 7.0% 1,8-cineole | | Yes | 2 | 3 | 0.007 | 0.021 |
| Ketoprofen | 10% | KET2223 | KET146 | Ethanol | Propylene glycol | 30:70 | Eucalyptus oil | 7.0% 1,8-cineole | | Yes | 4 | 3 | 0.069 | 0.207 |
| Ketoprofen | 10% | KET2224 | KET146 | Ethanol | Propylene glycol | 30:70 | Eucalyptus oil | 7.0% 1,8-cineole | | Yes | 6 | 3 | 0.01 | 0.03 |
| Ketoprofen | 10% | KET2225 | KET146 | Ethanol | Propylene glycol | 30:70 | Eucalyptus oil | 7.0% 1,8-cineole | | Yes | 8 | 3 | 0.049 | 0.147 |
| Ketoprofen | 20% | KET2226 | KET147 | Ethanol | Isopropyl myristate | 70:30 | Eucalyptus oil | 3.5% 1,8-cineole | | No | 0.5 | 1 | 0.062 | 0.186 |
| Ketoprofen | 20% | KET2227 | KET147 | Ethanol | Isopropyl myristate | 70:30 | Eucalyptus oil | 3.5% 1,8-cineole | | No | 2 | 1 | 0.231 | 0.693 |
| Ketoprofen | 20% | KET2228 | KET147 | Ethanol | Isopropyl myristate | 70:30 | Eucalyptus oil | 3.5% 1,8-cineole | | No | 4 | 1 | 0.195 | 0.585 |
| Ketoprofen | 20% | KET2229 | KET147 | Ethanol | Isopropyl myristate | 70:30 | Eucalyptus oil | 3.5% 1,8-cineole | | No | 6 | 1 | 0.441 | 1.323 |
| Ketoprofen | 20% | KET2230 | KET147 | Ethanol | Isopropyl myristate | 70:30 | Eucalyptus oil | 3.5% 1,8-cineole | | No | 8 | 1 | 1.119 | 3.357 |
| Ketoprofen | 20% | KET2231 | KET147 | Ethanol | Isopropyl myristate | 70:30 | Eucalyptus oil | 3.5% 1,8-cineole | | No | 0.5 | 2 | 0.036 | 0.108 |
| Ketoprofen | 20% | KET2232 | KET147 | Ethanol | Isopropyl myristate | 70:30 | Eucalyptus oil | 3.5% 1,8-cineole | | No | 2 | 2 | 3.345 | 10.035 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 20% | KET2233 | KET147 | Ethanol | Isopropyl myristate | 70:30 | Eucalyptus oil | 3.5% 1,8-cineole | | No | 4 | 2 | 0.201 | 0.603 |
| Ketoprofen | 20% | KET2234 | KET147 | Ethanol | Isopropyl myristate | 70:30 | Eucalyptus oil | 3.5% 1,8-cineole | | No | 6 | 2 | 18.947 | 56.841 |
| Ketoprofen | 20% | KET2235 | KET147 | Ethanol | Isopropyl myristate | 70:30 | Eucalyptus oil | 3.5% 1,8-cineole | | No | 8 | 2 | 27.13 | 81.39 |
| Ketoprofen | 20% | KET2236 | KET147 | Ethanol | Isopropyl myristate | 70:30 | Eucalyptus oil | 3.5% 1,8-cineole | | No | 0.5 | 3 | 0.045 | 0.135 |
| Ketoprofen | 20% | KET2237 | KET147 | Ethanol | Isopropyl myristate | 70:30 | Eucalyptus oil | 3.5% 1,8-cineole | | No | 2 | 3 | 0.118 | 0.354 |
| Ketoprofen | 20% | KET2238 | KET147 | Ethanol | Isopropyl myristate | 70:30 | Eucalyptus oil | 3.5% 1,8-cineole | | No | 4 | 3 | 0.13 | 0.39 |
| Ketoprofen | 20% | KET2239 | KET147 | Ethanol | Isopropyl myristate | 70:30 | Eucalyptus oil | 3.5% 1,8-cineole | | No | 6 | 3 | 2.423 | 7.269 |
| Ketoprofen | 20% | KET2240 | KET147 | Ethanol | Isopropyl myristate | 70:30 | Eucalyptus oil | 3.5% 1,8-cineole | | No | 8 | 3 | 5.49 | 16.47 |
| Ketoprofen | 20% | KET2241 | KET148 | Ethanol | Isopropyl myristate | 70:30 | Eucalyptus oil | 3.5% 1,8-cineole | | Yes | 0.5 | 1 | 0.042 | 0.126 |
| Ketoprofen | 20% | KET2242 | KET148 | Ethanol | Isopropyl myristate | 70:30 | Eucalyptus oil | 3.5% 1,8-cineole | | Yes | 2 | 1 | 0.072 | 0.216 |
| Ketoprofen | 20% | KET2243 | KET148 | Ethanol | Isopropyl myristate | 70:30 | Eucalyptus oil | 3.5% 1,8-cineole | | Yes | 4 | 1 | 10.198 | 30.594 |
| Ketoprofen | 20% | KET2244 | KET148 | Ethanol | Isopropyl myristate | 70:30 | Eucalyptus oil | 3.5% 1,8-cineole | | Yes | 6 | 1 | 0.368 | 1.104 |
| Ketoprofen | 20% | KET2245 | KET148 | Ethanol | Isopropyl myristate | 70:30 | Eucalyptus oil | 3.5% 1,8-cineole | | Yes | 8 | 1 | 0.764 | 2.292 |
| Ketoprofen | 20% | KET2246 | KET148 | Ethanol | Isopropyl myristate | 70:30 | Eucalyptus oil | 3.5% 1,8-cineole | | Yes | 0.5 | 2 | 0.035 | 0.105 |
| Ketoprofen | 20% | KET2247 | KET148 | Ethanol | Isopropyl myristate | 70:30 | Eucalyptus oil | 3.5% 1,8-cineole | | Yes | 2 | 2 | 2.67 | 8.01 |
| Ketoprofen | 20% | KET2248 | KET148 | Ethanol | Isopropyl myristate | 70:30 | Eucalyptus oil | 3.5% 1,8-cineole | | Yes | 4 | 2 | 0.987 | 2.961 |
| Ketoprofen | 20% | KET2249 | KET148 | Ethanol | Isopropyl myristate | 70:30 | Eucalyptus oil | 3.5% 1,8-cineole | | Yes | 6 | 2 | 13.131 | 39.393 |
| Ketoprofen | 20% | KET2250 | KET148 | Ethanol | Isopropyl myristate | 70:30 | Eucalyptus oil | 3.5% 1,8-cineole | | Yes | 8 | 2 | 17.996 | 53.988 |
| Ketoprofen | 20% | KET2251 | KET148 | Ethanol | Isopropyl myristate | 70:30 | Eucalyptus oil | 3.5% 1,8-cineole | | Yes | 0.5 | 3 | 0.03 | 0.09 |
| Ketoprofen | 20% | KET2252 | KET148 | Ethanol | Isopropyl myristate | 70:30 | Eucalyptus oil | 3.5% 1,8-cineole | | Yes | 2 | 3 | 0.46 | 1.38 |
| Ketoprofen | 20% | KET2253 | KET148 | Ethanol | Isopropyl myristate | 70:30 | Eucalyptus oil | 3.5% 1,8-cineole | | Yes | 4 | 3 | 0.206 | 0.618 |
| Ketoprofen | 20% | KET2254 | KET148 | Ethanol | Isopropyl myristate | 70:30 | Eucalyptus oil | 3.5% 1,8-cineole | | Yes | 6 | 3 | 2.409 | 7.227 |
| Ketoprofen | 20% | KET2255 | KET148 | Ethanol | Isopropyl myristate | 70:30 | Eucalyptus oil | 3.5% 1,8-cineole | | Yes | 8 | 3 | 5.535 | 16.605 |

TABLE 13-continued

NSAID and vehicle screening data

| NSAID | Drug conc | Sample # | Vehicle ID | Alcohol solvent Solvent | Solvent conc | Co-solvent conc | Co-solvent | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 20% | KET2256 | KET149 | Ethanol | Propylene glycol | 30:70 | Eucalyptus oil | 7.0% 1,8-cineole | | No | 0.5 | 1 | 0.021 | 0.063 |
| Ketoprofen | 20% | KET2257 | KET149 | Ethanol | Propylene glycol | 30:70 | Eucalyptus oil | 7.0% 1,8-cineole | | No | 2 | 1 | 2.229 | 6.687 |
| Ketoprofen | 20% | KET2258 | KET149 | Ethanol | Propylene glycol | 30:70 | Eucalyptus oil | 7.0% 1,8-cineole | | No | 4 | 1 | 9.642 | 28.926 |
| Ketoprofen | 20% | KET2259 | KET149 | Ethanol | Propylene glycol | 30:70 | Eucalyptus oil | 7.0% 1,8-cineole | | No | 6 | 1 | 7.797 | 23.391 |
| Ketoprofen | 20% | KET2260 | KET149 | Ethanol | Propylene glycol | 30:70 | Eucalyptus oil | 7.0% 1,8-cineole | | No | 8 | 1 | 25.76 | 77.28 |
| Ketoprofen | 20% | KET2261 | KET149 | Ethanol | Propylene glycol | 30:70 | Eucalyptus oil | 7.0% 1,8-cineole | | No | 0.5 | 2 | 0.008 | 0.024 |
| Ketoprofen | 20% | KET2262 | KET149 | Ethanol | Propylene glycol | 30:70 | Eucalyptus oil | 7.0% 1,8-cineole | | No | 2 | 2 | 0.093 | 0.279 |
| Ketoprofen | 20% | KET2263 | KET149 | Ethanol | Propylene glycol | 30:70 | Eucalyptus oil | 7.0% 1,8-cineole | | No | 4 | 2 | 1.287 | 3.861 |
| Ketoprofen | 20% | KET2264 | KET149 | Ethanol | Propylene glycol | 30:70 | Eucalyptus oil | 7.0% 1,8-cineole | | No | 6 | 2 | 1.223 | 3.669 |
| Ketoprofen | 20% | KET2265 | KET149 | Ethanol | Propylene glycol | 30:70 | Eucalyptus oil | 7.0% 1,8-cineole | | No | 8 | 2 | 7.323 | 21.969 |
| Ketoprofen | 20% | KET2266 | KET149 | Ethanol | Propylene glycol | 30:70 | Eucalyptus oil | 7.0% 1,8-cineole | | No | 0.5 | 3 | 0.017 | 0.051 |
| Ketoprofen | 20% | KET2267 | KET149 | Ethanol | Propylene glycol | 30:70 | Eucalyptus oil | 7.0% 1,8-cineole | | No | 2 | 3 | 0.061 | 0.183 |
| Ketoprofen | 20% | KET2268 | KET149 | Ethanol | Propylene glycol | 30:70 | Eucalyptus oil | 7.0% 1,8-cineole | | No | 4 | 3 | 0.12 | 0.36 |
| Ketoprofen | 20% | KET2269 | KET149 | Ethanol | Propylene glycol | 30:70 | Eucalyptus oil | 7.0% 1,8-cineole | | No | 6 | 3 | 0.133 | 0.399 |
| Ketoprofen | 20% | KET2270 | KET149 | Ethanol | Propylene glycol | 30:70 | Eucalyptus oil | 7.0% 1,8-cineole | | No | 8 | 3 | 0.965 | 2.895 |
| Ketoprofen | 20% | KET2271 | KET150 | Ethanol | Isopropyl myristate | 30:70 | Eucalyptus oil | 7.0% 1,8-cineole | | No | 0.5 | 1 | 0.041 | 0.123 |
| Ketoprofen | 20% | KET2272 | KET150 | Ethanol | Isopropyl myristate | 30:70 | Eucalyptus oil | 7.0% 1,8-cineole | | No | 2 | 1 | 0.097 | 0.291 |
| Ketoprofen | 20% | KET2273 | KET150 | Ethanol | Isopropyl myristate | 30:70 | Eucalyptus oil | 7.0% 1,8-cineole | | No | 4 | 1 | 8.058 | 24.174 |
| Ketoprofen | 20% | KET2274 | KET150 | Ethanol | Isopropyl myristate | 30:70 | Eucalyptus oil | 7.0% 1,8-cineole | | No | 6 | 1 | 0.482 | 1.446 |
| Ketoprofen | 20% | KET2275 | KET150 | Ethanol | Isopropyl myristate | 30:70 | Eucalyptus oil | 7.0% 1,8-cineole | | No | 8 | 1 | 1.472 | 4.416 |
| Ketoprofen | 20% | KET2276 | KET150 | Ethanol | Isopropyl myristate | 30:70 | Eucalyptus oil | 7.0% 1,8-cineole | | No | 0.5 | 2 | 0.033 | 0.099 |
| Ketoprofen | 20% | KET2277 | KET150 | Ethanol | Isopropyl myristate | 30:70 | Eucalyptus oil | 7.0% 1,8-cineole | | No | 2 | 2 | 0.083 | 0.249 |
| Ketoprofen | 20% | KET2278 | KET150 | Ethanol | Isopropyl myristate | 30:70 | Eucalyptus oil | 7.0% 1,8-cineole | | No | 4 | 2 | 8.576 | 25.728 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 20% | KET2279 | KET150 | Ethanol | Isopropyl myristate | 30:70 | Eucalyptus oil | 7.0% 1,8-cineole | | No | 6 | 2 | 1.173 | 3.519 |
| Ketoprofen | 20% | KET2280 | KET150 | Ethanol | Isopropyl myristate | 30:70 | Eucalyptus oil | 7.0% 1,8-cineole | | No | 8 | 2 | 2.574 | 7.722 |
| Ketoprofen | 20% | KET2281 | KET150 | Ethanol | Isopropyl myristate | 30:70 | Eucalyptus oil | 7.0% 1,8-cineole | | No | 0.5 | 3 | 0.047 | 0.141 |
| Ketoprofen | 20% | KET2282 | KET150 | Ethanol | Isopropyl myristate | 30:70 | Eucalyptus oil | 7.0% 1,8-cineole | | No | 2 | 3 | 0.066 | 0.198 |
| Ketoprofen | 20% | KET2283 | KET150 | Ethanol | Isopropyl myristate | 30:70 | Eucalyptus oil | 7.0% 1,8-cineole | | No | 4 | 3 | 0.87 | 2.61 |
| Ketoprofen | 20% | KET2284 | KET150 | Ethanol | Isopropyl myristate | 30:70 | Eucalyptus oil | 7.0% 1,8-cineole | | No | 6 | 3 | 0.25 | 0.75 |
| Ketoprofen | 20% | KET2285 | KET150 | Ethanol | Isopropyl myristate | 30:70 | Eucalyptus oil | 7.0% 1,8-cineole | | No | 8 | 3 | 1.015 | 3.045 |
| Ketoprofen | 20% | KET2286 | KET151 | Ethanol | Propylene glycol | 30:70 | Eucalyptus oil | 7.0% 1,8-cineole | | Yes | 0.5 | 1 | 0.01 | 0.03 |
| Ketoprofen | 20% | KET2287 | KET151 | Ethanol | Propylene glycol | 30:70 | Eucalyptus oil | 7.0% 1,8-cineole | | Yes | 2 | 1 | 0.023 | 0.069 |
| Ketoprofen | 20% | KET2288 | KET151 | Ethanol | Propylene glycol | 30:70 | Eucalyptus oil | 7.0% 1,8-cineole | | Yes | 4 | 1 | 0.087 | 0.261 |
| Ketoprofen | 20% | KET2289 | KET151 | Ethanol | Propylene glycol | 30:70 | Eucalyptus oil | 7.0% 1,8-cineole | | Yes | 6 | 1 | 0.046 | 0.138 |
| Ketoprofen | 20% | KET2290 | KET151 | Ethanol | Propylene glycol | 30:70 | Eucalyptus oil | 7.0% 1,8-cineole | | Yes | 8 | 1 | 0.388 | 1.164 |
| Ketoprofen | 20% | KET2291 | KET151 | Ethanol | Propylene glycol | 30:70 | Eucalyptus oil | 7.0% 1,8-cineole | | Yes | 0.5 | 2 | 0.009 | 0.027 |
| Ketoprofen | 20% | KET2292 | KET151 | Ethanol | Propylene glycol | 30:70 | Eucalyptus oil | 7.0% 1,8-cineole | | Yes | 2 | 2 | 0.014 | 0.042 |
| Ketoprofen | 20% | KET2293 | KET151 | Ethanol | Propylene glycol | 30:70 | Eucalyptus oil | 7.0% 1,8-cineole | | Yes | 4 | 2 | 0.046 | 0.138 |
| Ketoprofen | 20% | KET2294 | KET151 | Ethanol | Propylene glycol | 30:70 | Eucalyptus oil | 7.0% 1,8-cineole | | Yes | 6 | 2 | 0.027 | 0.081 |
| Ketoprofen | 20% | KET2295 | KET151 | Ethanol | Propylene glycol | 30:70 | Eucalyptus oil | 7.0% 1,8-cineole | | Yes | 8 | 2 | 0.1 | 0.3 |
| Ketoprofen | 20% | KET2296 | KET151 | Ethanol | Propylene glycol | 30:70 | Eucalyptus oil | 7.0% 1,8-cineole | | Yes | 0.5 | 3 | 0.073 | 0.219 |
| Ketoprofen | 20% | KET2297 | KET151 | Ethanol | Propylene glycol | 30:70 | Eucalyptus oil | 7.0% 1,8-cineole | | Yes | 2 | 3 | 0.074 | 0.222 |
| Ketoprofen | 20% | KET2298 | KET151 | Ethanol | Propylene glycol | 30:70 | Eucalyptus oil | 7.0% 1,8-cineole | | Yes | 4 | 3 | 0.294 | 0.882 |
| Ketoprofen | 20% | KET2299 | KET151 | Ethanol | Propylene glycol | 30:70 | Eucalyptus oil | 7.0% 1,8-cineole | | Yes | 6 | 3 | 0.172 | 0.516 |
| Ketoprofen | 20% | KET2300 | KET151 | Ethanol | Propylene glycol | 30:70 | Eucalyptus oil | 7.0% 1,8-cineole | | Yes | 8 | 3 | 1.418 | 4.254 |
| Ketoprofen | 30% | KET2301 | KET152 | Ethanol | Isopropyl myristate | 70:30 | Eucalyptus oil | 3.5% 1,8-cineole | | No | 0.5 | 1 | 0.038 | 0.114 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 30% | KET2302 | KET152 | Ethanol | Isopropyl myristate | 70:30 | Eucalyptus oil | 3.5% 1,8-cineole | | No | 2 | 1 | 0.04 | 0.12 |
| Ketoprofen | 30% | KET2303 | KET152 | Ethanol | Isopropyl myristate | 70:30 | Eucalyptus oil | 3.5% 1,8-cineole | | No | 4 | 1 | 0.09 | 0.27 |
| Ketoprofen | 30% | KET2304 | KET152 | Ethanol | Isopropyl myristate | 70:30 | Eucalyptus oil | 3.5% 1,8-cineole | | No | 6 | 1 | 0.381 | 1.143 |
| Ketoprofen | 30% | KET2305 | KET152 | Ethanol | Isopropyl myristate | 70:30 | Eucalyptus oil | 3.5% 1,8-cineole | | No | 8 | 1 | 1.379 | 4.137 |
| Ketoprofen | 30% | KET2306 | KET152 | Ethanol | Isopropyl myristate | 70:30 | Eucalyptus oil | 3.5% 1,8-cineole | | No | 0.5 | 2 | 0.032 | 0.096 |
| Ketoprofen | 30% | KET2307 | KET152 | Ethanol | Isopropyl myristate | 70:30 | Eucalyptus oil | 3.5% 1,8-cineole | | No | 2 | 2 | 0.05 | 0.15 |
| Ketoprofen | 30% | KET2308 | KET152 | Ethanol | Isopropyl myristate | 70:30 | Eucalyptus oil | 3.5% 1,8-cineole | | No | 4 | 2 | 0.055 | 0.165 |
| Ketoprofen | 30% | KET2309 | KET152 | Ethanol | Isopropyl myristate | 70:30 | Eucalyptus oil | 3.5% 1,8-cineole | | No | 6 | 2 | 0.193 | 0.579 |
| Ketoprofen | 30% | KET2310 | KET152 | Ethanol | Isopropyl myristate | 70:30 | Eucalyptus oil | 3.5% 1,8-cineole | | No | 8 | 2 | 1.023 | 3.069 |
| Ketoprofen | 30% | KET2311 | KET152 | Ethanol | Isopropyl myristate | 70:30 | Eucalyptus oil | 3.5% 1,8-cineole | | No | 0.5 | 3 | 0.051 | 0.153 |
| Ketoprofen | 30% | KET2312 | KET152 | Ethanol | Isopropyl myristate | 70:30 | Eucalyptus oil | 3.5% 1,8-cineole | | No | 2 | 3 | 0.072 | 0.216 |
| Ketoprofen | 30% | KET2313 | KET152 | Ethanol | Isopropyl myristate | 70:30 | Eucalyptus oil | 3.5% 1,8-cineole | | No | 4 | 3 | 0.18 | 0.54 |
| Ketoprofen | 30% | KET2314 | KET152 | Ethanol | Isopropyl myristate | 70:30 | Eucalyptus oil | 3.5% 1,8-cineole | | No | 6 | 3 | 1.263 | 3.789 |
| Ketoprofen | 30% | KET2315 | KET152 | Ethanol | Isopropyl myristate | 70:30 | Eucalyptus oil | 3.5% 1,8-cineole | | No | 8 | 3 | 4.731 | 14.193 |
| Ketoprofen | 30% | KET2316 | KET153 | Ethanol | Isopropyl myristate | 70:30 | Eucalyptus oil | 3.5% 1,8-cineole | | Yes | 0.5 | 1 | 0.093 | 0.279 |
| Ketoprofen | 30% | KET2317 | KET153 | Ethanol | Isopropyl myristate | 70:30 | Eucalyptus oil | 3.5% 1,8-cineole | | Yes | 2 | 1 | 1.385 | 4.155 |
| Ketoprofen | 30% | KET2318 | KET153 | Ethanol | Isopropyl myristate | 70:30 | Eucalyptus oil | 3.5% 1,8-cineole | | Yes | 4 | 1 | 7.738 | 23.214 |
| Ketoprofen | 30% | KET2319 | KET153 | Ethanol | Isopropyl myristate | 70:30 | Eucalyptus oil | 3.5% 1,8-cineole | | Yes | 6 | 1 | 18.018 | 54.054 |
| Ketoprofen | 30% | KET2320 | KET153 | Ethanol | Isopropyl myristate | 70:30 | Eucalyptus oil | 3.5% 1,8-cineole | | Yes | 8 | 1 | 24.483 | 73.449 |
| Ketoprofen | 30% | KET2321 | KET153 | Ethanol | Isopropyl myristate | 70:30 | Eucalyptus oil | 3.5% 1,8-cineole | | Yes | 0.5 | 2 | 0.712 | 2.136 |
| Ketoprofen | 30% | KET2322 | KET153 | Ethanol | Isopropyl myristate | 70:30 | Eucalyptus oil | 3.5% 1,8-cineole | | Yes | 2 | 2 | 8.676 | 26.028 |
| Ketoprofen | 30% | KET2323 | KET153 | Ethanol | Isopropyl myristate | 70:30 | Eucalyptus oil | 3.5% 1,8-cineole | | Yes | 4 | 2 | 17.707 | 53.121 |
| Ketoprofen | 30% | KET2324 | KET153 | Ethanol | Isopropyl myristate | 70:30 | Eucalyptus oil | 3.5% 1,8-cineole | | Yes | 6 | 2 | 28.258 | 84.774 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 30% | KET2325 | KET153 | Ethanol | Isopropyl myristate | 70:30 | Eucalyptus oil | 3.5% 1,8-cineole | | Yes | 8 | 2 | 32.167 | 96.501 |
| Ketoprofen | 30% | KET2326 | KET153 | Ethanol | Isopropyl myristate | 70:30 | Eucalyptus oil | 3.5% 1,8-cineole | | Yes | 0.5 | 3 | 0.083 | 0.249 |
| Ketoprofen | 30% | KET2327 | KET153 | Ethanol | Isopropyl myristate | 70:30 | Eucalyptus oil | 3.5% 1,8-cineole | | Yes | 2 | 3 | 0.632 | 1.896 |
| Ketoprofen | 30% | KET2328 | KET153 | Ethanol | Isopropyl myristate | 70:30 | Eucalyptus oil | 3.5% 1,8-cineole | | Yes | 4 | 3 | 4.565 | 13.695 |
| Ketoprofen | 30% | KET2329 | KET153 | Ethanol | Isopropyl myristate | 70:30 | Eucalyptus oil | 3.5% 1,8-cineole | | Yes | 6 | 3 | 11.565 | 34.695 |
| Ketoprofen | 30% | KET2330 | KET153 | Ethanol | Isopropyl myristate | 70:30 | Eucalyptus oil | 3.5% 1,8-cineole | | Yes | 8 | 3 | 20.652 | 61.956 |
| Ketoprofen | 30% | KET2331 | KET154 | Ethanol | Propylene glycol | 30:70 | Eucalyptus oil | 7.0% 1,8-cineole | | No | 0.5 | 1 | 0.021 | 0.063 |
| Ketoprofen | 30% | KET2332 | KET154 | Ethanol | Propylene glycol | 30:70 | Eucalyptus oil | 7.0% 1,8-cineole | | No | 2 | 1 | 0.03 | 0.09 |
| Ketoprofen | 30% | KET2333 | KET154 | Ethanol | Propylene glycol | 30:70 | Eucalyptus oil | 7.0% 1,8-cineole | | No | 4 | 1 | 0.036 | 0.108 |
| Ketoprofen | 30% | KET2334 | KET154 | Ethanol | Propylene glycol | 30:70 | Eucalyptus oil | 7.0% 1,8-cineole | | No | 6 | 1 | 0.026 | 0.078 |
| Ketoprofen | 30% | KET2335 | KET154 | Ethanol | Propylene glycol | 30:70 | Eucalyptus oil | 7.0% 1,8-cineole | | No | 8 | 1 | 1.066 | 3.198 |
| Ketoprofen | 30% | KET2336 | KET154 | Ethanol | Propylene glycol | 30:70 | Eucalyptus oil | 7.0% 1,8-cineole | | No | 0.5 | 2 | 0.01 | 0.03 |
| Ketoprofen | 30% | KET2337 | KET154 | Ethanol | Propylene glycol | 30:70 | Eucalyptus oil | 7.0% 1,8-cineole | | No | 2 | 2 | 0.008 | 0.024 |
| Ketoprofen | 30% | KET2338 | KET154 | Ethanol | Propylene glycol | 30:70 | Eucalyptus oil | 7.0% 1,8-cineole | | No | 4 | 2 | 0.059 | 0.177 |
| Ketoprofen | 30% | KET2339 | KET154 | Ethanol | Propylene glycol | 30:70 | Eucalyptus oil | 7.0% 1,8-cineole | | No | 6 | 2 | 0.13 | 0.39 |
| Ketoprofen | 30% | KET2340 | KET154 | Ethanol | Propylene glycol | 30:70 | Eucalyptus oil | 7.0% 1,8-cineole | | No | 8 | 2 | 1.574 | 4.722 |
| Ketoprofen | 30% | KET2341 | KET154 | Ethanol | Propylene glycol | 30:70 | Eucalyptus oil | 7.0% 1,8-cineole | | No | 0.5 | 3 | 0.01 | 0.03 |
| Ketoprofen | 30% | KET2342 | KET154 | Ethanol | Propylene glycol | 30:70 | Eucalyptus oil | 7.0% 1,8-cineole | | No | 2 | 3 | 0.017 | 0.051 |
| Ketoprofen | 30% | KET2343 | KET154 | Ethanol | Propylene glycol | 30:70 | Eucalyptus oil | 7.0% 1,8-cineole | | No | 4 | 3 | 0.337 | 1.011 |
| Ketoprofen | 30% | KET2344 | KET154 | Ethanol | Propylene glycol | 30:70 | Eucalyptus oil | 7.0% 1,8-cineole | | No | 6 | 3 | 0.553 | 1.659 |
| Ketoprofen | 30% | KET2345 | KET154 | Ethanol | Propylene glycol | 30:70 | Eucalyptus oil | 7.0% 1,8-cineole | | No | 8 | 3 | 2.203 | 6.609 |
| Ketoprofen | 30% | KET2346 | KET155 | Ethanol | Isopropyl myristate | 30:70 | Eucalyptus oil | 7.0% 1,8-cineole | | No | 0.5 | 1 | 0.193 | 0.579 |
| Ketoprofen | 30% | KET2347 | KET155 | Ethanol | Isopropyl myristate | 30:70 | Eucalyptus oil | 7.0% 1,8-cineole | | No | 2 | 1 | 5.319 | 15.957 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 30% | KET2348 | KET155 | Ethanol | Isopropyl myristate | 30:70 | Eucalyptus oil | 7.0% 1,8-cineole | | No | 4 | 1 | 15.556 | 46.668 |
| Ketoprofen | 30% | KET2349 | KET155 | Ethanol | Isopropyl myristate | 30:70 | Eucalyptus oil | 7.0% 1,8-cineole | | No | 6 | 1 | 29.995 | 89.985 |
| Ketoprofen | 30% | KET2350 | KET155 | Ethanol | Isopropyl myristate | 30:70 | Eucalyptus oil | 7.0% 1,8-cineole | | No | 8 | 1 | 37.981 | 113.943 |
| Ketoprofen | 30% | KET2351 | KET155 | Ethanol | Isopropyl myristate | 30:70 | Eucalyptus oil | 7.0% 1,8-cineole | | No | 0.5 | 2 | 0.069 | 0.207 |
| Ketoprofen | 30% | KET2352 | KET155 | Ethanol | Isopropyl myristate | 30:70 | Eucalyptus oil | 7.0% 1,8-cineole | | No | 2 | 2 | 0.563 | 1.689 |
| Ketoprofen | 30% | KET2353 | KET155 | Ethanol | Isopropyl myristate | 30:70 | Eucalyptus oil | 7.0% 1,8-cineole | | No | 4 | 2 | 2.736 | 8.208 |
| Ketoprofen | 30% | KET2354 | KET155 | Ethanol | Isopropyl myristate | 30:70 | Eucalyptus oil | 7.0% 1,8-cineole | | No | 6 | 2 | 9.287 | 27.861 |
| Ketoprofen | 30% | KET2355 | KET155 | Ethanol | Isopropyl myristate | 30:70 | Eucalyptus oil | 7.0% 1,8-cineole | | No | 8 | 2 | 16.473 | 49.419 |
| Ketoprofen | 30% | KET2356 | KET155 | Ethanol | Isopropyl myristate | 30:70 | Eucalyptus oil | 7.0% 1,8-cineole | | No | 0.5 | 3 | 0.121 | 0.363 |
| Ketoprofen | 30% | KET2357 | KET155 | Ethanol | Isopropyl myristate | 30:70 | Eucalyptus oil | 7.0% 1,8-cineole | | No | 2 | 3 | 0.262 | 0.786 |
| Ketoprofen | 30% | KET2358 | KET155 | Ethanol | Isopropyl myristate | 30:70 | Eucalyptus oil | 7.0% 1,8-cineole | | No | 4 | 3 | 1.626 | 4.878 |
| Ketoprofen | 30% | KET2359 | KET155 | Ethanol | Isopropyl myristate | 30:70 | Eucalyptus oil | 7.0% 1,8-cineole | | No | 6 | 3 | 6.184 | 18.552 |
| Ketoprofen | 30% | KET2360 | KET155 | Ethanol | Isopropyl myristate | 30:70 | Eucalyptus oil | 7.0% 1,8-cineole | | No | 8 | 3 | 13.16 | 39.48 |
| Ketoprofen | 30% | KET2361 | KET156 | Ethanol | Propylene glycol | 30:70 | Eucalyptus oil | 7.0% 1,8-cineole | | Yes | 0.5 | 1 | 0.01 | 0.03 |
| Ketoprofen | 30% | KET2362 | KET156 | Ethanol | Propylene glycol | 30:70 | Eucalyptus oil | 7.0% 1,8-cineole | | Yes | 2 | 1 | 0.012 | 0.036 |
| Ketoprofen | 30% | KET2363 | KET156 | Ethanol | Propylene glycol | 30:70 | Eucalyptus oil | 7.0% 1,8-cineole | | Yes | 4 | 1 | 0.126 | 0.378 |
| Ketoprofen | 30% | KET2364 | KET156 | Ethanol | Propylene glycol | 30:70 | Eucalyptus oil | 7.0% 1,8-cineole | | Yes | 6 | 1 | 0.178 | 0.534 |
| Ketoprofen | 30% | KET2365 | KET156 | Ethanol | Propylene glycol | 30:70 | Eucalyptus oil | 7.0% 1,8-cineole | | Yes | 8 | 1 | 0.562 | 1.686 |
| Ketoprofen | 30% | KET2366 | KET156 | Ethanol | Propylene glycol | 30:70 | Eucalyptus oil | 7.0% 1,8-cineole | | Yes | 0.5 | 2 | 0.02 | 0.06 |
| Ketoprofen | 30% | KET2367 | KET156 | Ethanol | Propylene glycol | 30:70 | Eucalyptus oil | 7.0% 1,8-cineole | | Yes | 2 | 2 | 0.014 | 0.042 |
| Ketoprofen | 30% | KET2368 | KET156 | Ethanol | Propylene glycol | 30:70 | Eucalyptus oil | 7.0% 1,8-cineole | | Yes | 4 | 2 | 0.057 | 0.171 |
| Ketoprofen | 30% | KET2369 | KET156 | Ethanol | Propylene glycol | 30:70 | Eucalyptus oil | 7.0% 1,8-cineole | | Yes | 6 | 2 | 0.213 | 0.639 |
| Ketoprofen | 30% | KET2370 | KET156 | Ethanol | Propylene glycol | 30:70 | Eucalyptus oil | 7.0% 1,8-cineole | | Yes | 8 | 2 | 0.766 | 2.298 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 30% | KET2371 | KET156 | Ethanol | Propylene glycol | 30:70 | Eucalyptus oil | 7.0% 1,8-cineole | | Yes | 0.5 | 3 | 0.01 | 0.03 |
| Ketoprofen | 30% | KET2372 | KET156 | Ethanol | Propylene glycol | 30:70 | Eucalyptus oil | 7.0% 1,8-cineole | | Yes | 2 | 3 | 0.01 | 0.03 |
| Ketoprofen | 30% | KET2373 | KET156 | Ethanol | Propylene glycol | 30:70 | Eucalyptus oil | 7.0% 1,8-cineole | | Yes | 4 | 3 | 0.029 | 0.087 |
| Ketoprofen | 30% | KET2374 | KET156 | Ethanol | Propylene glycol | 30:70 | Eucalyptus oil | 7.0% 1,8-cineole | | Yes | 6 | 3 | 0.046 | 0.138 |
| Ketoprofen | 30% | KET2375 | KET156 | Ethanol | Propylene glycol | 30:70 | Eucalyptus oil | 7.0% 1,8-cineole | | Yes | 8 | 3 | 0.653 | 1.959 |
| Ketoprofen | 10% | KET2376 | KET157 | Ethanol | Isopropyl myristate | 30:70 | Eucalyptus oil | 7.0% 1,8-cineole | | Yes | 0.5 | 1 | 0.062 | 0.186 |
| Ketoprofen | 10% | KET2377 | KET157 | Ethanol | Isopropyl myristate | 30:70 | Eucalyptus oil | 7.0% 1,8-cineole | | Yes | 2 | 1 | 0.105 | 0.315 |
| Ketoprofen | 10% | KET2378 | KET157 | Ethanol | Isopropyl myristate | 30:70 | Eucalyptus oil | 7.0% 1,8-cineole | | Yes | 4 | 1 | 1.085 | 3.255 |
| Ketoprofen | 10% | KET2379 | KET157 | Ethanol | Isopropyl myristate | 30:70 | Eucalyptus oil | 7.0% 1,8-cineole | | Yes | 6 | 1 | 0.199 | 0.597 |
| Ketoprofen | 10% | KET2380 | KET157 | Ethanol | Isopropyl myristate | 30:70 | Eucalyptus oil | 7.0% 1,8-cineole | | Yes | 8 | 1 | 0.378 | 1.134 |
| Ketoprofen | 10% | KET2381 | KET157 | Ethanol | Isopropyl myristate | 30:70 | Eucalyptus oil | 7.0% 1,8-cineole | | Yes | 0.5 | 2 | 0.079 | 0.237 |
| Ketoprofen | 10% | KET2382 | KET157 | Ethanol | Isopropyl myristate | 30:70 | Eucalyptus oil | 7.0% 1,8-cineole | | Yes | 2 | 2 | 0.572 | 1.716 |
| Ketoprofen | 10% | KET2383 | KET157 | Ethanol | Isopropyl myristate | 30:70 | Eucalyptus oil | 7.0% 1,8-cineole | | Yes | 4 | 2 | 0.521 | 1.563 |
| Ketoprofen | 10% | KET2384 | KET157 | Ethanol | Isopropyl myristate | 30:70 | Eucalyptus oil | 7.0% 1,8-cineole | | Yes | 6 | 2 | 3.888 | 11.664 |
| Ketoprofen | 10% | KET2385 | KET157 | Ethanol | Isopropyl myristate | 30:70 | Eucalyptus oil | 7.0% 1,8-cineole | | Yes | 8 | 2 | 4.691 | 14.073 |
| Ketoprofen | 10% | KET2386 | KET157 | Ethanol | Isopropyl myristate | 30:70 | Eucalyptus oil | 7.0% 1,8-cineole | | Yes | 0.5 | 3 | 0.062 | 0.186 |
| Ketoprofen | 10% | KET2387 | KET157 | Ethanol | Isopropyl myristate | 30:70 | Eucalyptus oil | 7.0% 1,8-cineole | | Yes | 2 | 3 | 0.539 | 1.617 |
| Ketoprofen | 10% | KET2388 | KET157 | Ethanol | Isopropyl myristate | 30:70 | Eucalyptus oil | 7.0% 1,8-cineole | | Yes | 4 | 3 | 0.085 | 0.255 |
| Ketoprofen | 10% | KET2389 | KET157 | Ethanol | Isopropyl myristate | 30:70 | Eucalyptus oil | 7.0% 1,8-cineole | | Yes | 6 | 3 | 3.897 | 11.691 |
| Ketoprofen | 10% | KET2390 | KET157 | Ethanol | Isopropyl myristate | 30:70 | Eucalyptus oil | 7.0% 1,8-cineole | | Yes | 8 | 3 | 5.128 | 15.384 |
| Ketoprofen | 10% | KET2391 | KET158 | Ethanol | Propylene glycol | 50:50 | Eucalyptus oil | 7.0% 1,8-cineole | | No | 0.5 | 1 | 0.008 | 0.024 |
| Ketoprofen | 10% | KET2392 | KET158 | Ethanol | Propylene glycol | 50:50 | Eucalyptus oil | 7.0% 1,8-cineole | | No | 2 | 1 | 0.019 | 0.057 |
| Ketoprofen | 10% | KET2393 | KET158 | Ethanol | Propylene glycol | 50:50 | Eucalyptus oil | 7.0% 1,8-cineole | | No | 4 | 1 | 0.057 | 0.171 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/EVAP | sample time (hrs) | Replicate | analysis conc | Concentration (μg/mL) |
|---|---|---|---|---|---|---|---|---|---|---|---|---|---|---|
| Ketoprofen | 10% | KET2394 | KET158 | Ethanol | Propylene glycol | 50:50 | Eucalyptus oil | 7.0% 1,8-cineole | | No | 6 | 1 | 0.02 | 0.06 |
| Ketoprofen | 10% | KET2395 | KET158 | Ethanol | Propylene glycol | 50:50 | Eucalyptus oil | 7.0% 1,8-cineole | | No | 8 | 1 | 0.09 | 0.27 |
| Ketoprofen | 10% | KET2396 | KET158 | Ethanol | Propylene glycol | 50:50 | Eucalyptus oil | 7.0% 1,8-cineole | | No | 0.5 | 2 | 0.012 | 0.036 |
| Ketoprofen | 10% | KET2397 | KET158 | Ethanol | Propylene glycol | 50:50 | Eucalyptus oil | 7.0% 1,8-cineole | | No | 2 | 2 | 0.012 | 0.036 |
| Ketoprofen | 10% | KET2398 | KET158 | Ethanol | Propylene glycol | 50:50 | Eucalyptus oil | 7.0% 1,8-cineole | | No | 4 | 2 | 0.211 | 0.633 |
| Ketoprofen | 10% | KET2399 | KET158 | Ethanol | Propylene glycol | 50:50 | Eucalyptus oil | 7.0% 1,8-cineole | | No | 6 | 2 | 0.604 | 1.812 |
| Ketoprofen | 10% | KET2400 | KET158 | Ethanol | Propylene glycol | 50:50 | Eucalyptus oil | 7.0% 1,8-cineole | | No | 8 | 2 | 1.757 | 5.271 |
| Ketoprofen | 10% | KET2401 | KET158 | Ethanol | Propylene glycol | 50:50 | Eucalyptus oil | 7.0% 1,8-cineole | | No | 0.5 | 3 | 0.014 | 0.042 |
| Ketoprofen | 10% | KET2402 | KET158 | Ethanol | Propylene glycol | 50:50 | Eucalyptus oil | 7.0% 1,8-cineole | | No | 2 | 3 | 0.203 | 0.609 |
| Ketoprofen | 10% | KET2403 | KET158 | Ethanol | Propylene glycol | 50:50 | Eucalyptus oil | 7.0% 1,8-cineole | | No | 4 | 3 | 4.025 | 12.075 |
| Ketoprofen | 10% | KET2404 | KET158 | Ethanol | Propylene glycol | 50:50 | Eucalyptus oil | 7.0% 1,8-cineole | | No | 6 | 3 | 4.648 | 13.944 |
| Ketoprofen | 10% | KET2405 | KET158 | Ethanol | Propylene glycol | 50:50 | Eucalyptus oil | 7.0% 1,8-cineole | | No | 8 | 3 | 19.304 | 57.912 |
| Ketoprofen | 10% | KET2406 | KET158 | Ethanol | Propylene glycol | 50:50 | Eucalyptus oil | 7.0% 1,8-cineole | | No | 0.5 | 1 | 0.07 | 0.21 |
| Ketoprofen | 10% | KET2407 | KET159 | Ethanol | Isopropyl myristate | 50:50 | Eucalyptus oil | 7.0% 1,8-cineole | | No | 2 | 1 | 0.42 | 1.26 |
| Ketoprofen | 10% | KET2408 | KET159 | Ethanol | Isopropyl myristate | 50:50 | Eucalyptus oil | 7.0% 1,8-cineole | | No | 4 | 1 | 0.189 | 0.567 |
| Ketoprofen | 10% | KET2409 | KET159 | Ethanol | Isopropyl myristate | 50:50 | Eucalyptus oil | 7.0% 1,8-cineole | | No | 6 | 1 | 2.76 | 8.28 |
| Ketoprofen | 10% | KET2410 | KET159 | Ethanol | Isopropyl myristate | 50:50 | Eucalyptus oil | 7.0% 1,8-cineole | | No | 8 | 1 | 3.769 | 11.307 |
| Ketoprofen | 10% | KET2411 | KET159 | Ethanol | Isopropyl myristate | 50:50 | Eucalyptus oil | 7.0% 1,8-cineole | | No | 0.5 | 2 | 0.06 | 0.18 |
| Ketoprofen | 10% | KET2412 | KET159 | Ethanol | Isopropyl myristate | 50:50 | Eucalyptus oil | 7.0% 1,8-cineole | | No | 2 | 2 | 0.484 | 1.452 |
| Ketoprofen | 10% | KET2413 | KET159 | Ethanol | Isopropyl myristate | 50:50 | Eucalyptus oil | 7.0% 1,8-cineole | | No | 4 | 2 | 7.984 | 23.952 |
| Ketoprofen | 10% | KET2414 | KET159 | Ethanol | Isopropyl myristate | 50:50 | Eucalyptus oil | 7.0% 1,8-cineole | | No | 6 | 2 | 3.159 | 9.477 |
| Ketoprofen | 10% | KET2415 | KET159 | Ethanol | Isopropyl myristate | 50:50 | Eucalyptus oil | 7.0% 1,8-cineole | | No | 8 | 2 | 4.48 | 13.44 |
| Ketoprofen | 10% | KET2416 | KET159 | Ethanol | Isopropyl myristate | 50:50 | Eucalyptus oil | 7.0% 1,8-cineole | | No | 0.5 | 3 | 0.059 | 0.177 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/EVAP | sample time (hrs) | Replicate | analysis conc | Concentration (µg/mL) |
|---|---|---|---|---|---|---|---|---|---|---|---|---|---|---|
| Ketoprofen | 10% | KET2417 | KET159 | Ethanol | Isopropyl myristate | 50:50 | Eucalyptus oil | 7.0% 1,8-cineole | | No | 2 | 3 | 0.124 | 0.372 |
| Ketoprofen | 10% | KET2418 | KET159 | Ethanol | Isopropyl myristate | 50:50 | Eucalyptus oil | 7.0% 1,8-cineole | | No | 4 | 3 | 4.989 | 14.967 |
| Ketoprofen | 10% | KET2419 | KET159 | Ethanol | Isopropyl myristate | 50:50 | Eucalyptus oil | 7.0% 1,8-cineole | | No | 6 | 3 | 0.869 | 2.607 |
| Ketoprofen | 10% | KET2420 | KET159 | Ethanol | Isopropyl myristate | 50:50 | Eucalyptus oil | 7.0% 1,8-cineole | | No | 8 | 3 | 3.86 | 11.58 |
| Ketoprofen | 10% | KET2421 | KET160 | Ethanol | Propylene glycol | 50:50 | Eucalyptus oil | 7.0% 1,8-cineole | | Yes | 0.5 | 1 | 0.015 | 0.045 |
| Ketoprofen | 10% | KET2422 | KET160 | Ethanol | Propylene glycol | 50:50 | Eucalyptus oil | 7.0% 1,8-cineole | | Yes | 2 | 1 | 0.017 | 0.051 |
| Ketoprofen | 10% | KET2423 | KET160 | Ethanol | Propylene glycol | 50:50 | Eucalyptus oil | 7.0% 1,8-cineole | | Yes | 4 | 1 | 0.297 | 0.891 |
| Ketoprofen | 10% | KET2424 | KET160 | Ethanol | Propylene glycol | 50:50 | Eucalyptus oil | 7.0% 1,8-cineole | | Yes | 6 | 1 | 0.583 | 1.749 |
| Ketoprofen | 10% | KET2425 | KET160 | Ethanol | Propylene glycol | 50:50 | Eucalyptus oil | 7.0% 1,8-cineole | | Yes | 8 | 1 | 3.951 | 11.853 |
| Ketoprofen | 10% | KET2426 | KET160 | Ethanol | Propylene glycol | 50:50 | Eucalyptus oil | 7.0% 1,8-cineole | | Yes | 0.5 | 2 | 0.011 | 0.033 |
| Ketoprofen | 10% | KET2427 | KET160 | Ethanol | Propylene glycol | 50:50 | Eucalyptus oil | 7.0% 1,8-cineole | | Yes | 2 | 2 | 0.008 | 0.024 |
| Ketoprofen | 10% | KET2428 | KET160 | Ethanol | Propylene glycol | 50:50 | Eucalyptus oil | 7.0% 1,8-cineole | | Yes | 4 | 2 | 0.012 | 0.036 |
| Ketoprofen | 10% | KET2429 | KET160 | Ethanol | Propylene glycol | 50:50 | Eucalyptus oil | 7.0% 1,8-cineole | | Yes | 6 | 2 | 0.064 | 0.192 |
| Ketoprofen | 10% | KET2430 | KET160 | Ethanol | Propylene glycol | 50:50 | Eucalyptus oil | 7.0% 1,8-cineole | | Yes | 8 | 2 | 0.484 | 1.452 |
| Ketoprofen | 10% | KET2431 | KET160 | Ethanol | Propylene glycol | 50:50 | Eucalyptus oil | 7.0% 1,8-cineole | | Yes | 0.5 | 3 | 0.012 | 0.036 |
| Ketoprofen | 10% | KET2432 | KET160 | Ethanol | Propylene glycol | 50:50 | Eucalyptus oil | 7.0% 1,8-cineole | | Yes | 2 | 3 | 0.012 | 0.036 |
| Ketoprofen | 10% | KET2433 | KET160 | Ethanol | Propylene glycol | 50:50 | Eucalyptus oil | 7.0% 1,8-cineole | | Yes | 4 | 3 | 0.246 | 0.738 |
| Ketoprofen | 10% | KET2434 | KET160 | Ethanol | Propylene glycol | 50:50 | Eucalyptus oil | 7.0% 1,8-cineole | | Yes | 6 | 3 | 0.271 | 0.813 |
| Ketoprofen | 10% | KET2435 | KET160 | Ethanol | Propylene glycol | 50:50 | Eucalyptus oil | 7.0% 1,8-cineole | | Yes | 8 | 3 | 2.103 | 6.309 |
| Ketoprofen | 10% | KET2436 | KET161 | Ethanol | Isopropyl myristate | 50:50 | Eucalyptus oil | 7.0% 1,8-cineole | | Yes | 0.5 | 1 | 0.094 | 0.282 |
| Ketoprofen | 10% | KET2437 | KET161 | Ethanol | Isopropyl myristate | 50:50 | Eucalyptus oil | 7.0% 1,8-cineole | | Yes | 2 | 1 | 0.767 | 2.301 |
| Ketoprofen | 10% | KET2438 | KET161 | Ethanol | Isopropyl myristate | 50:50 | Eucalyptus oil | 7.0% 1,8-cineole | | Yes | 4 | 1 | 1.838 | 5.514 |
| Ketoprofen | 10% | KET2439 | KET161 | Ethanol | Isopropyl myristate | 50:50 | Eucalyptus oil | 7.0% 1,8-cineole | | Yes | 6 | 1 | 0.652 | 1.956 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 10% | KET2440 | KET161 | Ethanol | Isopropyl myristate | Eucalyptus oil | 50:50 | 7.0% 1,8-cineole | | Yes | 8 | 1 | 1.516 | 4.548 |
| Ketoprofen | 10% | KET2441 | KET161 | Ethanol | Isopropyl myristate | Eucalyptus oil | 50:50 | 7.0% 1,8-cineole | | Yes | 0.5 | 2 | 0.051 | 0.153 |
| Ketoprofen | 10% | KET2442 | KET161 | Ethanol | Isopropyl myristate | Eucalyptus oil | 50:50 | 7.0% 1,8-cineole | | Yes | 2 | 2 | 0.242 | 0.726 |
| Ketoprofen | 10% | KET2443 | KET161 | Ethanol | Isopropyl myristate | Eucalyptus oil | 50:50 | 7.0% 1,8-cineole | | Yes | 4 | 2 | 1.415 | 4.245 |
| Ketoprofen | 10% | KET2444 | KET161 | Ethanol | Isopropyl myristate | Eucalyptus oil | 50:50 | 7.0% 1,8-cineole | | Yes | 6 | 2 | 3.33 | 9.99 |
| Ketoprofen | 10% | KET2445 | KET161 | Ethanol | Isopropyl myristate | Eucalyptus oil | 50:50 | 7.0% 1,8-cineole | | Yes | 8 | 2 | 4.133 | 12.399 |
| Ketoprofen | 10% | KET2446 | KET161 | Ethanol | Isopropyl myristate | Eucalyptus oil | 50:50 | 7.0% 1,8-cineole | | Yes | 0.5 | 3 | 0.064 | 0.192 |
| Ketoprofen | 10% | KET2447 | KET161 | Ethanol | Isopropyl myristate | Eucalyptus oil | 50:50 | 7.0% 1,8-cineole | | Yes | 2 | 3 | 0.264 | 0.792 |
| Ketoprofen | 10% | KET2448 | KET161 | Ethanol | Isopropyl myristate | Eucalyptus oil | 50:50 | 7.0% 1,8-cineole | | Yes | 4 | 3 | 5.348 | 16.044 |
| Ketoprofen | 10% | KET2449 | KET161 | Ethanol | Isopropyl myristate | Eucalyptus oil | 50:50 | 7.0% 1,8-cineole | | Yes | 6 | 3 | 4.038 | 12.114 |
| Ketoprofen | 10% | KET2450 | KET161 | Ethanol | Isopropyl myristate | Eucalyptus oil | 50:50 | 7.0% 1,8-cineole | | Yes | 8 | 3 | 1.22 | 3.66 |
| Ketoprofen | 10% | KET2451 | KET162 | Ethanol | Isopropyl myristate | Eucalyptus oil | 30:70 | 7.0% 1,8-cineole | | Yes | 0.5 | 1 | 0.117 | 0.351 |
| Ketoprofen | 20% | KET2452 | KET162 | Ethanol | Isopropyl myristate | Eucalyptus oil | 30:70 | 7.0% 1,8-cineole | | Yes | 2 | 1 | 0.106 | 0.318 |
| Ketoprofen | 20% | KET2453 | KET162 | Ethanol | Isopropyl myristate | Eucalyptus oil | 30:70 | 7.0% 1,8-cineole | | Yes | 4 | 1 | 0.204 | 0.612 |
| Ketoprofen | 20% | KET2454 | KET162 | Ethanol | Isopropyl myristate | Eucalyptus oil | 30:70 | 7.0% 1,8-cineole | | Yes | 6 | 1 | 0.852 | 2.556 |
| Ketoprofen | 20% | KET2455 | KET162 | Ethanol | Isopropyl myristate | Eucalyptus oil | 30:70 | 7.0% 1,8-cineole | | Yes | 8 | 1 | 1.787 | 5.361 |
| Ketoprofen | 20% | KET2456 | KET162 | Ethanol | Isopropyl myristate | Eucalyptus oil | 30:70 | 7.0% 1,8-cineole | | Yes | 0.5 | 2 | 0.087 | 0.261 |
| Ketoprofen | 20% | KET2457 | KET162 | Ethanol | Isopropyl myristate | Eucalyptus oil | 30:70 | 7.0% 1,8-cineole | | Yes | 2 | 2 | 1.066 | 3.198 |
| Ketoprofen | 20% | KET2458 | KET162 | Ethanol | Isopropyl myristate | Eucalyptus oil | 30:70 | 7.0% 1,8-cineole | | Yes | 4 | 2 | 6.232 | 18.696 |
| Ketoprofen | 20% | KET2459 | KET162 | Ethanol | Isopropyl myristate | Eucalyptus oil | 30:70 | 7.0% 1,8-cineole | | Yes | 6 | 2 | 15.057 | 45.171 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 20% | KET2460 | KET162 | Ethanol | Isopropyl myristate | 30:70 | Eucalyptus oil | 7.0% 1,8-cineole | | Yes | 8 | 2 | 18.571 | 55.713 |
| Ketoprofen | 20% | KET2461 | KET162 | Ethanol | Isopropyl myristate | 30:70 | Eucalyptus oil | 7.0% 1,8-cineole | | Yes | 0.5 | 3 | 0.09 | 0.27 |
| Ketoprofen | 20% | KET2462 | KET162 | Ethanol | Isopropyl myristate | 30:70 | Eucalyptus oil | 7.0% 1,8-cineole | | Yes | 2 | 3 | 0.324 | 0.972 |
| Ketoprofen | 20% | KET2463 | KET162 | Ethanol | Isopropyl myristate | 30:70 | Eucalyptus oil | 7.0% 1,8-cineole | | Yes | 4 | 3 | 2.459 | 7.377 |
| Ketoprofen | 20% | KET2464 | KET162 | Ethanol | Isopropyl myristate | 30:70 | Eucalyptus oil | 7.0% 1,8-cineole | | Yes | 6 | 3 | 7.619 | 22.857 |
| Ketoprofen | 20% | KET2465 | KET162 | Ethanol | Isopropyl myristate | 30:70 | Eucalyptus oil | 7.0% 1,8-cineole | | Yes | 8 | 3 | 10.657 | 31.971 |
| Ketoprofen | 20% | KET2466 | KET163 | Ethanol | Propylene glycol | 50:50 | Eucalyptus oil | 7.0% 1,8-cineole | | No | 0.5 | 1 | 0.01 | 0.03 |
| Ketoprofen | 20% | KET2467 | KET163 | Ethanol | Propylene glycol | 50:50 | Eucalyptus oil | 7.0% 1,8-cineole | | No | 2 | 1 | 0.154 | 0.462 |
| Ketoprofen | 20% | KET2468 | KET163 | Ethanol | Propylene glycol | 50:50 | Eucalyptus oil | 7.0% 1,8-cineole | | No | 4 | 1 | 3.099 | 9.297 |
| Ketoprofen | 20% | KET2469 | KET163 | Ethanol | Propylene glycol | 50:50 | Eucalyptus oil | 7.0% 1,8-cineole | | No | 6 | 1 | 8.957 | 26.871 |
| Ketoprofen | 20% | KET2470 | KET163 | Ethanol | Propylene glycol | 50:50 | Eucalyptus oil | 7.0% 1,8-cineole | | No | 8 | 1 | 23.383 | 70.149 |
| Ketoprofen | 20% | KET2471 | KET163 | Ethanol | Propylene glycol | 50:50 | Eucalyptus oil | 7.0% 1,8-cineole | | No | 0.5 | 2 | 0.007 | 0.021 |
| Ketoprofen | 20% | KET2472 | KET163 | Ethanol | Propylene glycol | 50:50 | Eucalyptus oil | 7.0% 1,8-cineole | | No | 2 | 2 | 0.035 | 0.105 |
| Ketoprofen | 20% | KET2473 | KET163 | Ethanol | Propylene glycol | 50:50 | Eucalyptus oil | 7.0% 1,8-cineole | | No | 4 | 2 | 2.742 | 8.226 |
| Ketoprofen | 20% | KET2474 | KET163 | Ethanol | Propylene glycol | 50:50 | Eucalyptus oil | 7.0% 1,8-cineole | | No | 6 | 2 | 3.286 | 9.858 |
| Ketoprofen | 20% | KET2475 | KET163 | Ethanol | Propylene glycol | 50:50 | Eucalyptus oil | 7.0% 1,8-cineole | | No | 8 | 2 | 15.666 | 46.998 |
| Ketoprofen | 20% | KET2476 | KET163 | Ethanol | Propylene glycol | 50:50 | Eucalyptus oil | 7.0% 1,8-cineole | | No | 0.5 | 3 | 0.007 | 0.021 |
| Ketoprofen | 20% | KET2477 | KET163 | Ethanol | Propylene glycol | 50:50 | Eucalyptus oil | 7.0% 1,8-cineole | | No | 2 | 3 | 0.01 | 0.03 |
| Ketoprofen | 20% | KET2478 | KET163 | Ethanol | Propylene glycol | 50:50 | Eucalyptus oil | 7.0% 1,8-cineole | | No | 4 | 3 | 0.183 | 0.549 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 20% | KET2479 | KET163 | Ethanol | Propylene glycol | 50:50 | Eucalyptus oil | 7.0% 1,8-cineole | | No | 6 | 3 | 0.469 | 1.407 |
| Ketoprofen | 20% | KET2480 | KET163 | Ethanol | Propylene glycol | 50:50 | Eucalyptus oil | 7.0% 1,8-cineole | | No | 8 | 3 | 1.298 | 3.894 |
| Ketoprofen | 20% | KET2481 | KET164 | Ethanol | Isopropyl myristate | 50:50 | Eucalyptus oil | 7.0% 1,8-cineole | | No | 0.5 | 1 | 0.047 | 0.141 |
| Ketoprofen | 20% | KET2482 | KET164 | Ethanol | Isopropyl myristate | 50:50 | Eucalyptus oil | 7.0% 1,8-cineole | | No | 2 | 1 | 0.234 | 0.702 |
| Ketoprofen | 20% | KET2483 | KET164 | Ethanol | Isopropyl myristate | 50:50 | Eucalyptus oil | 7.0% 1,8-cineole | | No | 4 | 1 | 1.212 | 3.636 |
| Ketoprofen | 20% | KET2484 | KET164 | Ethanol | Isopropyl myristate | 50:50 | Eucalyptus oil | 7.0% 1,8-cineole | | No | 6 | 1 | 3.845 | 11.535 |
| Ketoprofen | 20% | KET2485 | KET164 | Ethanol | Isopropyl myristate | 50:50 | Eucalyptus oil | 7.0% 1,8-cineole | | No | 8 | 1 | 6.208 | 18.624 |
| Ketoprofen | 20% | KET2486 | KET164 | Ethanol | Isopropyl myristate | 50:50 | Eucalyptus oil | 7.0% 1,8-cineole | | No | 0.5 | 2 | 0.056 | 0.168 |
| Ketoprofen | 20% | KET2487 | KET164 | Ethanol | Isopropyl myristate | 50:50 | Eucalyptus oil | 7.0% 1,8-cineole | | No | 2 | 2 | 0.228 | 0.684 |
| Ketoprofen | 20% | KET2488 | KET164 | Ethanol | Isopropyl myristate | 50:50 | Eucalyptus oil | 7.0% 1,8-cineole | | No | 4 | 2 | 3.9 | 11.7 |
| Ketoprofen | 20% | KET2489 | KET164 | Ethanol | Isopropyl myristate | 50:50 | Eucalyptus oil | 7.0% 1,8-cineole | | No | 6 | 2 | 3.446 | 10.338 |
| Ketoprofen | 20% | KET2490 | KET164 | Ethanol | Isopropyl myristate | 50:50 | Eucalyptus oil | 7.0% 1,8-cineole | | No | 8 | 2 | 6.828 | 20.484 |
| Ketoprofen | 20% | KET2491 | KET164 | Ethanol | Isopropyl myristate | 50:50 | Eucalyptus oil | 7.0% 1,8-cineole | | No | 0.5 | 3 | 0.112 | 0.336 |
| Ketoprofen | 20% | KET2492 | KET164 | Ethanol | Isopropyl myristate | 50:50 | Eucalyptus oil | 7.0% 1,8-cineole | | No | 2 | 3 | 1.762 | 5.286 |
| Ketoprofen | 20% | KET2493 | KET164 | Ethanol | Isopropyl myristate | 50:50 | Eucalyptus oil | 7.0% 1,8-cineole | | No | 4 | 3 | 1.296 | 3.888 |
| Ketoprofen | 20% | KET2494 | KET164 | Ethanol | Isopropyl myristate | 50:50 | Eucalyptus oil | 7.0% 1,8-cineole | | No | 6 | 3 | 9.296 | 27.888 |
| Ketoprofen | 20% | KET2495 | KET164 | Ethanol | Isopropyl myristate | 50:50 | Eucalyptus oil | 7.0% 1,8-cineole | | No | 8 | 3 | 16.225 | 48.675 |
| Ketoprofen | 20% | KET2496 | KET165 | Ethanol | Propylene glycol | 50:50 | Eucalyptus oil | 7.0% 1,8-cineole | | Yes | 0.5 | 1 | 0.016 | 0.048 |
| Ketoprofen | 20% | KET2497 | KET165 | Ethanol | Propylene glycol | 50:50 | Eucalyptus oil | 7.0% 1,8-cineole | | Yes | 2 | 1 | 0.015 | 0.045 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (µg/mL) |
|---|---|---|---|---|---|---|---|---|---|---|---|---|---|---|
| Ketoprofen | 20% | KET2498 | KET165 | Ethanol | Propylene glycol | Eucalyptus oil | 50:50 | 7.0% 1,8-cineole | | Yes | 4 | 1 | 0.147 | 0.441 |
| Ketoprofen | 20% | KET2499 | KET165 | Ethanol | Propylene glycol | Eucalyptus oil | 50:50 | 7.0% 1,8-cineole | | Yes | 6 | 1 | 0.45 | 1.35 |
| Ketoprofen | 20% | KET2500 | KET165 | Ethanol | Propylene glycol | Eucalyptus oil | 50:50 | 7.0% 1,8-cineole | | Yes | 8 | 1 | 2.557 | 7.671 |
| Ketoprofen | 20% | KET2501 | KET165 | Ethanol | Propylene glycol | Eucalyptus oil | 50:50 | 7.0% 1,8-cineole | | Yes | 0.5 | 2 | 0.008 | 0.024 |
| Ketoprofen | 20% | KET2502 | KET165 | Ethanol | Propylene glycol | Eucalyptus oil | 50:50 | 7.0% 1,8-cineole | | Yes | 2 | 2 | 0.014 | 0.042 |
| Ketoprofen | 20% | KET2503 | KET165 | Ethanol | Propylene glycol | Eucalyptus oil | 50:50 | 7.0% 1,8-cineole | | Yes | 4 | 2 | 0.147 | 0.441 |
| Ketoprofen | 20% | KET2504 | KET165 | Ethanol | Propylene glycol | Eucalyptus oil | 50:50 | 7.0% 1,8-cineole | | Yes | 6 | 2 | 0.185 | 0.555 |
| Ketoprofen | 20% | KET2505 | KET165 | Ethanol | Propylene glycol | Eucalyptus oil | 50:50 | 7.0% 1,8-cineole | | Yes | 8 | 2 | 0.525 | 1.575 |
| Ketoprofen | 20% | KET2506 | KET165 | Ethanol | Propylene glycol | Eucalyptus oil | 50:50 | 7.0% 1,8-cineole | | Yes | 0.5 | 3 | 0.013 | 0.039 |
| Ketoprofen | 20% | KET2507 | KET165 | Ethanol | Propylene glycol | Eucalyptus oil | 50:50 | 7.0% 1,8-cineole | | Yes | 2 | 3 | 0.007 | 0.021 |
| Ketoprofen | 20% | KET2508 | KET165 | Ethanol | Propylene glycol | Eucalyptus oil | 50:50 | 7.0% 1,8-cineole | | Yes | 4 | 3 | 0.331 | 0.993 |
| Ketoprofen | 20% | KET2509 | KET165 | Ethanol | Propylene glycol | Eucalyptus oil | 50:50 | 7.0% 1,8-cineole | | Yes | 6 | 3 | 0.573 | 1.719 |
| Ketoprofen | 20% | KET2510 | KET165 | Ethanol | Propylene glycol | Eucalyptus oil | 50:50 | 7.0% 1,8-cineole | | Yes | 8 | 3 | 1.374 | 4.122 |
| Ketoprofen | 20% | KET2511 | KET166 | Ethanol | Isopropyl myristate | Eucalyptus oil | 50:50 | 7.0% 1,8-cineole | | Yes | 0.5 | 1 | 0.085 | 0.255 |
| Ketoprofen | 20% | KET2512 | KET166 | Ethanol | Isopropyl myristate | Eucalyptus oil | 50:50 | 7.0% 1,8-cineole | | Yes | 2 | 1 | 0.986 | 2.958 |
| Ketoprofen | 20% | KET2513 | KET166 | Ethanol | Isopropyl myristate | Eucalyptus oil | 50:50 | 7.0% 1,8-cineole | | Yes | 4 | 1 | 4.006 | 12.018 |
| Ketoprofen | 20% | KET2514 | KET166 | Ethanol | Isopropyl myristate | Eucalyptus oil | 50:50 | 7.0% 1,8-cineole | | Yes | 6 | 1 | 8.567 | 25.701 |
| Ketoprofen | 20% | KET2515 | KET166 | Ethanol | Isopropyl myristate | Eucalyptus oil | 50:50 | 7.0% 1,8-cineole | | Yes | 8 | 1 | 15.529 | 46.587 |
| Ketoprofen | 20% | KET2516 | KET166 | Ethanol | Isopropyl myristate | Eucalyptus oil | 50:50 | 7.0% 1,8-cineole | | Yes | 0.5 | 2 | 0.112 | 0.336 |
| Ketoprofen | 20% | KET2517 | KET166 | Ethanol | Isopropyl myristate | Eucalyptus oil | 50:50 | 7.0% 1,8-cineole | | Yes | 2 | 2 | 2.146 | 6.438 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 20% | KET2518 | KET166 | Ethanol | Isopropyl myristate | 50:50 | Eucalyptus oil | 7.0% 1,8-cineole | | Yes | 4 | 2 | 9.022 | 27.066 |
| Ketoprofen | 20% | KET2519 | KET166 | Ethanol | Isopropyl myristate | 50:50 | Eucalyptus oil | 7.0% 1,8-cineole | | Yes | 6 | 2 | 15.756 | 47.268 |
| Ketoprofen | 20% | KET2520 | KET166 | Ethanol | Isopropyl myristate | 50:50 | Eucalyptus oil | 7.0% 1,8-cineole | | Yes | 8 | 2 | 20.915 | 62.745 |
| Ketoprofen | 20% | KET2521 | KET166 | Ethanol | Isopropyl myristate | 50:50 | Eucalyptus oil | 7.0% 1,8-cineole | | Yes | 0.5 | 3 | 0.045 | 0.135 |
| Ketoprofen | 20% | KET2522 | KET166 | Ethanol | Isopropyl myristate | 50:50 | Eucalyptus oil | 7.0% 1,8-cineole | | Yes | 2 | 3 | 0.876 | 2.628 |
| Ketoprofen | 20% | KET2523 | KET166 | Ethanol | Isopropyl myristate | 50:50 | Eucalyptus oil | 7.0% 1,8-cineole | | Yes | 4 | 3 | 4.699 | 14.097 |
| Ketoprofen | 20% | KET2524 | KET166 | Ethanol | Isopropyl myristate | 50:50 | Eucalyptus oil | 7.0% 1,8-cineole | | Yes | 6 | 3 | 8.932 | 26.796 |
| Ketoprofen | 20% | KET2525 | KET166 | Ethanol | Isopropyl myristate | 50:50 | Eucalyptus oil | 7.0% 1,8-cineole | | Yes | 8 | 3 | 13.891 | 41.673 |
| Ketoprofen | 30% | KET2526 | KET167 | Ethanol | Isopropyl myristate | 30:70 | Eucalyptus oil | 7.0% 1,8-cineole | | Yes | 0.5 | 1 | 0.111 | 0.333 |
| Ketoprofen | 30% | KET2527 | KET167 | Ethanol | Isopropyl myristate | 30:70 | Eucalyptus oil | 7.0% 1,8-cineole | | Yes | 2 | 1 | 0.174 | 0.522 |
| Ketoprofen | 30% | KET2528 | KET167 | Ethanol | Isopropyl myristate | 30:70 | Eucalyptus oil | 7.0% 1,8-cineole | | Yes | 4 | 1 | 2.104 | 6.312 |
| Ketoprofen | 30% | KET2529 | KET167 | Ethanol | Isopropyl myristate | 30:70 | Eucalyptus oil | 7.0% 1,8-cineole | | Yes | 6 | 1 | 6.267 | 18.801 |
| Ketoprofen | 30% | KET2530 | KET167 | Ethanol | Isopropyl myristate | 30:70 | Eucalyptus oil | 7.0% 1,8-cineole | | Yes | 8 | 1 | 12.945 | 38.835 |
| Ketoprofen | 30% | KET2531 | KET167 | Ethanol | Isopropyl myristate | 30:70 | Eucalyptus oil | 7.0% 1,8-cineole | | Yes | 0.5 | 2 | 0.112 | 0.336 |
| Ketoprofen | 30% | KET2532 | KET167 | Ethanol | Isopropyl myristate | 30:70 | Eucalyptus oil | 7.0% 1,8-cineole | | Yes | 2 | 2 | 0.397 | 1.191 |
| Ketoprofen | 30% | KET2533 | KET167 | Ethanol | Isopropyl myristate | 30:70 | Eucalyptus oil | 7.0% 1,8-cineole | | Yes | 4 | 2 | 4.412 | 13.236 |
| Ketoprofen | 30% | KET2534 | KET167 | Ethanol | Isopropyl myristate | 30:70 | Eucalyptus oil | 7.0% 1,8-cineole | | Yes | 6 | 2 | 10.328 | 30.984 |
| Ketoprofen | 30% | KET2535 | KET167 | Ethanol | Isopropyl myristate | 30:70 | Eucalyptus oil | 7.0% 1,8-cineole | | Yes | 8 | 2 | 18.162 | 54.486 |
| Ketoprofen | 30% | KET2536 | KET167 | Ethanol | Isopropyl myristate | 30:70 | Eucalyptus oil | 7.0% 1,8-cineole | | Yes | 0.5 | 3 | 0.083 | 0.249 |
| Ketoprofen | 30% | KET2537 | KET167 | Ethanol | Isopropyl myristate | 30:70 | Eucalyptus oil | 7.0% 1,8-cineole | | Yes | 2 | 3 | 1.142 | 3.426 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 30% | KET2538 | KET167 | Ethanol | Isopropyl myristate | 30:70 | Eucalyptus oil | 7.0% 1,8-cineole | | Yes | 4 | 3 | 8.465 | 25.395 |
| Ketoprofen | 30% | KET2539 | KET167 | Ethanol | Isopropyl myristate | 30:70 | Eucalyptus oil | 7.0% 1,8-cineole | | Yes | 6 | 3 | 12.84 | 38.52 |
| Ketoprofen | 30% | KET2540 | KET167 | Ethanol | Isopropyl myristate | 30:70 | Eucalyptus oil | 7.0% 1,8-cineole | | Yes | 8 | 3 | 19.458 | 58.374 |
| Ketoprofen | 30% | KET2541 | KET168 | Ethanol | Propylene glycol | 50:50 | Eucalyptus oil | 7.0% 1,8-cineole | | No | 0.5 | 1 | 5.977 | 17.931 |
| Ketoprofen | 30% | KET2542 | KET168 | Ethanol | Propylene glycol | 50:50 | Eucalyptus oil | 7.0% 1,8-cineole | | No | 2 | 1 | 7.033 | 21.099 |
| Ketoprofen | 30% | KET2543 | KET168 | Ethanol | Propylene glycol | 50:50 | Eucalyptus oil | 7.0% 1,8-cineole | | No | 4 | 1 | 7.901 | 23.703 |
| Ketoprofen | 30% | KET2544 | KET168 | Ethanol | Propylene glycol | 50:50 | Eucalyptus oil | 7.0% 1,8-cineole | | No | 6 | 1 | 12.529 | 37.587 |
| Ketoprofen | 30% | KET2545 | KET168 | Ethanol | Propylene glycol | 50:50 | Eucalyptus oil | 7.0% 1,8-cineole | | No | 8 | 1 | 20.847 | 62.541 |
| Ketoprofen | 30% | KET2546 | KET168 | Ethanol | Propylene glycol | 50:50 | Eucalyptus oil | 7.0% 1,8-cineole | | No | 0.5 | 2 | 0.499 | 1.497 |
| Ketoprofen | 30% | KET2547 | KET168 | Ethanol | Propylene glycol | 50:50 | Eucalyptus oil | 7.0% 1,8-cineole | | No | 2 | 2 | 0.661 | 1.983 |
| Ketoprofen | 30% | KET2548 | KET168 | Ethanol | Propylene glycol | 50:50 | Eucalyptus oil | 7.0% 1,8-cineole | | No | 4 | 2 | 1.092 | 3.276 |
| Ketoprofen | 30% | KET2549 | KET168 | Ethanol | Propylene glycol | 50:50 | Eucalyptus oil | 7.0% 1,8-cineole | | No | 6 | 2 | 1.361 | 4.083 |
| Ketoprofen | 30% | KET2550 | KET168 | Ethanol | Propylene glycol | 50:50 | Eucalyptus oil | 7.0% 1,8-cineole | | No | 8 | 2 | 1.431 | 4.293 |
| Ketoprofen | 30% | KET2551 | KET168 | Ethanol | Propylene glycol | 50:50 | Eucalyptus oil | 7.0% 1,8-cineole | | No | 0.5 | 3 | 0.118 | 0.354 |
| Ketoprofen | 30% | KET2552 | KET168 | Ethanol | Propylene glycol | 50:50 | Eucalyptus oil | 7.0% 1,8-cineole | | No | 2 | 3 | 0.269 | 0.807 |
| Ketoprofen | 30% | KET2553 | KET168 | Ethanol | Propylene glycol | 50:50 | Eucalyptus oil | 7.0% 1,8-cineole | | No | 4 | 3 | 3.847 | 11.541 |
| Ketoprofen | 30% | KET2554 | KET168 | Ethanol | Propylene glycol | 50:50 | Eucalyptus oil | 7.0% 1,8-cineole | | No | 6 | 3 | 3.485 | 10.455 |
| Ketoprofen | 30% | KET2555 | KET168 | Ethanol | Propylene glycol | 50:50 | Eucalyptus oil | 7.0% 1,8-cineole | | No | 8 | 3 | 5.79 | 17.37 |
| Ketoprofen | 30% | KET2556 | KET169 | Ethanol | Isopropyl myristate | 50:50 | Eucalyptus oil | 7.0% 1,8-cineole | | No | 0.5 | 1 | 0.095 | 0.285 |
| Ketoprofen | 30% | KET2557 | KET169 | Ethanol | Isopropyl myristate | 50:50 | Eucalyptus oil | 7.0% 1,8-cineole | | No | 2 | 1 | 0.168 | 0.504 |
| Ketoprofen | 30% | KET2558 | KET169 | Ethanol | Isopropyl myristate | 50:50 | Eucalyptus oil | 7.0% 1,8-cineole | | No | 4 | 1 | 2.63 | 7.89 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 30% | KET2559 | KET169 | Ethanol | Isopropyl myristate | 50:50 | Eucalyptus oil | 7.0% 1,8-cineole | | No | 6 | 1 | 7.315 | 21.945 |
| Ketoprofen | 30% | KET2560 | KET169 | Ethanol | Isopropyl myristate | 50:50 | Eucalyptus oil | 7.0% 1,8-cineole | | No | 8 | 1 | 14.825 | 44.475 |
| Ketoprofen | 30% | KET2561 | KET169 | Ethanol | Isopropyl myristate | 50:50 | Eucalyptus oil | 7.0% 1,8-cineole | | No | 0.5 | 2 | 0.056 | 0.168 |
| Ketoprofen | 30% | KET2562 | KET169 | Ethanol | Isopropyl myristate | 50:50 | Eucalyptus oil | 7.0% 1,8-cineole | | No | 2 | 2 | 1.259 | 3.777 |
| Ketoprofen | 30% | KET2563 | KET169 | Ethanol | Isopropyl myristate | 50:50 | Eucalyptus oil | 7.0% 1,8-cineole | | No | 4 | 2 | 7.345 | 22.035 |
| Ketoprofen | 30% | KET2564 | KET169 | Ethanol | Isopropyl myristate | 50:50 | Eucalyptus oil | 7.0% 1,8-cineole | | No | 6 | 2 | 16.244 | 48.732 |
| Ketoprofen | 30% | KET2565 | KET169 | Ethanol | Isopropyl myristate | 50:50 | Eucalyptus oil | 7.0% 1,8-cineole | | No | 8 | 2 | 25.968 | 77.904 |
| Ketoprofen | 30% | KET2566 | KET169 | Ethanol | Isopropyl myristate | 50:50 | Eucalyptus oil | 7.0% 1,8-cineole | | No | 0.5 | 3 | 0.04 | 0.12 |
| Ketoprofen | 30% | KET2567 | KET169 | Ethanol | Isopropyl myristate | 50:50 | Eucalyptus oil | 7.0% 1,8-cineole | | No | 2 | 3 | 0.529 | 1.587 |
| Ketoprofen | 30% | KET2568 | KET169 | Ethanol | Isopropyl myristate | 50:50 | Eucalyptus oil | 7.0% 1,8-cineole | | No | 4 | 3 | 4.881 | 14.643 |
| Ketoprofen | 30% | KET2569 | KET169 | Ethanol | Isopropyl myristate | 50:50 | Eucalyptus oil | 7.0% 1,8-cineole | | No | 6 | 3 | 12.469 | 37.407 |
| Ketoprofen | 30% | KET2570 | KET169 | Ethanol | Isopropyl myristate | 50:50 | Eucalyptus oil | 7.0% 1,8-cineole | | No | 8 | 3 | 22.167 | 66.501 |
| Ketoprofen | 30% | KET2571 | KET170 | Ethanol | Propylene glycol | 50:50 | Eucalyptus oil | 7.0% 1,8-cineole | | Yes | 0.5 | 1 | 0.027 | 0.081 |
| Ketoprofen | 30% | KET2572 | KET170 | Ethanol | Propylene glycol | 50:50 | Eucalyptus oil | 7.0% 1,8-cineole | | Yes | 2 | 1 | 0 | 0 |
| Ketoprofen | 30% | KET2573 | KET170 | Ethanol | Propylene glycol | 50:50 | Eucalyptus oil | 7.0% 1,8-cineole | | Yes | 4 | 1 | 0.1 | 0.3 |
| Ketoprofen | 30% | KET2574 | KET170 | Ethanol | Propylene glycol | 50:50 | Eucalyptus oil | 7.0% 1,8-cineole | | Yes | 6 | 1 | 0.238 | 0.714 |
| Ketoprofen | 30% | KET2575 | KET170 | Ethanol | Propylene glycol | 50:50 | Eucalyptus oil | 7.0% 1,8-cineole | | Yes | 8 | 1 | 0.899 | 2.697 |
| Ketoprofen | 30% | KET2576 | KET170 | Ethanol | Propylene glycol | 50:50 | Eucalyptus oil | 7.0% 1,8-cineole | | Yes | 0.5 | 2 | 0.034 | 0.102 |
| Ketoprofen | 30% | KET2577 | KET170 | Ethanol | Propylene glycol | 50:50 | Eucalyptus oil | 7.0% 1,8-cineole | | Yes | 2 | 2 | 0.029 | 0.087 |
| Ketoprofen | 30% | KET2578 | KET170 | Ethanol | Propylene glycol | 50:50 | Eucalyptus oil | 7.0% 1,8-cineole | | Yes | 4 | 2 | 0.121 | 0.363 |
| Ketoprofen | 30% | KET2579 | KET170 | Ethanol | Propylene glycol | 50:50 | Eucalyptus oil | 7.0% 1,8-cineole | | Yes | 6 | 2 | 0.172 | 0.516 |
| Ketoprofen | 30% | KET2580 | KET170 | Ethanol | Propylene glycol | 50:50 | Eucalyptus oil | 7.0% 1,8-cineole | | Yes | 8 | 2 | 0.42 | 1.26 |
| Ketoprofen | 30% | KET2581 | KET170 | Ethanol | Propylene glycol | 50:50 | Eucalyptus oil | 7.0% 1,8-cineole | | Yes | 0.5 | 3 | 0.454 | 1.362 |

TABLE 13-continued

NSAID and vehicle screening data

| NSAID | Drug conc | Sample # | Vehicle ID | Alcohol solvent Solvent | Solvent conc | Co-solvent | Co-solvent conc | Terpene | Terpene concentration (mg/mL) | Buffer/ EVAP | sample time (hrs) | Replicate | analysis conc | Concentration (μg/mL) |
|---|---|---|---|---|---|---|---|---|---|---|---|---|---|---|
| Ketoprofen | 30% | KET2582 | KET170 | Ethanol | Propylene glycol | Eucalyptus oil | 50:50 | 7.0% 1,8-cineole | | Yes | 2 | 3 | 0.421 | 1.263 |
| Ketoprofen | 30% | KET2583 | KET170 | Ethanol | Propylene glycol | Eucalyptus oil | 50:50 | 7.0% 1,8-cineole | | Yes | 4 | 3 | 5.979 | 17.937 |
| Ketoprofen | 30% | KET2584 | KET170 | Ethanol | Propylene glycol | Eucalyptus oil | 50:50 | 7.0% 1,8-cineole | | Yes | 6 | 3 | 5.739 | 17.217 |
| Ketoprofen | 30% | KET2585 | KET170 | Ethanol | Propylene glycol | Eucalyptus oil | 50:50 | 7.0% 1,8-cineole | | Yes | 8 | 3 | 8.202 | 24.606 |
| Ketoprofen | 30% | KET2586 | KET171 | Ethanol | Isopropyl myristate | Eucalyptus oil | 50:50 | 7.0% 1,8-cineole | | Yes | 0.5 | 1 | 0.644 | 1.932 |
| Ketoprofen | 30% | KET2587 | KET171 | Ethanol | Isopropyl myristate | Eucalyptus oil | 50:50 | 7.0% 1,8-cineole | | Yes | 2 | 1 | 6.599 | 19.797 |
| Ketoprofen | 30% | KET2588 | KET171 | Ethanol | Isopropyl myristate | Eucalyptus oil | 50:50 | 7.0% 1,8-cineole | | Yes | 4 | 1 | 21.617 | 64.851 |
| Ketoprofen | 30% | KET2589 | KET171 | Ethanol | Isopropyl myristate | Eucalyptus oil | 50:50 | 7.0% 1,8-cineole | | Yes | 6 | 1 | 30.099 | 90.297 |
| Ketoprofen | 30% | KET2590 | KET171 | Ethanol | Isopropyl myristate | Eucalyptus oil | 50:50 | 7.0% 1,8-cineole | | Yes | 8 | 1 | 35.084 | 105.252 |
| Ketoprofen | 30% | KET2591 | KET171 | Ethanol | Isopropyl myristate | Eucalyptus oil | 50:50 | 7.0% 1,8-cineole | | Yes | 0.5 | 2 | 0.231 | 0.693 |
| Ketoprofen | 30% | KET2592 | KET171 | Ethanol | Isopropyl myristate | Eucalyptus oil | 50:50 | 7.0% 1,8-cineole | | Yes | 2 | 2 | 3.496 | 10.488 |
| Ketoprofen | 30% | KET2593 | KET171 | Ethanol | Isopropyl myristate | Eucalyptus oil | 50:50 | 7.0% 1,8-cineole | | Yes | 4 | 2 | 12.012 | 36.036 |
| Ketoprofen | 30% | KET2594 | KET171 | Ethanol | Isopropyl myristate | Eucalyptus oil | 50:50 | 7.0% 1,8-cineole | | Yes | 6 | 2 | 16.294 | 48.882 |
| Ketoprofen | 30% | KET2595 | KET171 | Ethanol | Isopropyl myristate | Eucalyptus oil | 50:50 | 7.0% 1,8-cineole | | Yes | 8 | 2 | 20.867 | 62.601 |
| Ketoprofen | 30% | KET2596 | KET171 | Ethanol | Isopropyl myristate | Eucalyptus oil | 50:50 | 7.0% 1,8-cineole | | Yes | 0.5 | 3 | 0.659 | 1.977 |
| Ketoprofen | 30% | KET2597 | KET171 | Ethanol | Isopropyl myristate | Eucalyptus oil | 50:50 | 7.0% 1,8-cineole | | Yes | 2 | 3 | 6.032 | 18.096 |
| Ketoprofen | 30% | KET2598 | KET171 | Ethanol | Isopropyl myristate | Eucalyptus oil | 50:50 | 7.0% 1,8-cineole | | Yes | 4 | 3 | 16.236 | 48.708 |
| Ketoprofen | 30% | KET2599 | KET171 | Ethanol | Isopropyl myristate | Eucalyptus oil | 50:50 | 7.0% 1,8-cineole | | Yes | 6 | 3 | 20.343 | 61.029 |
| Ketoprofen | 30% | KET2600 | KET171 | Ethanol | Isopropyl myristate | Eucalyptus oil | 50:50 | 7.0% 1,8-cineole | | Yes | 8 | 3 | 24.634 | 73.902 |

DISCUSSION

To Confirm Transdermal Penetration of Candidate Formulations Using In Vitro Techniques

Regional Differences in Transdermal Drug Penetration

This study has shown that there are significant differences in the penetration of lignocaine hydrochloride through different regions of cattle skin in vitro. Regional differences in transdermal drug penetration has also been reported in cats (Hill et al., 2015), horses (Mills and Cross, 2006b, 2007a, b) and dogs (Mills et al., 2004b, a, 2005). However, the specific differences between regions will depend on both the active drug and the vehicle used. In the current study, lignocaine hydrochloride was dissolved in an alcohol-based vehicle containing a surfactant, which was associated with a significantly higher penetration of active drug through skin harvested from the thorax and scrotal regions.

Specific reasons for the regional differences are uncertain, although the scrotal skin was observed to be grossly thinner with finer hair present on the skin, compared to the skin from dorsal midline, thorax and ventral abdomen. Regional differences may relate to the thickness of the stratum corneum (Monteiro-Riviere et al., 1990), regional cutaneous blood flow (Monteiro-Riviere et al., 1990), the size of corneocytes (Kashibuchi et al., 2002; McEwan et al., 2009) and density of hair follicles (Damodaram and Seshadri, 1984; Steelman et al., 1997). Since the current study used in vitro diffusion cells, cutaneous blood flow did not contribute to the outcomes, although it is generally higher in the ventral abdomen compared to the buttocks, ear and shoulder and dorsal midline (Monteiro-Riviere et al., 1990). In contrast, the epidermis thickness in the skin from ventral abdomen is generally lower than other regions. However, the primary barrier to drug penetration is the stratum corneum and can be directly evaluated using diffusion cells in vitro (Mills and Cross, 2006).

The selection of the four regions used in the current study was based on potential sites where topical drug may be applied to cattle. The scrotal skin is incised during castration and an effective local anaesthetic would significantly reduce pain associated with this procedure, yet could be applied by lay operators. Topical drugs are usually applied to the thorax or dorsal midline for convenience, but this also facilitates larger volumes of formulation to be applied, if required, for adequate systemic effects. Moreover, many pour-on drugs applied along the dorsal midline will tend to run ventrally over the thorax. The abdomen was included in this study since studies in other species have demonstrated that some drugs will penetrate through the abdomen and/or groin region to a greater extent than other regions (Mills et al., 2004a, b; Mills and Cross, 2006b, 2007a, b). However, the current study showed that the thorax was more permeable to the specific formulation used, although lignocaine hydrochloride also penetrated through the other regions tested.

Screening of NSAID and Vehicle Combinations to Maximise Active Drug Penetration Through Cattle Skin Of the four NSAIDs currently registered for use in cattle in Australia, only ketoprofen and flunixin meglumine actually penetrated through skin in the vehicles tested. Tolfenamic acid was poorly soluble in almost every vehicle tested, while meloxicam had poor percutaneous penetration. It was therefore decided to move forward with ketoprofen since it penetrated through bovine skin significantly higher, in terms of rate and extent, than flunixin meglumine. The combination with *eucalyptus* oil was interesting, since a number of the commercially-available vehicles (from Croda) had a basis in eucalyptol, while the terpenes were generally useful vehicle excipients to enhance drug movement through the skin.

Optimising the Candidate Formulations

The final formulation was determined based of a number of factors. It was considered advisable that isopropanol would be preferable in any topical preparation due to its low flammability. Occupational health and Safety were a consideration when spraying a potentially flammable mixture on cattle. However, isopropanol did not enhance active drug movement as well as ethanol, so the latter was retained. Similarly, IPM was selected as a solubilising agent, proving superior to other potential agents, including propylene glycol and oleyl alcohol. The 50:50 combination of ethanol and IPM maximally enhanced the movement of ketoprofen through cattle skin, supported by 10% *eucalyptus* oil.

The amount of active drug required in the formulation was unknown. Other commercial formulations containing NSIDs for human topical application contain 10+% of active drug. Up to 30% ketoprofen could be dissolved in the final vehicle formulation, although some precipitation occurred, while 20% dissolved easily without precipitation. Since it was uncertain how much drug would actually get through cattle skin in vivo, it was decided to incorporate 20% active into the final formulation. This would also minimise the volume of formulation that needed to be applied.

Stability Studies of the Final Formulation

The stability study was intended as a preliminary assessment to provide some support for the final formulation if advanced to production. The environmental conditions used (0, 20 and 40° C.) approximated potential storage or use conditions in the field. Despite a mild colour change after several months at 40° C., the concentration of active drug remained stable (20±1%). It was concluded that the formulation was quite stable under a range of conditions and storage.

Analysis of Ketoprofen in Biological Samples

The analytical methodology was reliable and consistent, with a low and appropriate limit of detection. The use of mass spectrometry ensured that parent drug was detected and any metabolites identified.

SUMMARY

To Determine the Efficacy of Candidate Transdermal Formulations to Control Pain Associated with Surgical Husbandry Formulations

Pilot Study 1 and 2

Despite the in vitro data, it was uncertain how much active drug would reach the systemic circulation and how quickly. In vitro studies using Franz cells are widely acknowledged as useful for proof-of-concept studies and to screen large numbers of potential drug and vehicle combinations. However, other factors must be considered when applying formulations to the living animal, including metabolism in the skin (both phase 1 and phase 2 metabolism occurs), the effects of cutaneous blood flow and the potential of the active to move away for the dermis and enter the systemic circulation (Mills and Cross, 2006a). Significant concentrations of ketoprofen were detected systemically in plasma following transdermal application of the novel formulation. The 40 mL dose resulted in obvious precipitation of the skin of the calves and resulted in peak ($C_{MAX}$) concentrations of up to 43 µg/mL in the plasma, with drug appearing within 30 min (this was the first blood collection time) and peaking at ~2 hr. This was much faster than expected. The study was repeated with only the 10 mL dose, which resulted in a $C_{MAX}$ of 3-10 µg/mL, again around 2 hr, within initial drug appearing in the plasma after ~30 min. These concentrations approached what had been reported following IM administration (3 mg/kg) and, as such, could be considered therapeutic (see Plessers et al 2015). No adverse effects were observed in the cattle.

Bioavailability Study

This was a major study to determine the bioavailability of ketoprofen from the transdermal formulation and to compare the pharmacokinetics with IM administration. The use of a cross-over study with animals in the target age group (i.e. when dehorning is normally undertaken) added power and relevance to the study design.

The bioavailability of ketoprofen was ~50%, which is a good outcome for a topically-administered drug. More importantly, the lag phase (the time between application and first appearance in the plasma) was exceptionally short for the transdermal route, with drug appearing within 10-15 min. Furthermore, the $C_{MAX}$ and AUC were almost twice that measured after IM administration, although the $T_{MAX}$ for IM (74 min) was faster than transdermal delivery (115 min). These pharmacokinetic findings suggest that the transdermal route is a rapid and effective route to deliver ketoprofen to calves. Further modelling and dose administration should be undertaken, but a smaller dose rate (i.e. volume) of the transdermal formulation could be applied to achieve a similar efficacy (determined by $C_{MAX}$ and AUC) as IM administration. Moreover, reducing the volume of drug applied could also reduce the $T_{MAX}$, meaning that the transdermal formulation could have a similar pharmacokinetic profile as IM administration.

The skin irritation and excoriation noted in the bioavailability study was a concern and had not been observed in the calves in the pilot studies or the clinical study. It should be noted, however, that the formulation had not been washed off in the other studies. The exact cause of this irritation is uncertain, although ketoprofen is a known photosensitising agent (Guy, et al., 2014; Seto et al., 2015). Since the active drug was absorbed so rapidly following topical administration, less of the active drug should have remained on the skin.

To Develop a Formulation Containing an NSAID to Control Pain Associated with Routine Surgical Interventions for Up to 24 hr Clinical Study This study was performed on calves at an age when they would normally be dehorned. A cornual nerve block was not used (this was approved by the animal ethics committee) since this represents the industry standard currently. A sham-handled group was used as a negative control to allow for the stress induced by handling and multiple blood samples collected. The remaining calves were all dehorned and no adverse effects were observed.

An important consideration for the clinical study was that the bioavailability study had already demonstrated that the transdermal formulation resulted in a higher systemic concentration of ketoprofen than the IM administration and, while slower in onset, persisted in the plasma for longer. These findings suggested that the efficacy of the transdermal formulation would be similar, if not better than, IM ketoprofen, from a bioequivalence perspective. The literature has already shown that IM ketoprofen has an analgesic effect lasting at least 24 hr in cattle following surgical husbandry procedures.

Conventional Parameters to Assessment Pain and Inflammation

All the conventional parameters indicated that ketoprofen had a significant analgesic effect in the cattle. Total plasma cortisol and body weight gain were significantly different between treated and untreated calves, but there were no significant difference between the routes of administration of the ketoprofen. Dehorned calves that received ketoprofen had a body weight gain that was similar to the sham-treated cattle and significantly higher than the placebo-treated cattle. These findings indicated that transdermal ketoprofen had a similar or higher efficacy than IM ketoprofen and this significantly reduced pain and stress in cattle following dehorning.

Proteomic Assessment of Pain and Inflammation

Unfortunately, the analysis of the proteomic data was continuing while this report was being combined. Over 300 proteins had been isolated and identified, consisting of two or more peptides each. The software packages to automatically identify the proteins proved inaccurate and much of the spectral library was confirmed manually. Irrespective, some important trends were emerging, backing up the conventional parameters. The response to dehorning (FIG. 19b) was substantially different from sham. There was a difference between untreated and treated cattle, meaning that ketoprofen significantly affected key biomarkers of pain and inflammation, while the transdermal ketoprofen appeared to have greater efficacy than IM delivery.

Conclusions/Recommendations

Drug Movement Through Cattle Skin

The transdermal route appears to be an effective and useful approach to delivering analgesic drugs to cattle. It is more convenient and able to be applied by lay (untrained) operators. There are regional differences in the permeability of cattle skin to topically applied drugs, with thoracic/backline skin being the highest.

It was possible to move NSAIDs through cattle skin, although, of the NSAIDs registered for cattle use in Australia, only ketoprofen and flunixin meglumine were suitable, while tolfenamic acid and meloxicam did not penetrate cattle skin. Ketoprofen penetrated skin to a significantly higher extent, but flunixin meglumine did penetrate to some degree and could be considered for other potential formulations.

Optimising a Transdermal NSAID Formulation

A combination of 20% ketoprofen in a vehicle consisting of a combination of 50:50 ethanol and IPM, mixed with 10% *eucalyptus* oil (~7% 1,8-cineole), meaning that ethanol and IPM are actually at 45% each, was the most effective transdermal formulation.

This formulation was stable under a range of conditions, such as may be expected under use in the field.

Pilot studies revealed that 10 mL of the transdermal formulation delivered systemic ketofen concentrations that were likely to be effective to control pain and inflammation.

Determining the Efficacy of the Transdermal Ketoprofen Formulation

A bioequivalence study revealed that the bioavailability of the transdermal ketoprofen formulation was ~50%. Importantly, the lag time was low, with active drug appearing in the systemic circulation after 15-20 min and a peak concentration ~2 hr. A comparison with IM administration revealed that 10 mL of the transdermal formulation had a slightly longer lag time and delay to peak ($C_{MAX}$), but the overall $C_{MAX}$ and AUC were both higher than an IM dose of 3 mg/kg. These outcomes suggest that the transdermal formulation should therefore have similar efficacy as IM delivery.

The clinical study confirmed that similar efficacy between IM and transdermal ketoprofen occurred when used during a routine surgical husbandry procedure, dehorning. Total plasma cortisol concentrations and body weight gain showed that ketoprofen, by either route, reduced stress and pain associated with dehorning. Behavioural parameters supported the analgesic effects of ketoprofen and, while not demonstrating overall significance, the trends were all towards analgesia and may have been significant in the study had sufficient power. Some individual behaviour parameters, such as head shaking, were significantly different from the placebo group, demonstrating that ketoprofen significantly reduced this indicator of pain.

The outcome from this project was that a formulation has been developed to effectively move ketoprofen through cattle skin. When applied to the backline, a 10 mL provided similar if not greater efficacy to control stress and pain as IM (3 mg/kg) administration. Pharmacokinetic modelling also demonstrated a similar extent and duration of active drug following topical administration as from IM, in itself providing strong support for efficacy.

The transdermal ketoprofen formulation is easy to administer, effective and relatively cheap, providing a highly encouraging means of providing analgesia for surgical husbandry procedures in Australia. This will be encouraging for producers, veterinarians and welfare advocates.

Proteomics has the potential to replace or at least support more traditional methods of assessing pain, such as plasma cortisol and behavioural parameters. Further analysis is required to finalise the protein spectral library for cattle, before a single blood sample could accurately and quantitatively assess pain and stress.

BIBLIOGRAPHY

Ahlstrom L. A., Cross S. E. and Mills, P. C. (2007a). The effects of freezing skin on transdermal drug penetration kinetics. *J Vet. Pharm. Ther.* 30(5), 456-63.

Ahlstrom, L. A., Cross, S. E., Morton, J. M., Mills, P. C., 2009. The effects of surface preparation on the penetration of hydrocortisone through canine skin. Veterinary Journal 180, 48-54.

Allen K A, et al., 2013. The effect of timing of oral meloxicam administration on physiological responses in calves after cautery dehorning with local anesthesia. *Journal of Dairy Science* 96(8): 5194-5205.

Bell, L. N., Lee, L., Saxena, R., Bemis, K. G., Wang, M., Theodorakis, J. L., Vuppalanchi, R., Alloosh, M., Sturek, M., Chalasani, N., 2010. Serum proteomic analysis of diet-induced steatohepatitis and metabolic syndrome in the Ossabaw miniature swine. American Journal of Physiology—Gastrointestinal and Liver Physiology 298, 746-754.

Cross, S. E., Anissimov, Y. G., Magnusson, B. M., Roberts, M. S., 2003a. Bovine-serum-albumin-containing receptor phase better predicts transdermal absorption parameters for lipophilic compounds. Journal of Investigative Dermatology 120, 589-591.

Cross, S. E., Magnusson, B. M., Winckle, G., Anissimov, Y., Roberts, M. S., 2003b. Determination of the effect of lipophilicity on the in vitro permeability and tissue reservoir characteristics of topically applied solutes in human skin layers. Journal of Investigative Dermatology 120, 759-764.

Faulkner P. M. and Weary D. M. (2000). Reducing Pain After Dehorning in Dairy Calves. J Dairy Sci 83:2037-2041.

Goonewardene L A, Hand R K, 1991, Studies on dehorning steers in Alberta feedlots. Canadian J An Sc 71; 1249-1252.

Guy, R. H., Kuma, H., Nakanishi, M. (2014). Serious photocontact dermatitis induced by topical ketoprofen depends on the formulation. Eur J Dermatol. 24(3):365-71.

Faulkner, S., Elia, G., Mullen, M. P., O'Boyle, P., Dunn, M. J., Morris, D., 2012. A comparison of the bovine uterine and plasma proteome using iTRAQ proteomics. Proteomics 12, 2014-2023.

Hemsworth P, Arnold A, 2006. Animal Welfare and how it relates to cattle. Proceedings of the Australian Cattle Veterinarians Annual Conference, Hobart, May 2006.

Hoofnagle, A. N., Wener, M. H., 2009. The fundamental flaws of immunoassays and potential solutions using tandem mass spectrometry. J. Immunol. Methods 347, 3-11.

Horadagoda, N. U., Knox, K. M., Gibbs, H. A., Reid, S. W., Horadagoda, A., Edwards, S. E., Eckersall, P. D., 1999. Acute phase proteins in cattle: discrimination between acute and chronic inflammation. The Veterinary record 144, 437-441.

Ignacio Viñuela-Fernández, Emma Jones, Elizabeth M. Welsh, Susan M. Fleetwood-Walker 2007. Pain mechanisms and their implication doer the management of pain in farm and companion animals. The Vet J, 174; 227-239.

Liu, Y. J., Zhang, K. S., Zheng, H. X., Shang, Y. J., Guo, J. H., Tian, H., Lu, G. D., Jin, Y., He, J. J., Cai, X. P., Li, X. T., 2011. Proteomics Analysis of Porcine Serum Proteins by LC-MS/MS after Foot-and-Mouth Disease Virus (FMDV) Infection. J. Vet. Med. Sci. 73, 1569-1572.

Loxton I D, Toleman M A, Holmes A E, 1982. The effect of dehorning Brahman crossbred animals of four age groups on subsequent bodyweight gain. Aust Vet J 58; 191-193.

Mann, M., Aebersold, R., 2003. Mass spectrometry-based proteomics. Nature 422, 198-207.

Mellor D, Stafford K, 1999. Assessing and minimising the distress caused by painful husbandry procedures in ruminants. In Practice, September 436-446.

Mills P. C. (2007). Vehicle effects on the penetration of testosterone through equine skin. *Vet. Res. Comm.* 31(2), 227-233.

Mills P. C. and Cross S. E. (2006a). Transdermal Drug Delivery: Basic Principles for the Veterinarian. *Vet. J.* 172(2), 218-233.

Mills P. C. and Cross S. E. (2006b). The effects of equine skin preparation on transdermal drug penetration in vitro. *Can. J Vet. Res.* 70(4), 317-320.

Mills P. C. and Cross S. E. (2006c). Regional differences in the in vitro penetration of hydrocortisone through equine skin. *J. Vet. Pharm. Ther.* 29, 25-30.

Mills P. C. and Cross S. E. (2007a). Regional differences in the in vitro penetration of methylsalicylate through equine skin. *Vet. J.* 173, 59-63.

Mills P. C. and Cross S. E. (2007b). Regional differences in transdermal penetration of fentanyl through equine skin. *Res. Vet. Sci.* 82(2), 252-256.

Mills P. C., Magnusson B. M. and Cross S. E. (2004a). Investigation of in vitro transdermal absorption of fentanyl from patches placed on skin samples obtained from various anatomic regions of dogs. *Am. J. Vet. Res.* 65(12), 1697-1700.

Mills P. C., Magnusson B. M. and Cross S. E. (2004b). The effect of region of application on absorption through canine skin. *Res. Vet. Sci.* 76, 37-41.

Mills P. C., Magnusson B. M. and Cross S. E. (2005). The effects of vehicle and region of application on absorption of hydrocortisone through canine skin. *Am. J Vet. Res.* 66(1), 43-47.

Mills P. C., Magnusson B. M. and Cross S. E. (2006). The effects of vehicle and region of application on absorption of testosterone through canine skin. *Vet J.* 171, 276-280.

Nesvizhskii, A. I., Aebersold, R., 2005. Interpretation of shotgun proteomic data—The protein inference problem. MOLECULAR & CELLULAR PROTEOMICS 4, 1419-1440.

Petherick, JC, McCosker, K., Mayer, DG., Letchford P., McGowan, M. (2013). Evaluation of the impacts of spaying by either the dropped ovary technique or ovariectomy via flank laparotomy on the welfare of *Bos indicus* beef heifers and cows. *J Anim Sci* 91:382-394.

Phillips C 2006. Industry perceptions of animal welfare in the red meat industry. Report to MLA.

Seto, Y., Ohtake, H., Kato, M., Onoue, S. (2015). Phototoxic Risk Assessments on Benzophenone Derivatives: Photobiochemical Assessments and Dermal Cassette-Dosing Pharmacokinetic Study. J Pharmacol Exp Ther. 354(2), 195-202

Stafford et al. 2003. The effect of different combinations of lignocaine, ketoprofen, xylazine and tolazoline on the acute cortisol response to dehorning in calves. NZ vet J 51, 219-226.

Stafford K J, Mellor D J, 2005. Dehorning and disbudding distress and its alleviation in calves. The Vet J 169; 337-349.

Sun, D., Zhang, H., Guo, D., Sun, A., Wang, H., 2013. Shotgun Proteomic Analysis of Plasma from Dairy Cattle Suffering from Footrot: Characterization of Potential Disease-Associated Factors. PLoS ONE 8, e55973.

Williams, A. C. 2003. Experimental design. In: Williams, A. C., (Ed.). Transdermal and Topical Drug Delivery. Pharmaceutical Press, London, UK, pp. 27-49.

Winks L, Holmes A E, O'Rourke P K, 1977, Effect of dehorning and tipping on liveweight gain of mature Brahman crossbred steers. Aust J Exp Ag Anim Husb. 17: 16-19.

The invention claimed is:

1. A method of treating inflammation in a subject, the method including the step of topically administering to an area of the subject a therapeutically effective amount of a transdermal liquid formulation comprising:
   (a) a therapeutically effective amount of ketoprofen or a pharmaceutically acceptable salt thereof; and
   (b) a dermal penetration enhancer comprising an alcohol, an emollient and *eucalyptus* oil;
   to thereby provide a therapeutically effective plasma concentration of ketoprofen or a pharmaceutically acceptable salt thereof to the subject to thereby treat inflammation in the subject,
   wherein:
   the subject is bovine;
   the inflammation is systemic, or is located at a site of the subject which is not at the area of administration of the transdermal liquid formulation;
   the ketoprofen is present in the transdermal liquid formulation in an amount from 100 mg/mL to 300 mg/mL;
   the alcohol is ethanol, and is present in the transdermal liquid formulation in an amount from 100 mg/mL to 700 mg/mL;
   the emollient is selected from the group consisting of propylene glycol, oleyl alcohol, dimethyl isosorbide, PPG-3 benzyl ether myristate, di-PPG2-myreth-10-adipate, 1-ethyl-2-pryrrolidone, isomyristate, isopropyl myristate and any combination thereof, and is present in the transdermal liquid formulation in an amount from 100 mg/mL to 700 mL/L; and
   the *eucalyptus* oil is present in an amount from 25 mL/L to 150 mL/L.

2. A method of treating pain in a subject, the method including the step of topically administering to an area of the subject a therapeutically effective amount of a transdermal liquid formulation comprising:
   (a) a therapeutically effective amount of ketoprofen or a pharmaceutically acceptable salt thereof; and
   (b) a dermal penetration enhancer comprising an alcohol, an emollient and *eucalyptus* oil;
   to thereby provide a therapeutically effective plasma concentration of ketoprofen or a pharmaceutically acceptable salt thereof to the subject to thereby treat pain in the subject,
   wherein:
   the subject is bovine;
   the pain is systemic, or is located at a site of the subject which is not at the area of administration of the transdermal liquid formulation;
   the ketoprofen is present in the transdermal liquid formulation in an amount from 100 mg/mL to 300 mg/mL;
   the alcohol is ethanol, and is present in the transdermal liquid formulation in an amount from 100 mg/mL to 700 mg/mL;
   the emollient is selected from the group consisting of propylene glycol, oleyl alcohol, dimethyl isosorbide, PPG-3 benzyl ether myristate, di-PPG2-myreth-10-adipate, 1-ethyl-2-pryrrolidone, isomyristate, isopropyl myristate and any combination thereof, and is present in the transdermal liquid formulation in an amount from 100 mg/mL to 700 mL/L; and
   the *eucalyptus* oil is present in an amount from 25 mL/L to 150 mL/L.

3. A method of treating a lameness and/or a loss of mobility in a subject, the method including the step of topically administering to the subject a therapeutically effective amount of a transdermal liquid formulation comprising:
   (a) a therapeutically effective amount of ketoprofen or a pharmaceutically acceptable salt thereof; and
   (b) a dermal penetration enhancer comprising an alcohol, an emollient and *eucalyptus* oil;
   to thereby treat the lameness and/or the loss of mobility in the subject,
   wherein:
   the subject is bovine;
   the lameness and/or loss of mobility is located at a site of the subject which is not at the area of administration of the transdermal liquid formulation;
   the ketoprofen is present in the transdermal liquid formulation in an amount from 100 mg/mL to 300 mg/mL;
   the alcohol is ethanol, and is present in the transdermal liquid formulation in an amount from 100 mg/mL to 700 mg/mL;
   the emollient is selected from the group consisting of propylene glycol, oleyl alcohol, dimethyl isosorbide, PPG-3 benzyl ether myristate, di-PPG2-myreth-10-adipate, 1-ethyl-2-pryrrolidone, isomyristate, isopropyl myristate and any combination thereof, and is present in the transdermal liquid formulation in an amount from 100 mg/mL to 700 mL/L; and
   the *eucalyptus* oil is present in an amount from 25 mL/L to 150 mL/L.

4. The method of claim 1, wherein the emollient is selected from the group consisting of propylene glycol, isopropyl myristate and any combination thereof.

5. The method of claim 2, wherein the emollient is selected from the group consisting of propylene glycol, isopropyl myristate and any combination thereof.

6. The method of claim 3, wherein the emollient is selected from the group consisting of propylene glycol, isopropyl myristate and any combination thereof.

\* \* \* \* \*